(12) United States Patent
Guo et al.

(10) Patent No.: US 9,718,838 B2
(45) Date of Patent: Aug. 1, 2017

(54) INHIBITORS OF EZH2

(71) Applicant: Eli Lilly and Company, Indianapolis, IN (US)

(72) Inventors: Deqi Guo, Carmel, IN (US); Anh-Quan Hannah Nguyen, Carmel, IN (US); Michael Enrico Richett, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/242,638

(22) Filed: Aug. 22, 2016

(65) Prior Publication Data

US 2017/0066780 A1    Mar. 9, 2017

(30) Foreign Application Priority Data

Aug. 27, 2015  (EP) ..................................... 15382433
Dec. 11, 2015  (EP) ..................................... 15382615

(51) Int. Cl.
| | | |
|---|---|---|
| *C07D 495/04* | (2006.01) |
| *A61K 31/5377* | (2006.01) |
| *A61K 31/337* | (2006.01) |
| *A61K 31/282* | (2006.01) |
| *A61K 31/55* | (2006.01) |
| *A61K 33/24* | (2006.01) |
| *A61K 31/7068* | (2006.01) |
| *A61K 31/444* | (2006.01) |
| *A61K 31/4745* | (2006.01) |

(52) U.S. Cl.
CPC .......... *C07D 495/04* (2013.01); *A61K 31/282* (2013.01); *A61K 31/337* (2013.01); *A61K 31/444* (2013.01); *A61K 31/4745* (2013.01); *A61K 31/5377* (2013.01); *A61K 31/55* (2013.01); *A61K 31/7068* (2013.01); *A61K 33/24* (2013.01)

(58) Field of Classification Search
None
See application file for complete search history.

(56) References Cited

U.S. PATENT DOCUMENTS

| | | |
|---|---|---|
| 8,691,507 B2 | 4/2014 | Copeland et al. |
| 2012/0071418 A1 | 3/2012 | Copeland et al. |
| 2013/0040906 A1 | 2/2013 | Kuntz et al. |
| 2014/0107122 A1 | 4/2014 | Kuntz et al. |
| 2015/0368229 A1 | 12/2015 | Albrecht et al. |
| 2016/0009718 A1 | 1/2016 | Albrecht et al. |
| 2016/0185757 A1 | 6/2016 | Albrecht et al. |
| 2016/0228447 A1 | 8/2016 | Keilhack et al. |

FOREIGN PATENT DOCUMENTS

| | | |
|---|---|---|
| WO | 2004/074301 A2 | 9/2004 |
| WO | 2011/140324 A1 | 11/2011 |
| WO | 2011/140325 A1 | 11/2011 |
| WO | 2012/005805 A1 | 1/2012 |
| WO | 2012/034132 A2 | 3/2012 |
| WO | 2012/068589 A2 | 5/2012 |
| WO | 2012/075080 | 6/2012 |
| WO | 2012/118812 A2 | 9/2012 |
| WO | 2012/142504 A1 | 10/2012 |
| WO | 2012/142513 A1 | 10/2012 |
| WO | 2013/039988 A1 | 3/2013 |
| WO | 2013/049770 A2 | 4/2013 |
| WO | 2013/067296 A1 | 5/2013 |
| WO | 2013/067300 A1 | 5/2013 |
| WO | 2013/067302 A1 | 5/2013 |
| WO | 2013/075083 A1 | 5/2013 |
| WO | 2013/075084 A1 | 5/2013 |
| WO | 2013/078320 A1 | 5/2013 |
| WO | 2013/120104 A2 | 8/2013 |
| WO | 2013/138361 A1 | 9/2013 |
| WO | 2013/155317 A1 | 10/2013 |
| WO | 2013/155434 | 10/2013 |
| WO | 2013/155464 A1 | 10/2013 |
| WO | 2013/173441 | 11/2013 |
| WO | 2014/049488 | 4/2014 |
| WO | 2014/062720 A2 | 4/2014 |
| WO | 2014/097041 A1 | 6/2014 |
| WO | 2014/100080 A1 | 6/2014 |
| WO | 2014/100646 A1 | 6/2014 |
| WO | 2014/100665 A1 | 6/2014 |
| WO | 2014/107277 A1 | 7/2014 |
| WO | 2014/124418 A1 | 8/2014 |
| WO | 2014/151142 A1 | 9/2014 |
| WO | 2014/177982 A1 | 11/2014 |
| WO | 2015/004618 A1 | 1/2015 |
| WO | 2015/010049 A1 | 1/2015 |
| WO | 2015/010078 A2 | 1/2015 |
| WO | 2015/077193 A1 | 5/2015 |
| WO | 2015/077194 A1 | 5/2015 |

(Continued)

OTHER PUBLICATIONS

Pei-Pei Kung, et al_Design and synthesis of pyridine containing 3,4-dihydroisoquinoline-1(2H)-ones as a novel class of enhancer of zeste homolog 2 (EZH2) inhibitors_Journal of Medicinal Chemistry_2016_pp. 1-72.

*Primary Examiner* — Brian J Davis
(74) *Attorney, Agent, or Firm* — Tina M. Tucker

(57) ABSTRACT

The present invention relates to compounds that inhibit activity of the histone lysine methyltransferase, Enhancer of Zeste Homolog 2 (EZH2), pharmaceutical compositions comprising the compounds, and methods of using the compounds to treat cancer, such as hematologic and solid tumors.

15 Claims, No Drawings

(56) References Cited

FOREIGN PATENT DOCUMENTS

| WO | 2015/104677 A1 | 7/2015 |
|----|----------------|--------|
| WO | 2015/141616    | 9/2015 |
| WO | 2015/193765 A1 | 12/2015 |
| WO | 2015/193768 A1 | 12/2015 |
| WO | 2015/195848 A1 | 12/2015 |
| WO | 2015/196064 A1 | 12/2015 |
| WO | 2015/200650 A1 | 12/2015 |
| WO | 2016/066697    | 5/2016 |
| WO | 2016/089804 A1 | 6/2016 |
| WO | 2016/102493 A1 | 6/2016 |
| WO | 2016/130396 A1 | 8/2016 |
| WO | 2016/140501 A1 | 9/2016 |
| WO | 2017002064     | 1/2017 |

INHIBITORS OF EZH2

The present invention relates to compounds that inhibit activity of the histone lysine methyltransferase, Enhancer of Zeste Homolog 2 (EZH2), pharmaceutical compositions comprising the compounds, and methods of using the compounds to treat cancer, such as hematologic and solid tumors.

EZH2 is encoded by the EZH2 gene, and is the catalytic component within polycomb repressive complex 2 (PRC2) that is responsible for the methylation of lysine 27 on histone 3 (H3K27) on chromatin. EZH2 overexpression is thought to promote cancer as a result of increases in histone methylation which silences the expression of tumor suppressor genes. The catalytic activity of EZH2 is mediated by a 130 amino acid Su(var)3-9, enhancer of Zeste and trithorax (SET) domain, which provides the binding pockets for S-adenosylmethionine (SAM) cofactor and the lysine substrate residue. The core PRC2 complex is comprised of EZH2 and proteins EED (Embryonic Ectoderm Development), SUZ12 (Suppressor of Zeste 12 homolog) and RbAp46/48 (also known as RBBP7/4), and can also include other proteins such as JARID2, AEBP2, and Polycomblike (PCL) 1/2/3.

In addition to overexpression of EZH2, increased H3K27 methylation can also arise due to mutations which increase the catalytic efficiency of EZH2, such as Y641N, A677G, and A678V. In addition, it is also reported that levels of H3K27 methylation can be modulated in solid tumors through various signaling pathways, such as those involving VEGFR2 and PI3K/AKT.

The SWI/SNF and PRC2 complexes play antagonistic roles in the activation and repression of transcription, respectively. Tumors that lack or are defective in SWI/SNF protein SNF5 (also known as SMARCB1/INI1) can demonstrate aberrant methylation and repression by PRC2 and are growth-inhibited following treatment with EZH2 small molecule inhibitors. In addition, tumors that lack or are defective in SWI/SNF protein ARID1A (also known as BAF250), combined with constitutively activating mutations in components of the PI3K pathway such as PIK3CA, are also growth-inhibited following treatment with EZH2 small molecule inhibitors. In addition, tumors that lack or are defective in both SMARCA2 (also known as BRM) and SMARCA4 (also known as BRG1) are also growth-inhibited following treatment with EZH2 small molecule inhibitors.

H3K4 methyltransferase (also known as MLL or COMPASS) complexes cooperate with the SWI/SNF complex in antagonizing the repressive effects of PRC2 (reviewed in Van der Meulen, J. et al. (2014) Epigenetics 9:658-68, Xu, B. et al. (2015) Exp. Hematol. 43:698-712) Tumors that lack or are defective in H3K4 methyltransferase complex components, including but not limited to MLL2 (data shown herein for combination treatment with an EZH2 inhibitor plus Standard of Care chemotherapy in patient-derived xenograft models of gastric cancer), MLL3 (data shown herein for combination treatment with an EZH2 inhibitor plus Standard of Care chemotherapy in patient-derived xenograft models of lung cancer), Lysine-specific demethylase 6A, also known as Ubiquitously transcribed tetratricopeptide repeat, X chromosome (UTX, also known as KDM6A [Ezponda, T. et al. (2014) Blood 124:611]), alone or in combination with the lack or defect in components of the SWI/SNF complex described above, including but not limited to ARID1A (data shown herein for combination treatment with an EZH2 inhibitor plus Standard of Care chemotherapy in patient-derived xeno graft models of gastric cancer), are growth-inhibited following treatment with EZH2 small molecule inhibitors as a single-agent or in combination with Standard of Care (SOC) chemotherapeutic agents. Lymphomas with germinal center B-cell origins are growth-inhibited with perturbations in EZH2 (Beguelin et al. (2013) Cancer Cell 23:677-92; Velichutina, I. et al. (2010) Blood 116:5247-5255) and also have a high frequency of mutations in MLL2, CREBBP, EP300, ARID1A and SMARCA4 (Lunning, M. A. and Green, M. R. (2015) Blood Cancer Journal 5, e361; Carbone, A. et al. (2014) Ann. Hematol. 93:1263-1277).

Some EZH2 inhibitors are already known in the literature. See for example, WO2012/142504, WO2012/142513, WO2013/120104, WO2013/173441, WO2013/075083, WO2014/177982, WO2014/097041, and WO2016/066697.

There remains a need to provide alternative EZH2 inhibitors for treatment of cancer. Accordingly, the present invention provides certain inhibitors of EZH2 which may be useful for treating cancer.

The present invention provides a compound of the formula:

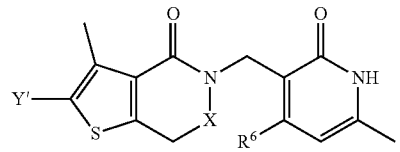

wherein:
X is —CH$_2$— or —CH$_2$—CH$_2$—;
Y' is —NR$^4$R$^5$, CH(CH$_3$)-cyclohex-4-yl-dimethylamino, CH(CH$_3$)-cyclohex-4-yl-N-methyl-N-methoxyethylamino, or —CH(CH$_3$)-cyclohex-4-yl-azetidin-1-yl wherein the azetidin-1-yl is optionally substituted with methoxy, 2-propoxy, methoxymethyl, methoxyethoxy, cyclopropyloxy, cyclopropylmethoxy, N-triazolyl, N-pyrrolidinyl, morpholinyl, tetrahydrofuran-3-yloxy, or N-pyrazolyl optionally substituted with methyl;
R$^4$ is piperidin-4-yl or cyclohex-4-yl substituted with dimethylamino, N-methyl-N-methoxyethylamino, N-methyl-N-cyclopropylamino, or azetidin-1-yl wherein the azetidin-1-yl is substituted with methoxy, ethoxy, methoxyethoxy, cyclopropyloxy, or N-pyrazolyl optionally substituted with methyl;
R$^5$ is methyl or ethyl; and
R$^6$ is methyl or chloro; or
a pharmaceutically acceptable salt thereof.

The present invention also provides a compound of the formula:

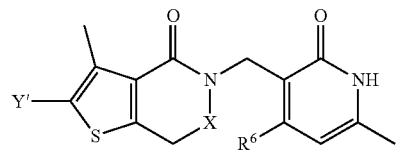

wherein:
X is —CH$_2$— or —CH$_2$—CH$_2$—;
Y' is —NR$^4$R$^5$, —CH(CH$_3$)-cyclohexyl-4-yl-N-methyl-N-methoxyethyl, or —CH(CH$_3$)-cyclohex-4-yl-azetidin-1-yl wherein the azetidin-1-yl is optionally substituted with methoxy, 2-propoxy, methoxymethyl, methoxyethoxy, cyclopropyloxy, cyclopropylmethoxy, pyrazolyl, methylpyrazolyl, triazolyl, pyrrolidinyl, tetrahydrofuranyloxy, or morpholinyl;

$R^4$ is cyclohex-4-yl substituted with N-methyl-N-methoxyethylamino, N-methyl-N-cyclopropylamino, or azetidin-1-yl wherein the azetidin-1-yl is substituted with methoxy, ethoxy, methoxyethoxy, cyclopropyloxy, or pyrazolyl;

$R^5$ is methyl or ethyl; and $R^6$ is methyl or chloro; or a pharmaceutically acceptable salt thereof.

The present invention also provides a compound of the formula:

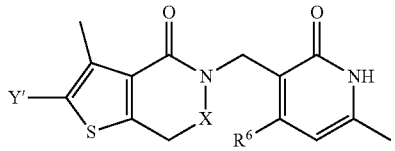

wherein:

X is —CH$_2$—;

Y' is —NR$^4$R$^5$, CH(CH$_3$)-cyclohex-4-yl-dimethylamino, CH(CH$_3$)-cyclohex-4-yl-N-methyl-N-methoxyethylamino, or —CH(CH$_3$)-cyclohex-4-yl-azetidin-1-yl wherein the azetidin-1-yl is optionally substituted with methoxy, 2-propoxy, methoxymethyl, methoxyethoxy, cyclopropyloxy, cyclopropylmethoxy, N-triazolyl, N-pyrrolidinyl, morpholinyl, tetrahydrofuran-3-yloxy, or N-pyrazolyl optionally substituted with methyl;

$R^4$ is cyclohex-4-yl substituted with dimethylamino, N-methyl-N-methoxyethylamino, N-methyl-N-cyclopropylamino, or azetidin-1-yl wherein the azetidin-1-yl is substituted with methoxy, ethoxy, methoxyethoxy, cyclopropyloxy, or N-pyrazolyl optionally substituted with methyl;

$R^5$ is methyl or ethyl; and $R^6$ is methyl or chloro; or a pharmaceutically acceptable salt thereof.

The present invention also provides a compound of the formula:

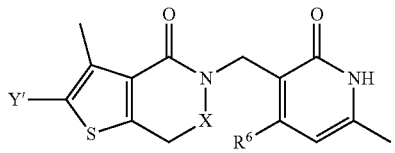

wherein:

X is —CH$_2$—;

Y' is —NR$^4$R$^5$, CH(CH$_3$)-cyclohex-4-yl-N-methyl-N-methoxyethylamino, or —CH(CH$_3$)-cyclohex-4-yl-azetidin-1-yl wherein the azetidin-1-yl is optionally substituted with methoxy, 2-propoxy, methoxymethyl, methoxyethoxy, cyclopropyloxy, cyclopropylmethoxy, N-triazolyl, N-pyrrolidinyl, morpholinyl, tetrahydrofuran-3-yloxy, or N-pyrazolyl optionally substituted with methyl;

$R^4$ is cyclohex-4-yl substituted with N-methyl-N-methoxyethylamino, N-methyl-N-cyclopropylamino, or azetidin-1-yl wherein the azetidin-1-yl is substituted with methoxy, ethoxy, methoxyethoxy, cyclopropyloxy, or N-pyrazolyl optionally substituted with methyl;

$R^5$ is methyl or ethyl; and $R^6$ is methyl or chloro; or a pharmaceutically acceptable salt thereof.

The present invention also provides a compound of the formula:

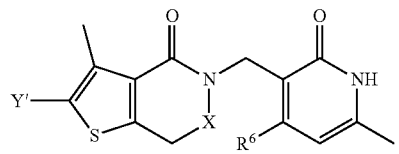

wherein:

X is —CH$_2$— or —CH$_2$—CH$_2$—;

Y' is —CH(CH$_3$)-cyclohex-4-yl-azetidin-1-yl wherein the azetidin-1-yl is optionally substituted with methoxy, propoxy, methylmethoxy, methoxyethoxy, cyclopropyloxy, cyclopropylmethoxy, morpholinyl, N-triazolyl, N-pyrrolidinyl, tetrahydrofuran-3-yloxy, or N-pyrazolyl optionally substituted with methyl; and $R^6$ is methyl; or a pharmaceutically acceptable salt thereof.

The present invention also provides a compound of the formula:

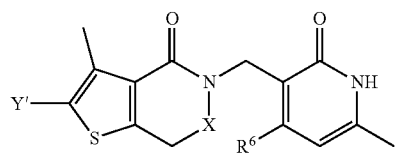

wherein:

X is —CH$_2$—;

Y' is —CH(CH$_3$)-cyclohex-4-yl-azetidin-1-yl wherein the azetidin-1-yl is optionally substituted with methoxy, propoxy, methylmethoxy, methoxyethoxy, cyclopropyloxy, cyclopropylmethoxy, morpholinyl, N-triazolyl, N-pyrrolidinyl, tetrahydrofuran-3-yloxy, or N-pyrazolyl optionally substituted with methyl; and $R^6$ is methyl; or a pharmaceutically acceptable salt thereof.

The present invention also provides a compound of the formula:

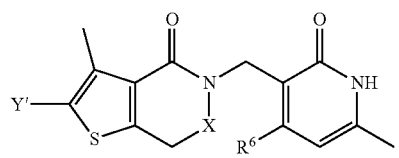

wherein:

X is —CH$_2$—CH$_2$—;

Y' is —CH(CH$_3$)-cyclohex-4-yl-azetidin-1-yl wherein the azetidin-1-yl is optionally substituted with methoxy, propoxy, methylmethoxy, methoxyethoxy, cyclopropyloxy, cyclopropylmethoxy, morpholinyl, N-triazolyl, N-pyrrolidinyl, tetrahydrofuran-3-yloxy, or N-pyrazolyl optionally substituted with methyl; and $R^6$ is methyl; or a pharmaceutically acceptable salt thereof.

The present invention also provides a compound of the formula:

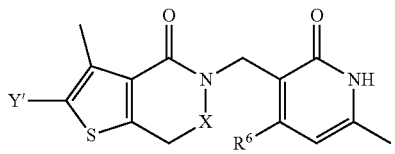

wherein:
X is —CH$_2$— or —CH$_2$—CH$_2$—;
Y' is —NR$^4$R$^5$;
R$^4$ is cyclohex-4-yl-azetidin-1-yl, wherein the azetidin-1-yl is substituted with methoxy, ethoxy, methoxyethoxy, cyclopropyloxy, or N-pyrazolyl optionally substituted with methyl; and
R$^5$ is methyl or ethyl; and
R$^6$ is methyl or chloro; or
a pharmaceutically acceptable salt thereof.

The present invention also provides a compound of the formula:

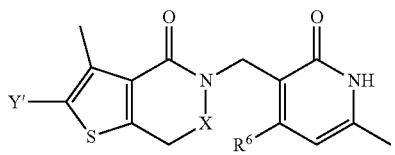

wherein:
X is —CH$_2$—;
Y' is —NR$^4$R$^5$;
R$^4$ is cyclohex-4-yl-azetidin-1-yl, wherein the azetidin-1-yl is substituted with methoxy, ethoxy, methoxyethoxy, cyclopropyloxy, or N-pyrazolyl optionally substituted with methyl;
R$^5$ is methyl or ethyl; and
R$^6$ is methyl or chloro; or
a pharmaceutically acceptable salt thereof.

The present invention also provides a compound of the formula:

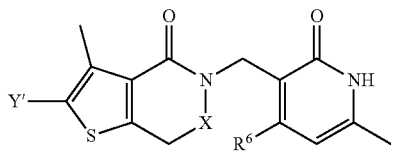

wherein:
X is —CH$_2$—CH$_2$—;
Y' is —NR$^4$R$^5$;
R$^4$ is cyclohex-4-yl-azetidin-1-yl, wherein the azetidin-1-yl is substituted with methoxy, ethoxy, methoxyethoxy, cyclopropyloxy, or N-pyrazolyl optionally substituted with methyl;
R$^5$ is methyl or ethyl; and
R$^6$ is methyl; or
a pharmaceutically acceptable salt thereof.

The present invention also provides a compound of the formula:

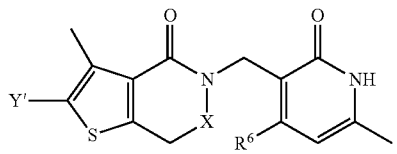

wherein:
X is —CH$_2$— or —CH$_2$—CH$_2$—;
Y' is —CH(CH$_3$)-cyclohex-4-yl-azetidin-1-yl wherein the azetidin-1-yl is optionally substituted with methoxy, propoxy, methylmethoxy, methoxyethoxy, cyclopropyloxy, cyclopropylmethoxy, morpholinyl, N-triazolyl, N-pyrrolidinyl, tetrahydrofuran-3-yloxy, or N-pyrazolyl optionally substituted with methyl; and
R$^6$ is methyl or chloro; or a pharmaceutically acceptable salt thereof; wherein the carbon attached at the 2 position of the 6,7-dihydrothieno[3,2-c]pyridin-4(5H)-one is in the (R) configuration.

The present invention also provides a compound of the formula:

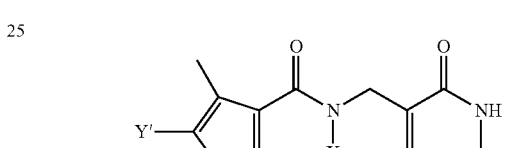

wherein:
X is —CH$_2$— or —CH$_2$—CH$_2$—;
Y' is —CH[CH$_3$]-cyclohex-4-yl-azetidin-1-yl wherein the azetidin-1-yl is optionally substituted with methoxy, propoxy, methylmethoxy, methoxyethoxy, cyclopropyloxy, cyclopropylmethoxy, morpholinyl, N-triazolyl, N-pyrrolidinyl, tetrahydrofuran-3-yloxy, or N-pyrazolyl optionally substituted with methyl; and
R$^6$ is methyl or chloro; or
a pharmaceutically acceptable salt thereof; wherein the carbon attached at the 2 position of the 6,7-dihydrothieno[3,2-c]pyridin-4(5H)-one is in the (R) configuration and the cyclohexane ring is in the trans configuration.

The present invention also provides a compound of the formula:

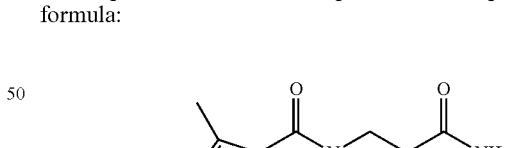

wherein:
X is —CH$_2$— or —CH$_2$—CH$_2$—;
Y' is —NR$^4$R$^5$;
R$^4$ is cyclohex-4-yl-azetidin-1-yl, wherein the azetidin-1-yl is substituted with methoxy, ethoxy, methoxyethoxy, cyclopropyloxy, or N-pyrazolyl optionally substituted with methyl;
R$^5$ is methyl or ethyl; and
R$^6$ is methyl or chloro; or a pharmaceutically acceptable salt thereof; wherein the cyclohexane ring is in the trans configuration.

The present invention also provides a compound of the formula:

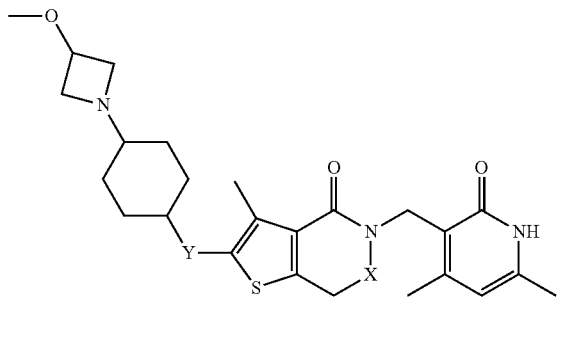

wherein:
X is —CH₂— or —CH₂—CH₂—; and
Y is CHCH₃, N(CH₃), or N(CH₂CH₃); or
a pharmaceutically acceptable salt thereof.

The present invention also provides a compound of the formula:

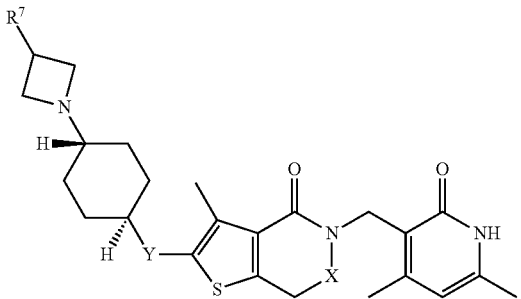

wherein:
X is —CH₂— or —CH₂—CH₂—; and
Y is CHCH₃, N(CH₃), or N(CH₂CH₃); and
R⁷ is hydrogen, methoxy, ethoxy, propoxy, methylmethoxy, methoxyethoxy, cyclopropyloxy, cyclopropylmethoxy, morpholinyl, N-triazolyl, N-pyrrolidinyl, tetrahydrofuran-3-yloxy, or N-pyrazolyl optionally substituted with methyl; or a pharmaceutically acceptable salt thereof.

The present invention also provides a compound of the formula:

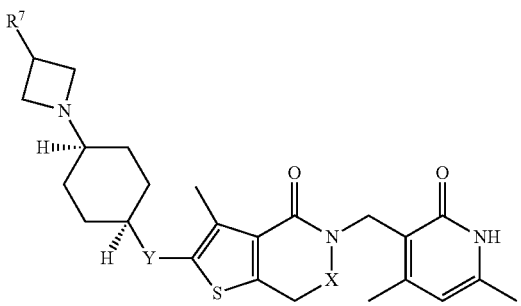

wherein:
X is —CH₂— or —CH₂—CH₂—;
Y is CHCH₃, N(CH₃), or N(CH₂CH₃); and
R⁷ is hydrogen, methoxy, ethoxy, propoxy, methylmethoxy, methoxyethoxy, cyclopropyloxy, cyclopropylmethoxy, morpholinyl, N-triazolyl, N-pyrrolidinyl, tetrahydrofuran-3-yloxy, or N-pyrazolyl optionally substituted with methyl; or a pharmaceutically acceptable salt thereof.

The present invention also provides a compound of the formula:

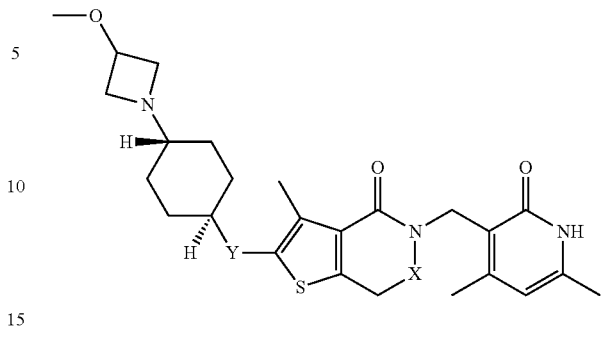

wherein:
X is —CH₂— or —CH₂—CH₂—; and
Y is CHCH₃, N(CH₃), or N(CH₂CH₃); or
a pharmaceutically acceptable salt thereof.

The present invention provides a compound which is

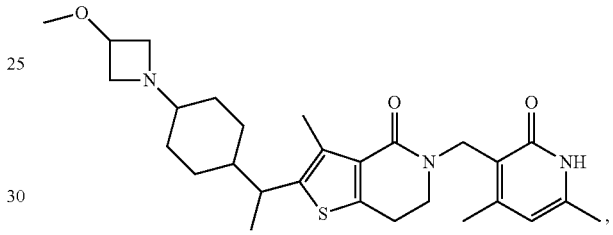

or a pharmaceutically acceptable salt thereof.

The present invention provides a compound which is

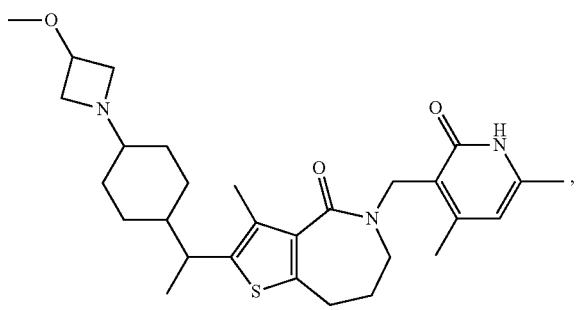

or a pharmaceutically acceptable salt thereof.

The present invention provides a compound which is

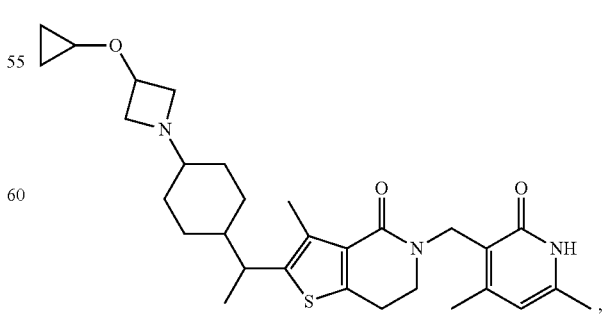

or a pharmaceutically acceptable salt thereof.

The present invention provides a compound which is

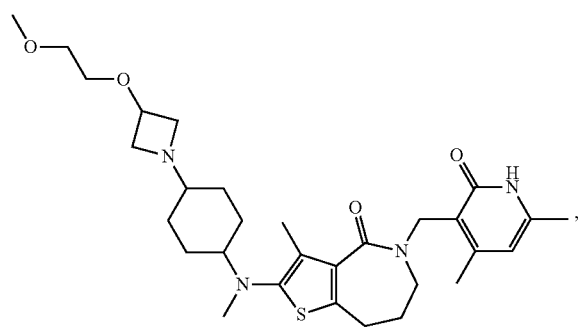

or a pharmaceutically acceptable salt thereof.

The present invention provides a compound which is

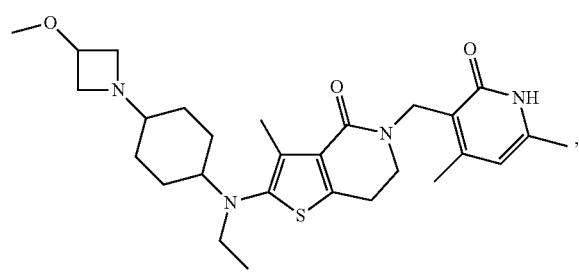

or a pharmaceutically acceptable salt thereof.

The present invention provides a compound which is

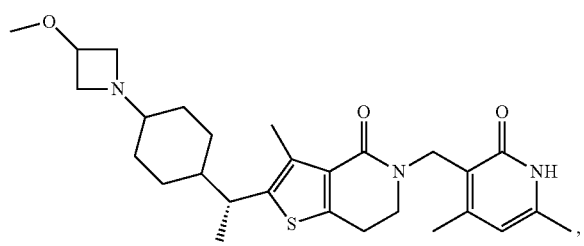

or a pharmaceutically acceptable salt thereof.

The present invention provides a compound which is

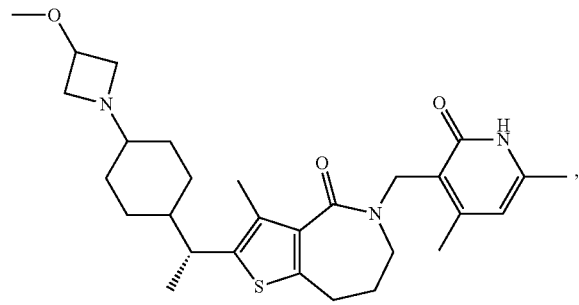

or a pharmaceutically acceptable salt thereof.

The present invention provides a compound which is

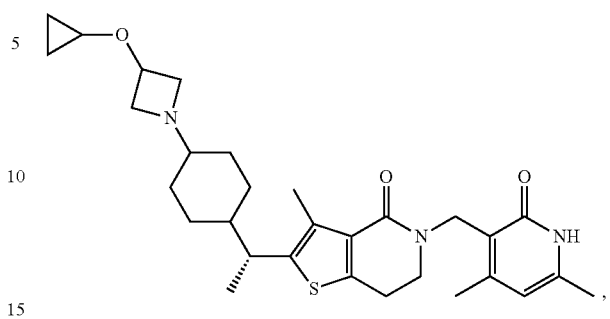

or a pharmaceutically acceptable salt thereof.

The present invention provides a compound which is

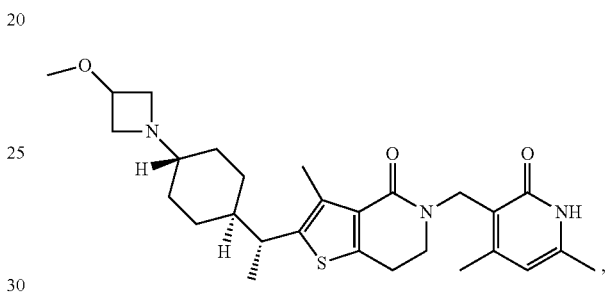

or a pharmaceutically acceptable salt thereof.

The present invention provides a compound which is

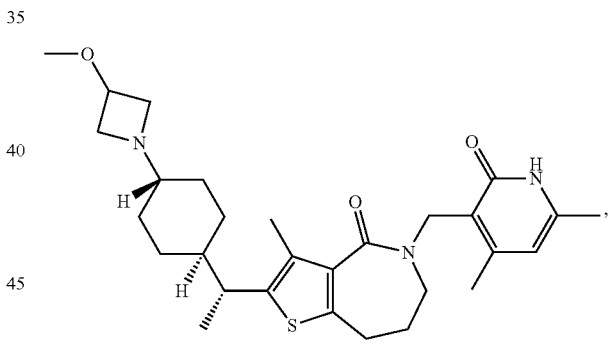

or a pharmaceutically acceptable salt thereof.

The present invention provides a compound which is

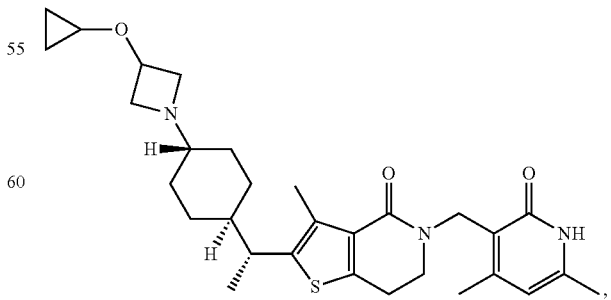

or a pharmaceutically acceptable salt thereof.

The present invention provides a compound which is

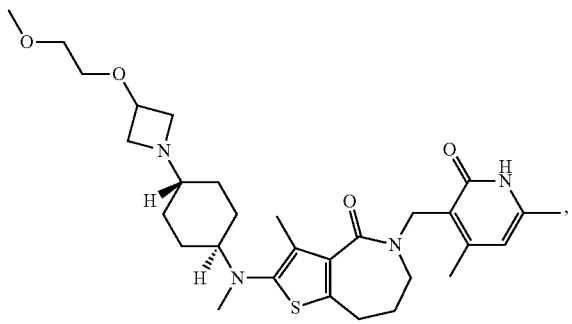

or a pharmaceutically acceptable salt thereof.

The present invention provides a compound which is

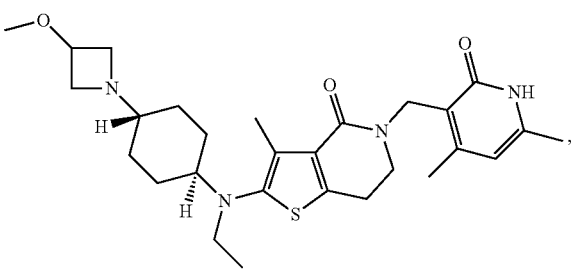

or a pharmaceutically acceptable salt thereof.

The present invention provides a method of treating cancer in a patient, wherein the cancer is selected from the group consisting of lymphomas, rhabdoid tumors, tumors which lack or are defective in one or more components of the SWI/SNF complex (for instance, SNF5), MLL complexes, and constitutively active PI3K pathway, sarcomas, multiple myeloma, melanoma, gastric cancer, colorectal cancer, lung cancer, kidney cancer, breast cancer, ovarian cancer, and prostate cancer comprising administering to the patient an effective amount of a compound or salt thereof of the present invention. Preferably the cancer is diffuse large B-cell lymphoma or follicular lymphoma. Preferably the cancer is diffuse large B-cell lymphoma. Preferably the cancer is gastric cancer. Preferably the cancer is ovarian cancer. Preferably the cancer is multiple myeloma. Preferably the cancer is lung cancer. Preferably the cancer is colorectal cancer. Preferably the cancer is a solid or hematological tumor that bears wild type (WT) EZH2 as well as a solid or hematological tumor that bears mutant EZH2. Preferably the cancer is a solid or hematological tumor that bears WT EZH2. Preferably the cancer is a solid or hematological tumor that bears mutant EZH2.

The present invention also provides for a method of treating ovarian cancer in a patient comprising administering to the patient a compound or salt thereof of the present invention in combination with carboplatin and paclitaxel.

The present invention also provides for a method of treating gastric cancer in a patient comprising administering to the patient a compound or salt thereof of the present invention in combination with oxaliplatin and paclitaxel.

The present invention also provides for a method of treating lung cancer in a patient comprising administering to the patient a compound or salt thereof of the present invention in combination with gemcitabine and cisplatin.

The present invention also provides for a method of treating colorectal cancer in a patient comprising administering to the patient a compound or salt thereof of the present invention in combination with irinotecan and oxaliplatin.

The present invention also provides a pharmaceutical composition comprising a compound or salt thereof of the present invention and one or more pharmaceutically acceptable excipients, carriers, or diluents.

According to another aspect of the present invention, there is presented a kit comprising a compound or salt thereof of the present invention and carboplatin and paclitaxel for the treatment of ovarian cancer.

According to another aspect of the present invention, there is presented a kit comprising a compound or salt thereof of the present invention with one or more pharmaceutically acceptable carriers, diluents, or excipients, and carboplatin with one or more pharmaceutically acceptable carriers, diluents, or excipients and paclitaxel with one or more pharmaceutically acceptable carriers, diluents, or excipients for the treatment of ovarian cancer.

According to another aspect of the present invention, there is presented a kit comprising a compound or salt thereof of the present invention and oxaliplatin and paclitaxel for the treatment of gastric cancer.

According to another aspect of the present invention, there is presented a kit comprising a compound or salt thereof of the present invention with one or more pharmaceutically acceptable carriers, diluents, or excipients, and oxaliplatin with one or more pharmaceutically acceptable carriers, diluents, or excipients and paclitaxel with one or more pharmaceutically acceptable carriers, diluents, or excipients for the treatment of gastric cancer.

According to another aspect of the present invention, there is presented a kit comprising a compound or salt thereof of the present invention and gemcitabine and cisplatin for the treatment of lung cancer.

According to another aspect of the present invention, there is presented a kit comprising a compound or salt thereof of the present invention with one or more pharmaceutically acceptable carriers, diluents, or excipients, and gemcitabine with one or more pharmaceutically acceptable carriers, diluents, or excipients and cisplatin with one or more pharmaceutically acceptable carriers, diluents, or excipients for the treatment of lung cancer.

According to another aspect of the present invention, there is presented a kit comprising a compound or salt thereof of the present invention and irinotecan and oxaliplatin for the treatment of colorectal cancer.

According to another aspect of the present invention, there is presented a kit comprising a compound or salt thereof of the present invention with one or more pharmaceutically acceptable carriers, diluents, or excipients, and irinotecan with one or more pharmaceutically acceptable carriers, diluents, or excipients and oxaliplatin with one or more pharmaceutically acceptable carriers, diluents, or excipients for the treatment of colorectal cancer.

This invention also provides a compound or salt thereof of the present invention for use in therapy. Additionally, this invention provides a compound or salt thereof of the present invention for use in the treatment of cancer wherein the cancer is selected from the group consisting of lymphomas, rhabdoid tumors, tumors which lack or are defective in one or more components of the SWI/SNF complex (for instance, SNF5), MLL complexes, and constitutively active PI3K pathway, sarcomas, multiple myeloma, melanoma, gastrointestinal cancer, colorectal cancer, lung cancer, kidney cancer, breast cancer, ovarian cancer, and prostate cancer.

Preferably the cancer is diffuse large B-cell lymphoma or follicular lymphoma. Preferably the cancer is diffuse large B-cell lymphoma. Preferably the cancer is gastric cancer. Preferably the cancer is ovarian cancer. Preferably the cancer is multiple myeloma. Preferably the cancer is lung cancer. Preferably the cancer is colorectal cancer. Preferably the cancer is a solid or hematological tumor that bears wild type (WT) EZH2 as well as a solid or hematological tumor that bears mutant EZH2. Preferably the cancer is a solid or hematological tumor that bears WT EZH2. Preferably the cancer is a solid or hematological tumor that bears mutant EZH2.

Furthermore, this invention provides the use of a compound or a salt thereof of the present invention in the manufacture of a medicament for treating cancer wherein the cancer is selected from the group consisting of lymphomas, rhabdoid tumors, tumors which lack or are defective in one or more components of the SWI/SNF complex (for instance, SNF5), MLL complexes, and constitutively active PI3K pathway, sarcomas, multiple myeloma, melanoma, gastrointestinal cancer, colorectal cancer, lung cancer, kidney cancer, breast cancer, ovarian cancer, and prostate cancer. Preferably the cancer is diffuse large B-cell lymphoma or follicular lymphoma. Preferably the cancer is diffuse large B-cell lymphoma. Preferably the cancer is gastric cancer. Preferably the cancer is ovarian cancer. Preferably the cancer is multiple myeloma. Preferably the cancer is lung cancer. Preferably the cancer is colorectal cancer. Preferably the cancer is a solid or hematological tumor that bears wild type (WT) EZH2 as well as a solid or hematological tumor that bears mutant EZH2. Preferably the cancer is a solid or hematological tumor that bears WT EZH2. Preferably the cancer is a solid or hematological tumor that bears mutant EZH2.

According to another aspect of the present invention, there is presented a combination comprising a compound or salt thereof of the present invention and carboplatin and paclitaxel for simultaneous, separate, or sequential use in the treatment of ovarian cancer.

According to another aspect of the present invention, there is presented a compound or salt thereof of the present invention for use in simultaneous, separate or sequential combination with carboplatin and paclitaxel in the treatment of ovarian cancer.

According to another aspect of the present invention, there is presented carboplatin for use in simultaneous, separate, or sequential combination with a compound or salt thereof of the present invention and paclitaxel in the treatment of ovarian cancer.

According to another aspect of the present invention, there is presented paclitaxel for use in simultaneous, separate, or sequential combination with a compound or salt thereof of the present invention and carboplatin in the treatment of ovarian cancer.

The present invention also provides for use of a compound or salt thereof of the present invention in the manufacture of a medicament for the treatment of ovarian cancer wherein the compound or salt thereof of the present invention is to be administered in simultaneous, separate or sequential combination with carboplatin and paclitaxel.

The present invention also provides for use of carboplatin in the manufacture of a medicament for the treatment of ovarian cancer wherein the carboplatin is to be administered in simultaneous, separate, or sequential combination with a compound or salt thereof of the present invention and paclitaxel.

The present invention also provides for use of paclitaxel in the manufacture of a medicament for the treatment of ovarian cancer wherein the paclitaxel is to be administered in simultaneous, separate, or sequential combination with a compound or salt thereof of the present invention and carboplatin.

According to another aspect of the present invention, there is presented a combination comprising a compound or salt thereof of the present invention and oxaliplatin and paclitaxel for simultaneous, separate, or sequential use in the treatment of gastric cancer.

According to another aspect of the present invention, there is presented a compound or salt thereof of the present invention for use in simultaneous, separate or sequential combination with oxaliplatin and paclitaxel in the treatment of gastric cancer.

According to another aspect of the present invention, there is presented oxaliplatin for use in simultaneous, separate, or sequential combination with a compound or salt thereof of the present invention and paclitaxel in the treatment of gastric cancer.

According to another aspect of the present invention, there is presented paclitaxel for use in simultaneous, separate, or sequential combination with a compound or salt thereof of the present invention and oxaliplatin in the treatment of gastric cancer.

The present invention also provides for use of a compound or salt thereof of the present invention in the manufacture of a medicament for the treatment of gastric cancer wherein the compound or salt thereof of the present invention is to be administered in simultaneous, separate or sequential combination with oxaliplatin and paclitaxel.

The present invention also provides for use of oxaliplatin in the manufacture of a medicament for the treatment of gastric cancer wherein the oxaliplatin is to be administered in simultaneous, separate, or sequential combination with a compound or salt thereof of the present invention and paclitaxel.

The present invention also provides for use of paclitaxel in the manufacture of a medicament for the treatment of gastric cancer wherein the paclitaxel is to be administered in simultaneous, separate, or sequential combination with a compound or salt thereof of the present invention and oxaliplatin.

According to another aspect of the present invention, there is presented a combination comprising a compound or salt thereof of the present invention and gemcitabine and cisplatin for simultaneous, separate, or sequential use in the treatment of lung cancer.

According to another aspect of the present invention, there is presented a compound or salt thereof of the present invention for use in simultaneous, separate or sequential combination with gemcitabine and cisplatin in the treatment of lung cancer.

According to another aspect of the present invention, there is presented gemcitabine for use in simultaneous, separate, or sequential combination with a compound or salt thereof of the present invention and cisplatin in the treatment of lung cancer.

According to another aspect of the present invention, there is presented cisplatin for use in simultaneous, separate, or sequential combination with a compound or salt thereof of the present invention and gemcitabine in the treatment of lung cancer.

The present invention also provides for use of a compound or salt thereof of the present invention in the manufacture of a medicament for the treatment of lung cancer wherein the compound or salt thereof of the present invention is to be administered in simultaneous, separate or sequential combination with gemcitabine and cisplatin.

The present invention also provides for use of gemcitabine in the manufacture of a medicament for the treatment of lung cancer wherein the gemcitabine is to be administered in simultaneous, separate, or sequential combination with a compound or salt thereof of the present invention and cisplatin.

The present invention also provides for use of cisplatin in the manufacture of a medicament for the treatment of lung cancer wherein the cisplatin is to be administered in simultaneous, separate, or sequential combination with a compound or salt thereof of the present invention and gemcitabine.

According to another aspect of the present invention, there is presented a combination comprising a compound or salt thereof of the present invention and irinotecan and oxaliplatin for simultaneous, separate, or sequential use in the treatment of colorectal cancer.

According to another aspect of the present invention, there is presented a compound or salt thereof of the present invention for use in simultaneous, separate or sequential combination with irinotecan and oxaliplatin in the treatment of colorectal cancer.

According to another aspect of the present invention, there is presented irinotecan for use in simultaneous, separate, or sequential combination with a compound or salt thereof of the present invention and oxaliplatin in the treatment of colorectal cancer.

According to another aspect of the present invention, there is presented oxaliplatin for use in simultaneous, separate, or sequential combination with a compound or salt thereof of the present invention and irinotecan in the treatment of colorectal cancer.

The present invention also provides for use of a compound or salt thereof of the present invention in the manufacture of a medicament for the treatment of colorectal cancer wherein the compound or salt thereof of the present invention is to be administered in simultaneous, separate or sequential combination with irinotecan and oxaliplatin.

The present invention also provides for use of irinotecan in the manufacture of a medicament for the treatment of colorectal cancer wherein the irinotecan is to be administered in simultaneous, separate, or sequential combination with a compound or salt thereof of the present invention and oxaliplatin.

The present invention also provides for use of oxaliplatin in the manufacture of a medicament for the treatment of colorectal cancer wherein the oxaliplatin is to be administered in simultaneous, separate, or sequential combination with a compound or salt thereof of the present invention and irinotecan.

The following paragraphs describe preferred classes of the present invention:
a) X is —CH$_2$—
b) X is —CH$_2$—CH$_2$—;
c) Y' is —CH(CH$_3$)-cyclohex-4-yl-azetidin-1-yl wherein the azetidin-1-yl is optionally substituted with methoxy, cyclopropyloxy, or tetrahydrofuran-3-yloxy;
d) Y' is NR$^4$R$^5$;
e) R$^4$ is cyclohex-4-yl-azetidin-1-yl, wherein the azetidin-1-yl is substituted with methoxy or methoxyethoxy;
f) R$^5$ is ethyl;
g) R$^6$ is methyl;
h) X is —CH$_2$—, Y' is —CH(CH$_3$)-cyclohex-4-yl-azetidin-1-yl wherein the azetidin-1-yl is substituted with methoxy, and R$^6$ is methyl;
i) X is —CH$_2$—, Y' is —CH(CH$_3$)-cyclohex-4-yl-azetidin-1-yl wherein the azetidin-1-yl is substituted with cyclopropyloxy, and R$^6$ is methyl;
j) X is —CH$_2$—, Y' is —CH(CH$_3$)-cyclohex-4-yl-azetidin-1-yl wherein the azetidin-1-yl is substituted with tetrahydrofuran-3-yloxy, and R$^6$ is methyl;
k) X is —CH$_2$—, Y' is NR$^4$R$^5$, R$^4$ is cyclohex-4-yl-azetidin-1-yl, wherein the azetidin-1-yl is substituted with methoxy, R$^5$ is ethyl, and R$^6$ is methyl;
l) X is —CH$_2$—CH$_2$—, Y' is NR$^4$R$^5$, R$^4$ is cyclohex-4-yl-azetidin-1-yl, wherein the azetidin-1-yl is substituted with methoxyethoxy, R$^5$ is ethyl, and R$^6$ is methyl; and
m) X is —CH$_2$—CH$_2$—, Y' is —CH(CH$_3$)-cyclohex-4-yl-azetidin-1-yl wherein the azetidin-1-yl is substituted with methoxy, and R$^6$ is methyl.

It will be understood by one of ordinary skill in the art that the term "trans-" is as depicted below wherein substituents at the 1,4 positions around the cyclohexyl moiety are trans-relative to one another:

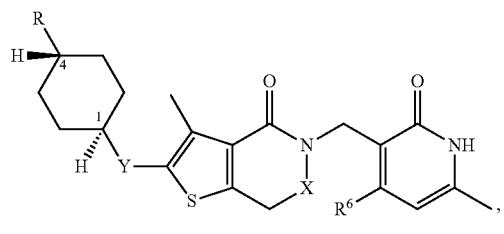

wherein R is selected from among dimethylamino, N-methyl-N-methoxyethylamino, N-cyclopropyl-N-methylamino, or azetidin-1-yl, optionally substituted with methoxy, ethoxy, propoxy, methylmethoxy, methoxyethoxy, cyclopropyloxy, cyclopropylmethoxy, morpholinyl, N-triazolyl, pyrrolidin-4-yl, tetrahydrofuran-3-yloxy, or N-pyrazolyl optionally substituted with methyl and X and Y are as previously defined.

It will be understood by the skilled reader that a compound of the present invention is capable of forming salts. The compound of the present invention is a base, and accordingly reacts with any of a number of inorganic and organic acids to form pharmaceutically acceptable salts. Such pharmaceutically acceptable acid addition salts and common methodology for preparing them are well known in the art. See, for example, P. Stahl, et al., HANDBOOK OF PHARMACEUTICAL SALTS: PROPERTIES, SELECTION AND USE, (VCHA/Wiley-VCH, 2008); S. M. Berge, et al., "Pharmaceutical Salts", *Journal of Pharmaceutical Sciences*, Vol 66, No. 1, January 1977.

A compound or salt thereof of the present invention may be prepared by a variety of procedures known in the art, some of which are illustrated in the Preparations and Examples below. The specific synthetic steps described may be combined in different ways to prepare compounds or salts of the present invention. The products of the synthetic steps can be recovered by conventional methods well known in the art, including extraction, evaporation, precipitation, chromatography, filtration, trituration, and crystallization. The reagents and starting materials are readily available to one of ordinary skill in the art.

Some intermediates or compounds of the present invention may have one or more chiral centers. The present invention contemplates all individual enantiomers or diastereomers, as well as mixtures of the enantiomers and diastereomers of said compounds including racemates. It is preferred that compounds of the present invention containing at least one chiral center exist as single enantiomers or diastereomers. The single enantiomers or diastereomers may be prepared beginning with chiral reagents or by stereoselective or stereospecific synthetic techniques. Alternatively, the single enantiomers or diastereomers may be isolated from mixtures by standard chiral chromatographic or crystallization techniques. The skilled artisan will appreciate that in some circumstances the elution order of enantiomers or diastereomers may be different due to different chromatographic columns and mobile phases.

Certain stereochemical centers have been left unspecified and certain substituents have been eliminated in the following schemes for the sake of clarity and are not intended to limit the teaching of the schemes in any way. Furthermore, individual isomers, enantiomers, or diastereomers may be separated or resolved by one of ordinary skill in the art at any convenient point in the synthesis of compounds of the present invention by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994). Additionally, the intermediates described in the following schemes contain a number of nitrogen protecting groups. The variable protecting group may be the same or different in each occurrence depending on the particular reaction conditions and the particular transformations to be performed. The protection and deprotection conditions are well known to the skilled artisan and are described in the literature (See for example "*Greene's Protective Groups in Organic Synthesis*", Fourth Edition, by Peter G. M. Wuts and Theodora W. Greene, John Wiley and Sons, Inc. 2007).

Certain abbreviations are defined as follows: "AcOH" refers to acetic acid or glacial acetic acid; "ACN" refers to acetonitrile; "AdoMet" refers to S-adenosyl-L-methionine; "AEBP" refers to adipocyte-enhancer binding protein; "AUC" refers to Area Under the Curve; "BOC" refers to tert-butoxycarbonyl; "bid" refers to twice a day dosing; "bm" refers to broad multiplet; "Bn" refers to benzyl; "BSA" refers to Bovine Serum Albumin; "c" refers to concentration in grams per milliliter; "CAT. #" Refers to catalog number; "CDI" refers to carbonyldiimidazole; "$CO_2$" refers to carbon dioxide; "CV" refers to column volume; "Ci" refers to Curie; "CPM" refers to counts per million; "cPr" refers to cyclopropyl; "DCE" refers to 1,2-dichloroethane; "DCM" refers to methylene chloride or dichloromethane; "DIBAL-H" refers to diisobutyl aluminum hydride; "DIPEA" refers to diisopropylethyl amine; "dm" refers to decimeters or 10 centimeters; "DMA" refers to dimethylacetamide; "DMEA" refers to N, N-dimethylethylamine; "DMF" refers to dimethylformamide or N,N-dimethylformamide; "DMSO" refers to dimethyl sulfoxide; "DNase" refers to deoxyribonuclease; "DTT" refers to dithiothreitol; "EED" refers to embryonic ectoderm development; "$Et_2O$" refers to diethyl ether; "EtOAc" refers to ethyl acetate; "ES/MS" refers to electrospray mass spectrometry; "EtOH" refers to ethanol or ethyl alcohol; "Ex" refers to example; "GAPDH" refers to glyceraldehyde 3-phosphate dehydrogenase; "hr" refers to hour or hours; "HEC" refers to hydroxy ethyl cellulose; "HOAt" refers to hydroxyazabenzotriazole; "HOBt" refers to hydroxybenzotriazole; "HSQC" refers to Heteronuclear Single Quantum Coherence; "IPAm" refers to isopropylamine, propan-2-amine, or 2-aminopropane; "iPr" refers to isopropyl or 1-methylethyl; "IrMeO(COD)$_2$" refers to (1,5-cyclooctadiene)(methoxy)iridium(I) dimer or bis(1,5-cyclooctadiene) di-µ-methoxydiiridium(I); "kPa" refers to kilopascal or kilopascals; "KHMDS" refers to potassium bis(trimethylsilyl) amide; "KOtBu" refers to potassium-tert-butoxide or potassium-t-butoxide; "LAH" refers to lithium aluminum hydride; "LiBH$_4$" refers to lithium borohydride; "LC" refers to liquid chromatography; "LiHMDS" refers to lithium bis(trimethylsilyl)amide; "LOF" refers to Loss of Function; "$^3$H-SAM" refers to adenosyl-L-methionine, S[methyl-$^3$H]; "IC$_{50}$" refers to the concentration of an agent that produces 50% of the maximal inhibitory response possible for that agent; "Me" refers to methyl; "MgSO$_4$" refers to magnesium sulfate; "mpk" refers to milligrams per kilogram; "min" refers to minute or minutes; "NaH" refers to sodium hydride; "NBS" refers to N-bromosuccinimide; "NH$_3$" refers to ammonia; "nm" refers to nanometer or nanometers; "MeOH" refers to methanol or methyl alcohol; "MsOH" refers to methanesulfonic acid; "MTBE" refers to methyl tert-butyl ether; "mut" refers to mutant; "OAc" refers to acetate; "PBS" refers to phosphate buffered saline; "PCR" refers to polymerase chain reaction; "PDX" refers to patient-derived xenograft; "PRC2" refers to Polycomb Repressive Complex 2"; "Prep" refers to preparation; "psi" refers to pounds per square inch; "PTSA" refers to para-toluene sulfonic acid; "quantitative yield" refers to essentially greater than 99% yield; "RBBP4" refers to retinoblastoma binding protein 4; "RNase" refers to ribonuclease; "rpm" refers to revolutions per minute; "RT" refers to room temperature; "R$_t$" refers to retention time in minutes; "RuPhos-G3-Palladacycle" refers to (2-dicyclohexylphosphino-2',6'-diisopropoxy-1,1'-biphenyl)[2-(2'-amino-1,1'-biphenyl)] palladium(II) methanesulfonate; "SCX" refers to selective cation exchange; "SFC" refers to supercritical fluid chromatography; "SPA" refers to scintillation proximity assay; "NaHCO$_3$" refers to sodium bicarbonate; "Na$_2$SO$_4$" refers to sodium sulfate; "SoC" refers to Standard of Care; "THF" refers to tetrahydrofuran, "TEA" refers to triethylamine; "Tris" refers to tris(hydroxymethyl)-aminomethane; "WT" refers to wild type; "XPhos Pd Gen 2" refers to chloro(2-dicyclohexylphosphino-2',4',6'-triisopropyl-1,1'-biphenyl)-[2-(2'-amino-1,1'-biphen-yl)]-palladium(II); "A" refers to angstrom or angstroms; "λ" refers to wavelength; and "$[\pi]_D^{20}$" refers to the optical rotation of a compound that rotates plane-polarized light using the D-line of a sodium lamp (wavelength 589.3 nm) in a polarimeter, with an observed polarimetry measurement a, in a suitable solvent such as MeOH, measured at 20° C., at a defined concentration c, a volume of 2 mL, and a path length of 1 dm.

In the schemes below, all substituents, unless otherwise indicated, are as previously defined. The reagents and starting materials are readily available to one of ordinary skill in the art. The following schemes, preparations, examples, and assays further illustrate the invention, but should not be construed to limit the scope of the invention in any way.

PREPARATIONS AND EXAMPLES

The following Preparations and Examples further illustrate the invention and represent typical synthesis of the compounds of the invention. The reagents and starting materials are readily available or may be readily synthesized by one of ordinary skill in the art. It should be understood that the Preparations and Examples are set forth by way of illustration and not limitation, and that various modifications may be made by one of ordinary skill in the art.

The R- or S-configuration of the compounds of the invention may be determined by standard techniques such as X-ray analysis. $^1$H NMR, chiral HPLC, and correlation with chiral-HPLC retention time may be used to further elucidate stereoisomerism if one center is known.

LC-ES/MS is performed on an Agilent HP1100 liquid chromatography system. Electrospray mass spectrometry measurements (acquired in positive and/or negative mode) are performed on a Mass Selective Detector quadrupole mass spectrometer interfaced to the HP1100 HPLC. LC-MS conditions (low pH): column: Phenomenex GEMINI® NX C-18 2.1×50 mm 3.0 µm; gradient: 5-100% B in 3 min, then 100% B for 0.75 mM column temperature: 50° C.+/−10° C.; flow rate: 1.2 mL/min; Solvent A: deionized water with 0.1% HCOOH; Solvent B: ACN with 0.1% formic acid; wavelength 214 nm. Alternate LC-MS conditions (high pH): column: WATERS™ XTERRA® MS C-18 columns 2.1×50 min, 3.5 µm; gradient: 5% of solvent A for 0.25 mM, gradient from 5% to 100% of solvent B in 3 mM and 100% of solvent B for 0.5 min or 10% to 100% of solvent B in 3 mM and at 100% of solvent B for 0.75 min; column temperature: 50° C.+/−10° C.; flow rate: 1.2 mL/min; Solvent A: 10 mM NH$_4$HCO$_3$ pH 9; Solvent B: ACN; wavelength: 214 nm.

Preparative reversed phase chromatography is performed on an Agilent 1200 LC-ES/MS equipped with a Mass Selective Detector mass spectrometer and a Leap autosampler/fraction collector. High pH methods are run on a 75×30 mm Phenomenex GEMINI®-NX, 5 µm particle size column with a 10×20 mm guard. Flow rate of 85 mL/min. Eluent is 10 mM ammonium bicarbonate (pH 10) in ACN.

NMR spectra are performed on a Bruker AVIII HD 400 MHz NMR Spectrometer, obtained as CDCl$_3$ or (CD$_3$)$_2$SO solutions reported in ppm, using residual solvent [CDCl$_3$, 7.26 ppm; (CD$_3$)$_2$SO, 2.50 ppm] as a reference standard. When peak multiplicities are reported, the following abbreviations may be used: s (singlet), d (doublet), t (triplet), q (quartet), m (multiplet), br-s (broad singlet), dd (doublet of doublets), dt (doublet of triplets). Coupling constants (J), when reported, are reported in hertz (Hz).

Scheme 1

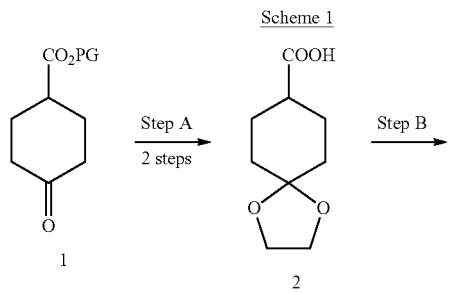

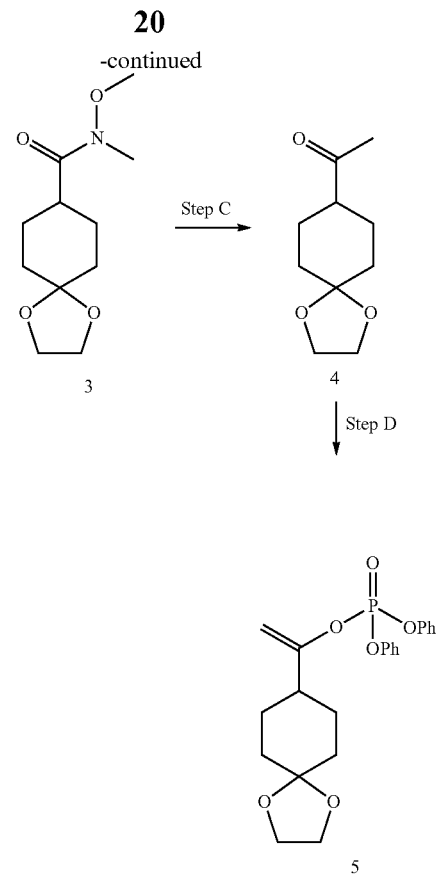

PG = protecting group

Scheme 1 illustrates the formation of a substituted 1,4-dioxaspirol[4,5]decane (compound 5) starting from a protected 4-oxocyclohexanecarboxylate (compound 1). The protected 4-oxocyclohexanecarboxylate may be treated with p-toluenesulfonic acid, triethyl orthoformate and ethylene glycol in a solvent such as EtOH to give the protected 1,4-dioxaspirol[4,5]decane-8-carboxylic ester which may then be deprotected by procedures well known in the art, such as by using an aqueous base, to give 1,4-dioxaspirol[4,5]decane-8-carboxylic acid over 2 steps (compound 2, Scheme 1, Step A). The Weinreb amide (compound 3) may be prepared from the acid product of Step A with the addition of a coupling reagent such as CDI or HOBt in small portions followed by the addition of N-methoxymethanamine hydrochloride in small portions (Scheme 1, Step B). The Weinreb amide (compound 3) may be converted to the ketone (compound 4) using an organometallic reagent such as a Grignard reagent or an organolithium reagent (Scheme 1, Step C). More specifically, methyl magnesium bromide may be added in an appropriate solvent such as Et$_2$O and/or THF to give the methyl ketone (compound 4). The methyl ketone (compound 4) may be converted to the vinyl phosphonate (compound 5) with drop wise addition of a non-nucleophilic base such as LiHMDS in a solvent such as THF with the addition of diphenyl phosphorochloridate (Scheme 1, Step D).

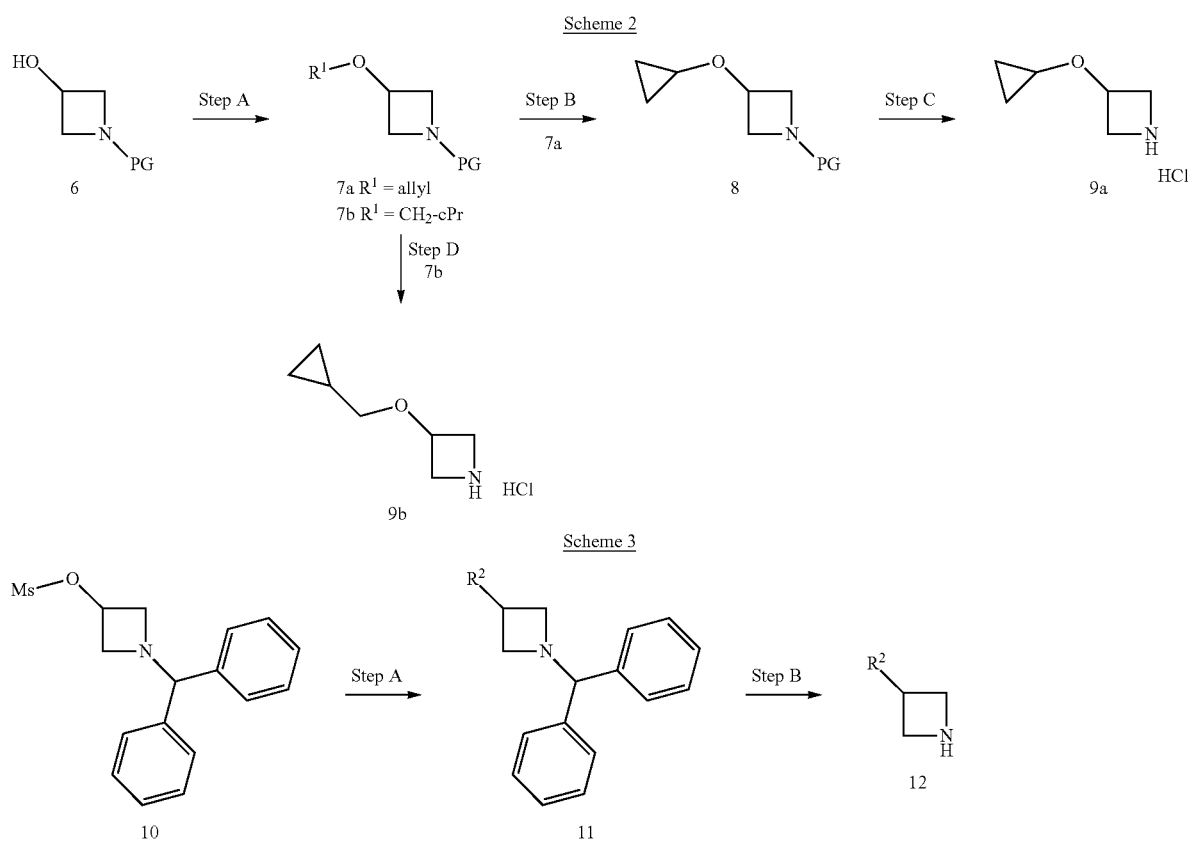

Scheme 2

Scheme 3

R² = OCH₃, OCH₂CH₃, O-cPr, O-iPr, OCH₂-cPr, CH₂OCH₃, O(CH₂)₂O CH₃, N-pyrazolyl, N-(substituted pyrazolyl), N-triazolyl, tetrahydrofuran-3-yl, morpholinyl, N-pyrrolidinyl Schemes 2 and 3 illustrate the syntheses of substituted azetidines. N-Protected vinyloxyazetidine (compound 7a, R¹=allyl) may be prepared by alkylating the appropriately substituted 3-hydroxyazetidine (compound 6) with an alkyl halide and a non-nucleophilic base such as DIPEA, or, alternatively, by a metal-mediated etherification with a palladium (II) source in the presence of a dibasic ligand such as 1,10-phenanthroline in the presence of a non-nucleophilic base such as DIPEA or TEA using an unsymmetrical vinyl ether as the solvent. One skilled in the art will recognize that the azetidine may be protected with a wide array of protecting groups such as an alkyl group, a substituted alkyl, an aralkyl, an amide, or an alkyl carbamate. More specifically, a solution of N-BOC-3-hydroxyazetidine may be treated with palladium(II) acetate in the presence of TEA and 4,7-diphenyl-1,10-phenanthroline in n-butyl vinyl ether to give the N-protected vinyloxyazetidine (compound 7a, R¹=allyl, Scheme 2, Step A). The vinyl group may be converted to the protected 3-cyclopropoxyazetidine (compound 8) by a Simmons-Smith reaction or similar carbene-generating conditions, for example, using chloroiodomethane and an alkylzinc reagent in DCE, as shown in Scheme 2, Step B. Deprotection of the protected 3-cyclopropoxyazetidine (compound 8) under standard conditions as those well described in the art, followed by treatment of the free base with a solution of mineral acid in organic solvent, such as HCl in diethyl ether or 1,4-dioxane, may provide the stable azetidine salt (compound 9a). More specifically, when the protecting group is BOC, one skilled in the art will recognize that treatment of the protected 3-cyclopropoxyazetidine (compound 8) with an acid such as HCl in 1,4-dioxane, followed by solvent evaporation, may afford the crude 3-cyclopropoxyazetidine hydrochloride (compound 9a, Scheme 2, Step C). Additionally, the cyclopropylmethoxyazetidine (compound 7b, R¹=cyclopropylmethyl, Scheme 2, Step A) may be prepared by alkylation of the appropriately substituted 3-hydroxyazetidine (compound 6) with bromomethylcyclopropane under strongly basic deprotonation conditions, for example, with NaH in a polar solvent such as DMF or DMSO, with subsequent deprotection of the protected cyclopropylmethoxyazetidine (compound 7b, R¹=cyclopropylmethyl) to obtain the crude cyclopropylmethoxyazetidine hydrochloride (compound 9b, Scheme 2, Step D).

Other substituted azetidines may be prepared from the commercially available benzhydrylazetidine mesylate (compound 10) by treatment with a wide variety of N, O, C and S containing nucleophiles under nucleophilic substitution conditions using an appropriate base such NaHCO₃, K₂CO₃, DIPEA or TEA and microwave heating, or by treatment with a strong base such as NaH, KOtBu or LHMDS and heating in a polar organic solvent such as DMF or DMSO, to give a substituted benzhydrylazetidine (compound 11, Scheme 3, Step A). Subsequent deprotection under catalytic hydrogenation (Scheme 3, Step B) may yield the desired substituted azetidine (compound 12).

Scheme 4

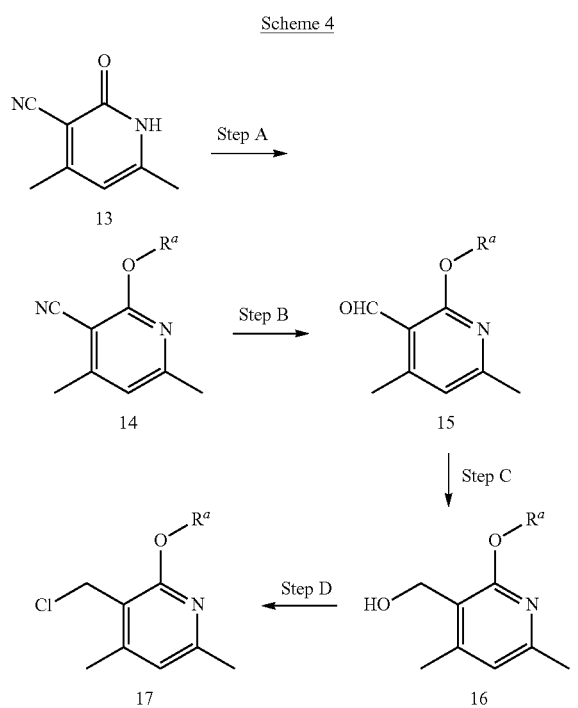

Scheme 4 depicts the preparation of 2-alkoxy-3-chloromethyl-4,6-dimethyl-pyridines (compound 17, where $R^a$ is $CH_3$, $CH_2CH_3$, or Bn), which may be prepared starting from commercially available 3-cyano-4,6-dimethylpyridone (compound 13). Alkylation of the 3-cyano-4,6-dimethylpyridone (compound 13) with the appropriate alkyl halide under standard literature conditions known to one skilled in the art, may provide the desired 2-alkoxy-3-cyano-4,6-dimethylpyridine (compound 14). Specifically, treatment of 3-cyano-4,6-dimethylpyridone (compound 13) with methyl iodide or benzyl chloride with $AgCO_3$ or $Ag_2O$ in an aprotic solvent such as 1,4-dioxane, DMF, toluene, or $CHCl_3$ with subsequent heating, may give the requisite 2-methoxy- or 2-benzyloxy-3-cyano-4,6-dimethylpyridine (compound 14, Scheme 4, Step A). Subsequent reduction of the cyano group in the 2-alkoxy-3-cyano-4,6-dimethylpyridine (compound 14) under standard conditions well known in the literature to one skilled in the art, such as slow treatment with a reducing agent such as DIBAL-H in an aprotic solvent such as DCM at 0° C. or RT may give the corresponding pyridine aldehyde (compound 15, Scheme 4, Step B). Further reduction to the carbinol (compound 16, Scheme 4, Step C) may be realized by standard conditions well known to one skilled in the art; specifically, treating the pyridine aldehyde (compound 15) portion wise with a common reducing agent such as $NaBH_4$ at 0° C. or lower temperature, to obtain the carbinol (compound 16). Subsequent chlorination of the carbinol (compound 16) with a typical chlorinating agent such as $SOCl_2$ or $POCl_3$ in an aprotic solvent such as DCM at low temperatures such as −40° C. to −60° C. may give the requisite chloromethylpyridine (compound 17, Scheme 4, Step D).

Scheme 5

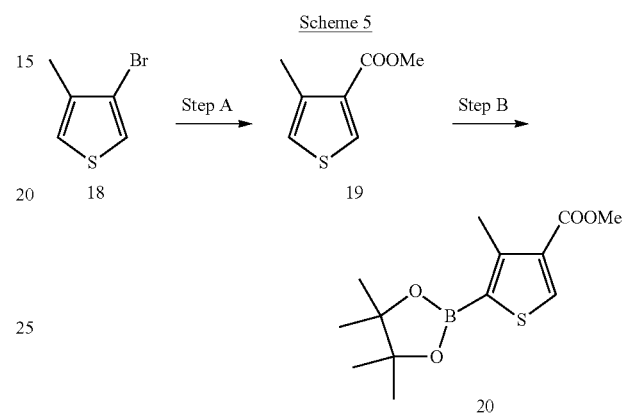

Scheme 5 illustrates the synthesis of methyl 4-methyl-5-(4,4,5,5-tetramethyl-1,3,2-dioxaborolan-2-yl)thiophene-3-carboxylate (compound 20). As is well known in the art, the aryl bromide (compound 18) may be carbonylated using an array of palladium(II) catalysts and a variety of appropriate phosphine ligands, specifically palladium(II) acetate and 1,1′-bis(diphenylphosphino)ferrocene, in the presence of an alcohol such as MeOH in a polar solvent such as DMF or DMA with or without a non-nucleophilic organic base such as DIPEA or TEA, under a pressurized atmosphere of carbon monoxide, to obtain the ester (compound 19, Scheme 5, Step A). Subsequent borolane esterification may be effected either by deprotonation with an alkyl metallating reagent such as n-butyl-, s-butyl-, or t-butyllithium with quenching of the aryl anion with a borate ester, or by transition-metal coordination complexes using palladium(II), iridium(I), or iron(III), to obtain the desired boronic ester. Specifically, the ester (compound 19) may be treated with bis(1,5-cyclooctadiene)di-μ-methoxydiiridium(I) and 4,4,5,5-tetramethyl-1,3,2-dioxaborolane portion wise in a nonpolar solvent such as cyclohexane with concomitant heating to obtain methyl 4-methyl-5-(4,4,5,5-tetramethyl-1,3,2-dioxaborolan-2-yl)thiophene-3-carboxylate (compound 20, Scheme 5, Step B).

Scheme 6

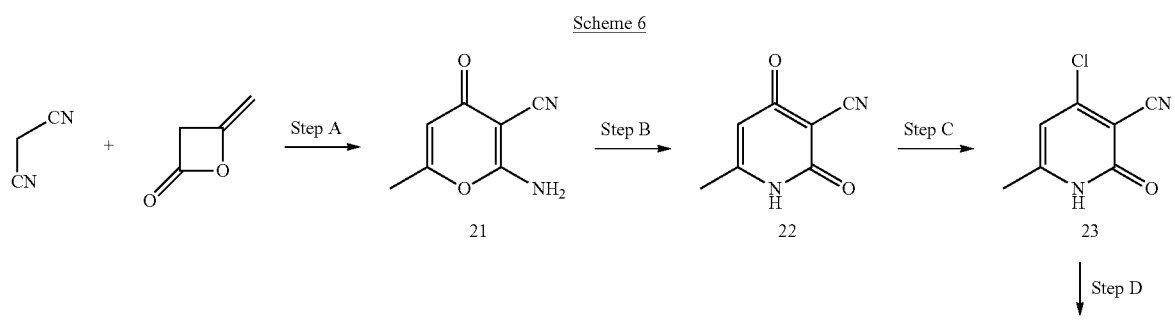

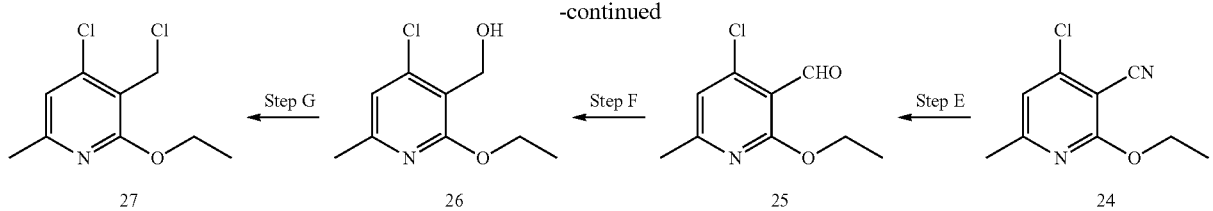

The 2-ethoxypyridine (compound 27) may be prepared according to the route depicted in Scheme 6, starting with condensation of malononitrile with acetyl ketene under basic conditions in an appropriate polar organic solvent, such as sodium hydride and THF, to obtain the 2-amino-3-cyano-pyranone (compound 21, Scheme 6, Step A). Subsequent thermal rearrangement with an inorganic acid, such as HCl, may give the 3-cyano-4-hydroxy-6-methylpyridone (compound 22, Scheme 6, Step B). Chlorination to the 4-chloropyridone (compound 23) may be effected using many chlorinating agents well known in the art, more specifically a mixture of $POCl_3$ and $PCl_5$ (Scheme 6, Step C); alkylation of the resulting pyridone (compound 23) may be achieved via metal-mediated etherification with an alkyl halide in an appropriate non-polar organic solvent, more specifically using silver(I) oxide and iodoethane in toluene, to give the 2-ethoxy-3-cyano-4-chloropyridine (compound 24, Scheme 6, Step D). Two-step reduction using reducing agents such as DIBAL-H followed by $NaBH_4$ or $NaCNBH_3$ may give the alcohol (compound 26, Scheme 6, Steps E-F), and subsequent chlorination with a chlorinating agent such as $POCl_3$ or $PCl_5$ in an appropriate organic solvent may yield the ethoxypyridine (compound 27). More specifically, chlorination of the alcohol (compound 26) may be achieved via in situ preparation of the mesylate by treatment with methanesulfonyl chloride in DCM from 0° C. to RT to give the ethoxypyridine (compound 27, Scheme 6, Step G).

Scheme 7

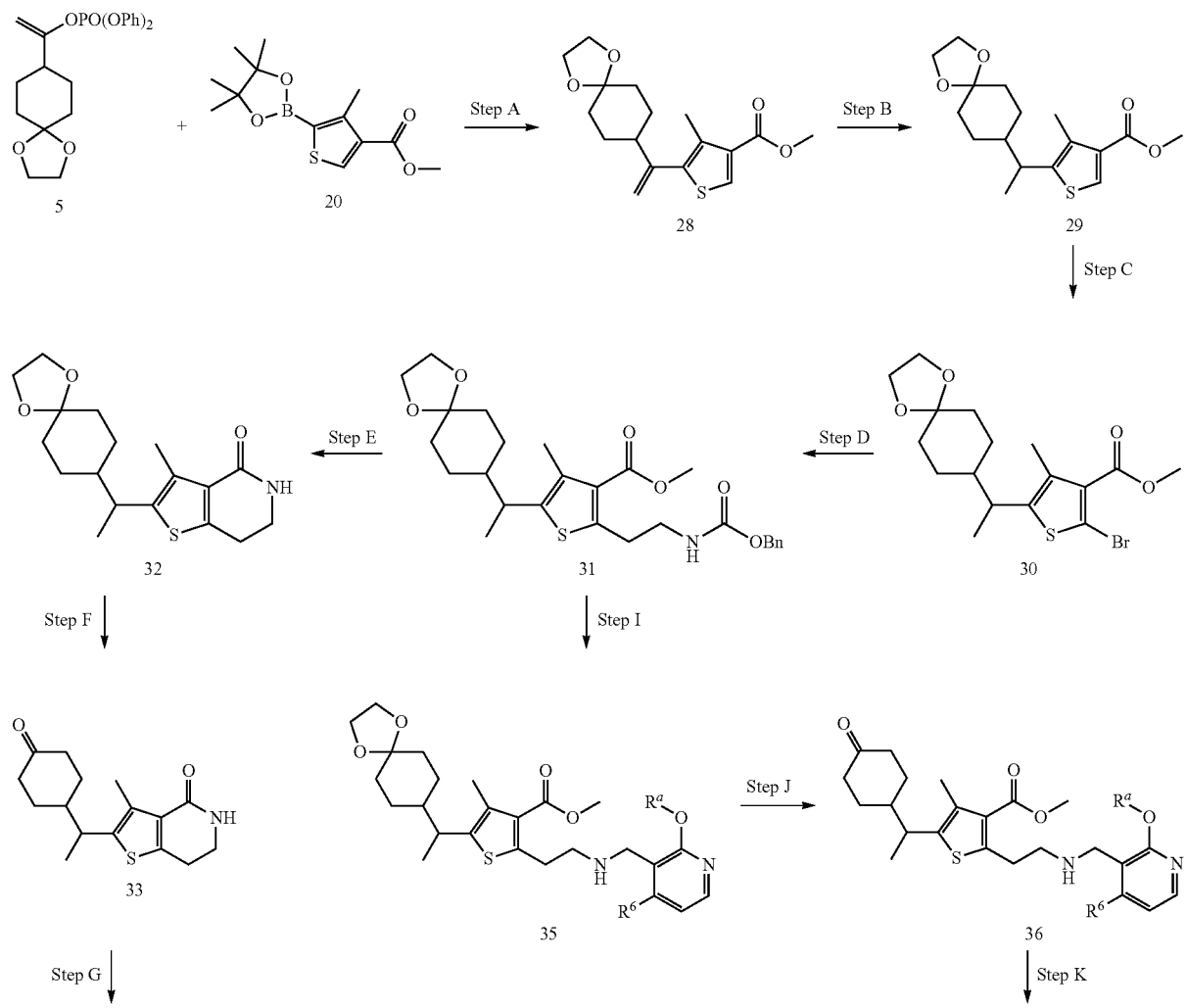

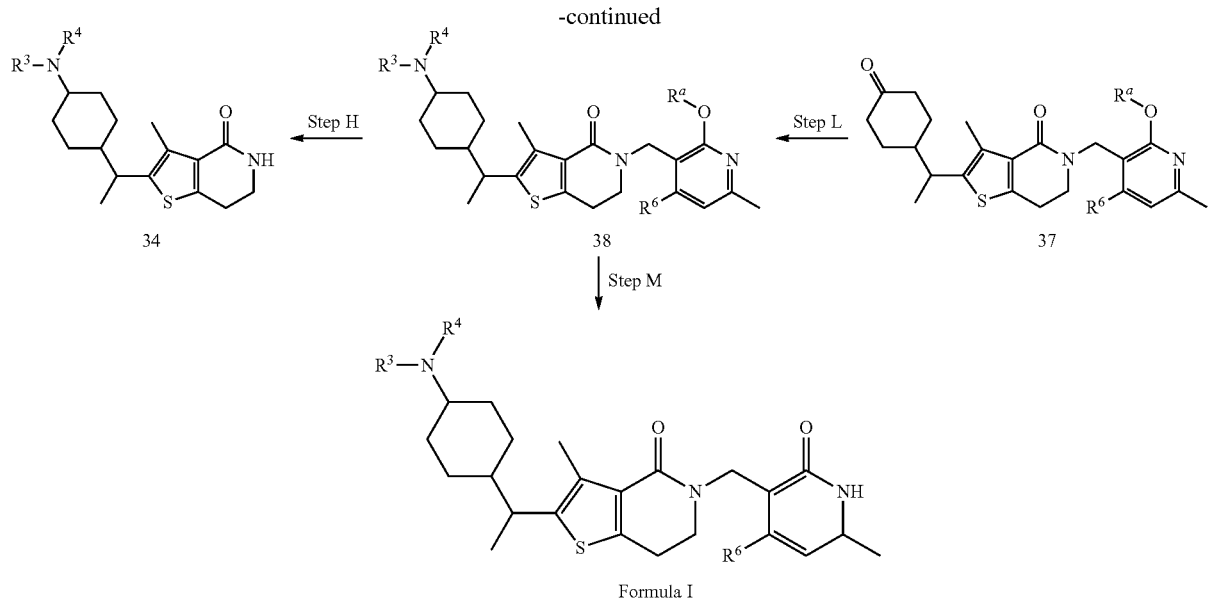

$R^6 = CH_3, Cl$

Scheme 7 depicts the synthesis of compounds of Formula I. Coupling of the prepared vinyl phosphate (compound 5, Scheme 1, Step D) with the aryl boronate ester (compound 20, Scheme 5, Step B) under standard Suzuki-type coupling conditions utilizing a palladium(II) catalyst and a phosphine ligand with a mild inorganic base such as K$_3$PO$_4$ in a polar organic solvent such as 1,4-dioxane may give the vinyl thiophene ester (compound 28, Scheme 7, Step A). Reduction of the vinyl moiety may be accomplished by procedures well documented in the art to obtain the α-methyl thiophene ester (compound 29, Scheme 7, Step B). Stereoselective reduction of the vinyl group may be achieved using an array of catalysts and ligands well documented in the art, especially with an iridium(I) catalyst/ligand complex such as [(4R,5R)-(+)-O-[1-benzyl-1-(5-methyl-2-phenyl-4,5-dihydrooxazol-4-yl)-2-phenylethyl]] (dicyclohexylphosphinite) (1,5-COD) iridium(I) tetrakis (3,5-bis(trifluoromethyl) phenylborate to yield the desired stereospecific ester (compound 29). Subsequent bromination in Scheme 7, Step C, to give the 5-bromothiophene ester (compound 30), may be effected using a brominating agent such as elemental bromine or NBS in a suitable organic solvent such as CHCl$_3$, DCM, EtOAc, 1,4-dioxane or CCl$_4$. Alkylation to methyl 2-[2-(benzyloxycarbonylamino)ethyl]-5-[1-(1,4-dioxaspiro[4.5]decan-8-yl)ethyl]-4-methyl-thiophene-3-carboxylate (compound 31) under standard palladium-mediated coupling conditions, specifically using RuPhos-G3-palladacycle (Scheme 7, Step D) followed by deprotection of the carbobenzyloxy amine (compound 31) under typical hydrogenolysis conditions well known in the art, specifically, in situ cyclization in a polar organic alcoholic solvent such as MeOH (Scheme 7, Step E) and unmasking to the ketone under standard acidic conditions, for example, using HCl in a suitable polar solvent such as THF or EtOH, may be accomplished to give 3-methyl-2-[1-(4-oxocyclohexyl)ethyl]-6,7-dihydro-5H-thieno[3,2-c]pyridin-4-one (compound 33, Scheme 7, Step F). Reductive amination may be effected in the presence of a Lewis acid such as titanium isopropoxide and a reducing agent such as NaBH$_4$, Na(OAc$_3$)BH, or NaCNBH$_3$ in a suitable solvent such as DCM or MeOH, to obtain a mixture of the trans- and cis-cyclohexane (compound 34, Scheme 7, Step G), which may be separable by crystallization or chromatography methods well known in the art. Further, one skilled in the art may recognize that utilization of LiBH$_4$ as a reducing agent may lead primarily to the trans-stereoisomer. Alkylation under well-known conditions with an appropriately substituted aralkyl halide, such as benzyl halide, followed by either demethylation or debenzylation under acidic conditions, for example using LiCl in the presence of PTSA with heating, may give the compound of Formula I (Scheme 7, Steps H and M).

Alternatively, the carbobenzyloxy amine (compound 31, Scheme 7, Step D) may be subjected to hydrogenolysis using conditions well known in the art, for example with Pd(OH)$_2$ on carbon in a suitable organic solvent such as MeOH, and hydrogenolysis may be effected in the presence of a pyridine aldehyde (e.g., compound 15, Scheme 4, Step B), to give methyl 5-[1-(1,4-dioxaspiro[4.5]decan-8-yl)ethyl]-4-methyl-2-[2-[(6-methyl-3-pyridyl)methylamino]ethyl]thiophene-3-carboxylate (compound 35, Scheme 7, Step I). Subsequent unmasking to the ketone, reductive amination, cyclization under thermal acidic conditions, and O-deprotection as above may yield the compounds of Formula I (Scheme 7, Steps J-M).

Alternatively, an amine such as compound 38, in which $R^3$=H, $R^4$=benzyl, may be subjected to hydrogenolysis using conditions well known in the art to provide an amine in which $R^3$=$R^4$=H. Subjecting this amine to reductive amination conditions and O-deprotection as above may yield compounds of Formula I. Specifically, use of acid, formaldehyde and triacetoxyborohydride may result in a reductive amination product in which $R^3$=$R^4$=Me.

Scheme 8

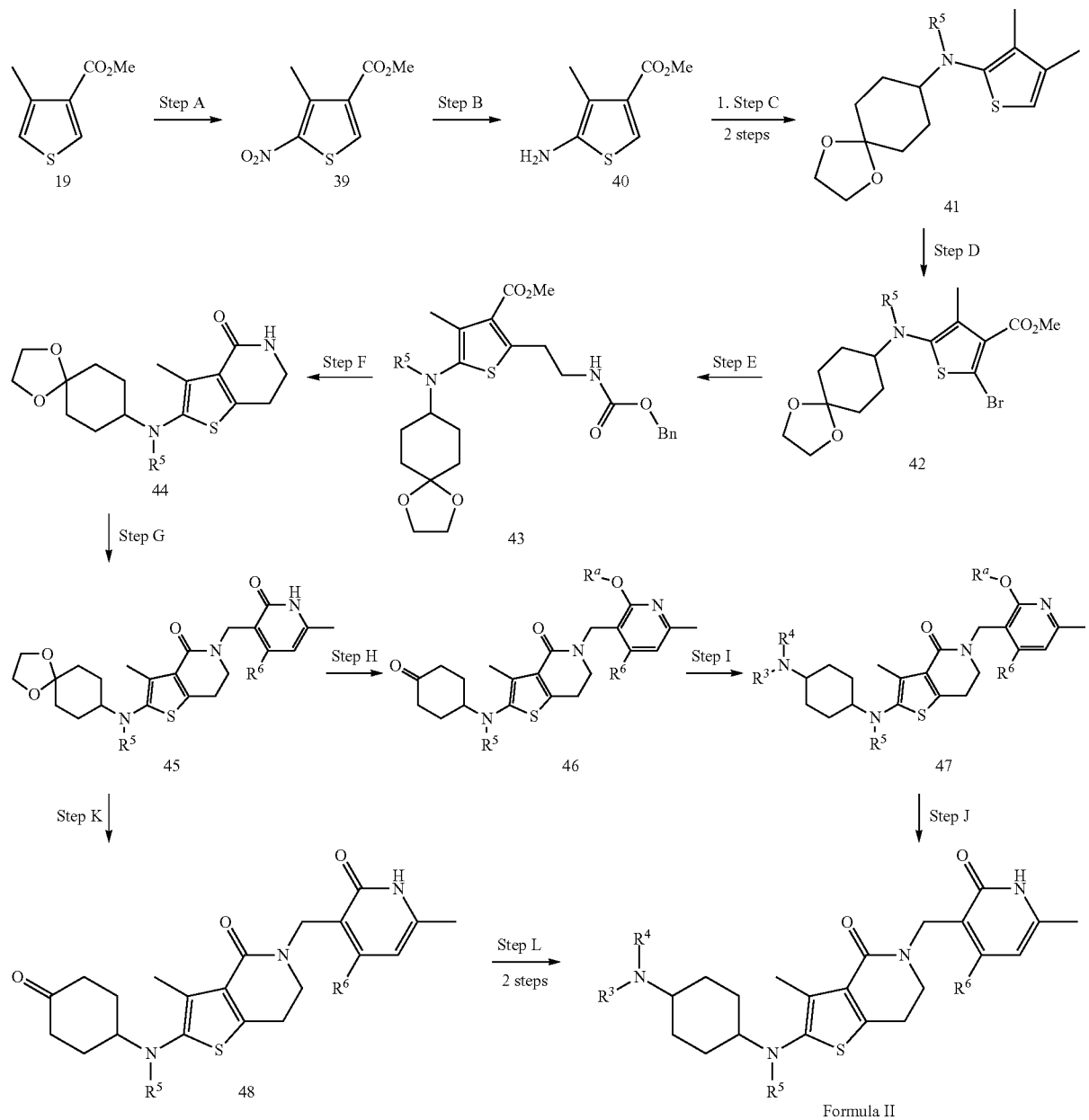

Scheme 8 depicts the synthesis of compounds of Formula II. Nitration of the ester (compound 19, Scheme 5, Step A) with subsequent nitro reduction under standard conditions may yield methyl 5-amino-4-methyl-thiophene-3-carboxylate (compound 40, Scheme 8, Steps A-B). Amino protection with a suitable amine protecting group, such as BOC, and subsequent alkylation under typical conditions, for example alkylating with methyl iodide in the presence of a mild base such as $K_2CO_3$ or $Cs_2CO_3$ in a polar solvent such as DMF, may yield an appropriately N-alkylated protected amino thiophene, which may be followed by in situ carbamate cleavage and subsequent reductive amination, for example with a cyclohexanone, such as 1,4-dioxaspirol[4.5]decan-8-one, and $Na(OAc_3)BH$ or $NaCHBH_3$, in a suitable organic solvent such as DCE, to obtain the requisite tertiary amine (compound 41, Scheme 8, Step C, where $R^5=CH_3$). Alternately, 5-amino-4-methyl-thiophene-3-carboxylate (compound 40) may first be subjected to reductive amination conditions with a cyclohexanone, such as 1,4-dioxaspirol[4.5]decan-8-one, in the presence of $Na(OAc)_3BH$ or $NaCNBH_3$ in a suitable organic solvent such as DCE, followed by a second reductive amination in situ with acetaldehyde, to obtain the requisite tertiary amine (compound 41, Scheme 8, Step C, where $R^5=CH_2CH_3$). Subsequent bromination, metal-mediated alkylation, cyclization to the bicyclic lactam (compound 44), lactam N-alkylation, unmasking to the ketone, reductive amination and final demethylation or debenzylation all may be performed similarly to the methods of Scheme 7 to obtain the final compounds of Formula II (Scheme 8, steps D-J).

Alternatively, the ketal (compound 45, Scheme 8, Step G) may first be dealkylated to obtain the pyridone ketone (compound 48, Scheme 8, Step K) under similar conditions described in Scheme 7. Subsequent alkylation followed by reductive amination or double reductive amination (under conditions similar to Scheme 8, Step C) may be performed to obtain the compounds of Formula II (Scheme 8, Step L)

dichloride, and a non-nucleophilic organic base such as TEA, to obtain the alkyne (compound 49, Scheme 9, Step A). Subsequent reduction of the alkyne and deprotection of the amine moiety is well known in the art. Specifically, treatment of the alkyne (compound 49) under standard catalytic hydrogenation conditions and in situ hydrogenoly-

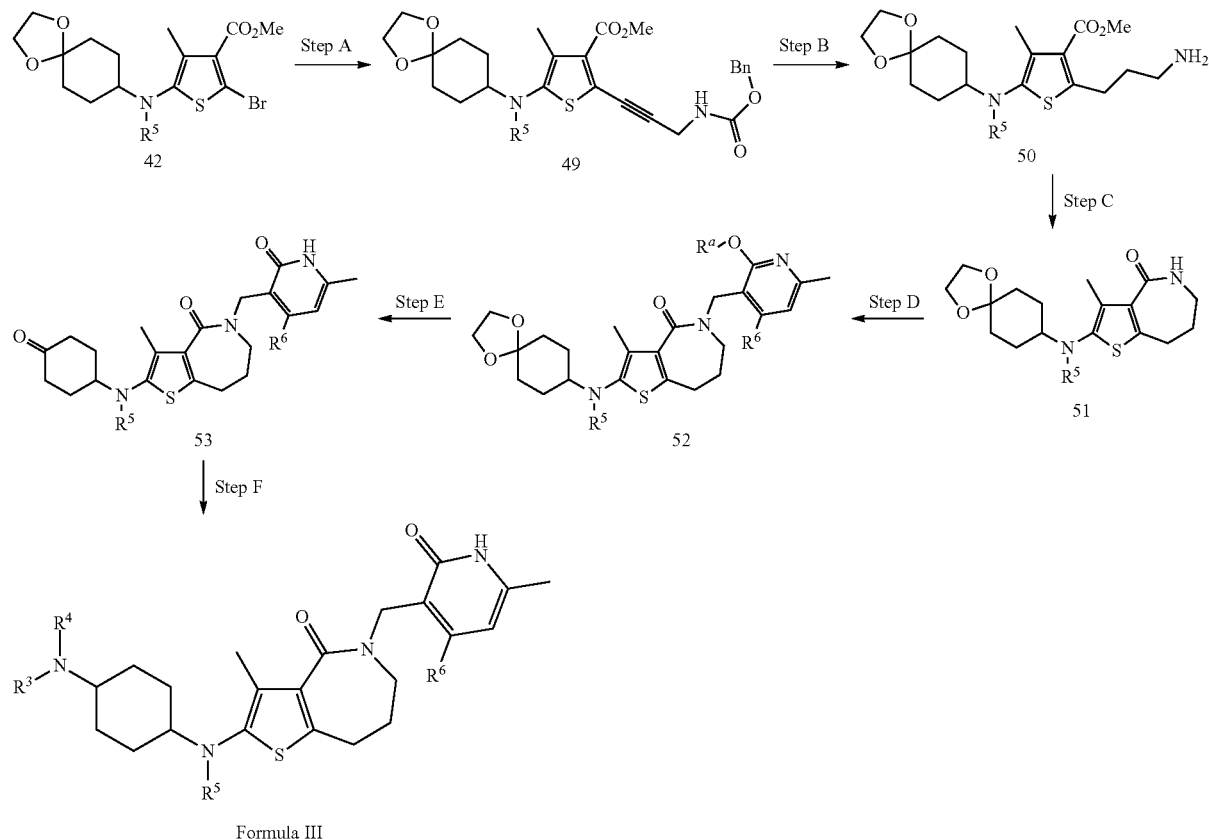

Scheme 9 depicts the synthesis of compounds of Formula III. An N-alkylated methyl 2-bromo-5-[$R^5$-(1,4-dioxaspirol[4.5]decan-8-yl)amino]-4-methyl-thiophene-3-carboxylate (compound 42, Scheme 8, Step D) may be alkynylated via transition-metal mediated coupling procedures well known in the art. More specifically, the bromothiophene (compound 42) may be treated with benzyl prop-2-yn-1-yl carbamate in the presence of CuI, an appropriate palladium(II)-ligand complex, such as bis(triphenylphosphine)palladium(II)

sis with $H_2$ in the presence of Pd on carbon or Pd(OH)$_2$ on carbon in a suitable organic solvent such as MeOH, EtOH, or EtOAc under pressure, may give the amine (compound 50, Scheme 9, step B), which may be subsequently cyclized under basic conditions such as KOtBu and heating to obtain the lactam (compound 51, Scheme 9, Step C). Alkylation of the lactam nitrogen, unmasking to the ketone, reductive amination and final dealkylation all may be performed similarly to what is described in Scheme 8 to obtain the compounds of Formula III (Scheme 9, Steps D-F).

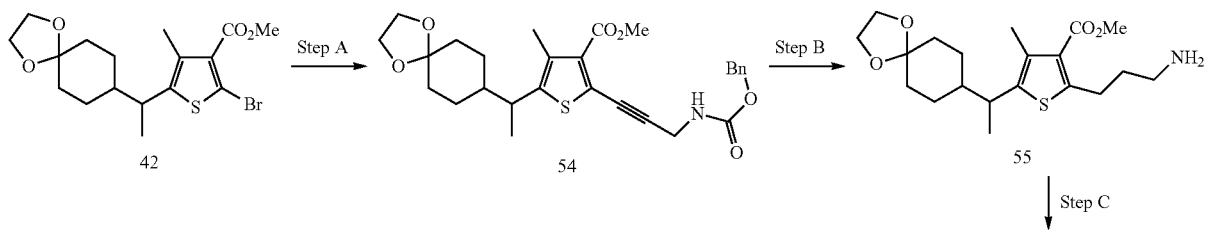

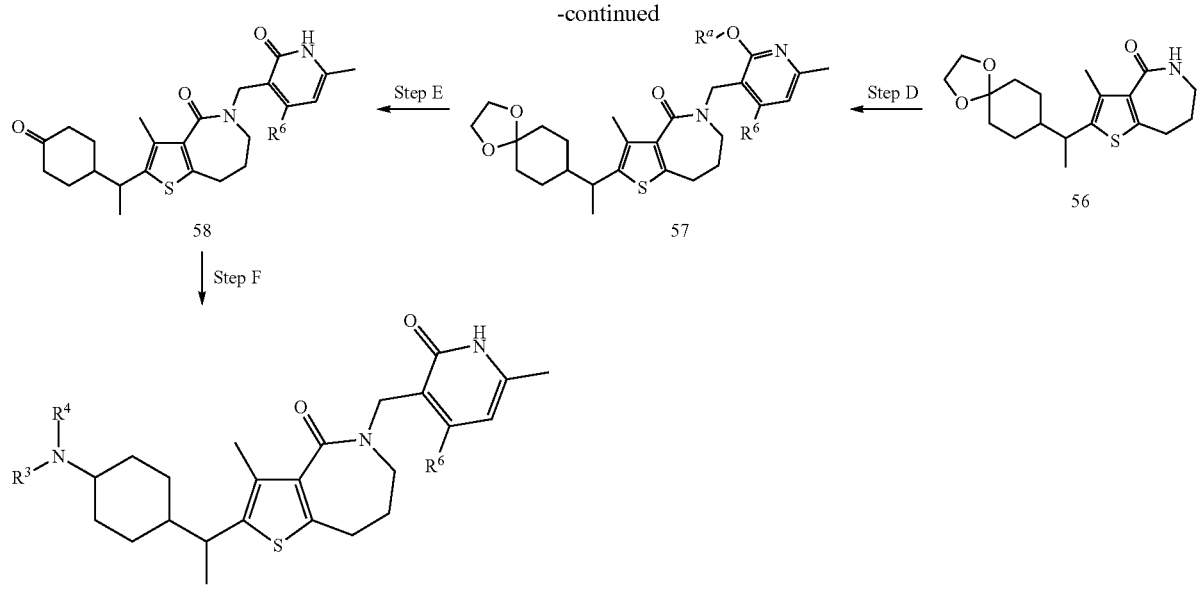

Scheme 10 depicts the synthesis of compounds of Formula IV starting with the appropriately substituted 5-bromothiophene ester (compound 30), utilizing methods similar to those described in Scheme 9 (Scheme 10, Steps A-F).

The preparation of compounds of Formula V is depicted in Scheme 11. Treating the aminothiophene (compound 40, Scheme 8, Step B) with an appropriately protected aminoalkyl ketone under reductive amination conditions well

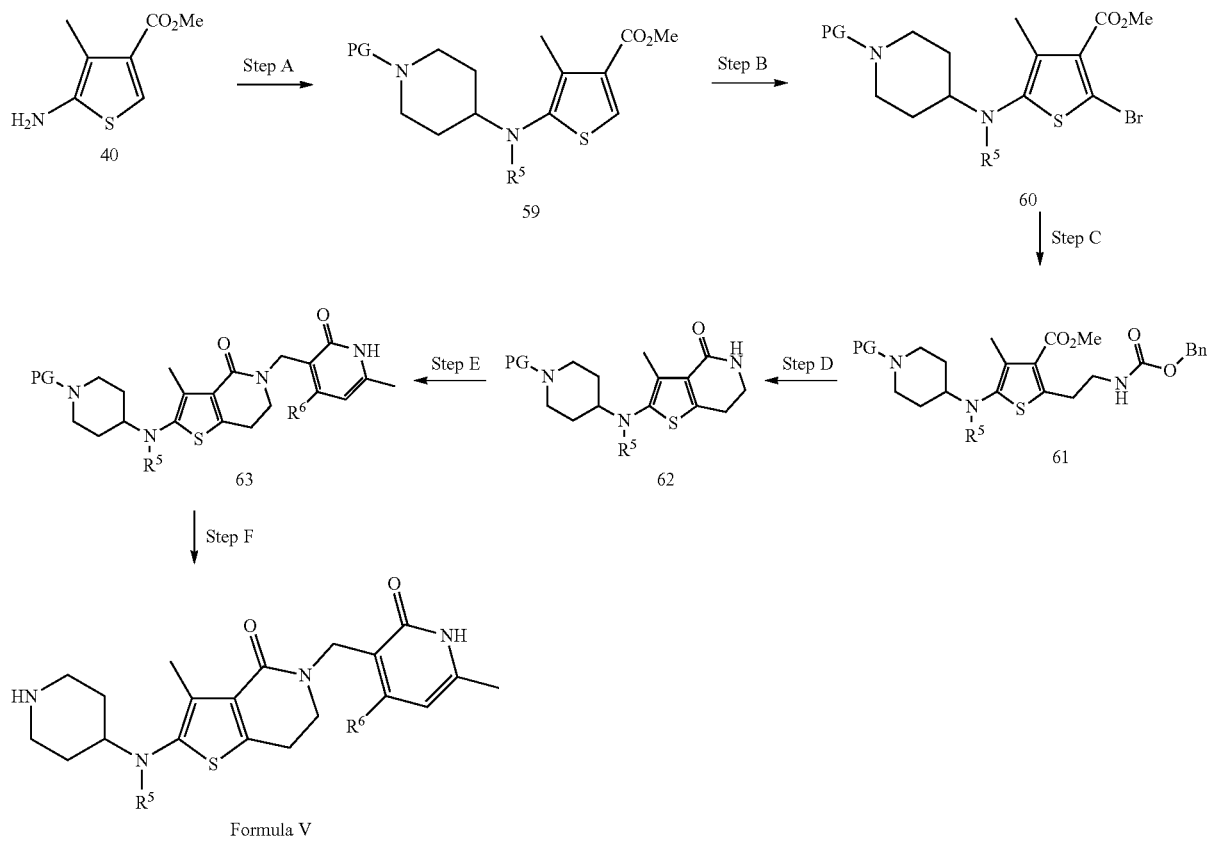

known in the art with subsequent alkylation, using an alkylating agent such as $CH_3I$ or $CH_3CH_2I$ under basic conditions with an appropriate base such as NaH or $K_2CO_3$, or alkylation via a second reductive amination with, for example, acetaldehyde, (Scheme 11, Step A), may give the N-alkylated N-piperidinyl thiophene ester (compound 59). More specifically, 3,4-dimethylthiophen-2-amine (compound 40) may be treated with tert-butyl-4-oxopiperidine-1-carboxylate in an appropriate organic solvent such as DCE with portion wise addition of a suitable reducing agent such as $Na(OAc)_3BH$ with subsequent addition of formaldehyde or acetaldehyde to obtain the N-alkylated N-piperidinyl thiophene (compound 59). Subsequent bromination, alkylation of the aryl bromide (compound 60) under Pd-catalyzed coupling conditions to obtain alkylthiophene (compound 61), cyclization to the lactam, lactam-N alkylation, and finally deprotection in a manner similar to that described in Scheme 8, may give compounds of Formula V (Scheme 11, Steps B-F).

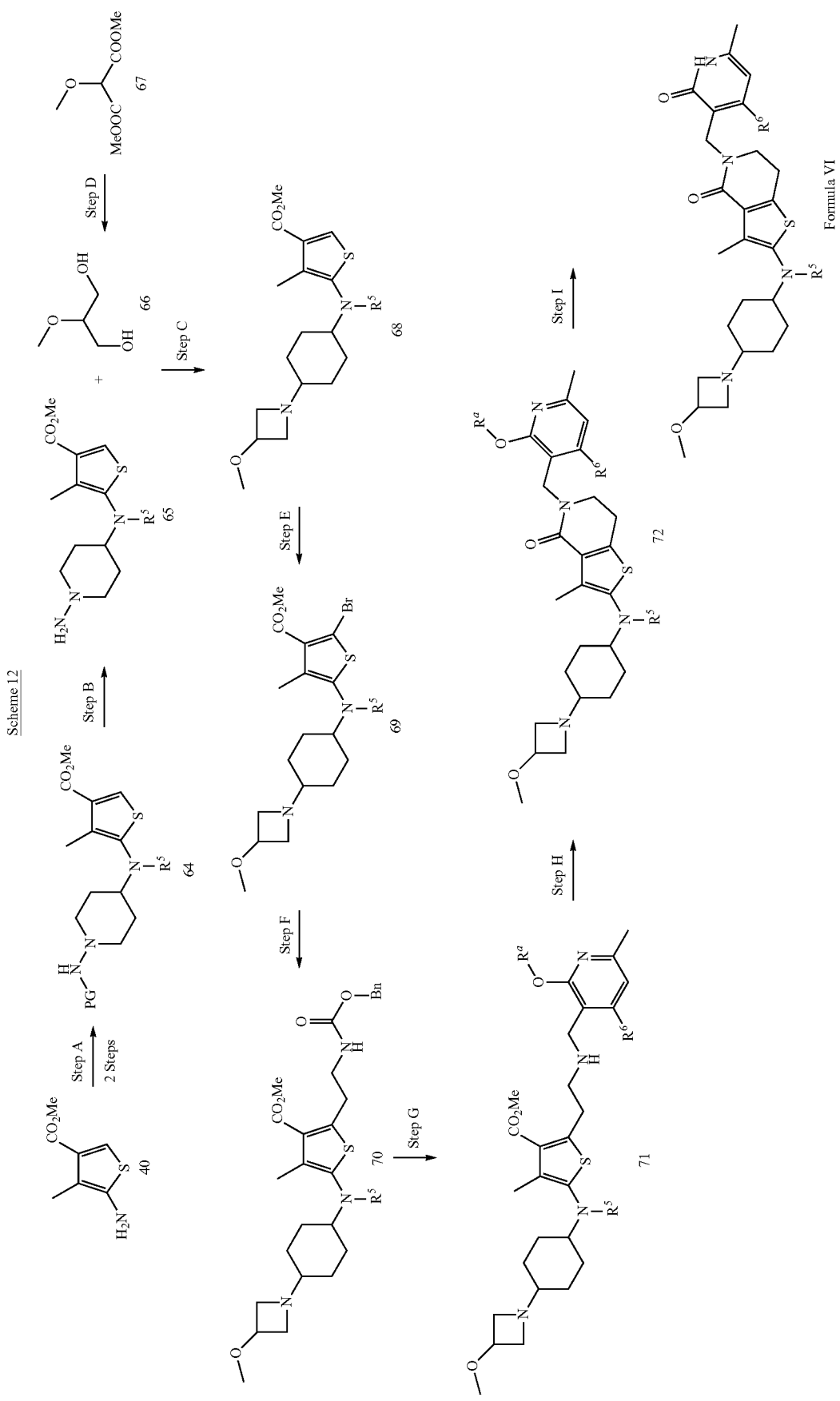

Scheme 12 shows the synthesis of compounds of Formula VI. Double alkylation of the aminothiophene (compound 40) under reductive amination conditions, specifically using first an appropriately protected 4-aminocyclohexanone and then acetaldehyde in the presence of Na(OAc)₃BH, may give the N-alkylated thienylcyclohexylamine (compound 64, Scheme 12, Step A). Additionally, N-methylation to this N-alkylated thienylcyclohexyl amine (compound 64) may be effected by first protecting the amino thiophene with an appropriate amine protecting group, such as BOC, followed by treatment of the subsequent carbamate with a strong base, such as NaH or KOtBu, treatment of the resulting anion with an alkyl halide such as CH₃I, removal of the amine protecting group, and finally reductive amination with an appropriately protected 4-aminocyclohexanone. Deprotection of the cyclohexylamino group yielding the 4-aminocyclohexane (compound 65) may be accomplished readily via an array of conditions well recognized to one skilled in the art (Scheme 12, Step B). Alkylation (Scheme 12, Step C) of this 4-aminocyclohexane (compound 65, Scheme 12, Step C) may be effected using the in situ-generated triflate of 2-methoxypropane-1,3-diol (compound 66), and subsequent bromination, using either elemental bromine or NBS, gives the bromothiophene (compound 69, Scheme 12, Step E). Alkylation of the arylbromide (compound 69) under palladium catalyzed conditions, for example using a substituted potassium trifluoroborate salt with catalytic RuPhos-G3-Palladacycle in a mixture of toluene and water in the presence of an inorganic base such as K₂CO₃ and heating, may result in the N-alkylated methyl 2-[2-(benzyloxycarbonylamino)ethyl]-5-[[4-(3-methoxyazetidin-1-yl)cyclohexyl]amino]-4-methyl-thiophene-3-carboxylate (compound 70, Scheme 12, Step F). Deprotection under conditions well described in the art, with concomitant reductive amination in situ using an appropriately substituted heteroaryl aldehyde, for example, in the presence of Pd(OH)₂ on carbon in an alcoholic solvent, such as EtOH, under pressure and heating, may give the substituted aminomethyl pyridine (compound 71, Rᵃ=CH₃ or Bn, Scheme 12, Step G). Subsequent cyclization and deprotection under conditions similar to those described in Scheme 8, may yield compounds of Formula VI (Scheme 12, Steps H-I).

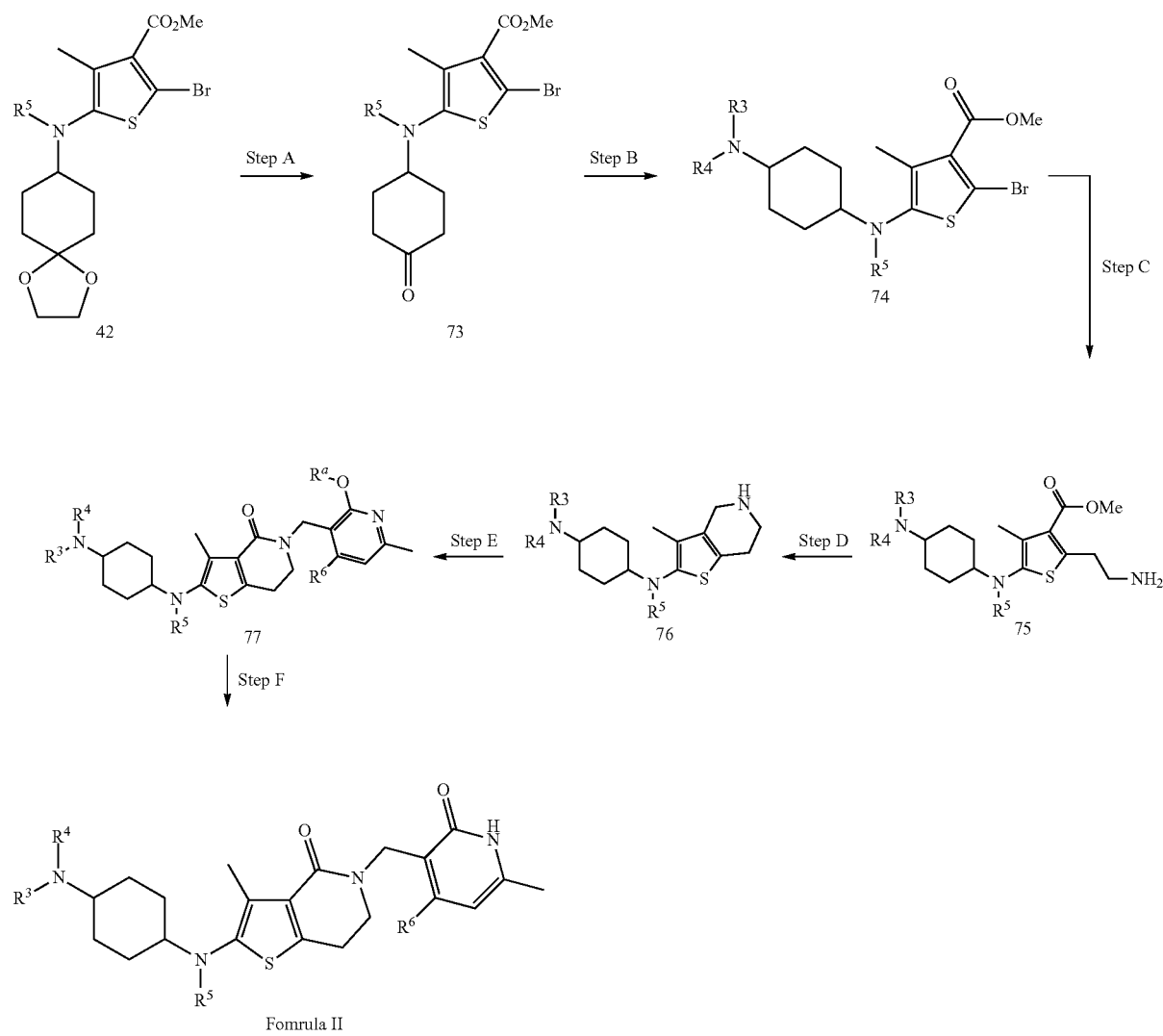

Scheme 13 depicts an alternative synthesis of compounds of Formula II. Unmasking the ketal (compound 42, Scheme 8, Step D) under acidic conditions similar to those described in Scheme 7, Step J or Scheme 8, Step K, may give the corresponding ketone (compound 73, Scheme 13, Step A). Double reductive amination under conditions similar to Scheme 8, Step L, may result in the cyclohexylamine (compound 74, Scheme 13, Step B), and subsequent transition-metal mediated coupling under conditions described in Scheme 7, Step D, followed by amine deprotection well described in the literature, may give aminocyclohexane (compound 75, Scheme 13, Step C). Cyclization to the 6,7-dihydro-5H-thieno[3,2-c]pyridin-4-one (compound 76) under similarly described conditions in Scheme 11, Step D, followed by alkylation conditions similarly described in Scheme 7, Step H, may give the substituted pyridine (compound 77, Scheme 13, Step E), and final dealkylation under similarly described conditions in Scheme 7, Step M, may result in the compound of Formula II (Scheme 13, Step F).

may be accomplished using standard techniques well known in the art, for example, either by using standard flash chromatography on silica and an appropriate organic solvent mixture (e.g., EtOAc/hexanes) or by reverse phase chromatography over C-18 silica using an appropriate water/organic solvent mixture (e.g., $H_2O$ buffered with $NH_4OAc$ or $NH_4HCO_3$ and ACN).

Preparation 1 tert-Butyl 3-hydroxyazetidine-1-carboxylate

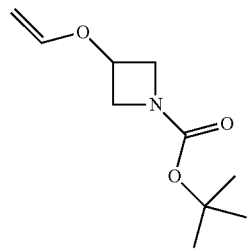

Scheme 14

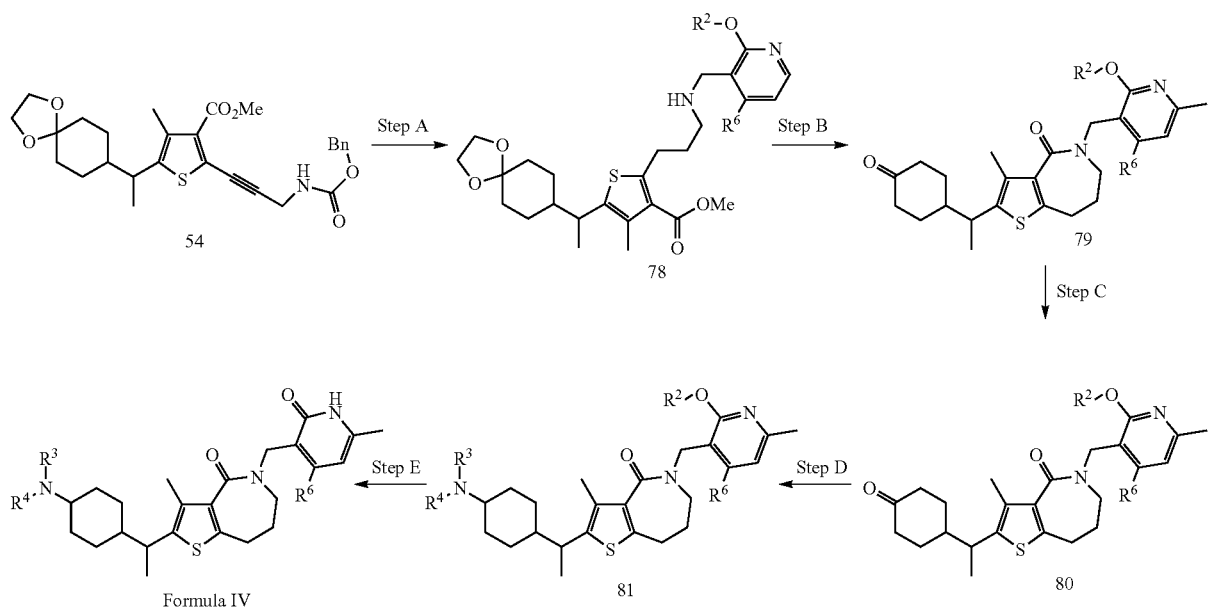

Scheme 14 illustrates an alternative synthetic pathway to compounds of Formula IV. The alkyne compound 54 (Scheme 10, step A) may be simultaneously reduced and deprotected using an array of techniques well known in the art, such as catalytic hydrogenation with palladium(II) hydroxide, and in situ reductive amination with an appropriately substituted 2-alkoxypyridine, such as 4,6-dimethyl-2-alkoxypyridine, may be accomplished under conditions similar to those depicted in Scheme 9, step B to give ketal compound 78. Subsequent unmasking to the ketone compound 79, cyclization to the lactam compound 80, reductive amination with an appropriately substituted amine to obtain compound 81, and final dealkylation, all under similarly described conditions depicted in Scheme 7 (steps J-M), may yield compounds of Formula IV.

One skilled in the art will recognize that separation of all relevant trans- and cis-isomers described in Schemes 7-12

Add tert-butyl 3-hydroxyazetidine-1-carboxylate (12.0 g, 69.3 mmol), n-butyl vinyl ether (125.0 mL, 961 mmol), and TEA (4.1 mL, 29 mmol) to a sealed flask. Bubble the mixture with $N_2$ vigorously for 10 min. Add 4,7-diphenyl-1,10-phenanthroline (1.0 g, 2.92 mmol) and Pd(OAc)$_2$ (0.66 g, 2.91 mmol). Seal the flask and stir the mixture under $N_2$ at 80° C. for 7 days. Filter the mixture through diatomaceous earth and rinse the filter cake with EtOAc. Concentrate the filtrate and subject the resulting residue to chromatography on silica, eluting with a gradient of 0-20% EtOAc in hexanes, to give the title compound (9.95 g, 72% yield) as yellow oil after solvent evaporation. $^1$H NMR (400.1 MHz, CDCl$_3$) δ 1.44 (s, 9H), 3.90 (dd, J=4.2, 10.1 Hz, 2H), 3.97 (dd, J=2.5, 14.5 Hz, 1H), 4.08 (dd, J=2.5, 6.8 Hz, 1H), 4.17 (dd, J=6.5, 10.1 Hz, 2H), 4.55-4.61 (m, 1H), 6.37 (dd, J=6.8, 14.5 Hz, 1H).

Preparation 2 tert-Butyl 3-(cyclopropoxy)azetidine-1-carboxylate

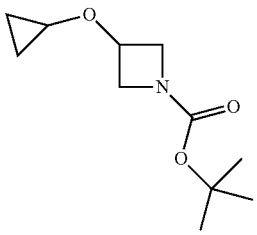

Cool a solution of tert-butyl 3-vinyloxyazetidine-1-carboxylate (9.9 g, 50 mmol) and chloroiodomethane (12 mL, 159.8 mmol) in DCE (50 mL) to −5° C., and then add a solution of 1M diethylzinc in heptane (80 mL, 80 mmol) drop wise over 60 min while maintaining the internal temperature between 0 and −5° C. Warm to RT and stir the mixture for 30 min. Re-cool the mixture in an ice bath and quench the reaction with saturated aqueous NH$_4$Cl solution. Add concentrated NH$_4$OH solution, and then extract the resulting mixture three times with MTBE. Wash the combined extracts with saturated aqueous NH$_4$Cl solution, dry over anhydrous K$_2$CO$_3$, filter, and concentrate in vacuo. Subject the resulting residue to chromatography on silica, eluting with a gradient of 0-20% EtOAc in hexanes, to give the title compound (4.90 g, 46% yield) as colorless oil after solvent evaporation. $^1$H NMR (400.1 MHz, CDCl$_3$) δ 0.45-0.50 (m, 2H), 0.57-0.62 (m, 2H), 1.43 (s, 9H), 3.21-3.26 (m, 1H), 3.85 (dd, J=4.2, 9.8 Hz, 2H), 4.08 (dd, J=6.6, 9.8 Hz, 2H), 4.32 (m, 1H).

Preparation 3

3-(Cyclopropoxy)azetidine hydrochloride

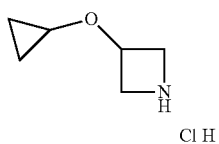

Cool a solution of tert-butyl 3-(cyclopropoxy)azetidine-1-carboxylate (4.45 g, 20.9 mmol) in THF (10 mL, 123 mmol) in an ice bath and drop wise add a solution of 4N HCl in 1,4-dioxane (20 mL, 80 mmol). Stir the solution at RT for 3 hr and concentrate in vacuo. Dissolve the residue in 2-propanol, concentrate, and dry in vacuo to give the title compound (3.0 g, 96% yield) which may be used without additional purification. $^1$H NMR (400.1 MHz, CD$_3$OD) δ 0.48-0.54 (m, 2H), 0.56-0.61 (m, 2H), 3.35-3.40 (m, 1H), 3.98 (dd, J=4.8, 11.8 Hz, 2H), 4.29 (dd, J=6.8, 11.8 Hz, 2H), 4.51-4.58 (m, 1H).

Preparation 4

1-Benzhydryl-3-[(3S)-tetrahydrofuran-3-yl]oxy-azetidine

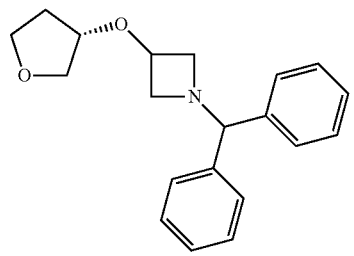 [SMILES: c1ccc(C(c2ccccc2)N2CC(O[C@H]3CCOC3)C2)cc1]

Heat a mixture of (3S)-tetrahydrofuran-3-ol (10 mL, 122.0 mmol) and 1-benzhydrylazetidin-3-yl methanesulfonate (3.0 g, 9.3 mmol) at 100° C. in a microwave for 20 min. Cool the mixture to RT and dilute with EtOAc and saturated aqueous Na$_2$CO$_3$ solution. Separate the layers, wash the organic layer sequentially with water and saturated aqueous NaCl, and dry over Mg$_2$SO$_4$. Filter and concentrate in vacuo. Subject the resulting residue to chromatography on silica, eluting with a gradient of 10-30% EtOAc in hexanes to give the title compound (0.9 g, 30% yield) as colorless oil after solvent evaporation. ES/MS (m/z): 310 (M+H).

Prepare Preparation 5 essentially by the method of Preparation 4 using (3R)-tetrahydrofuran-3-ol.

| Prep No. | Chemical name | Structure | ES/MS (m/z) (M + H) |
|---|---|---|---|
| 5 | 1-Benzhydryl-3-[(3R)-tetrahydrofuran-3-yl]oxy-azetidine | 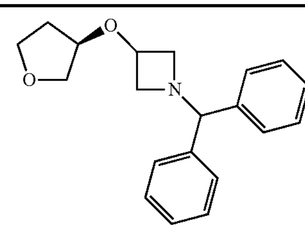 | 310 |

Preparation 6

3-[(3S)-Tetrahydrofuran-3-yl]oxyazetidine

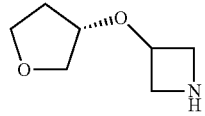

Flush N$_2$ through a mixture of 1-benzhydryl-3-[(3S)-tetrahydrofuran-3-yl]oxy-azetidine (0.85 g, 2.7 mmol), MeOH (20 mL), EtOAc (5 mL) and AcOH (1 mL) for 10 min. Add 10% Pd on carbon (0.50 g) and stir the resulting slurry under H$_2$ at 60 psi for 18 hr. Remove the catalyst by filtration and rinse the filter cake with MeOH. Concentrate and dry the residue in vacuo to give the title compound (0.39 g, 95% yield) suitable for use without further purification. $^1$H NMR (400.1 MHz, CDCl$_3$): δ 1.85-2.05 (m, 2H), 2.05

(bs, 1H), 3.58-3.72 (m, 5H), 3.74 (d, 1H), 3.80 (m, 1H), 3.89 (m 1H), 4.07 (m, 1H), 4.34 (m, 1H).

Prepare Preparation 7 essentially by the method of Preparation 6 using 1-benzhydryl-3-[(3R)-tetrahydrofuran-3-yl]oxy-azetidine.

| Prep No. | Chemical name | Structure | $^1$H NMR (400.1 MHz, CDCl$_3$) δ |
|---|---|---|---|
| 7 | 3-[(3R)-Tetrahydrofuran-3-yl]oxyazetidine | 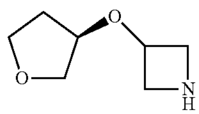 | 1.85-2.02 (m, 2H), 2.48 (bs, 1H), 3.56-3.78 (bm, 5H), 3.74 (d, 1H), 3.80 (m, 1H), 3.89 (m 1H), 4.08 (m, 1H), 4.36 (m, 1H) |

Preparation 8

1-[1-(Diphenylmethyl)azetidin-3-yl]-3-methyl-1H-pyrazole and 1-(1-benzhydrylazetidin-3-yl)-5-methyl-pyrazole (mixture of regioisomers)

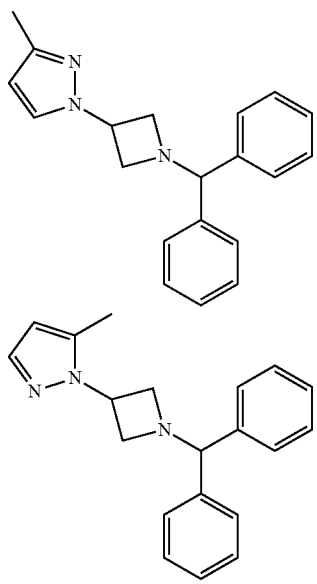

To a sealed tube, add to a solution of (1-benzhydrylazetidin-3-yl) methanesulfonate (7 g, 22.05 mmol) in DMF (15 mL), 3-methyl-1H-pyrazole (2.17 g, 26.47 mmol) and Cs$_2$CO$_3$ (8.6 g, 26.47 mmol) and stir the mixture at 120° C. for 24 hr. Cool to RT, pour the mixture into ice water, and extract with a solution of 5% MeOH in DCM. Separate the layers, dry the organic phase over Na$_2$SO$_4$, filter, and concentrate the filtrate in vacuo. Subject the resulting residue to chromatography on silica gel, eluting with a gradient of 7-30% EtOH in hexanes, to afford the title compound as a mixture of regioisomers as yellow oil (3.5 g, 49% yield) after solvent evaporation. ES/MS (m/z): 304 (M+H).

Prepare the following compounds essentially by the method of Preparation 8.

| Prep No. | Chemical name | Structure | ES/MS (m/z) |
|---|---|---|---|
| 9 | 1-[1-(Diphenylmethyl)-azetidin-3-yl]-4-methyl-1H-pyrazole | 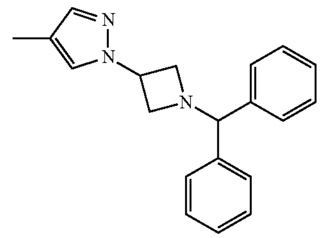 [SMILES: Cc1cnn(C2CN(C(c3ccccc3)c3ccccc3)C2)c1] | 304 (M + H) |
| 10 | 1-[1-(Diphenylmethyl)-azetidin-3-yl]-1H-1,2,3-triazole | 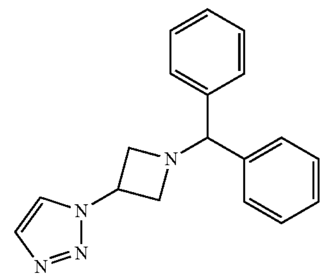 [SMILES: c1ccc(C(c2ccccc2)N2CC(n3ccnn3)C2)cc1] | 291 (M + H) |

Preparation 11

1-(Azetidin-3-yl)-3-methyl-1H-pyrazole and 1-(Azetidin-3-yl)-5-methyl-pyrazole (mixture of regioisomers)

To a 300 mL Parr autoclave, add a mixture of 1-[1-(diphenylmethyl)azetidin-3-yl]-3-methyl-1H-pyrazole (3.5 g, 11.5 mmol) and 1-(1-benzhydrylazetidin-3-yl)-5-methyl-pyrazole (mixture of regioisomers) with 10% Pd on carbon (3.5 g, 1 g/g) to a solution of MeOH (75 mL) and EtOAc (25 mL). Purge the vessel three times with H$_2$, charge to 50 psi of H$_2$, and stir vigorously at RT for 24 hr. Filter through a bed of diatomaceous earth and concentrate the filtrate in vacuo to afford the title compound as a mixture of regioisomers as colorless oil (1.58 g, 93% yield). ES/MS (m/z): 138 (M+H).

Prepare the following compounds essentially by the method of Preparation 11 using the corresponding 1-(diphenylmethyl)azetidine.

| Prep No. | Chemical name | Structure | ES/MS (m/z) |
|---|---|---|---|
| 12 | 1-(Azetidin-3-yl)-4-methyl-1H-pyrazole | 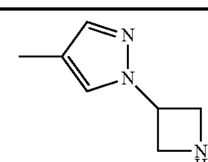 | 138 (M + H) |

| Prep No. | Chemical name | Structure | ES/MS (m/z) |
|---|---|---|---|
| 13 | 1-(Azetidin-3-yl)-1H-1,2,3-triazole | 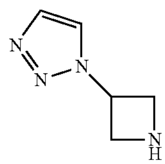 | 125 (M + H) |

Preparation 14 tert-Butyl 3-(cyclopropylmethoxy)azetidine-1-carboxylate

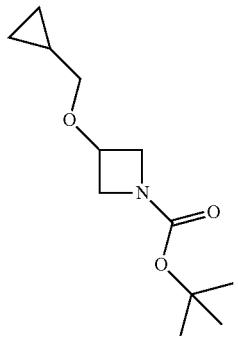 [SMILES: CC(C)(C)OC(=O)N1CC(OCC2CC2)C1]

Add NaH (60% in oil, 900 mg, 22.5 mmol) to a solution of tert-butyl 3-hydroxyazetidine-1-carboxylate (3 g, 17.32 mmol) in DMF (10 mL) at 0° C. Stir the mixture at RT for 1.5 hr, then slowly add bromomethylcyclopropane (2.80 g, 20.7 mmol) and stir over 72 hr. Dilute the mixture with EtOAc and Et$_2$O, wash twice with water, once with saturated aqueous NaCl, separate the layers, dry the organic extract over MgSO$_4$, filter, and concentrate the filtrate in vacuo. Subject the resulting residue to chromatography on silica, eluting with a gradient of 0-20% EtOAc in hexanes to give the title compound (1.91 g, 48% yield) as colorless oil after solvent evaporation. $^1$H NMR (400.1 MHz, CDCl$_3$) δ 0.18-0.22 (m, 2H), 0.54-0.58 (m, 2H), 1.00-1.04 (m, 1H), 1.43 (s, 9H), 3.23 (d, J=7.0 Hz, 2H), 3.85 (dd, J=4.3, 10.1 Hz, 2H), 4.06 (dd, J=6.5, 10.1 Hz, 2H), 4.20-4.26 (m, 1H).

Preparation 15

3-(Cyclopropylmethoxy)azetidine hydrochloride

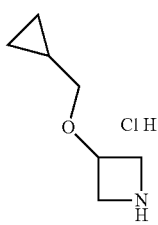

Add a 4N HCl solution in 1,4-dioxane (15 mL, 60 mmol) to tert-butyl 3-(cyclopropylmethoxy)-azetidine-1-carboxylate (1.91 g, 8.40 mmol) in a round bottom flask and stir at RT overnight. Concentrate the reaction mixture in vacuo and dry the resulting residue in vacuo to give the title compound (1.68 g, quantitative yield), suitable for use without further purification. $^1$H NMR (400.1 MHz, DMSO-d$_6$) δ 0.14-0.18 (m, 2H), 0.44-0.48 (m, 2H), 0.91-0.99 (m, 1H), 3.21 (d, J=7.0 Hz, 2H), 3.72-3.82 (m, 2H), 4.02-4.12 (m, 2H), 4.30-4.37 (m, 1H), 9.17 (bs, 2H).

Preparation 16

2-methoxy-4,6-dimethyl-pyridine-3-carbonitrile

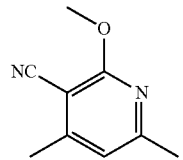

Add a solution of NaOCH$_3$ in MeOH (30 mass %, 175 mL, 940 mmol) drop wise to a solution of 2-chloro-4,6-dimethyl-pyridine-3-carbonitrile (75 g, 441.1 mmol) in MeOH (450 mL) in a water bath followed by another drop wise addition of NaOCH$_3$ in MeOH (25 mass %, 250 mL, 1090 mmol). Stir the resulting mixture for 1 hr, pour in ice cold water, stir for 30 min, and filter the resulting solid. Wash filter cake with hexane and dry in a vacuum oven overnight. Extract the aqueous filtrate with DCM, dry the organic phase over MgSO$_4$, filter and concentrate in vacuo. Combine the filtered solid and the evaporated residue to afford title compound as a solid (71.8 g, quantitative yield). ES/MS (m/z): 163 (M+H).

Preparation 17

2-methoxy-4,6-dimethyl-pyridine-3-carbaldehyde

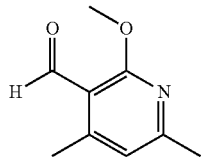

Add a 1M solution of DIBAL-H in toluene (240 mL, 240 mmol) to a solution of 2-methoxy-4,6-dimethyl-pyridine-3-carbonitrile (48 g, 295.95 mmol) in DCM (480 mL) at 0° C. over 2 hr. Remove the ice bath after 1 hr and stir at RT overnight. Cool in a water bath at RT and quench by slowly adding a mixture of 1M aqueous HCl (192 mL) and AcOH (192 mL). Add DCM, separate the layers, wash the organic phase with saturated aqueous NaCl, dry over Na$_2$SO$_4$, filter and concentrate in vacuo. Subject the resulting residue to chromatography on silica, eluting with a gradient of 0-20% EtOAc/hexane to afford title compound as a solid (22.6 g, 46% yield) after solvent evaporation. ES/MS (m/z): 166 (M+H). $^1$H NMR (400.1 MHz, CDCl$_3$) δ 2.43 (s, 3H), 2.54 (s, 3H), 4.01 (s, 3H), 6.61 (s, 1H), 10.48 (s, 1H).

Preparation 18

(2-Methoxy-4,6-dimethyl-3-pyridyl)methanol

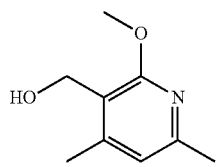

Add NaBH$_4$ (6.4 g, 170 mmol) portion wise to a solution of 2-methoxy-4,6-dimethyl-pyridine-3-carbaldehyde (22.6 g, 137 mmol) in MeOH (500 mL) at 0° C. Warm the solution to RT and stir overnight. Add additional NaBH$_4$ (1.0 g) and stir the mixture for 1 hr. Cool the flask to 0° C., add ice-cold water (50 mL), and concentrate the resulting mixture to ~½ volume in vacuo. Add saturated aqueous NaHCO$_3$ to the resulting residue, extract with DCM, separate the layers, wash the organic phase with saturated aqueous NaCl, and dry the organic phase over Na$_2$SO$_4$. Filter and concentrate the filtrate in vacuo to afford the title compound as oil (23 g, quantitative yield). ES/MS (m/z): 168 (M+H).

Preparation 19

3-(Chloromethyl)-2-methoxy-4,6-dimethyl-pyridine

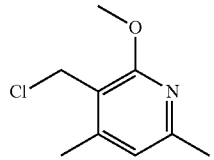

Add a solution of methanesulfonyl chloride (22 mL, 281 mmol) dissolved in DCM (100 mL) to a solution of (2-methoxy-4,6-dimethyl-3-pyridyl)methanol (39 g, 233.25 mmol) in DCM (500 mL) containing DIPEA (54 mL) at 0° C. Warm slowly to RT and stir over about 48 hr. Concentrate the reaction mixture in vacuo and subject the resulting residue to chromatography on silica, eluting with a gradient of 2-5% EtOAc/hexane, to afford the title compound as a solid (30.85 g, 71% yield) after solvent evaporation. H$^1$ NMR (399.8 MHz, DMSO-d$_6$): 2.28 (s, 3H), 2.30 (s, 3H), 3.84 (s, 3H), 4.69 (s, 2H), 6.70 (s, 1H).

Preparation 20

2-(Benzyloxy)4,6-dimethylpyridine-3-carbonitrile

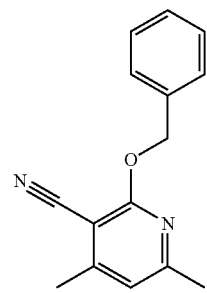 [SMILES: Cc1cc(C)c(C#N)c(OCc2ccccc2)n1]

Drop wise add benzyl chloride (100 mL, 859.5 mmol) to a mixture of 2-hydroxy-4,6-dimethyl-pyridine-3-carbonitrile (100 g, 675 mmol) and silver oxide (174 g, 747 mmol) in toluene (1 L) in a 2-L three-neck flask equipped with a mechanical stirrer. Stir the mixture at 110° C. for 6 hr. Cool the mixture to ~60° C., filter over diatomaceous earth, rinse with DCM and concentrate the filtrate in vacuo. Dissolve the crude product in DCM and drop wise add MeOH until a solid appears. Filter and collect the resulting solid to give the title product as a brown solid (144.9 g, 90% yield). ES/MS (m/z): 239 (M+H).

Preparation 21

2-(Benzyloxy)-4,6-dimethylpyridine-3-carbaldehyde

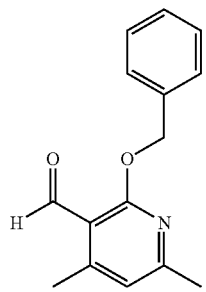 [SMILES: Cc1cc(C)c(C=O)c(OCc2ccccc2)n1]

Drop wise add a solution of 1M DIBAL-H in toluene (200 mL, 200 mmol) to a solution of 2-(benzyloxy)-4,6-dimethylpyridine-3-carbonitrile (40.3 g, 169 mmol) in DCM (400 mL) at 0° C. over 3 hr. Warm the reaction mixture to RT, and stir for 3 hr. Very slowly quench the reaction with a 1:1 mixture of 1N HCl (160 mL) and acetic acid (160 mL) at RT. Add saturated aqueous NaCl (100 mL) and extract with DCM. Separate the layers and dry the organic extracts over Na$_2$SO$_4$ overnight. Filter, concentrate the filtrate in vacuo, and subject the resulting residue to chromatography on silica, eluting with a gradient of 0-5% EtOAc in hexanes, to obtain the title compound (24.47 g, 60% yield) after solvent evaporation. ES/MS (m/z): 242 (M+H).

Preparation 22

(2-Benzyloxy-4,6-dimethyl-3-pyridyl)methanol

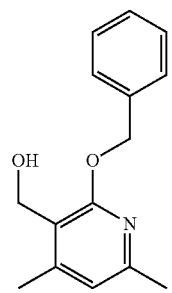 [SMILES: Cc1cc(C)c(CO)c(OCc2ccccc2)n1]

Dissolve 2-(benzyloxy)-4,6-dimethylpyridine-3-carbaldehyde (46.5 g, 193 mmol) in MeOH (1 L) in a 2-L three-neck flask in an ice bath equipped with a mechanical stirrer and add NaBH$_4$ (8.7 g, 230 mmol) in small portions over 1 hr. Warm the mixture to RT and stir for 3 hr. Re-cool the mixture to 0° C. and quench with ice-cold water (50 mL).

Concentrate the reaction mixture in vacuo and add saturated aqueous NaHCO₃ solution. Extract three times with DCM, wash the combined extracts with saturated aqueous NaCl, and dry over Na₂SO₄. Filter and concentrate the filtrate in vacuo to give the title compound (46.8 g, 99.8% yield) as colorless oil. ES/MS (m/z): 244 (M+H).

Preparation 23

2-Benzyloxy-3-(chloromethyl)-4,6-dimethyl-pyridine

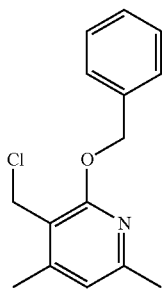 [SMILES: Cc1cc(C)c(CCl)c(OCc2ccccc2)n1]

Add SOCl₂ (4.0 g, 33 mmol) slowly to a solution of (2-benzyloxy-4,6-dimethyl-3-pyridyl)methanol (6.0 g, 25 mmol) in DCM (100 mL) at −60° C. under N₂ and then warm to −40° C. for 30 min. Pour the cold reaction mixture into ice/water (100 mL). Adjust the pH of the mixture with saturated aqueous NaHCO₃ until slightly basic, then sequentially extract the aqueous mixture twice with DCM, combine the organic extracts, and dry over MgSO₄. Filter and concentrate the filtrate in vacuo. Subject the resulting residue to chromatography on silica, eluting with a gradient of 0-30% EtOAc in hexanes to give the title compound (4.90 g, 76% yield) as a white solid. ¹H NMR (400.1 MHz, CDCl₃) δ 2.35 (s, 3H), 2.40 (s, 3H), 4.71 (s, 2H), 5.43 (s, 2H), 6.61 (s, 1H), 7.28-7.33 (m, 1H), 7.35-7.40 (m, 2H), 7.47-7.51 (m, 2H).

Preparation 24

2-Amino-6-methyl-4-oxo-4H-pyran-3-carbonitrile

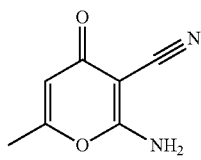

Cool a suspension of NaH (85.4 g, 2.10 mol) in anhydrous THF (0.70 L) to 0° C. Add neat malononitrile (238 g, 3.6 mol) drop wise to the stirred suspension. Stir at 0° C. for 10 min, then cool to −10° C. and add a solution of acetyl ketene (163 g, 1.91 mol) in THF (0.6 L) drop wise. Stir at −10 to 0° C. for 1 hr, then neutralize using concentrated HCl and dilute with water (1.0 L). Stir at RT for 16 h. Collect the solid by filtration and air dry to give yellow solid. Recrystallize from EtOH to obtain the title compound as a yellow powder (120 g, 42% yield). ¹H NMR (400.1 MHz, DMSO-d₆) δ 2.15 (3H, s) 5.87 (1H, s), 8.50 (2H, s).

Preparation 25

4-Hydroxy-6-methyl-2-oxo-1,2-dihydropyridine-3-carbonitrile

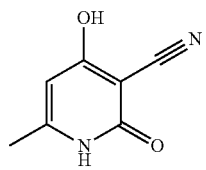

Heat a suspension of 2-amino-6-methyl-4-oxo-4H-pyran-3-carbonitrile (120 g, 0.80 mol) in 10% aqueous HCl (1.0 L) at 100° C. for 12 hr with stirring. Cool to RT and concentrate under reduced pressure. Add EtOH (0.40 L) to the resulting residue and collect the solid by filtration to afford the title compound as a white solid (103 g, 86% yield). ¹H NMR (400.1 MHz, DMSO-d₆) δ 2.15 (3H, s), 5.87 (1H, s), 11.68 (1H, s), 12.49 (bs).

Preparation 26

4-Chloro-6-methyl-2-oxo-1,2-dihydropyridine-3-carbonitrile

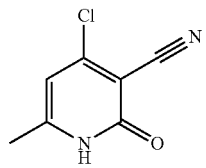

Suspend 4-hydroxy-6-methyl-2-oxo-1,2-dihydropyridine-3-carbonitrile (103 g, 0.69 mol) in CHCl₃ (1.0 L) and add phosphoryl chloride (210 g, 1.37 mol) and phosphorus pentachloride (286 g, 1.37 mol). Heat at 70° C. for 8 hr with stirring. Cool to RT, slowly pour into ice-water with vigorous stirring, neutralize the mixture using concentrated aqueous NH₃, and collect the resulting precipitate by filtration to afford the title compound as a brown solid (77 g, 65% yield) after drying in a vacuum oven. ¹H NMR (DMSO-d₆, 400.1 MHz, ppm) δ 2.27 (3H, s), 6.50 (1H, s).

Preparation 27

4-Chloro-2-ethoxy-6-methylpyridine-3-carbonitrile

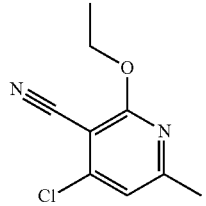

Add iodoethane (3.3 mL, 41 mmol) to a mixture of 4-chloro-6-methyl-2-oxo-1H-pyridine-3-carbonitrile (4.6 g, 27 mmol) and Ag₂O (13 g, 55.8 mmol) in toluene (250 mL)

and stir the resulting mixture at reflux for 4 hr. Cool the mixture to 60° C., filter through diatomaceous earth, and concentrate the filtrate in vacuo. Subject the resulting residue to chromatography on silica, eluting with a gradient of 0-100% EtOAc in hexanes, to afford the title compound (2.5 g, 47% yield) as a white solid after solvent evaporation. ES/MS (m/z): ($^{35}$Cl/$^{37}$Cl) 197/199 (M+H).

Preparation 28

4-Chloro-2-ethoxy-6-methylpyridine-3-carbaldehyde

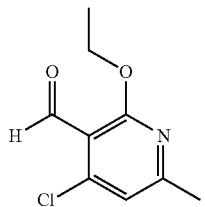

Add 1M DIBAL-H in toluene (18 mL, 18 mmol) to a solution of 4-chloro-2-ethoxy-6-methylpyridine-3-carbonitrile (2.2 g, 11 mmol) in DCM (100 mL) drop wise at 0° C. Gradually warm the mixture to RT, stir overnight, place the flask in a water bath at RT, and quench the reaction by adding a mixture of 1M aqueous HCl (9 mL) and AcOH (9 mL) drop wise. Dilute the resulting mixture with DCM, separate the resulting layers, wash the organic extract with saturated aqueous NaCl, and dry the organic extract over anhydrous Na$_2$SO$_4$. Filter and concentrate the filtrate in vacuo to afford the title compound (1.7 g, 76% yield) as an orange solid. ES/MS (m/z): ($^{35}$Cl/$^{37}$Cl) 200/202 (M+H).

Preparation 29

(4-Chloro-2-ethoxy-6-methylpyridin-3-yl)methanol

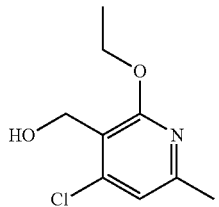

Add NaBH$_4$ (0.230 g, 6.08 mmol) to a solution of 4-chloro-2-ethoxy-6-methylpyridine-3-carbaldehyde (1 g, 5 mmol) in MeOH (50 mL) at 0° C. Gradually warm the mixture to RT, stir for approximately 2 hr, quench the mixture with saturated aqueous NaHCO$_3$ solution, concentrate the mixture in vacuo, dilute the resulting residue with saturated aqueous NaHCO$_3$ solution, and extract with DCM. Separate the layers, dry the organic layer over anhydrous Na$_2$SO$_4$, filter, and concentrate the filtrate in vacuo to afford the title compound (1.03 g, 82% yield) as yellow oil. ES/MS (m/z): ($^{35}$Cl/$^{37}$Cl) 202/204 (M+H).

Preparation 30

4-Chloro-3-(chloromethyl)-2-ethoxy-6-methylpyridine

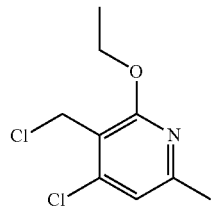

Add DIPEA (0.762 mL, 4.33 mmol) to a RT solution of (4-chloro-2-ethoxy-6-methylpyridin-3-yl)methanol (1.03 g, 4.09 mmol, 80% purity) in DCM (40 mL). Cool the solution to 0° C., then add methanesulfonyl chloride (0.335 mL, 4.28 mmol) drop wise. Gradually warm the solution to RT, stir the resulting mixture at RT for about 3 hr, and concentrate the mixture in vacuo. Add saturated aqueous NaHCO$_3$ solution and extract with EtOAc. Separate the layers, dry the organic extract over anhydrous Na$_2$SO$_4$, filter, and concentrate the filtrate in vacuo. Subject the resulting residue to chromatography on silica, eluting with a gradient of 5-30% EtOAc in hexanes, to afford the title compound (0.788 g, 88% yield) as yellow oil after solvent evaporation. $^1$H NMR δ (400.1 MHz, DMSO): 1.31 (t, J=7.0 Hz, 3H), 2.37 (s, 3H), 4.37 (q, J=7.0 Hz, 2H), 4.71 (s, 2H), 7.05 (s, 1H).

Preparation 31

1,4-Dioxaspiro[4.5]decane-8-carboxylic acid

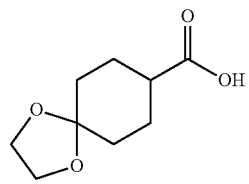 [SMILES: O=C(O)C1CCC2(CC1)OCCO2]

Add triethyl orthoformate (2.35 kg, 2.65 L, 15.9 mol), PTSA (2.8 g, 16 mmol) and ethylene glycol (1.64 kg, 26.4 mol) to a solution of ethyl 4-oxocyclohexanecarboxylate (900 g, 5.29 mol) in EtOH (4 L) and stir the mixture at 50° C. for 1 hr. Cool to RT and slowly add a 5M aqueous solution of NaOH (4.24 L, 21.18 mol) over 20 min; stir the resulting mixture for 2 hr. Evaporate most of the EtOH under reduced pressure, add water (5 L) and MTBE (4 L), stir, separate phases, and discard the organic phase. Cool the aqueous phase to 15° C. and acidify by slow addition of 5M aqueous HCl until pH-3.3 (~3.7 L). Add DCM (8 L), separate the layers, dry the organic phase over Na$_2$SO$_4$, filter, and concentrate the filtrate in vacuo to give the title compound as viscous oil that slowly solidifies on standing as a white low-melting solid (887 g, 90% yield), suitable for use in the next step without further purification. (GC-MS) MS (m/z): 99 (M-87).

Preparation 32

N-Methoxy-N-methyl-1,4-dioxaspiro[4.5]decane-8-carboxamide

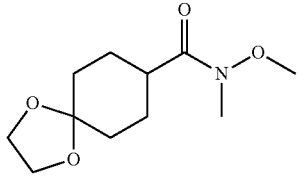 [SMILES: CON(C)C(=O)C1CCC2(CC1)OCCO2]

Slowly add CDI (915 g, 5.64 mol) in small portions over 20 min to a solution of 1,4-dioxaspirol[4.5]decane-8-carboxylic acid (988.6 g, 5.31 mol) in DCM (10 L) and stir for 1 hr. Add N-methoxymethanamine hydrochloride (577 g, 5.92 mol) in small portions over 15 min and stir for 12 hr. Add more N-methoxymethanamine hydrochloride (53 g, 0.55 mol) and stir for an additional 12 hr. Add water (10 L), separate phases, wash the organic phase sequentially with water (5 L) and saturated aqueous NaCl (5 L), dry over $Na_2SO_4$, filter, and concentrate the filtrate in vacuo to obtain the title compound as colorless oil (1.24 kg, quantitative yield) suitable for use in the next step without additional purification. ES/MS (m/z): 230 (M+H).

Preparation 33

1-(1,4-Dioxaspiro[4.5]dec-8-yl)ethanone

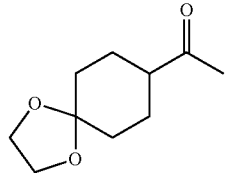

Cool a solution of N-methoxy-N-methyl-1,4-dioxaspirol[4.5]decane-8-carboxamide (400 g, 1.74 mol) in THF (3.5 L) to 0° C. under $N_2$ and add 3M MeMgBr solution in $Et_2O$ (697.87 mL, 2.1 mol) over 30 min Stir for 30 min while warming to RT. Quench the reaction by slow addition of aqueous saturated $NH_4Cl$ (1 L) and extract with MTBE (500 mL×3). Separate the layers and wash the organic layer with saturated aqueous NaCl. Dry over $Na_2SO_4$, filter, and concentrate the filtrate in vacuo to obtain the crude title compound as light yellow oil (275 g, 86% yield), suitable for use without further purification. (GC-MS) MS (m/z): 184 (M+).

Preparation 34

1-(1,4-Dioxaspiro[4.5]dec-8-yl)ethenyl diphenyl phosphate

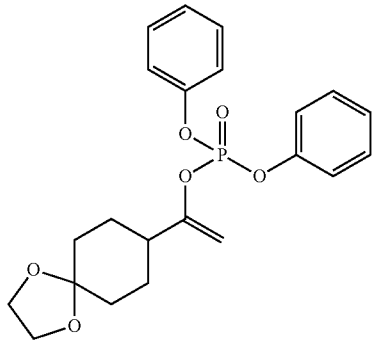 [SMILES: C=C(OP(=O)(Oc1ccccc1)Oc1ccccc1)C1CCC2(CC1)OCCO2]

Cool a solution of 1-(1,4-dioxaspirol[4.5]dec-8-yl)ethanone (150 g, 0.81 mol) in THF (1 L) to −70° C. and drop wise add a solution of 1M LiHMDS in THF (896 mL, 0.89 mol) over 30 min. Stir the mixture for 15 min at −60° C. and then drop wise add diphenyl phosphorochloridate (240.6 g, 896 mmol) in THF (450 mL) at −70° C. Stir the reaction mixture for 14 hr while warming to RT. Quench the reaction with saturated aqueous $NaHCO_3$ solution (1 L) and stir for 1 hr. Extract with MTBE (8 L×3), separate the layers, dry the combined organic extracts over $Na_2SO_4$, filter, and concentrate the filtrate in vacuo. Subject the resulting residue to chromatography on silica, eluting with a gradient of 2-33% EtOAc in hexanes, to afford the title compound as yellow oil (190 g, 56% yield) after solvent evaporation. ES/MS (m/z): 417 (M+H).

Preparation 35

Methyl 4-methylthiophene-3-carboxylate

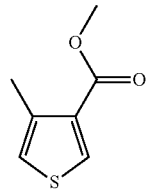

Mix 3-bromo-4-methylthiophene (200 g, 1.13 mol), MeOH (800 mL), DMA (1200 mL), TEA (390 mL, 2.8 mol) and purge with nitrogen for 10 mm Add 1,1'-bis(diphenylphosphino) ferrocene (50 g, 0.09 mol) and palladium (II) acetate (20 g, 0.09 mol) and stir under CO atmosphere at 60 psi for 30 hr at 80° C. Cool the mixture to RT, dilute with EtOAc, wash sequentially with water and saturated aqueous NaCl, and dry the organic phase over $Na_2SO_4$. Filter, and concentrate the filtrate in vacuo to afford the title compound (360 g) as yellow oil, sufficient for use without additional purification. ES/MS (m/z): 157 (M+H).

Alternative Preparation of Methyl 4-methylthiophene-3-carboxylate

Dissolve 3-bromo-4-methylthiophene (1.00 kg, 5.65 mol) and TEA (1.43 kg, 14.12 mol) in DMA (2.5 L) and MeOH (1.32 L) and add 1,1-bis-diphenylphophinoferrocene (187.9 g, 0.34 mol) followed by Pd(OAc)$_2$ (63.4 g, 0.28 mol). Stir the resulting mixture under an atmosphere of CO at 50 psi at 80° C. for 16 hr. After cooling to RT, add EtOAc (5 L), wash sequentially with 10% aqueous citric acid solution (1.6 L×2), saturated aqueous $NaHCO_3$ solution (1.6 L×2), water (1.2 L×2) and saturated aqueous NaCl (1 L×2). Separate the layers, dry the organic phase over $MgSO_4$, filter, and concentrate the filtrate in vacuo. Subject the resulting residue to chromatography on silica, eluting with 5% EtOAc in hexanes, to give the title compound as yellow oil (653 g, 74% yield) after solvent evaporation. ES/MS (m/z): 157 (M+H).

Preparation 36

Methyl 4-methy-5-(4,4,5,5-tetramethyl-1,3,2-dioxaborolan-2-yl)thiophene-3-carboxylate

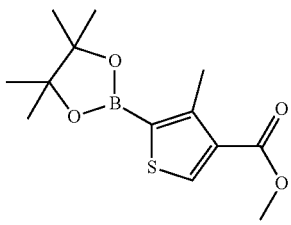 [SMILES: COC(=O)c1csc(B2OC(C)(C)C(C)(C)O2)c1C]

Mix methyl 4-methylthiophene-3-carboxylate (250 g, 1.60 mol), 4-tert-butyl-2-(4-tert-butyl-2-pyridyl)pyridine (8.59 g, 32.01 mmol) and [IrMeO(COD)]$_2$ (5.37 g, 8.00 mmol) in cyclohexane (2.5 L). Degas the mixture under vacuum, purge thoroughly with N$_2$, and then add 4,4,5,5-tetramethyl-1,3,2-dioxaborolane (409.67 g, 3.20 mol) in small portions over 1 hr. Stir the resulting mixture at 70° C. for 3 hr. Cool the mixture to RT, concentrate in vacuo, and subject the resulting residue to chromatography on silica, eluting with a gradient of 0-1% EtOAc in hexanes, to obtain the title compound as a solid (300 g, 66% yield) after solvent evaporation. ES/MS (m/z): 283 (M+H).

Preparation 37

Methyl 5-[1-(1,4-dioxaspiro[4.5]dec-8-yl)ethenyl]-4-methylthiophene-3-carboxylate

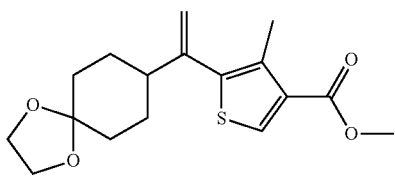 [SMILES: C=C(c1scc(C(=O)OC)c1C)C1CCC2(CC1)OCCO2]

Stir a mixture of 1-(1,4-dioxaspirol[4.5]dec-8-yl)ethenyl diphenyl phosphate (240 g, 576.37 mmol), methyl 4-methyl-5-(4,4,5,5-tetramethyl-1,3,2-dioxaborolan-2-yl)thiophene-3-carboxylate (211.4 g, 749.28 mmol) and an aqueous solution of 2M K$_3$PO$_4$ (367 g, 1.73 mol) in dioxane (2.4 L) at RT. Add chloro(2-dicyclohexylphosphino-2',4',6'-triisopropyl-1,1'-biphenyl)[2-(2'-amino-1,1'-biphenyl)]palladium (II) (9.07 g, 11.53 mmol) and stir at 80° C. for 3 hr. Evaporate the solvent under reduced pressure, extract with EtOAc (750 mL×2), separate the layers, sequentially wash the combined organic phases with water (150 mL) and saturated aqueous NaCl, dry over Na$_2$SO$_4$, filter, and concentrate the filtrate in vacuo. Subject the resulting residue to chromatography on silica, eluting with 5% EtOAc in hexanes, to afford the title compound as a solid (375 g, 67% yield) after solvent removal. ES/MS (m/z): 323 (M+H).

Preparation 38

Methyl 5-[(1R)-1-(1,4-dioxaspiro[4.5]dec-8-yl)(ethyl]-4-methylthiophene-3-carboxylate

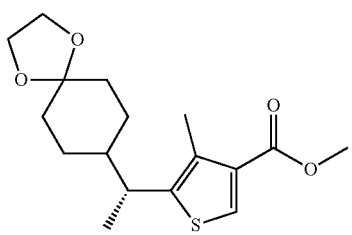 [SMILES: COC(=O)c1csc([C@H](C)C2CCC3(CC2)OCCO3)c1C]

Add [(4R,5R)-(+)-O-[1-benzyl-1-(5-methyl-2-phenyl-4,5-dihydrooxazol-4-yl)-2-phenylethyl] (dicyclohexylphosphinite) (1,5-COD) iridium(I) tetrakis (3,5-bis(trifluoromethyl) phenylborate (1.61 g, 0.93 mmol) to a solution of methyl 5-[1-(1,4-dioxaspirol[4.5]dec-8-yl)ethenyl]-4-methylthiophene-3-carboxylate (60 g, 186 mmol) in DCM (1.9 L) and elute the solution through a 48 mL stainless steel reactor at a hydrogen atmosphere of 80 parr at 12 mL/min for 2 hr at RT. Filter the solution and concentrate the filtrate in vacuo to obtain the crude title compound as brown oil (60 g, quantitative yield), suitable for use in the next step without further purification. ES/MS (m/z): 325 (M+H).

Preparation 39

Methyl 4-methyl-5-[(1R)-1-(4-oxocyclohexyl)ethyl]thiophene-3-carboxylate

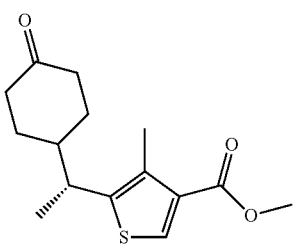 [SMILES: COC(=O)c1csc([C@H](C)C2CCC(=O)CC2)c1C]

Add to a solution of methyl 5-[(1R)-1-(1,4-dioxaspirol[4.5]dec-8-yl)ethyl]-4-methylthiophene-3-carboxylate (64.7 g, 178 mmol) in THF (450 mL) a solution of 1N HCl (450 mL, 5.53 mol) and stir for 16 hours at RT followed by 45° C. for 2 hours. Concentrate the reaction mixture in vacuo, add MTBE (500 mL) and separate phases. Wash the organic phase sequentially with water (200 mL), saturated aqueous NaHCO$_3$ solution (100 mL) and saturated aqueous NaCl (100 mL). Dry the organic phase over MgSO$_4$, filter, and concentrate the filtrate in vacuo to give the crude title compound as brown oil (53.3 g, 96% yield) which may be used without additional purification. ES/MS (m/z): 281 (M+H).

Preparation 40a

Methyl 5-[(1R)-1-[trans-4-(3-methoxyazetidin-1-yl)cyclohexyl]ethyl]-4-methylthiophene-3-carboxylate

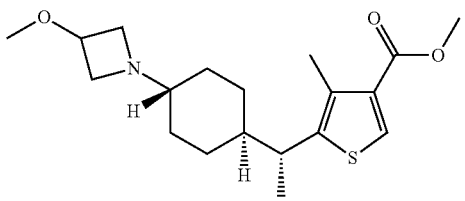

Stir a solution of 3-methoxyazetidine hydrochloride (43.4 g, 351 mmol) and DIPEA (65 mL, 373 mmol) in MeOH (500 mL) for 45 min at RT. Add this mixture to a solution of methyl 4-methyl-5-[(1R)-1-(4-oxocyclohexyl)ethyl]thiophene-3-carboxylate (50.0 g, 160 mmol) in THF (250 mL) and stir 40 min at RT. Cool the mixture at −70° C. and add LiBH$_4$ (4.9 g, 220 mmol) in five portions over 25 min. Allow to stir for 4 hr while warming to −20° C. Pour the mixture slowly into an aqueous solution of 1M HCl (500 mL) and stir for 10 min. Evaporate most of the organic solvent in vacuo, add DCM (500 mL) and an aqueous solution of 5M K$_2$CO$_3$ (~pH 9), separate the layers, and wash the aqueous phase again with DCM (250 mL). Combine the organic extracts, wash with saturated aqueous NaCl, dry the organic phase over MgSO$_4$, filter, and concentrate the filtrate in vacuo. Add EtOAc (50 mL) and concentrate in vacuo again. Subject the resulting residue to chromatography on silica, eluting with 20% EtOAc in 2% triethylamine/hexanes to give oil after solvent evaporation. Dissolve the resulting oil in MTBE (200 mL), wash with aqueous 1M HCl (200 mL) and add aqueous 2M K$_3$PO$_4$ to the aqueous phase (~pH 7.5). Extract the aqueous solution with EtOAc (2×300 mL), dry over MgSO$_4$, filter, and concentrate the filtrate in vacuo to obtain the title compound as pale yellow oil (15.5 g, 57% yield). ES/MS (m/z): 352 (M+H).

Preparation 40b

Methyl 5-[(1R)-1 [trans-4-(3-methoxyazetidin-1-yl)cyclohexyl]ethyl]-4-methylthiophene-3-carboxylate hydrochloride

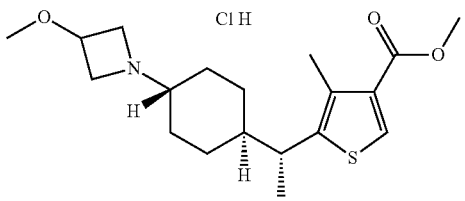

Methyl 5-[(1R)-1-[trans-4-(3-methoxyazetidin-1-yl)cyclohexyl]ethyl]-4-methyl-thiophene-3-carboxylate hydrochloride may be prepared essentially as described in Preparation 40a, with solvent evaporation of the crude reaction mixture following HCl quenching, and chromatography on silica, eluting with a gradient of 0-100% 2M NH$_3$/MeOH in DCM, to give oil after solvent evaporation, which partially crystallized upon drying in vacuo. Subsequent recrystallization from EtOAc and a trace of MeOH gives crystalline material sufficient for X-ray crystallography. ES/MS (m/z): 352 (M+H).

Prepare a single crystal of methyl 5-[(1R)-1-[trans-4-(3-methoxyazetidin-1-yl)cyclohexyl]ethyl]-4-methylthiophene-3-carboxylate hydrochloride by recrystallization in EtOAc and MeOH. Mount on a thin fiber at −173° C. Collect data using a Iµ CuK$_\alpha$ radiation source (λ=1.54178 Å) and a Bruker D8 based 3-circle goniometer diffractometer equipped with a SMART® 6000CCD area detector (crystal dimensions=0.150×0.080×0.020 mm). Perform cell refinement and data reduction using the SAINT program V8.32b. Index the unit cell, having monoclinic parameters of 12.2214(3) Å, b=7.0314(2) Å, c=12.8284(3) Å, and β=108.8099(15)° (cell volume from the crystal structure=1043.52(5) Å$^3$, calculated density of the structure=1.235 g/cm$^3$ at −173° C.). Determine the structure by direct methods using SHELXS program. Independently define all atomic parameters anisotropically except for the hydrogen atoms. Place at idealized calculated positions. Confirm the space group choice, namely P2$_1$, by successful convergence of the full-matrix least-squares refinement on F$^2$ using the SHELXL program, having a final goodness of fit of 1.110. The Final R indices (I≥2sigma(I)) are R1=0.0603, R2=0.1242. Refine the absolute structure parameter is to 0.081(12). Determine the structure. The structure is determined to be the hydrochloride salt and absolute structure is determined to be R-configuration at the stereocenter and trans-configuration around the cyclohexane ring.

Preparation 41

Methyl 2-bromo-5-[(1R)-1-(1,4-dioxaspiro[4.5]decan-8-yl)ethyl]-4-methyl-thiophene-3-carboxylate

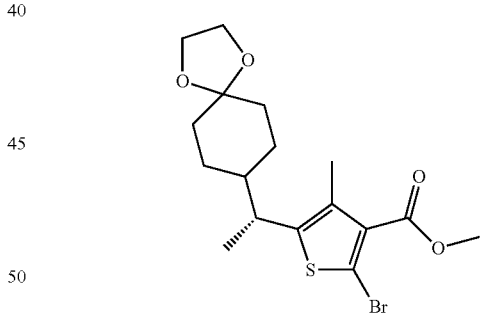

Add N-bromosuccinimide (6.18 g, 34.7 mmol) to a solution of methyl 5-[(1R)-1-(1,4-dioxaspirol[4.5]dec-8-yl)ethyl]-4-methylthiophene-3-carboxylate (15.56 g, 47.97 mmol) in EtOAc (60 mL) and stir the mixture at 55° C. for 30 min, then at 40° C. overnight. Wash the reaction mixture twice with saturated aqueous NaHSO$_3$ solution, separate the layers, and dry the combined organic layers over MgSO$_4$. Filter and concentrate the filtrate in vacuo. Subject the resulting residue to chromatography on silica, eluting with a gradient of 0-20% EtOAc in hexanes, to give the title compound (15.67 g, 81% yield) after solvent evaporation. ES/MS (m/z) ($^{79}$Br/$^{81}$Br): 403/405 (M+H).

Preparation 42

Methyl 2-(2-{[(benzyloxy)carbonyl]amino}ethyl)-5-[(1R)-1-(1,4-dioxaspiro[4.5]dec-8-yl)ethyl]-4-methylthiophene-3-carboxylate

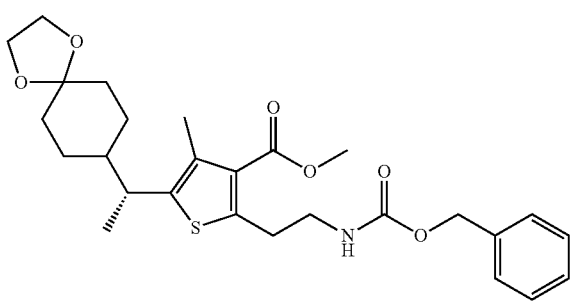 [SMILES: COC(=O)c1c(CCNC(=O)OCc2ccccc2)sc([C@H](C)C2CCC3(CC2)OCCO3)c1C]

Add methyl 2-bromo-5-[(1R)-1-(1,4-dioxaspiro[4.5]decan-8-yl)ethyl]-4-methyl-thiophene-3-carboxylate (15.44 g, 38.28 mmol), toluene (350 mL) and water (40 mL) into a 1-L three-neck flask equipped with a mechanical stirrer. Degas the mixture under house vacuum for 15 mm. Add potassium benzyl N-[2-(trifluoroboranuidyl)ethyl]carbamate (17.3 g, 57.6 mmol), $Cs_2CO_3$ (37.4 g, 115 mmol), and RuPhos-G3-Palladacycle (2.30 g, 2.69 mmol). Degas the mixture for an additional 15 min and then stir under $N_2$ at 80-85° C. overnight. Add saturated aqueous $NaHCO_3$ solution and extract three times with EtOAc; wash the combined extracts sequentially with water and saturated aqueous NaCl, dry over $MgSO_4$, filter, and concentrate the filtrate in vacuo. Subject the resulting residue to chromatography on silica, eluting with a gradient of 0-50% EtOAc in hexanes to afford the title compound (14.72 g, 76% yield) as oil. ES/MS (m/z): 502 (M+H).

Preparation 43

2-[(1R)-1-(1,4-Dioxaspiro[4.5]dec-8-yl)ethyl]-3-methyl-6,7-dihydrothieno[3,2-c]pyridin-4(5H)-one

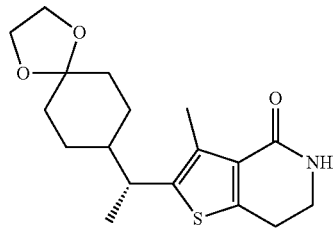 [SMILES: Cc1c([C@H](C)C2CCC3(CC2)OCCO3)sc2c1C(=O)NCC2]

Stir a mixture of methyl 2-(2-{[(benzyloxy)carbonyl]amino}ethyl)-5-[(1R)-1-(1,4-dioxaspirol[4.5]dec-8-yl)ethyl]-4-methylthiophene-3-carboxylate (14.72 g, 29.35 mmol) and dry 10% Pd on carbon (3.0 g) in MeOH (80 mL) under $H_2$ at 60 psi overnight. Filter the reaction mixture over diatomaceous earth, stir the filtrate at RT for 24 hr and concentrate in vacuo. Subject the resulting residue to chromatography on silica, eluting with a gradient of 20-100% EtOAc to hexanes and then a gradient of 10% MeOH in EtOAc, to give the title compound (8.20 g, 83% yield) after solvent evaporation. ES/MS (m/z): 336 (M+H).

Preparation 44

3-Methyl-2-[(1R)-1-(4-oxocyclohexyl)ethyl]-6,7-dihydrothieno[3,2-c]pyridin-4(5H)-one

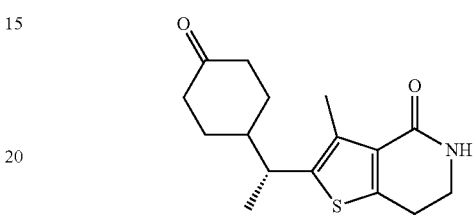

Stir a solution of 2-[(1R)-1-(1,4-dioxaspirol[4.5]dec-8-yl)ethyl]-3-methyl-6,7-dihydrothieno[3,2-c]pyridin-4(5H)-one (6.18 g, 18.4 mmol) in a mixture of THF (30 mL) and 1N HCl (30 mL) at RT overnight, then at 55° C. for 2 hr. Quench the reaction with solid $Na_2CO_3$ and extract with EtOAc. Wash the combined extracts with saturated aqueous NaCl and dry over $MgSO_4$. Subject the resulting residue to chromatography on silica, eluting with a gradient of 0-100% EtOAc in hexanes, to give the title compound (4.69 g, 87% yield) as foam after solvent removal. ES/MS (m/z): 292 (M+H).

Preparation 45

Methyl 4-methyl-5-nitrothiophene-3-carboxylate

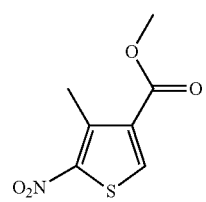

Add acetic anhydride (2.5 L) to a solution of methyl 4-methylthiophene-3-carboxylate (150 g, 0.96 mol) in AcOH (4.5 L) below 25° C. Cool the mixture to 10° C., slowly add fuming $HNO_3$ (220 mL), keeping the temperature below 15° C., warm to RT, and stir for 1 hr. Slowly pour the reaction into ice water and extract with EtOAc (2×3 L). Separate the resulting layers, sequentially wash the organic phase with water (4×3 L) and saturated aqueous $NaHCO_3$ solution, dry over $Na_2SO_4$, filter, and concentrate the filtrate in vacuo. Subject the resulting residue to chromatography on silica, eluting with 5% EtOAc/hexane, to afford the title compound (91 g, 47% yield) as an orange solid after solvent evaporation. $^1$H NMR (400.1 MHz, DMSO-$d_6$) δ 2.77 (s, 3H); 3.83 (s, 3H); 8.61 (s, 1H).

Preparation 46

Methyl 5-amino-4-methylthiophene-3-carboxylate

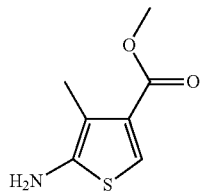

Add iron (166 g, 2.98 mol) slowly to a solution of methyl 4-methyl-5-nitrothiophene-3-carboxylate (120 g, 0.55 mol) in AcOH (1200 mL) and EtOH (1200 mL). Stir the mixture at 80° C. for 15 min Cool the reaction, pour slowly into ice water, and add a saturated aqueous solution of NaHCO₃ until pH 7-7.5. Extract with EtOAc (2×3 L), separate the layers, wash the combined organic layers with saturated aqueous NaCl, dry over Na₂SO₄, filter, and evaporate the filtrate in vacuo to obtain the title compound (98 g, 98% yield) as yellow oil, sufficient for use without additional purification. ES/MS (m/z): 172 (M+H).

Preparation 47

Methyl 5-[(tert-butoxycarbonyl)amino]-4-methylthiophene-3-carboxylate

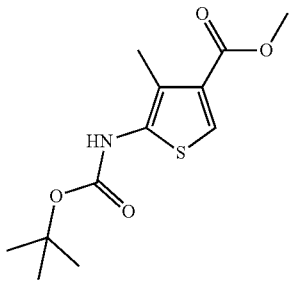 [SMILES: COC(=O)c1csc(NC(=O)OC(C)(C)C)c1C]

To a solution of methyl 5-amino-4-methylthiophene-3-carboxylate (7.79 g, 37.3 mmol) in 1,4-dioxane (40 mL), add tert-butoxycarbonyl tert-butyl carbonate (16.3 g, 74.6 mmol), heat at reflux for 2 hr, then cool to RT and concentrate the reaction mixture in vacuo. Subject the resulting residue to chromatography on silica, eluting with a gradient of 0-10% EtOAc in hexanes, to afford the title compound (8.88 g, 88% yield) as thick yellow oil after solvent evaporation. ES/MS (m/z): 272 (M+H).

Preparation 48

Methyl 5-[1,4-dioxaspiro[4.5]dec-8-yl(methyl) amino]-4-methylthiophene-3-carboxylate

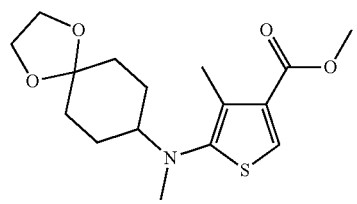 [SMILES: COC(=O)c1csc(N(C)C2CCC3(CC2)OCCO3)c1C]

To a solution of methyl 5-[tert-butoxycarbonyl)amino]-4-methylthiophene-3-carboxylate (2.01 g, 7.41 mmol) in DMF (20 mL) add Cs₂CO₃ (6.03 g, 18.5 mmol) and CH₃I (1.05 g, 7.41 mmol). Heat the mixture at 80° C. for 10 mm and cool the reaction mixture to RT. Dilute with DCM (50 mL) and water (10 mL), separate the organic layer, dry over Na₂SO₄, filter, and concentrate the filtrate in vacuo. Add MeOH (40 mL) and 5M aqueous HCl (20 mL) to the resulting residue, and heat at 50° C. for approximately 1 hr. Concentrate the mixture in vacuo, dilute with DCM and add solid NaHCO₃ until the mixture is neutralized to about pH 7. Separate the organic layer, dry over Na₂SO₄, filter, and concentrate the filtrate in vacuo to give crude methyl 4-methyl-5-(methylamino)-thiophene-3-carboxylate. ES/MS (m/z): 186 (M+H).

Dissolve the crude methyl 4-methyl-5-(methylamino)-thiophene-3-carboxylate in DCM (20 mL), add 1,4-dioxaspiro[4.5]decan-8-one (1.16 g, 7.40 mmol) while stirring for 30 min, then add sodium triacetoxyborohydride (3.13 g, 14.8 mmol) and stir at RT for an additional 30 mm Add additional 1,4-dioxaspiro[4.5]decan-8-one (0.289 g, 1.85 mmol), stir for 15 min, add more sodium triacetoxyborohydride (0.784 g, 3.70 mmol), and stir the resulting mixture overnight at RT. Dilute the reaction with saturated aqueous NaHCO₃ solution (10 mL) and DCM (40 mL), stir for 1 hr, separate the organic layer, dry over Na₂SO₄, filter, and concentrate the filtrate in vacuo. Subject the resulting residue to chromatography on silica, eluting with a gradient of 0-10% EtOAc in hexanes, to afford the title compound (1.21 g, 50% yield) as colorless oil after solvent evaporation. ES/MS (m/z): 326 (M+H).

Preparation 49

Methyl 2-bromo-5-[1,4-dioxaspiro[4.5]dec-8-yl (methyl)amino]-4-methylthiophene-3-carboxylate

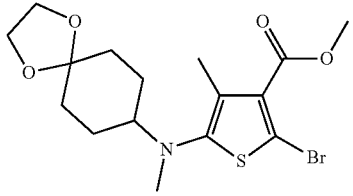 [SMILES: COC(=O)c1c(Br)sc(N(C)C2CCC3(CC2)OCCO3)c1C]

To methyl 5-[1,4-dioxaspiro[4.5]dec-8-yl(methyl) amino]-4-methylthiophene-3-carboxylate (1.13 g, 3.47 mmol) in DCM (11 mL) add N-bromosuccinimide (0.701 g, 3.82 mmol) at RT. After 5 min, dilute the reaction with DCM (40 mL) and wash with 0.1M NaOH (2×10 mL). Separate the organic layer, dry over Na₂SO₄, filter, and concentrate the filtrate in vacuo to afford the crude title compound (1.47 g, quantitative yield) as brown oil. ES/MS (m/z): (⁷⁹Br/⁸¹Br) 404/406 (M+H).

Preparation 50

Methyl 2-(2-{[(benzyloxy)carbonyl]amino}ethyl)-5-[1,4-dioxaspiro[4.5]dec-8-yl(methyl)amino]-4-methylthiophene-3-carboxylate

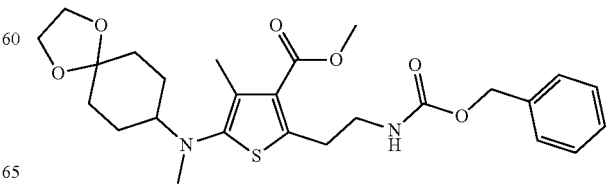

Add toluene (15 mL) and water (2.5 mL) to crude methyl 2-bromo-5-[1,4-dioxaspiro[4.5]dec-8-yl(methyl)amino]-4-methylthiophene-3-carboxylate (1.36 g, 3.20 mmol), potassium benzyl N-[2-(trifluoroboranuidyl)ethyl]carbamate (1.25 g, 4.15 mmol) and Cs$_2$CO$_3$ (3.64 g, 11.2 mmol) in a flask. Purge the mixture with N$_2$, then add RuPhos (0.0761 g, 0.160 mmol) and 2nd generation Ruphos precatalyst (0.124 g, 0.160 mmol). Stir the mixture vigorously and heat at 100° C. for 18 hr. Cool to RT and dilute the reaction with EtOAc (40 mL) and water (10 mL). Separate the organic layer, dry over Na$_2$SO$_4$, filter, and concentrate the filtrate in vacuo. Subject the resulting residue to chromatography on silica, eluting with a gradient of 0-30% EtOAc in hexanes, to afford the title compound (0.93 g, 58% yield) as orange oil after solvent evaporation. ES/MS (m/z): 503 (M+H).

Preparation 51

2-[1,4-Dioxaspiro[4.5]dec-8-yl(methyl)amino]-3-methyl-6,7-dihydrothieno[3,2-c]pyridin-4(5H)-one

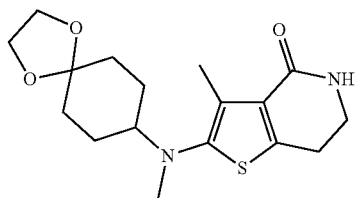 [SMILES: Cc1c(N(C)C2CCC3(CC2)OCCO3)sc2c1C(=O)NCC2]

To methyl 2-(2-{[(benzyloxy)carbonyl]amino}ethyl)-5-[1,4-dioxaspiro[4.5]dec-8-yl(methyl)amino]-4-methylthiophene-3-carboxylate (0.93 g, 1.86 mmol) in MeOH (10 mL), add 20% Pd(OH)$_2$ on carbon (0.500 g, 3.56 mmol) and TEA (0.78 mL, 5.57 mmol). Charge the reaction vessel with H$_2$ (345 kPa) and stir at RT. After about 1.5 hr remove the catalyst by filtration, then heat the mixture at 70° C. for 5 hr. Cool the mixture to RT and concentrate in vacuo to afford the title compound (0.513 g, 82% yield) as yellow foam, sufficient for use without additional purification. ES/MS (m/z): 337 (M+H).

Preparation 52

Methyl 5-[{trans-4-[(tert-butoxycarbonyl)amino]cyclohexyl}(ethyl)amino]-4-methylthiophene-3-carboxylate

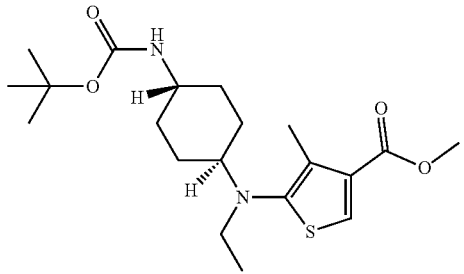 [SMILES: CCN(c1scc(C(=O)OC)c1C)[C@H]1CC[C@H](NC(=O)OC(C)(C)C)CC1]

Add sodium triacetoxyborohydride (441 g, 2.05 mol) to a solution of methyl 5-amino-4-methylthiophene-3-carboxylate (98 g, 0.57 mol) in DCE (1000 mL) containing tert-butyl r(4-oxocyclohexyl)carbamate (156.7 g, 0.75 mol) and AcOH (118 mL) at RT. Stir the resulting mixture for 30 min at RT, add acetaldehyde (63.7 mL, 1.15 mol), stir for another 45 min, and add water followed by saturated aqueous NaHCO$_3$ solution (pH ~9-10). Extract the aqueous mixture with EtOAc (2×3 L), wash combined organic extracts with saturated aqueous NaCl, dry over Na$_2$SO$_4$, filter, and concentrate the filtrate in vacuo. Subject the resulting residue to chromatography on silica, eluting with 5% EtOAc in hexanes, to give 337 g of cis-/trans-mixture after solvent removal. Separate the cis- and trans-isomers by multiple sequential chiral SFC runs (CHIRALPAK® AD, 5 μm, 5×25 cm; eluent: isocratic mixture of 5% MeOH in CO$_2$; Column Temp: 50° C.; Flow Rate: 400 g/min) to afford the pure trans-title compound (183 g, 76% yield) as a brown solid after solvent removal. R$_t$=3.54 min ES/MS (m/z): 397 (M+H).

Preparation 53

Methyl 5-[(trans-4-aminocyclohexyl)(ethyl)amino]-4-methylthiophene-3-carboxylate

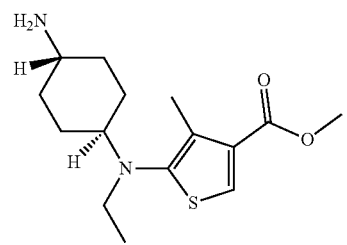 [SMILES: CCN(c1scc(C(=O)OC)c1C)[C@H]1CC[C@H](N)CC1]

Cool a solution of methyl 5-[[4-(tert-butoxycarbonylamino)cyclohexyl]-ethyl-amino]-4-methyl-thiophene-3-carboxylate (40 g, 100.9 mmol) in THF (200 mL) to 0° C. Add a solution of 4M HCl in dioxane (250 mL, 1000 mmol) drop wise, and stir the resulting mixture at RT for 16 hr. Concentrate in vacuo to ~1/4 volume, add EtOAc (400 mL) and saturated aqueous K$_2$CO$_3$ solution (200 mL), and stir the resulting mixture at RT for 1 hr. Separate the resulting phases, wash aqueous phase with EtOAc (2×100 mL), combine the organic layers, and wash sequentially with water (100 mL) and saturated aqueous NaCl (100 mL). Dry the organic layer over Na$_2$SO$_4$, filter, and concentrate the filtrate in vacuo to give the title compound (31.7 g, quantitative yield) as dark brown oil after solvent evaporation. ES/MS (m/z): 297 (M+H).

Preparation 54

2-Methoxypropane-1,3-diol

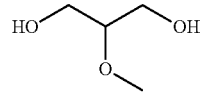

To a cold solution of dimethyl 2-methoxypropanedioate (25 g, 154.19 mmol) in THF (300 mL) at −15° C., add a solution of 2.3M LAH in 2-methyltetrahydrofuran (170 mL, 150 g, 385.47 mmol) drop wise at −15° C. and stir for 2 hr at 0° C., then for 1 hr at RT. Re-cool to −15° C. and slowly rquench with water (15 mL), 2N KOH (15 mL) and water (30 mL), and stir the resulting mixture for 30 mm at RT. Filter the resulting white solids, wash solids with EtOAc (250 mL) followed by 40% (v/v) MeOH/EtOAc (500 mL), and concentrate the filtrate in vacuo. Subject the resulting residue to chromatography on silica gel, eluting with a gradient of 0-20% MeOH in EtOAc, to afford the title compound as colorless oil (6.66 g, 40% yield) after solvent evaporation. $^1$H NMR (400.1 MHz, CDCl$_3$) δ 2.50 (bs, 2H), 3.47 (s, 3H), 3.36 (quintet, J=4.5 Hz, 1H), 3.69 (dd, J=4.6, 11.7 Hz, 2H), 3.79 (dd, J=4.2, 11.7 Hz, 2H).

Preparation 55

Methyl 5-{ethyl[trans-4-(3-methoxyazetidin-1 -yl)cyclohexyl]amino}-4-methylthiophene-3-carboxylate

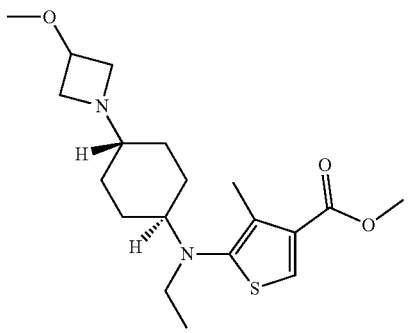

Drop wise add trifluoromethanesulfonic anhydride (36.47 mL, 61.16 g, 214.6 mmol) to a solution of 2-methoxypropane-1,3-diol (14.81 g, 139.6 mmol) in ACN (500 mL) at −20° C. over 45 min. Then add drop wise DIPEA (44.4 mL, 32.9 g, 255 mmol) over 35 min and stir the resulting mixture for 45 min at −15° C. Cool the mixture to −25° C. and add DIPEA (44.4 mL, 32.9 g, 255 mmol) drop wise over 20 min. Add a solution of methyl 5-[(trans-4-aminocyclohexyl)(ethyl)amino]-4-methylthiophene-3-carboxylate 31.72 g, 107.0 mmol) in ACN (300 mL) drop wise over 30 min. Warm the reaction to RT and then stir at 70° C. for an additional 1 hr. Cool the mixture to RT, dilute with EtOAc (500 mL) and water (500 mL), separate phases, and extract the aqueous phase with EtOAc (2×250 mL). Add a solution of 4M aqueous K$_2$CO$_3$ (250 mL) to the combined organic extracts and stir for 2 hr at RT. Separate phases, wash the organic layer with saturated aqueous NaCl (250 mL), dry organic layer over Na$_2$SO$_4$, filter, and concentrate the filtrate in vacuo. Subject the resulting residue to chromatography on silica, eluting with a gradient of 0-10% MeOH in EtOAc, to afford the title compound (29.2 g, 74% yield) as a brown solid after solvent evaporation. ES/MS (m/z): 367 (M+H).

Preparation 56

Methyl 2-bromo-5-{ethyl[trans-4-(3-methoxyazetidin-1-yl)cyclohexyl]amino}-4-methylthiophene-3-carboxylate

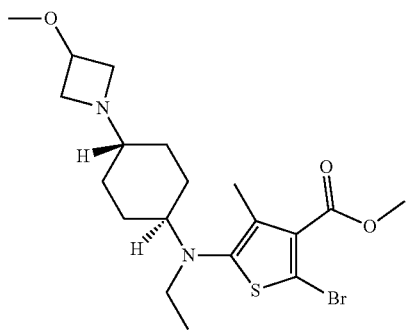

Mix methyl 5-{ethyl[trans-4-(3-methoxyazetidin-1-yl)cyclohexyl]amino}-4-methylthiophene-3-carboxylate (29.17 g, 79.59 mmol) and NBS (17.00 g, 95.51 mmol) in DMF (400 mL) and stir the resulting mixture for 2 hr at RT. Dilute with EtOAc (400 mL) and water (250 mL), separate the phases, and wash the organic layer sequentially with 4M aqueous K$_2$CO$_3$ solution (2×200 mL), water (200 mL), and saturated aqueous NaCl (200 mL). Dry the organic layer over Na$_2$SO$_4$, filter, and concentrate the filtrate in vacuo to give the title compound (32.4 g, 89% yield) as brown oil, suitable for use in the next step without further purification. ES/MS (m/z) ($^{79}$Br/$^{81}$Br): 445, 447 (M+H).

Preparation 57

Methyl 2-(2-{[(benzyloxy)carbonyl]amino}ethyl)-5-{ethyl[trans-4-(3-methoxyazetidin-1-yl)cyclohexyl]amino}-4-methylthiophene-3-carboxylate

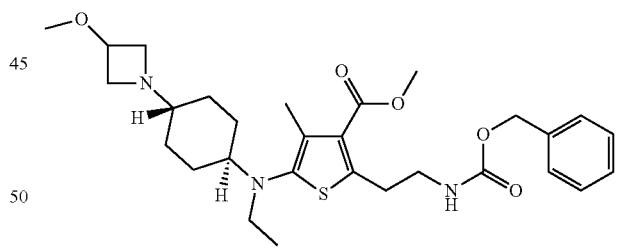

To a solution of K$_2$CO$_3$ (657.8 g, 414.3 mmol) in water (123 mL, 6828 mmol) add potassium benzyl N-[2-(trifluoroboranuidyl)ethyl]carbamate (23.62 g, 82.85 mmol) drop wise followed by a solution of methyl 2-bromo-5-{ethyl[trans-4-(3-methoxyazetidin-1-yl)cyclohexyl]amino}-4-methylthiophene-3-carboxylate (32.37 g, 69.04 mmol) in toluene (450 mL). Purge the mixture gently with N$_2$ while warming to 90° C. over 30 min, then add 2-dicyclohexylphosphino-2',6'-diisopropoxy-1,1'-biphenyl (2.46 g, 5.18 mmol) and chloro(2-dicyclohexylphosphino-2',6'-diisopropoxy-1,1'-biphenyl)[2-(2'-amino-1,1'-biphenyl)]palladium (II) (4.02 g, 5.18 mmol). Stir the resulting mixture at 105° C. for 4 hr, cool to RT, dilute with EtOAc (300 mL) and water (100 mL), separate the phases, extract the aqueous phase with EtOAc (3×100 mL), and wash the combined organic layers sequentially with 4M aqueous K$_2$CO$_3$ (2×100 mL), water (150 mL), and saturated aqueous NaCl (150 mL). Dry the organic layer over Na$_2$SO$_4$, concentrate the filtrate in vacuo, and subject the resulting residue to chromatography on silica, eluting with a gradient of 0-5% MeOH in EtOAc, to afford the title compound (23.1 g, 51% yield) as brown oil after solvent evaporation. ES/MS (m/z): 544 (M+H).

Preparation 58

Methyl 5-{ethyl[trans-4-(3-methoxyazetidin-1-yl)cyclohexyl]amino}-2-(2-{[(2-methoxy-4,6-dimethyl-pyridin-3-yl)methyl]anino}ethyl)-4-methylthiophene-3-carboxylate

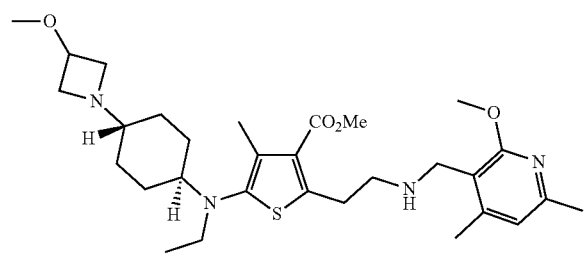

Add Pd(OH)$_2$ on carbon, 20% dry basis, water wet (5.75 g) to a mixture of methyl 2-(2-{[(benzyloxy)carbonyl]amino}ethyl)-5-{ethyl[trans-4-(3-methoxyazetidin-1-yl)cyclohexyl]amino}-4-methylthiophene-3-carboxylate (23.00 g, 35.11 mmol) and 2-methoxy-4,6-dimethyl-pyridine-3-carbaldehyde (7.03 g, 42.13 mmol) in EtOH (280 mL) and stir at 50° C. under H$_2$ (70 psi) for 24 hr. Filter the mixture through diatomaceous earth, rinse with EtOH, and concentrate the filtrate in vacuo. Subject the resulting residue to chromatography on silica, eluting with a gradient of 0-25% MeOH in DCM, to afford the title compound (18.4 g, 89% yield) as brown oil after solvent evaporation. ES/MS (m/z): 559 (M+H).

Preparation 59

2-{Ethyl[trans-4-(3-methoxyazetidin-1-yl)cyclohexyl]amino}-5-[(2-methoxy-4,6-dimethylpyridin-3-yl)methyl]-3-methyl-6,7-dihydrothieno[3,2-c]pyridin-4(5H)-one

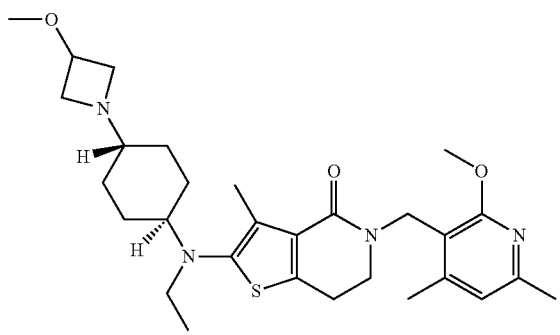

Stir a mixture of methyl 5-{ethyl[trans-4-(3-methoxyazetidin-1-yl)cyclohexyl]amino}-2-(2-{[(2-methoxy-4,6-dimethylpyridin-3-yl)methyl]amino}ethyl)-4-methylthiophene-3-carboxylate (18.35 g, 30.21 mmol) and AcOH (9.07 g, 151.1 mmol) in toluene (175 mL) at 110° C. for 3 hr. Cool the mixture, dilute with EtOAc (250 mL) and water (150 mL), separate phases, extract the aqueous phase with EtOAc (3×100 mL), wash the combined organic extracts sequentially with 4M aqueous K$_2$CO$_3$ solution (2×100 mL), water (150 mL), and saturated aqueous NaCl (150 mL). Dry the organic layer over Na$_2$SO$_4$, filter, and concentrate the filtrate in vacuo, to afford the title compound (16.42 g, 95% yield) as brown oil suitable for use without additional purification. ES/MS (m/z): 527 (M+H).

Preparation 60

Methyl 5-[1,4-dioxaspiro[4.5]dec-8-yl(ethyl)amino]-4-methylthiophene-3-carboxylate

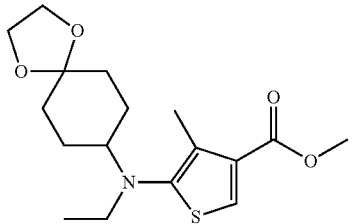 [SMILES: CCN(c1scc(C(=O)OC)c1C)C1CCC2(CC1)OCCO2]

To a solution of methyl 5-amino-4-methylthiophene-3-carboxylate (43 g, 251 mmol), 1,4-dioxaspiro[4.5]decan-8-one (39.23 g, 251 mmol) and AcOH (47 mL) in DCE (430 mL) slowly add sodium triacetoxyborohydride (159.6 g, 754 mmol) below 25° C. Stir the mixture at RT for 30 min and then add acetaldehyde (28 mL, 503 mmol). Stir the mixture at RT for 30 min Pour the contents of the mixture into ice water and basify by addition of a saturated aqueous NaHCO$_3$ solution until pH 7.0-7.5. Extract the resulting mixture with EtOAc (2×3 L), wash with saturated aqueous NaCl, dry over Na$_2$SO$_4$, filter, and concentrate the filtrate in vacuo. Subject the resulting residue to chromatography on silica, eluting with 5% EtOAc in hexanes, to afford the title compound (55 g, 67% yield) as a solid after solvent evaporation. ES/MS (m/z): 340 (M+H).

Preparation 61

Methyl 2-bromo-5-[1,4-dioxaspiro[4.5]dec-8-yl(ethyl)amino]-4-methylthiophene-3-carboxylate

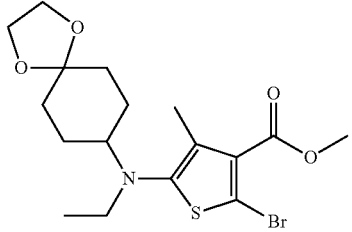 [SMILES: CCN(c1sc(Br)c(C(=O)OC)c1C)C1CCC2(CC1)OCCO2]

To a three-neck round bottom flask equipped with an addition funnel, add a solution of methyl 5-[1,4-dioxaspirol

[4.5]dec-8-yl(ethyl)amino]-4-methylthiophene-3-carboxylate (91 g, 268.1 mmol) in DCM (1.2 L). Cool the flask to 0° C., then add NBS (58.4 g, 322 mmol) portion-wise over 1 hr. Remove the ice bath and stir the reaction mixture at RT for 2 hr. Add water, separate the organic layer and concentrate the organic phase in vacuo. Subject the resulting residue to chromatography on silica in four batches, eluting each with 10-50% EtOAc in hexanes. Concentrate the combined fractions from the first two batches to afford oil. Dry the material in vacuo overnight to afford a white solid (40.9 g). Concentrate fractions from batches three and four to afford brown oil. Treat the resulting material with a small amount of hexanes until a solid appears, filter, and dry in vacuo overnight to afford a light brown solid (37.9 g). Combine the two resulting collected batches to afford the title compound (78.8 g, 70% yield) as brown oily solid. ES/MS (m/z): ($^{79}$Br/$^{81}$Br) 418/420 (M+H).

Preparation 62

Methyl 2-bromo-5-[ethyl(4-oxocyclohexyl)amino]-4-methylthiophene-3-carboxylate

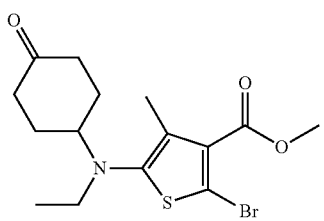 [SMILES: CCN(c1sc(Br)c(C(=O)OC)c1C)C1CCC(=O)CC1]

To methyl 2-bromo-5-[1,4-dioxaspirol[4.5]dec-8-yl(ethyl)amino]-4-methylthiophene-3-carboxylate (7.81 g, 18.7 mmol) in THF (140 mL) add 1M aqueous HCl (100 mL). Stir the reaction at RT for about 25 hr. Dilute the reaction mixture with EtOAc (200 mL) and separate the layers. Wash the organic layer with saturated aqueous NaHCO$_3$ (2×25 mL). Dry the organic layer over Na$_2$SO$_4$, filter, and concentrate the filtrate in vacuo to afford the crude title compound (6.71 g, 96% yield) as reddish brown thick oil, sufficient for use in the next step without additional purification. ES/MS (m/z): ($^{79}$Br/$^{81}$Br) 374/376 (M+H).

Preparation 63

Methyl 2-(2-{[(benzyloxy)carbonyl](amino}ethyl)-5-[1,4-dioxaspiro[4.5]dec-8-yl(ethyl)amino]-4-methylthiophene-3-carboxylate

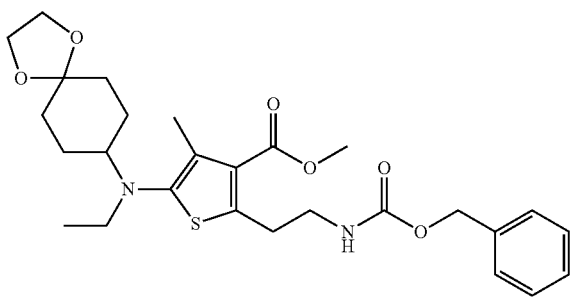 [SMILES: CCN(c1sc(CCNC(=O)OCc2ccccc2)c(C(=O)OC)c1C)C1CCC2(CC1)OCCO2]

In two separate batches, add toluene (428 mL) and water (100 mL) to a mixture of methyl 2-bromo-5-[1,4-dioxaspirol[4.5]dec-8-yl(ethyl)amino]-4-methylthiophene-3-carboxylate (20 g, 48 mmol), potassium benzyl N-[2-(trifluoroboranuidyl)ethyl]carbamate (17.5 g, 58.9 mmol), (2-dicyclohexylphosphino-2',6'-diisopropoxy-1,1'-biphenyl)[2-(2'-amino-1,1'-biphenyl)]palladium(II) methanesulfonate (4.1 g, 4.8 mmol) and Cs$_2$CO$_3$ (47 g, 144 mmol). Flush the reaction mixture with N$_2$, then heat at 80° C. for 4 hr. Pour the reaction mixture into ice-cold water, add EtOAc, separate the layers, filter the organic phase over diatomaceous earth, and concentrate the filtrate in vacuo. Subject the resulting residue to chromatography on silica, eluting with a gradient of 5-40% EtOAc in hexanes Concentrate the resulting desired fractions and dry in vacuo for 72 hr to afford the title compound (41.9 g combined mass, 85% combined yield from two runs) as brown oil. ES/MS (m/z): 517 (M+H).

Preparation 64

2-[1,4-Dioxaspiro[4.5]dec-8-yl(ethyl)amino]-3-methyl-6,7-dihydrothieno[3,2-c]pyridin-4(5H)-one

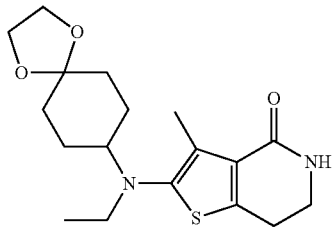 [SMILES: CCN(c1sc2c(c1C)C(=O)NCC2)C1CCC2(CC1)OCCO2]

Purge a Parr flask with N$_2$, add 20% Pd(OH)$_2$ on carbon (40 g, 284.9 mmol), purge the flask with N$_2$ again, and add TEA (150 mL, 1080 mmol), MeOH (500 mL) and a solution of methyl 2-(2-{[(benzyloxy)carbonyl]amino}ethyl)-5-[1,4-dioxaspirol[4.5]dec-8-yl(ethyl)amino]-4-methylthiophene-3-carboxylate (39.5 g, 76.5 mmol) in MeOH (500 mL). Seal the flask, purge with N$_2$, purge with H$_2$ gas, and fill the system with H$_2$ (414 kPa). Stir for about 4 hr at RT and allow the reaction mixture to sit for 72 hr. Filter the resulting suspension, concentrate the filtrate in vacuo, dissolve the resulting residue in EtOAc, and add a little Et$_2$O until a solid forms. Filter and collect the resulting solid to give the title compound (15.3 g) as a white solid. Concentrate the yellow filtrate and subject the resulting residue to chromatography on silica, eluting with a gradient of 10-60% EtOAc in hexanes, to afford additional title compound (8 g). Combine filtered and chromatographed material for further use (23.3 g, 86% yield). ES/MS (m/z): 351 (M+H).

Preparation 65 tert-Butyl 4-{ethyl[4-(methoxycarbonyl)-3-methyl-thiophen-2-yl]amino}piperidine-1-carboxylate

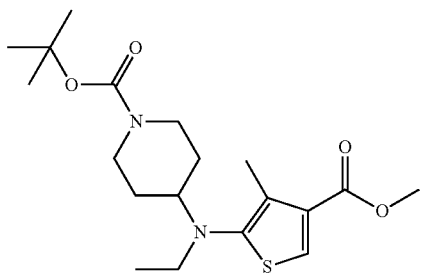 [SMILES: CCN(c1scc(C(=O)OC)c1C)C1CCN(C(=O)OC(C)(C)C)CC1]

To a round bottom flask, add methyl 5-amino-4-methyl-thiophene-3-carboxylate (~50% purity, 34 g, 99 mmol), tert-butyl-4-oxopiperidine-1-carboxylate (25.7 g, 129 mmol) in DCE (408 mL) and AcOH (17 mL, 297 mmol), stir at RT for 10 min, then cool to 0° C. and slowly add sodium triacetoxyborohydride (54.2 g, 248 mmol) portion-wise. Gradually warm the reaction mixture to RT and stir for 2 hr. Add acetaldehyde (11.1 mL, 199 mmol) drop wise, then stir for 72 hr. Cool the reaction mixture to 0° C., quench with saturated aqueous NaHCO$_3$ solution, and dilute with DCM. Separate the layers, extract the aqueous layer with DCM, combine the organic phases, dry over Na$_2$SO$_4$, filter, and concentrate the filtrate in vacuo. Subject the resulting residue to chromatography on silica, eluting with a gradient of 0-10% EtOAc in hexanes, to afford the title compound (6.4 g, 17% yield) as an orange solid after solvent evaporation. ES/MS (m/z): 383 (M+H).

Preparation 66 tert-Butyl 4-{[5-bromo-4-(methoxycarbonyl)-3-methylthiophen-2-yl](ethyl)amino}piperidine-1-carboxylate

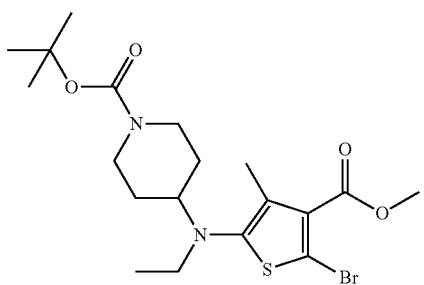 [SMILES: CCN(c1sc(Br)c(C(=O)OC)c1C)C1CCN(C(=O)OC(C)(C)C)CC1]

To a round bottom flask, add tert-butyl 4-{ethyl[4-(methoxycarbonyl)-3-methylthiophen-2-yl]amino}piperidine-1-carboxylate (6.4 g, 17 mmol) in DCM (84 mL), cool to 0° C., add NBS (3.3 g, 18 mmol) portion-wise, and stir for 1 hr. Dilute the reaction mixture with water, separate the layers, extract the aqueous layer with additional DCM, combine the organic phases, dry over Na$_2$SO$_4$, filter, and concentrate the filtrate in vacuo. Subject the resulting residue to chromatography on silica, eluting with a gradient of 0-20% EtOAc in hexanes, to afford the title compound (6.7 g, 87% yield) as orange oil after solvent removal. ES/MS (m/z): ($^{79}$Br/$^{81}$Br) 405/407 (M+H– t-butyl).

Preparation 67 tert-Butyl 4-{[5-(2-{[(benzyloxy)carbonyl]amino}ethyl)-4-(methoxycarbonyl)-3-methylthiophen-2-yl](ethyl)amino}piperidine-1-carboxylate

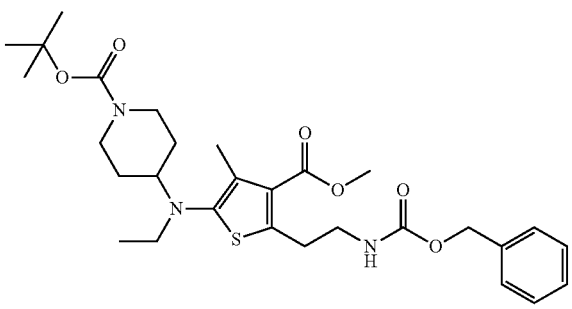 [SMILES: CCN(c1sc(CCNC(=O)OCc2ccccc2)c(C(=O)OC)c1C)C1CCN(C(=O)OC(C)(C)C)CC1]

In two separate batches, add tert-butyl 4-{[5-bromo-4-(methoxycarbonyl)-3-methylthiophen-2-yl](ethyl)amino}piperidine-1-carboxylate (0.900 g, 1.95 mmol), potassium benzyl N-[2-(trifluoroboranuidyl)ethyl]carbamate (0.695 g, 2.34 mmol), (2-dicyclohexyl-phosphino-2',6'-diisopropoxy-1,1'-biphenyl)[2-(2'-amino-1,1'-biphenyl)] palladium(II) methanesulfonate (0.167 g, 0.195 mmol), Cs$_2$CO$_3$ (1.91 g, 5.85 mmol), toluene (9.75 mL) and water (3.55 mL) to a round bottom flask. Degas each mixture with N$_2$ for 15 min, then heat at 90° C. overnight. Cool each reaction mixture to RT and combine. Quench with ice water, dilute with EtOAc, separate the layers, extract the aqueous layer with additional EtOAc, combine the organic phases, and dry over Na$_2$SO$_4$. Filter, and concentrate the filtrate in vacuo. Subject the resulting residue to chromatography on silica, eluting with a gradient of 0-30% EtOAc in hexanes, to afford the title compound (1.29 g, 59% yield) as yellow oil after solvent evaporation. ES/MS (m/z): 460 (M+H– BOC).

Preparation 68 tert-Butyl 4-[ethyl(3-methyl-4-oxo-4,5,6,7-tetrahydrothieno[3,2-c]pyridin-2-yl)amino]piperidine-1-carboxylate

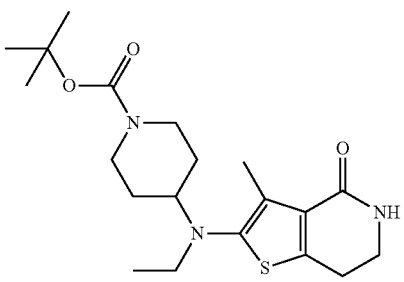 [SMILES: CCN(c1sc2c(c1C)C(=O)NCC2)C1CCN(C(=O)OC(C)(C)C)CC1]

To a round bottom flask, add tert-butyl 4-{[5-(2-{[(benzyloxy)carbonyl]amino}ethyl)-4-(methoxycarbonyl)-3-methylthiophen-2-yl](ethyl)amino}piperidine-1-carboxylate (1.29 g, 2.30 mmol) in MeOH (23 mL) and THF (15 mL), degas with N₂ for ~10 min, add 10% Pd on carbon (1.29 g) and TEA (0.400 mL, 2.84 mmol), then place under an atmosphere of H₂ and stir at RT for about 72 hr. Filter the reaction mixture through diatomaceous earth, wash with MeOH, and concentrate the filtrate in vacuo. Transfer the residue to a microwave vial, add TEA (0.300 mL), and heat at 90° C. for 2 hr. Cool to RT with stirring overnight, then concentrate the reaction mixture in vacuo. Subject the resulting residue to chromatography on silica, eluting with a gradient of 0-30% ACN in DCM, to afford the title compound (0.466 g, 51% yield) as yellow foam after solvent evaporation. ES/MS (m/z): 394 (M+H).

Preparation 69

Methyl 2-(3-{[(benzyloxy)carbonyl]-amino}prop-1-yn-1-yl)-5-[(1R)-1-(1,4-dioxaspiro[4.5]dec-8-yl)ethyl]-4-methyl-thiophene-3-carboxylate

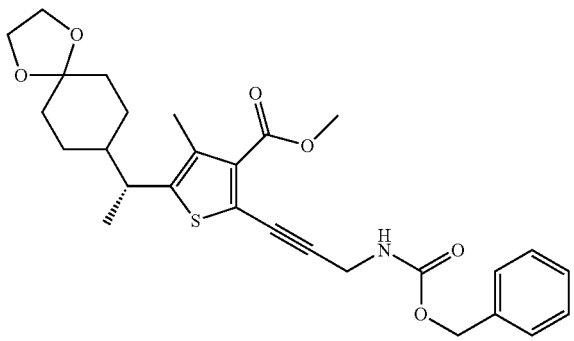 [SMILES: COC(=O)c1c(C#CCNC(=O)OCc2ccccc2)sc([C@H](C)C2CCC3(CC2)OCCO3)c1C]

To a mixture of crude methyl 2-bromo-5-[(1R)-1-(1,4-dioxaspirol[4.5]decan-8-yl)ethyl]-4-methyl-thiophene-3-carboxylate (10.1 g, 25.0 mmol), CuI (1.91 g, 10.0 mmol), and benzyl prop-2-yn-1-ylcarbamate (11.4 g, 60.3 mmol) in 1,4-dioxane (130 mL) add TEA (52 mL, 369 mmol). Degas and purge the mixture with N₂, then add bis(triphenylphosphine)palladium(II) dichloride (3.6 g, 5.1 mmol). Stir at 40° C. for 1 hr. Filter the mixture over diatomaceous earth and concentrate the filtrate in vacuo. Subject the resulting residue to chromatography on silica, eluting with a gradient of 0-20% EtOAc in hexanes, to afford the title compound (10.8 g, 80% yield) as light brown oil after solvent evaporation. ES/MS (m/z): 512 (M+H).

Preparation 70

Methyl 2-(3-aminopropyl)-5-[(1R)-1-(1,4-dioxaspiro[4.5]dec-8-yl)ethyl]-4-methylthiophene-3-carboxylate

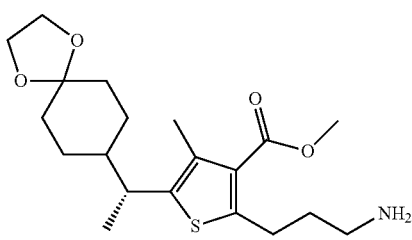 [SMILES: COC(=O)c1c(CCCN)sc([C@H](C)C2CCC3(CC2)OCCO3)c1C]

Add TEA (0.500 mL, 3.55 mmol) to a mixture of methyl 2-(3-{[(benzyloxy)carbonyl]-amino}prop-1-yn-1-yl)-5-[(1R)-1-(1,4-dioxaspiro[4.5]dec-8-yl)ethyl]-4-methyl-thiophene-3-carboxylate (10 g, 19.55 mmol) in MeOH (150 mL). Degas and purge the mixture with N₂, add 20% Pd(OH)₂ on carbon (4.10 g, 5.84 mmol), charge the reaction vessel with H₂ (414 kPa) and stir overnight. Add an additional portion of 20% Pd(OH)₂ on carbon (500 mg, 0.712 mmol) and TEA (0.500 mL, 3.55 mmol), degas with N₂ again and charge the reaction vessel with H₂ (414 kPa). Stir for an additional 6 hr, filter the reaction over diatomaceous earth, and concentrate the filtrate in vacuo to yellow oil. Subject the resulting oil to chromatography on silica, eluting with a gradient of 0-30% MeOH in DCM, to afford the title compound (6.6 g, 89% yield) as yellow oil after solvent evaporation. ES/MS (m/z): 382 (M+H).

Preparation 71

2-[(1R)-1-(1,4-Dioxaspiro[4.5]dec-8-yl)ethyl]-3-methyl-5,6,7,8-tetrahydro-4H-thieno[3,2-c]azepin-4-one

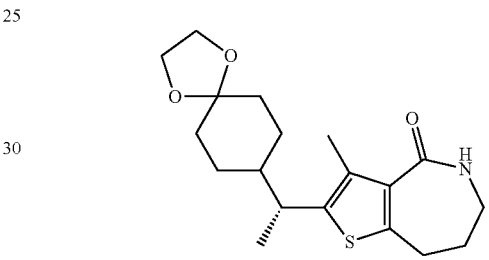

To a microwave vial, add a solution of methyl 2-(3-aminopropyl)-5-[(1R)-1-(1,4-dioxaspiro[4.5]dec-8-yl)ethyl]-4-methylthiophene-3-carboxylate (1.5 g, 3.9 mmol) in toluene (8 mL), then add KOtBu (940 mg, 7.87 mmol). Stir the mixture at 90° C. overnight. Pour the reaction into ice-cold saturated aqueous NaHCO₃ solution, extract with DCM, separate the layers, and concentrate the organic layer in vacuo. Subject the resulting residue to chromatography on silica, eluting with a gradient of 0-5% MeOH in DCM, to afford the title compound (1.3 g, 85% yield) as a light brown solid after solvent evaporation. ES/MS (m/z): 350 (M+H).

Preparation 72

2-[(1R)-1-(1,4-dioxaspiro[4.]dec-8-yl)ethyl]-5-[(2-methoxy-4,6-dimethylpyridin-3-yl)methyl]-3-methyl-5,6,7,8-tetrahydro-4H-thieno[3,2-c]azepin-4-one

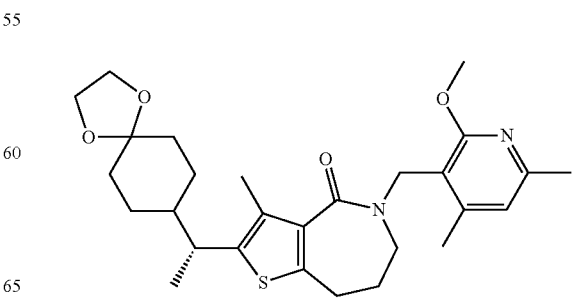

To a solution of 2-[(1R)-1-(1,4-dioxaspiro[4.5]dec-8-yl)ethyl]-3-methyl-5,6,7,8-tetrahydro-4H-thieno[3,2-c]azepin-4-one (1.1 g, 3.1 mmol) in THF (10 mL) add ground KOH (700 mg, 12.4 mmol). Stir for 30 min, then add 3-(chloromethyl)-2-methoxy-4,6-dimethyl-pyridine (700 mg, 3.77 mmol) dissolved in THF (1 mL), and stir the resulting mixture for 2 hr. Pour the reaction mixture into ice-cold saturated aqueous NaHCO₃ solution, extract with DCM, separate the layers, and concentrate the organic layer in vacuo. Dry the resulting residue under vacuum to afford the crude title compound (2.2 g, 87% yield) as brown oil, suitable for additional use without additional purification. ES/MS (m/z): 499 (M+H).

Preparation 73

5-[(4,6-Dimethyl-2-oxo-1,2-dihydropyridin-3-yl)methyl]-3-methyl-2-[(1R)-1-(4-oxocyclohexyl)ethyl]-5,6,7,8-tetrahydro-4H-thieno[3,2-c]azepin-4-one

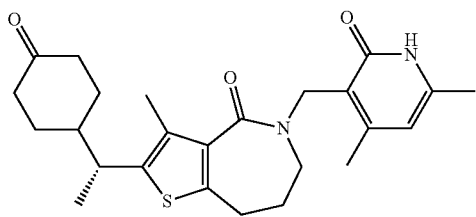 [SMILES: Cc1cc(C)c(CN2CCCc3sc([C@H](C)C4CCC(=O)CC4)c(C)c3C2=O)c(=O)[nH]1]

Add PTSA (1.3 g, 7.2 mmol) to crude 2-[(1R)-1-(1,4-dioxaspirol[4.5]dec-8-yl)ethyl]-5-[(2-methoxy-4,6-dimethylpyridin-3-yl)ethyl]-3-methyl-5,6,7,8-tetrahydro-4H-thieno[3,2-c]azepin-4-one (1.0 g, 1.2 mmol) in DMF (10 mL), and stir the resulting mixture at 70° C. for 2 hr. Pour the mixture into ice-cold saturated aqueous NaHCO₃ solution, extract with DCM, separate the layers, and concentrate the organic layer in vacuo. Subject the resulting residue to chromatography on silica, eluting with a gradient of 0-5% MeOH in DCM, to afford the title compound (680 mg, quantitative yield) as light brown oil after solvent evaporation. ES/MS (m/z): 441 (M+H).

Preparation 74

2-[(1R)-1-{Trans-4-[3-(cyclopropoxy)azetidin-1-yl]cyclohexyl}ethyl]-3-methyl-6,7-dihydrothieno[3,2-c]pyridin-4(5H)-one

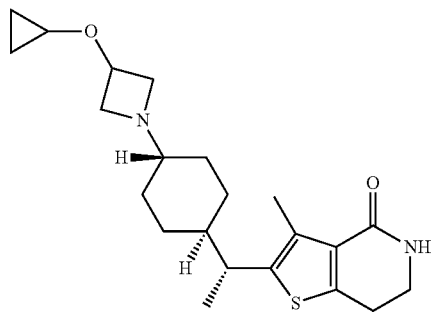 [SMILES: Cc1c([C@H](C)[C@H]2CC[C@H](N3CC(OC4CC4)C3)CC2)sc2c1C(=O)NCC2]

Add titanium(IV) isopropoxide (1.40 g, 4.9 mmol) and 3-(cyclopropyloxy)azetidine hydrochloride (0.74 g, 4.9 mmol) to a solution of 3-methyl-2-[(1R)-1-(4-oxocyclohexyl)ethyl]-6,7-dihydrothieno[3,2-c]pyridin-4(5H)-one (0.72 g, 2.5 mmol) in DCM (10 mL) containing DIPEA (0.87 mL, 4.9 mmol), stir the resulting reaction mixture at RT for 18 hr, and concentrate the reaction mixture in vacuo. Add THF (4 mL) and MeOH (6 mL) to the remaining residue and cool the resulting solution to −78° C. Add 2M LiBH₄ in THF (1.9 mL, 3.8 mmol) drop wise and gradually warm to RT over 3 hr. Dilute the reaction mixture with a 1:1 mixture of DCM/CHCl₃ (100 mL) and 50% saturated NaHCO₃ solution (50 mL), separate the resulting layers, dry the combined organic extracts over MgSO₄, filter, and concentrate the filtrate in vacuo. Subject the resulting residue to chromatography on silica, eluting with a gradient of 10-50% of a mixture of 10% MeOH in DCM and DCM to give the title compound (0.40 g, 42% yield) after solvent evaporation. ES/MS (m/z): 389 (M+H).

Prepare the following compounds essentially by the method of Preparation 74 using the corresponding substituted azetidine.

| Prep No. | Chemical name | Structure | ES/MS (m/z) (M + H) |
|---|---|---|---|
| 75 | 2-{(1R)-1-[Trans-4-(azetidin-1-yl)cyclohexyl]ethyl}-3-methyl-6,7-dihydrothieno[3,2-c]pyridin-4(5H)-one. | 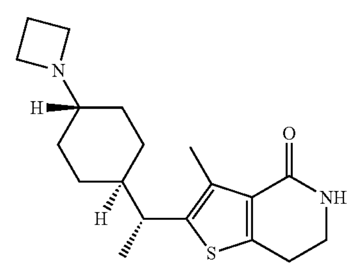 [SMILES: Cc1c([C@H](C)[C@H]2CC[C@H](N3CCC3)CC2)sc2c1C(=O)NCC2] | 333 |

-continued

| Prep No. | Chemical name | Structure | ES/MS (m/z) (M + H) |
|---|---|---|---|
| 76 | 2-[(1R)-1-{Trans-4-[3-(cyclopropylmethoxy)-azetidin-1-yl]cyclohexyl}ethyl]-3-methyl-6,7-dihydrothieno[3,2-c]pyridin-4(5H)-one | 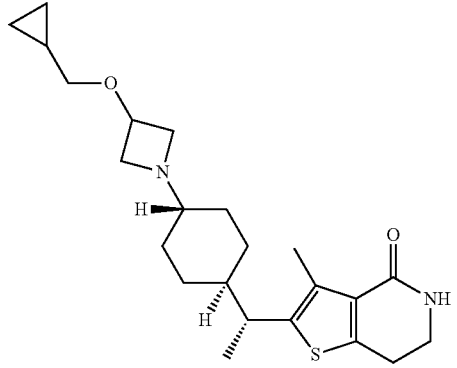 [SMILES: Cc1c([C@H](C)[C@H]2CC[C@H](N3CC(OCC4CC4)C3)CC2)sc2c1C(=O)NCC2] | 403 |
| 77 | 3-Methyl-2-[(1R)-1-{trans-4-[3-(propan-2-yloxy)azetidin-1-yl]cyclohexyl}ethyl]-6,7-dihydrothieno[3,2-c]pyridin-4(5H)-one | 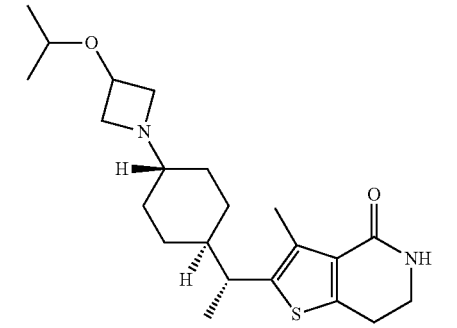 [SMILES: Cc1c([C@H](C)[C@H]2CC[C@H](N3CC(OC(C)C)C3)CC2)sc2c1C(=O)NCC2] | 391 |
| 78 | 3-Methyl-2-[(1R)-1-{trans-4-[3-(1H-pyrazol-1-yl)azetidin-1-yl]cyclohexyl}ethyl]-6,7-dihydrothieno[3,2-c]pyridin-4(5H)-one | 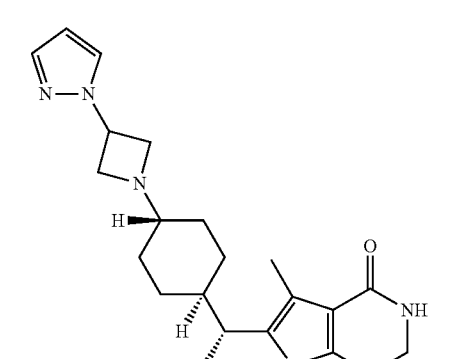 | 399 |
| 79 | 3-Methyl-2-[(1R)-1-(trans-4-{3-[(3S)-tetrahydrofuran-3-yloxy]azetidin-1-yl}cyclohexyl)ethyl]-6,7-dihydrothieno[3,2-c]pyridin-4(5H)-one | 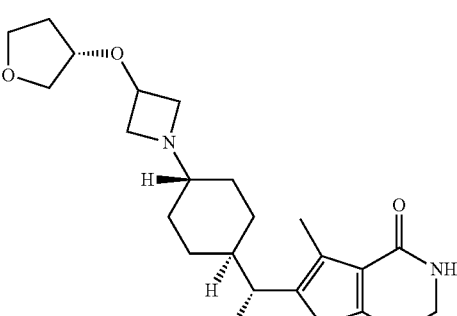 | 419 |

| Prep No. | Chemical name | Structure | ES/MS (m/z) (M + H) |
|---|---|---|---|
| 80 | 3-Methyl-2-[(1R)-1-(trans-4-{3-[(3R)-tetrahydrofuran-3-yloxy]azetidin-1-yl}cyclohexyl)ethyl]-6,7-dihydrothieno[3,2-c]pyridin-4(5H)-one | 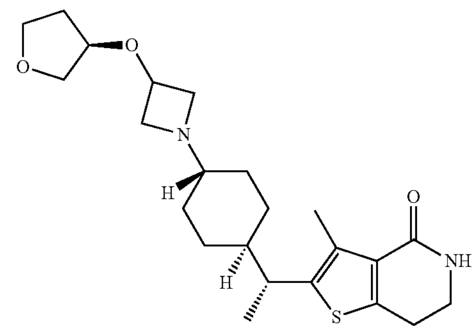 [SMILES: Cc1c([C@H](C)[C@H]2CC[C@H](N3CC(O[C@@H]4CCOC4)C3)CC2)sc2c1C(=O)NCC2] | 419 |

Preparation 81

2-[(1R)-1-{Trans-4-[3-(methoxymethyl)azetidin-1-yl]cyclohexyl}ethyl]-3-methyl-6,7-dihydrothieno[3,2-c]pyridin-4(5H)-one

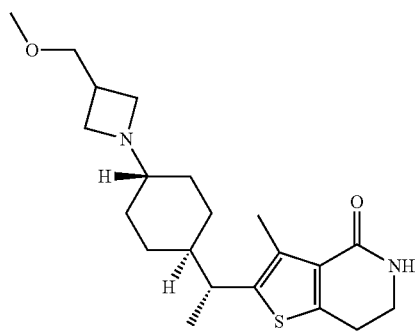 [SMILES: COCC1CN([C@H]2CC[C@H]([C@@H](C)c3sc4c(c3C)C(=O)NCC4)CC2)C1]

Stir a mixture of 3-(methoxymethyl)azetidine hydrochloride (368 mg, 2.67 mmol) and DIPEA (400 mg, 3.06 mmol) in MeOH (5 mL) under $N_2$ at RT for 10 min, add 3-methyl-2-[(1R)-1-(4-oxocyclohexyl)ethyl]-6,7-dihydrothieno[3,2-c]pyridin-4(5H)-one (400 mg, 1.37 mmol), and stir the mixture for 4 hr. Cool to −78° C., slowly add 2M $LiBH_4$ in THF (0.90 mL, 1.8 mmol), and gradually warm up to RT overnight. Concentrate the mixture in vacuo, dilute the resulting residue with saturated aqueous $NaHCO_3$ solution, extract with DCM, and separate the resulting layers. Dry the organic layer over $MgSO_4$, filter, and concentrate the filtrate in vacuo. Subject the resulting residue to chromatography on silica, eluting with a gradient of 0-80% of a mixture of (10% 2N $NH_3$ MeOH solution) in DCM and DCM. Combine the fractions containing the desired product and concentrate in vacuo. Subject the resulting residue to reverse-phase chromatography over C-18-silica (40 g), eluting with 10 mM $NH_4HCO_3$, pH 10, in 5% MeOH/water and ACN using a step gradient of 100% 10 mM $NH_4HCO_3$ in 5% MeOH/water for 5 min, then 25% ACN/10 mM $NH_4HCO_3$ in 5% MeOH/water for 5 min, then a linear gradient of 25%-90% ACN/10 mM $NH_4HCO_3$ in 5% MeOH/water. Combine the pure fractions and concentrate in vacuo to give the title compound (114 mg, 22% yield). ES/MS (m/z): 377 (M+H).

Preparation 82

5-{[2-(Benzyloxy)-4,6-dimethylpyridin-3-yl]methyl}-2-[(1R)-1-{trans-4-[3-(cyclopropyloxy)azetidin-1-yl]cyclohexyl}ethyl]-3-methyl-6,7-dihydrothieno[3,2-c]pyridin-4(5H)-one

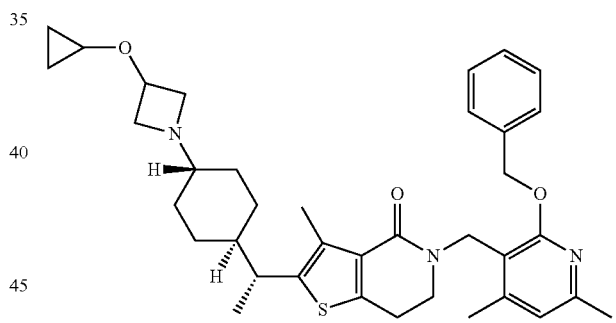

Slowly add 0.7M KHMDS in toluene (1.2 mL, 0.84 mmol) to a solution of 2-[(1R)-1-{trans-4-[3-(cyclopropoxy)azetidin-1-yl]cyclohexyl}ethyl]-3-methyl-6,7-dihydrothieno[3,2-c]pyridin-4(5H)-one (230 mg, 0.59 mmol) in THF (10 mL) at RT over 30 min, and stir an additional 30 min. Drop wise add a solution 2-benzyloxy-3-(chloromethyl)-4,6-dimethyl-pyridine (200 mg, 0.76 mmol) in THF (5 mL) and stir at RT for 18 hr. Heat the reaction mixture to 55° C., stir for 1 hr, cool to RT, pour into an ice-cold aqueous $NaHCO_3$ solution, and extract with EtOAc. Separate the layers, wash the organic extract with saturated aqueous NaCl, dry over $MgSO_4$, filter, and concentrate the filtrate in vacuo. Subject the resulting residue to chromatography on silica, eluting with a gradient 10-50% EtOAc in hexanes, to yield the title compound (210 mg, 57% yield) after solvent evaporation. ES/MS (m/z): 614 (M+H).

Prepare the following compounds essentially by the method of Preparation 82 and the appropriately substituted 6,7-dihydro-5H-thieno[3,2-c]pyridin-4-one.

| Prep No. | Chemical name | Structure | ES/MS (m/z) (M + H) |
|---|---|---|---|
| 83 | 2-{(1R)-1-[Trans-4-(azetidin-1-yl)cyclohexyl]ethyl}-5-{[2-(benzyloxy)-4,6-dimethylpyridin-3-yl]methyl}-3-methyl-6,7-dihydrothieno[3,2-c]pyridin-4(5H)-one | 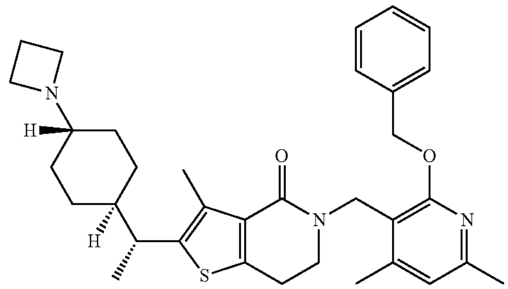 [SMILES: Cc1cc(C)c(CN2CCc3sc([C@H](C)[C@H]4CC[C@H](N5CCC5)CC4)c(C)c3C2=O)c(OCc2ccccc2)n1] | 558 |
| 84 | 5-{[2-(Benzyloxy)-4,6-dimethylpyridin-3-yl]methyl}-2-[(1R)-1-{trans-4-[3-(methoxymethyl)azetidin-1-yl]cyclohexyl}ethyl]-3-methyl-6,7-dihydrothieno[3,2-c]pyridin-4(5H)-one | 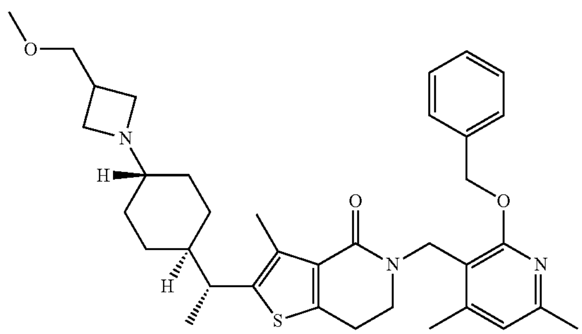 | 602 |
| 85 | 5-{[2-(Benzyloxy)-4,6-dimethylpyridin-3-yl]methyl}-2-[(1R)-1-{trans-4-[3-(cyclopropylmethoxy)-azetidin-1-yl]cyclohexyl}ethyl]-3-methyl-6,7-dihydrothieno[3,2-c]pyridin-4(5H)-one | 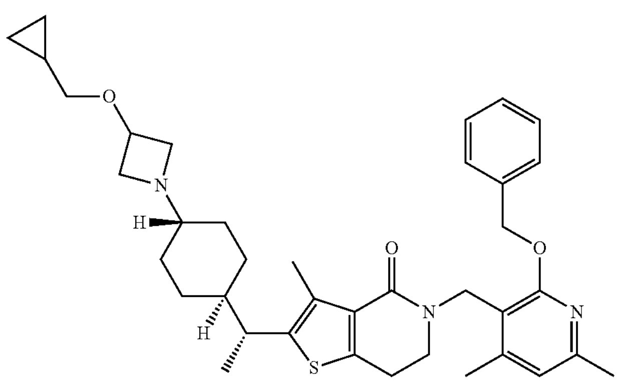 [SMILES: Cc1cc(C)c(CN2CCc3sc([C@H](C)[C@H]4CC[C@H](N5CC(OCC6CC6)C5)CC4)c(C)c3C2=O)c(OCc2ccccc2)n1] | 628 |
| 86 | 5-{[2-(Benzyloxy)-4,6-dimethylpyridin-3-yl]methyl}-3-methyl-2-[(1R)-1-{trans-4-[3-(propan-2-yloxy)azetidin-1-yl]cyclohexyl}ethyl]-6,7-dihydrothieno[3,2-c]pyridin-4(5H)-one | 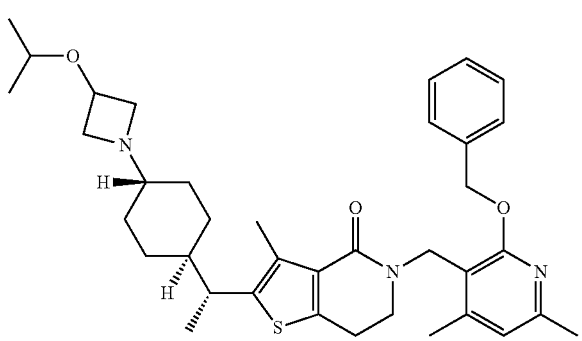 [SMILES: Cc1cc(C)c(CN2CCc3sc([C@H](C)[C@H]4CC[C@H](N5CC(OC(C)C)C5)CC4)c(C)c3C2=O)c(OCc2ccccc2)n1] | 616 |

-continued

| Prep No. | Chemical name | Structure | ES/MS (m/z) (M + H) |
|---|---|---|---|
| 87 | 5-{[2-(Benzyloxy)-4,6-dimethylpyridin-3-yl]methyl}-3-methyl-2-[(1R)-1-{trans-4-[3-(1H-pyrazol-1-yl)azetidin-1-yl]cyclohexyl}ethyl]-6,7-dihydrothieno[3,2-c]pyridin-4(5H)-one | 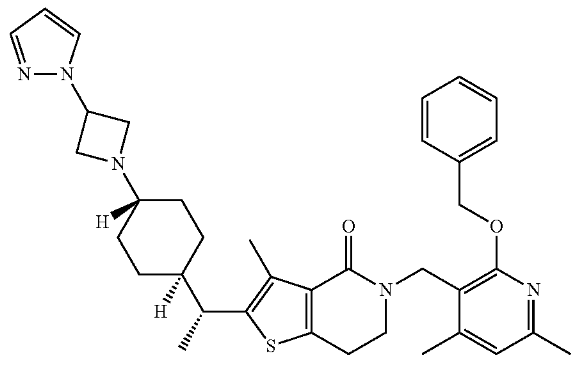 [SMILES: Cc1cc(C)c(CN2CCc3sc([C@H](C)[C@H]4CC[C@H](N5CC(n6cccn6)C5)CC4)c(C)c3C2=O)c(OCc2ccccc2)n1] | 624 |
| 88 | 5-{[2-(Benzyloxy)-4,6-dimethylpyridin-3-yl]methyl}-3-methyl-2-[(1R)-1-(trans-4-{3-[(3S)-tetrahydrofuran-3-yloxy]azetidin-1-yl}cyclohexyl)ethyl]-6,7-dihydrothieno[3,2-c]pyridin-4(5H)-one | 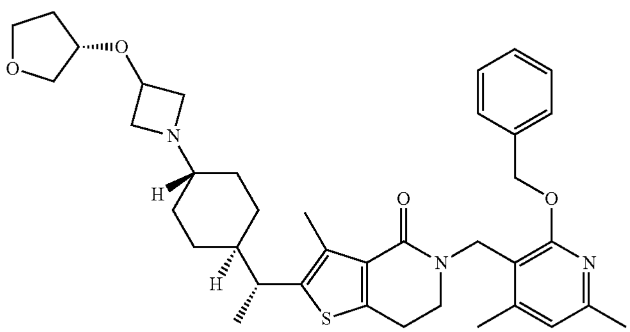 [SMILES: Cc1cc(C)c(CN2CCc3sc([C@H](C)[C@H]4CC[C@H](N5CC(O[C@H]6CCOC6)C5)CC4)c(C)c3C2=O)c(OCc2ccccc2)n1] | 644 |
| 89 | 5-{[2-(Benzyloxy)-4,6-dimethylpyridin-3-yl]methyl}-3-methyl-2-[(1R)-1-(trans-4-{3-[(3R)-tetrahydrofuran-3-yloxy]azetidin-1-yl}cyclohexyl)ethyl]-6,7-dihydrothieno[3,2-c]pyridin-4(5H)-one | 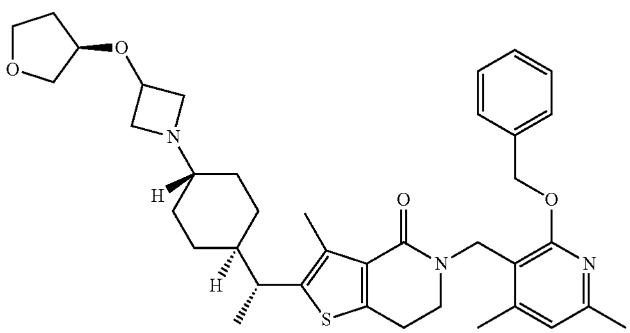 [SMILES: Cc1cc(C)c(CN2CCc3sc([C@H](C)[C@H]4CC[C@H](N5CC(O[C@@H]6CCOC6)C5)CC4)c(C)c3C2=O)c(OCc2ccccc2)n1] | 644 |

Preparation 90

Methyl 5-[(1R)-1-(1,4-dioxaspiro[4.5]dec-8-yl)ethyl]-2-(2-{[(2-methoxy-4,6-dimethylpyridin-3-yl)methyl]amino}elhyl)-4-methythiophene-3-carboxylate

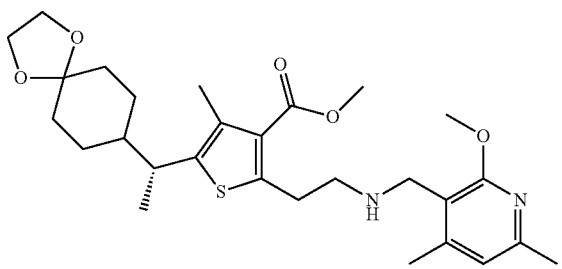 [SMILES: COC(=O)c1c(CCNCc2c(C)cc(C)nc2OC)sc([C@H](C)C2CCC3(CC2)OCCO3)c1C]

Dissolve methyl 2-(2-{[(benzyloxy)carbonyl]amino}ethyl)-5-[(1R)-1-(1,4-dioxaspiro[4.5]dec-8-yl)ethyl]-4-methylthiophene-3-carboxylate (77 g, 153.5 mmol) and 2-methoxy-4,6-dimethyl-pyridine-3-carbaldehyde (23.3 g, 140 mmol) in EtOH (500 mL) in a Parr reactor and add Pd(OH)$_2$ on carbon, 20% dry basis, water wet (11.5 g). Fill the vessel with H$_2$ (100 psi) and stir for 3.5 hr at 50° C. After cooling to RT, filter the mixture through diatomaceous earth and wash with EtOH. Concentrate the filtrate in vacuo, add toluene (800 mL) to the residue, and continue partial distillation of volatiles to a final weight of approximately 400 g, to obtain the title compound as a solution in toluene, suitable for use in the next step without additional purification. ES/MS of an evaporated sample (m/z): 517 (M+H).

Preparation 91

Methyl 2-(2-{[(2-methoxy-4,6-dimethylpyridin-3-yl)methyl]amino}ethyl)-4-methyl-5-[(1R)-1-(4-oxocyclohexyl)ethyl]thiophene-3-carboxylate

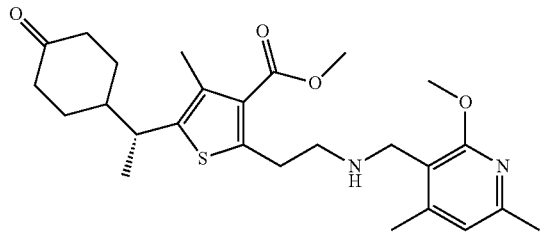 [SMILES: COC(=O)c1c(CCNCc2c(C)cc(C)nc2OC)sc([C@H](C)C2CCC(=O)CC2)c1C]

To the crude toluene solution (approximately 76 g) of methyl 5-[(1R)-1-(1,4-dioxaspiro[4.5]dec-8-yl)ethyl]-2-(2-{[(2-methoxy-4,6-dimethylpyridin-3-yl)methyl]amino}ethyl)-4-methylthiophene-3-carboxylate, from preparation 90, add 1M aqueous HCl (800 mL) and stir at RT for 1 hr. Separate the layers, wash the organic layer sequentially with 2M aqueous HCl (2×50 mL), and wash combined acidic aqueous layers with toluene (100 mL). Add toluene (0.4 L) to the aqueous layer and add 6M aqueous K₂CO₃ to pH 9, stir for 5 min, separate the phases, wash the organic layer with aqueous saturated NaCl, then pass through a short pad of Na₂SO₄. Further rinse Na₂SO₄ pad with toluene to obtain a crude toluene solution of the title compound (approximate volume 1 L), suitable for use in the next step without additional purification. ES/MS of an evaporated sample (m/z): 473 (M+H).

Preparation 92

5-[(2-Methoxy-4,6-dimethylpyridin-3-yl)methyl]-3-methyl-2-[(1R)-1-(4-oxocyclohexyl)ethyl]-6,7-dihydrothieno[3,2-c]pyridin-4(5H)-one

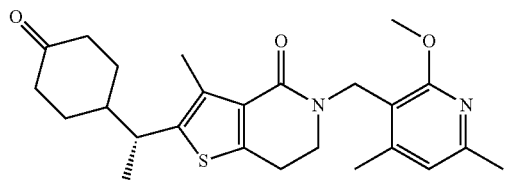 [SMILES: COc1nc(C)cc(C)c1CN1CCc2sc([C@H](C)C3CCC(=O)CC3)c(C)c2C1=O]

Add AcOH (9 mL, 157.1 mmol) to the crude solution of methyl 2-(2-{[(2-methoxy-4,6-dimethylpyridin-3-yl)methyl]amino}ethyl)-4-methyl-5-[(1R)-1-(4-oxocyclohexyl)ethyl]thiophene-3-carboxylate (1 L, approximately 79 g, from preparation 91) and stir at 90° C. for 2 hr. Wash the mixture twice with 2M aqueous HCl (total 0.15 L), and sequentially once each with water, 1M aqueous K₃PO₄, and saturated aqueous NaCl (each 0.1 L). Dry the organic layer over MgSO₄, filter, and evaporate the filtrate in vacuo to afford the title compound as orange viscous oil (40.98 g, 48.5% yield). ES/MS (m/z): 441 (M+H).

Preparation 93

5-[(2-Methoxy-4,6-dimethylpyridin-3-yl)methyl]-2-{(1R)-1-[trans-4-(3-methoxyazetidin-1-yl)cyclohexyl]ethyl}-3-methyl-6,7-dihydrothieno[3,2-c]pyridin-4(5H)-one

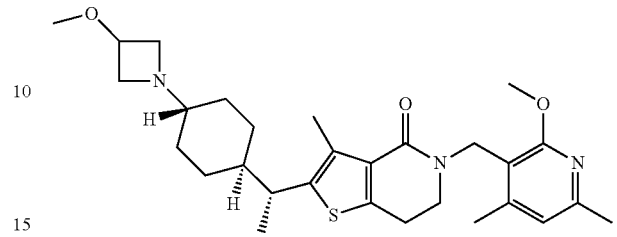

Add DIPEA (29 mL, 21.5 g, 166 mmol) to a solution of 3-methoxyazetidine hydrochloride (18.7 g, 151 mmol) in MeOH (280 mL) and stir at RT for 30 minutes. Add this mixture to 5-[(2-methoxy-4,6-dimethylpyridin-3-yl)methyl]-3-methyl-2-[(1R)-1-(4-oxocyclohexyl)ethyl]-6,7-dihydrothieno[3,2-c]pyridin-4(5H)-one (27.55 g, 56.28 mmol), stir at RT for 1.5 hours under N₂ and then add THF (50 mL). Cool the reaction to −70° C. and add 2M LiBH₄ in THF (40 mL, 80 mmol) over 30 minutes. Stir the reaction at the same temperature for 2 hr. Quench the reaction by slowly pouring the reaction into 1M aqueous HCl solution (about 1 L) over 10 minutes. Wash with MTBE (2×0.25 L), then treat the aqueous phase with 2M aqueous K₃PO₄ to pH 9 and extract with EtOAc (about 0.5 L). Wash the organic phase sequentially with 3M aqueous K₂CO₃ and saturated aqueous NaCl (each about 100 mL), dry over Na₂SO₄, filter and concentrate the filtrate in vacuo. Subject the resulting residue to chromatography on silica, eluting with a gradient of 10-25% of a 20% solution of 7N NH₃/MeOH in EtOAc to give the title compound as a white solid (19.5 g, 68% yield). ES/MS (m/z): 512 (M+H).

Preparation 94

5-[2-Methoxy-4,6-dimethylpyridin-3-yl)methyl]-3-methyl-2-[(1R)-1-{trans-4-[3-(3-methyl-1H-pyrazol-1-yl)azetidin-1-yl]cyclohexyl}ethyl]-6,7-dihydrothieno[3,2-c]pyridine-4(5H)-one and 5-[(2-methoxy-4,6-dimethyl-3-pyridyl)methyl]-3-methyl-2-[(1R)-1-[trans-4-[3-(5-methylpyrazol-1-yl)azetidin-1-yl]cyclohexyl]ethyl]-6,7-dihydrothieno[3,2-c]pyridin-4-one (mixture of regioisomers)

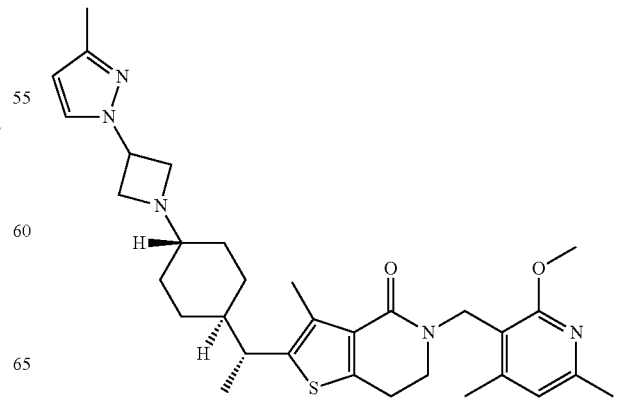

89
-continued

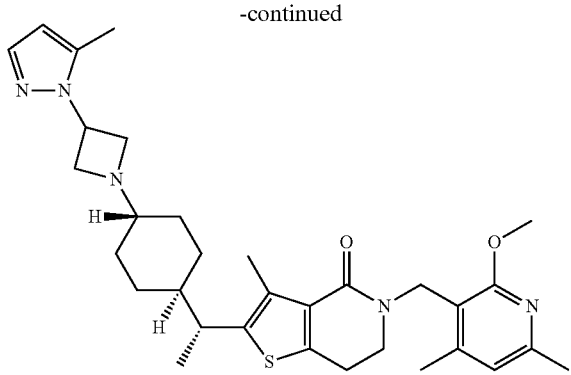

Stir a solution of a mixture of 1-(azetidin-3-yl)-3-methyl-1H-pyrazole and 1-(azetidin-3-yl)-5-methyl-pyrazole (0.53 g, 3.59 mmol, mixture of regioisomers), DIPEA (1.37 mL, 7.79 mmol) and 4N HCl in dioxane (1.8 mL, 7.190 mmol)

90 in MeOH (5 mL) for 30 min at RT. Add this to a solution of 5-[(2-methoxy-4,6-dimethylpyridin-3-yl)methyl]-3-methyl-2-[(1R)-1-(4-oxocyclohexyl)ethyl]-6,7-dihydrothieno[3,2-c]pyridin-4(5H)-one (600 mg, 1.2 mmol) in MeOH (19 mL) and stir 2 hr at RT. Cool the mixture to −78° C. and add a solution of 2M LiBH$_4$ in THF (0.78 mL, 1.56 mmol); gradually warm to RT and stir the reaction mixture overnight. Concentrate the reaction mixture in vacuo. Subject the resulting residue to chromatography over SCX (25 g cartridge), eluting with MeOH (2×100 mL) followed by a solution of 2N NH$_3$ in MeOH. Concentrate the MeOH in NH$_3$ fraction in vacuo to give the title compound as a mixture of regioisomers as pale yellow oil (0.51 g, 65% yield). ES/MS (m/z): 562 (M+H).

Prepare the following compounds essentially by the method of Preparation 94 using 5-[(2-methoxy-4,6-dimethylpyridin-3-yl)methyl]-3-methyl-2-[(1R)-1-(4-oxocyclohexyl)ethyl]-6,7-dihydrothieno[3,2-c]pyridin-4(5H)-one and the appropriately substituted azetidine.

| Prep No. | Chemical name | Structure | ES/MS (m/z) (M + H) |
|---|---|---|---|
| 95 | 5-[(2-methoxy-4,6-dimethylpyridin-3-yl)methyl]-3-methyl-2-[(1R)-1-{4-[3-(4-methyl-1H-pyrazol-1-yl)azetidin-1-yl]cyclohexyl}ethyl]-6,7-dihydrothieno[3,2-c]pyridin-4(5H)-one | 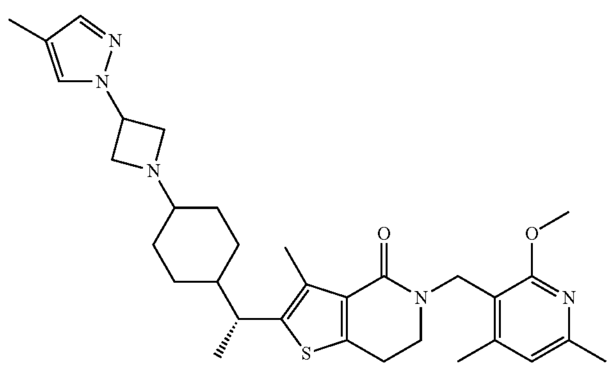 | 562 |
| 96 | 5-[(2-methoxy-4,6-dimethylpyridin-3-yl)methyl]-3-methyl-2-[(1R)-1-{4-[3-(pyrrolidin-1-yl)azetidin-1-yl]cyclohexyl}ethyl]-6,7-dihydrothieno[3,2-c]pyridin-4(5H)-one | 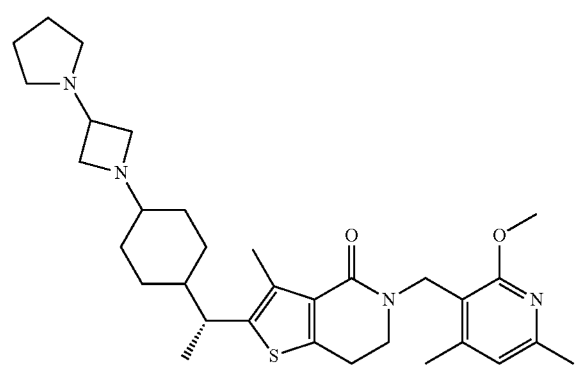 [SMILES: COc1nc(C)cc(C)c1CN1CCc2sc([C@H](C)C3CCC(N4CC(N5CCCC5)C4)CC3)c(C)c2C1=O] | 551 |

| Prep No. | Chemical name | Structure | ES/MS (m/z) (M + H) |
|---|---|---|---|
| 97 | 5-[(2-methoxy-4,6-dimethylpyridin-3-yl)methyl]-3-methyl-2-[(1R)-1-{4-[3-(morpholin-4-yl)azetidin-1-yl]cyclohexyl}ethyl]-6,7-dihydrothieno[3,2-c]pyridin-4(5H)-one | 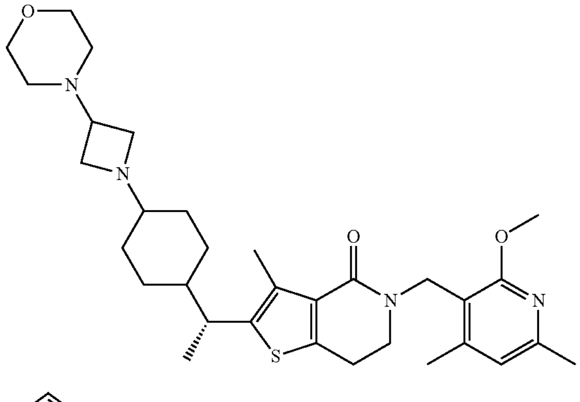 | 567 |
| 98 | 5-[(2-methoxy-4,6-dimethylpyridin-3-yl)methyl]-3-methyl-2-[(1R)-1-{4-[3-(1H-1,2,3-triazol-1-yl)azetidin-1-yl]cyclohexyl}ethyl]-6,7-dihydrothieno[3,2-c]pyridin-4(5H)-one | 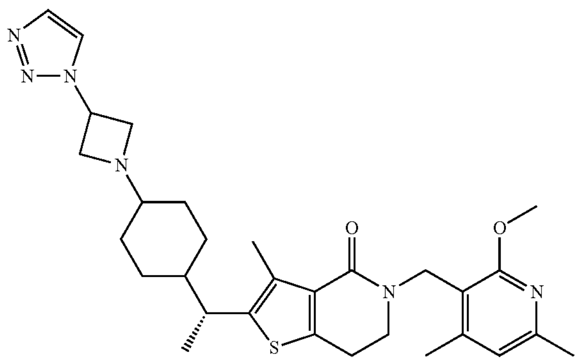 [SMILES: COc1nc(C)cc(C)c1CN1CCc2sc([C@H](C)C3CCC(N4CC(n5ccnn5)C4)CC3)c(C)c2C1=O] | 549 |

Preparation 99

5-[(2-Methoxy-4,6-dimethylpyridin-3-yl)methyl]-2-[(1R)-1-{4-[3-(2-methoxyethoxy)azetidin-1-yl]cyclohexyl}ethyl]-3-methyl-6,7-dihydrothieno[3,2-c]pyridin-4(5H)-one (mixture of diastereomers)

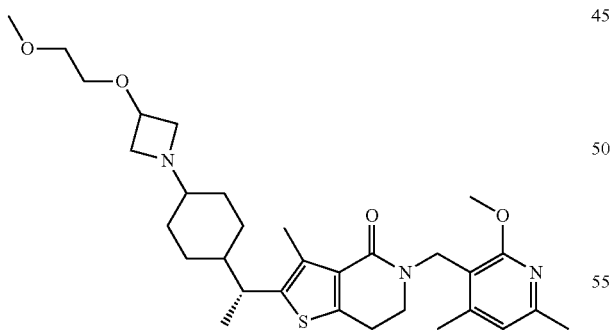

Add DIPEA (0.45 mL, 2.49 mmol) to a solution of 3-(2-methoxyethoxy)azetidine hydrochloride (0.42 g, 2.38 mmol) in MeOH (5.6 mL) and stir at RT for 30 min. Add 5-[(2-methoxy-4,6-dimethylpyridin-3-yl)methyl]-3-methyl-2-[(1R)-1-(4-oxocyclohexyl)ethyl]-6,7-dihydrothieno[3,2-c]pyridin-4(5H)-one (0.62 g, 1.12 mmol) and stir at RT overnight. Cool the mixture to −78° C., add a 2M solution of LiBH$_4$ in THF (0.74 mL, 1.47 mmol), warm to RT, and stir overnight. Add saturated aqueous NaHCO$_3$ solution, extract with EtOAc, and separate the layers. Dry the organic phase over Na$_2$SO$_4$, filter, and concentrate the filtrate in vacuo to afford title compound as oil (0.5 g, 98% yield). ES/MS (m/z): 556 (M+H).

Preparation 100

2-{(1R)-1-[Trans-4-(benzylamino)cyclohexyl]ethyl}-5-[(2-methoxy-4,6-dimethylpyridin-3-yl)methyl]-3-methyl-6,7-dihydrothieno[3,2-c]pyridin-4(5H)-one

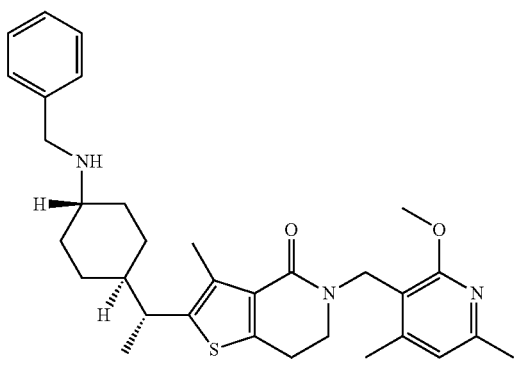 [SMILES: COc1nc(C)cc(C)c1CN1CCc2sc([C@H](C)[C@H]3CC[C@H](NCc4ccccc4)CC3)c(C)c2C1=O]

Stir a solution of benzyl amine (0.257 g, 2.397 mmol), DIPEA (0.95 mL, 5.39 mmol) and 4N HCl in dioxane (600 µL, 2.397 mmol) in MeOH (5 mL) for 30 min at RT. Add this mixture to a solution of the 5-[(2-methoxy-4,6-dimethyl-pyridin-3-yl)methyl]-3-methyl-2-[(1R)-1-(4-oxocyclohexyl)ethyl]-6,7-dihydrothieno[3,2-c]pyridin-4(5H)-one (0.6 g, 1.2 mmol) in MeOH (19 mL) and stir the resulting mixture for 18 hr at RT. Cool the mixture to −70° C. and add a solution of 2M LiBH$_4$ in THF (0.78 mL, 1.558 mmol). Allow to gradually warm up to room temperature. Add an ice-cold saturated NaHCO$_3$ solution, extract with EtOAc (100 mL), separate the layers, wash the organic extract with saturated aqueous NaCl, and dry the organic extract over Na$_2$SO$_4$. Filter and concentrate the filtrate in vacuo to afford the title compound as yellow oil (0.75 g, 99% yield) suitable for use without additional purification. ES/MS (m/z): 532 (M+H).

Preparation 101

2-[(1R)-1-(Trans-4-aminocyclohexyl)ethyl]-5-[(2-methoxy-4,6-dimethylpyridin-3-yl)methyl]-3-methyl-6,7-dihydrothieno[3,2-c]pyridin-4(5H)-one

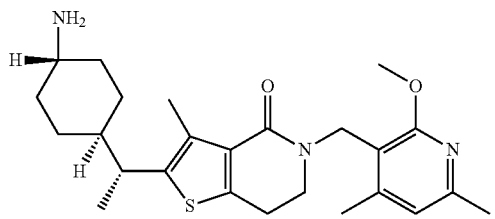 [SMILES: COc1nc(C)cc(C)c1CN1CCc2sc([C@H](C)[C@H]3CC[C@H](N)CC3)c(C)c2C1=O]

Stir a solution of 2-{(1R)-1-[trans-4-(benzylamino)cyclohexyl]ethyl}-5-[(2-methoxy-4,6-dimethylpyridin-3-yl)methyl]-3-methyl-6,7-dihydrothieno[3,2-c]pyridin-4(5H)-one (750 mg, 1.19 mmol) in MeOH (20 mL). Add 10% Pd—C(500 mg, 0.474 mmol) and stir under H$_2$ at 30 psi at RT overnight. Filter through diatomaceous earth and wash with MeOH. Evaporate the filtrate to afford the title compound as yellow oil (0.5 g, 80% yield), suitable for use without additional purification. ES/MS (m/z): 442 (M+H).

Preparation 102

2-{(1R)-1-[Trans-4-(dimethylamino)cyclohexyl]ethyl}-5-[(2-methoxy-4,6-dimethylpyridin-3-yl)methyl]-3-methyl-6,7-dihydrothieno[3,2-c]pyridin-4(5H)-one

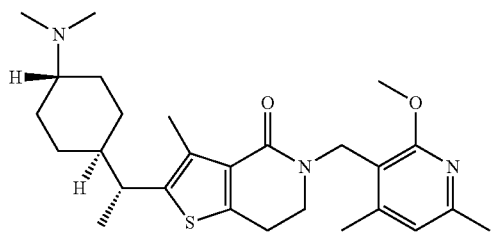 [SMILES: COc1nc(C)cc(C)c1CN1CCc2sc([C@H](C)[C@H]3CC[C@H](N(C)C)CC3)c(C)c2C1=O]

Stir a solution of 2-[(1R)-1-(trans-4-aminocyclohexyl)ethyl]-5-[(2-methoxy-4,6-dimethylpyridin-3-yl)methyl]-3-methyl-6,7-dihydrothieno[3,2-c]pyridin-4(5H)-one (0.5 g, 0.95 mmol) in MeOH (10 mL). Add AcOH (172 mg, 2.85 mmol), 37% aqueous formaldehyde (232 mg, 2.853 mmol). Cool the solution with an ice bath and add triacetoxyborohydride (605 mg, 2.853 mmol). Allow to gradually warm to RT and stir overnight. Add ice-cold saturated NaHCO$_3$ solution, and extract with DCM (2×100 mL). Separate the layers, combine the organic phases, and wash the combined organic extracts with saturated aqueous NaCl. Dry over Na$_2$SO$_4$, filter, and concentrate the filtrate in vacuo to afford the title compound as yellow oil (390 mg, 70% yield), suitable for use without additional purification. ES/MS (m/z): 470 (M+H).

Preparation 103

5-{[2-(Benzyloxy)-4,6-dimethylpyridin-3-yl]methyl}-2-[1,4-dioxaspiro[4.5]dec-8-yl(methyl)amino]-3-methyl-6,7-dihydrothieno[3,2-c]pyridin-4(5H)-one

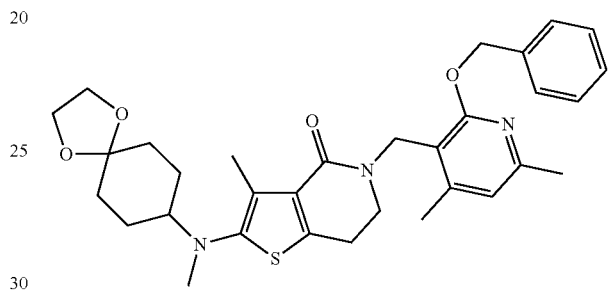

To 2-[1,4-dioxaspiro[4.5]dec-8-yl(methyl)amino]-3-methyl-6,7-dihydrothieno[3,2-c]pyridin-4(5H)-one (0.51 g, 1.53 mmol) in THF (5 mL) at 0° C., add a solution of 1M KHMDS in THF (2.14 mL, 2.14 mmol). Warm to RT and after 15 min add 2-benzyloxy-3-(chloromethyl)-4,6-dimethyl-pyridine (0.60 g, 2.29 mmol). Stir at RT for about 17 hr, then quench with saturated aqueous NH$_4$Cl solution (1 mL). Dilute the mixture with EtOAc (40 mL) and water (5 mL), separate the organic layer, dry over Na$_2$SO$_4$, filter, and concentrate the filtrate in vacuo to afford the title compound (0.94 g, 92% yield) as yellow oil, suitable for use without additional purification. ES/MS (m/z): 562 (M+H).

Preparation 104

5-[(4,6-Dimethyl-2-oxo-1,2-dihydropyridin-3-yl)methyl]-3-methyl-2-[methyl(4-oxyclohexyl)amino]-6,7-dihydrothieno[3,2-c]pyridin-4(5H)-one

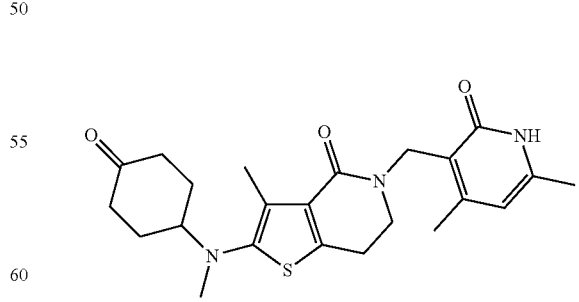

To crude 5-{[2-(benzyloxy)-4,6-dimethylpyridin-3-yl]methyl}-2-[1,4-dioxaspiro[4.5]dec-8-yl(methyl)amino]-3-methyl-6,7-dihydrothieno[3,2-c]pyridin-4(5H)-one (0.94 g, 1.4 mmol) in THF (14 mL), add 1M aqueous HCl (14 mL, 14 mmol), heat the mixture to 50° C. for 8 hr and stir at RT for 2 days. Add solid NaHCO$_3$ (1.8 g, 21 mmol) and EtOAc (125 mL), separate the organic layer, and dry over Na$_2$SO$_4$. Filter and concentrate the filtrate in vacuo. Subject the resulting residue to chromatography on silica, eluting with a gradient of 0-10% 7N methanolic NH$_3$ in DCM, to afford the title compound (0.408 g, 62% yield) as yellow foam after solvent evaporation. ES/MS (m/z): 428 (M+H).

Preparation 105

2-[1,4-Dioxaspiro[4.5]dec-8-yl(ethyl)amino]-5-[2-methoxy-4,6-dimetylpyridin-3-yl)methyl]-3-methyl-6,7-dihydroyhieno[3,2-c]pyridin-4(5H)-one

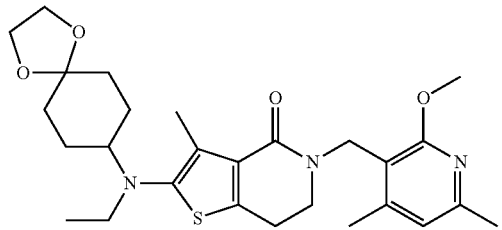 [SMILES: CCN(c1sc2c(c1C)C(=O)N(Cc1c(C)cc(C)nc1OC)CC2)C1CCC2(CC1)OCCO2]

In two separate batches, add a 0.91M solution of potassium bis(trimethylsilyl)amide in THF (22 mL, 20 mmol) slowly to a solution of 2-[1,4-dioxaspiro[4.5]dec-8-yl(ethyl)amino]-3-methyl-6,7-dihydrothieno[3,2-c]pyridin-4(5H)-one (6 g, 17.12 mmol) in THF (70 mL) at RT over 30 min. Stir the resulting mixtures for an additional 30 min at RT, then drop wise add 3-(chloromethyl)-2-methoxy-4,6-dimethyl-pyridine (3.4 g, 18 mmol) in THF (10 mL). Stir the resulting mixtures at RT overnight. Combine both mixtures, pour into an ice-cold saturated aqueous NaHCO$_3$ solution, and extract with EtOAc. Separate the phases, dry the organic extract over MgSO$_4$, filter, and concentrate the filtrate in vacuo to afford the title compound (total 18.55 g, quantitative yield) as yellow gum, suitable for use without additional purification. ES/MS (m/z): 500 (M+H).

Preparation 106

2-[Ethyl(4-oxocyclohexyl)amino]-5-[(2-methoxy-4,6-dimethylpyridin-3-yl)methyl]-3-methyl-6,7-dihydrothieno[3,2-c]pyridin-4(5H)-one

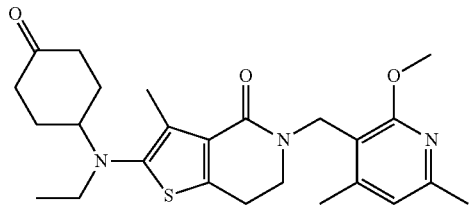 [SMILES: CCN(c1sc2c(c1C)C(=O)N(Cc1c(C)cc(C)nc1OC)CC2)C1CCC(=O)CC1]

Add 6M aqueous HCl (20 mL, 120 mmol) to solution of crude 2-[1,4-dioxaspiro[4.5]dec-8-yl(ethyl)amino]-5-[(2-methoxy-4,6-dimethylpyridin-3-yl)methyl]-3-methyl-6,7-dihydrothieno[3,2-c]pyridin-4(5H)-one (18.05 g, 36.12 mmol) in THF (20 mL). Heat the resulting mixture at 50° C. for 2 hr, and stir at RT overnight. Pour the reaction mixture into ice-cold saturated aqueous NaHCO$_3$, extract with DCM, separate the layers, and concentrate the organic layer in vacuo. Subject the resulting residue to chromatography on silica, eluting with a gradient of 10-50% EtOAc in hexanes to afford the title compound (4.01 g, 24% yield) as light yellow oil after solvent evaporation. ES/MS (m/z): 456 (M+H).

Preparation 107

5-[(4,6-Dimethyl-2-oxo-1,2-dihydropyridin-3-yl) methyl]-2-[ethyl(4-oxocyclohexyl)amino]-3-methyl-6,7-dihydrothieno[3,2-c]pyridin-4(5H)-one

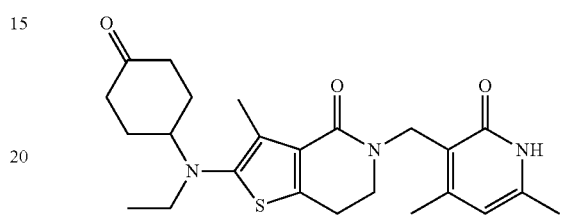

In a sealed tube, add a solution of 2-[ethyl(4-oxocyclohexyl)amino]-5-[(2-methoxy-4,6-dimethylpyridin-3-yl) methyl]-3-methyl-6,7-dihydrothieno[3,2-c]pyridin-4(5H)-one (6.3 g, 14 mmol) in DMF (50 mL), cool the tube to 0° C., and add LiCl (3 g, 70 mmol) followed by PTSA (13 g, 72 mmol). Heat the resulting mixture at 70° C. for 2 hr. Cool to RT, and slowly pour into ice-cold saturated aqueous NaHCO$_3$ (400 mL). Filter the precipitated solid and wash with water. Transfer the solid to a round bottom flask, dilute with MeOH, and concentrate in vacuo. Azeotrope the solid again with MeOH and THF in vacuo, then dry the residue in a vacuum oven overnight to afford the title compound (6.1 g, 100% yield) as a brown solid. ES/MS (m/z): 442 (M+H).

Preparation 108

2-{[Trans-4-(benzylamino)cyclohexyl](ethyl) amino}-5-[(4,6-dimethyl-2-oxo-1,2-dihydropyridin-3-yl)methyl]-3-methyl-6,7-dihydrothieno[3,2-c]pyridin-4(5H)-one

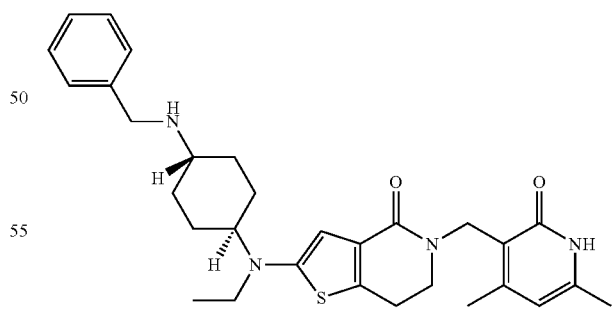

To a round bottom flask, add phenylmethanamine (0.445 mL, 4.076 mmol), 5-[(4,6-dimethyl-2-oxo-1,2-dihydropyridin-3-yl)methyl]-2-[ethyl(4-oxocyclohexyl)amino]-3-methyl-6,7-dihydrothieno[3,2-c]pyridin-4(5H)-one (0.600 g, 1.359 mmol) to THF (25 mL) and MeOH (5 mL), and stir at RT overnight. Cool the reaction mixture to −78° C. and drop wise add 2M LiBH$_4$ in THF (1.698 mL, 3.397 mmol). Place reaction in an ice bath and allow to warm to RT with stirring for 3 hr. Quench the reaction mixture with saturated aqueous NaHCO₃ solution and dilute with DCM. Separate the organic layer and additionally extract the aqueous layer with DCM. Combine the organic phases, dry over Na₂SO₄, filter, and concentrate the filtrate in vacuo. Subject the resulting residue to chromatography on silica, eluting with a gradient of 0-10% MeOH in DCM, and concentrate the resulting mixture of trans- and cis-isomers in vacuo. Subject the resulting mixture to reverse phase chromatography, eluting with a gradient of 10-75% ACN in 10 mM aqueous NH₄CO₃/water, to afford the title compound (0.132 g, 18% yield) as a white solid after solvent evaporation. ES/MS (m/z): 533 (M+H).

Preparation 109

2-[(Trans-4-aminocyclohexyl)(ethyl)amin]-5-[(4,6-dimethyl-2-oxo-1,2-dihydropyridin-3-yl)methyl]-3-methyl-6,7-dihydrothieno[3,2-c]pyridin-4(5H)-one

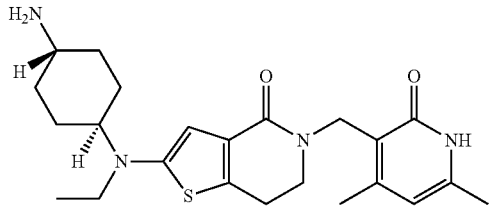 [SMILES: CCN(c1cc2c(s1)CCN(Cc1c(C)cc(C)[nH]c1=O)C2=O)[C@H]1CC[C@H](N)CC1]

To a round bottom flask, add 2-{[trans-4-(benzylamino)cyclohexyl](ethyl)amino}-5-[(4,6-dimethyl-2-oxo-1,2-dihydropyridin-3-yl)ethyl]-3-methyl-6,7-dihydrothieno[3,2-c]pyridin-4(5H)-one (0.095 g, 0.178 mmol), 10% Pd on carbon (0.095 g) and NH₄HCO₂ (0.057 g, 0.892 mmol) in wet 90% EtOH (0.89 mL). Degas with N₂ for 10 min, seal the reaction vessel, and heat at 90° C. overnight. Cool the reaction mixture to RT, filter through diatomaceous earth, and concentrate the filtrate in vacuo. Subject the resulting residue to chromatography on silica, eluting with a gradient of 7-100% 87.5:11:1.5 solution of DCM:MeOH:NH₄OH/DCM to afford the title compound (0.045 g, 57% yield) as a white powder after solvent evaporation. ES/MS (m/z): 443 (M+H).

Preparation 110 tert-Butyl 4-(ethyl{5-[(2-methoxy-4,6-dimethylpyridin-3-yl)methyl]-3-methyl-4-oxo-4,5,6,7-tetrahydrothieno[3,2-c]pyridin-2-yl}amino)piperidine-1-carboxylate

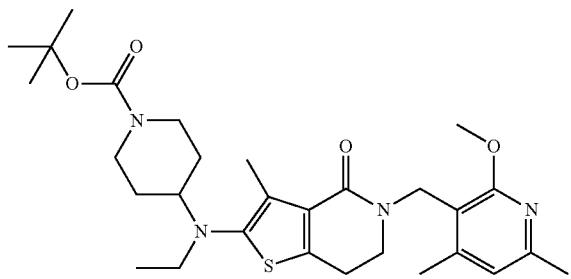 [SMILES: CCN(c1sc2c(c1C)C(=O)N(Cc1c(C)cc(C)nc1OC)CC2)C1CCN(C(=O)OC(C)(C)C)CC1]

To a round bottom flask, add tert-butyl 4-[ethyl(3-methyl-4-oxo-4,5,6,7-tetrahydrothieno[3,2-c]pyridin-2-yl)amino]piperidine-1-carboxylate (0.770 g, 1.957 mmol) and 3-(chloromethyl)-2-methoxy-4,6-dimethyl-pyridine (0.436 g, 2.348 mmol) in THF (20 mL) containing a solution of KHMDS in THF (0.91M, 2.6 mL, 2.348 mmol). Stir the reaction mixture at RT for 4 hr, quench with ice-cold saturated aqueous NaHCO₃, dilute with EtOAc, separate the layers, and extract the aqueous layer with additional EtOAc. Combine the organic phases, dry over Na₂SO₄, filter, and concentrate the filtrate in vacuo to afford the title compound (1.17 g, 99% yield) as yellow oil, sufficient for use without additional purification. ES/MS (m/z): 543 (M+H).

Preparation 111

2-(Ethyl{4-[(2-methoxyethyl)(methyl)amino]cyclohexyl}amino)-5-[(2-methoxy-4,6-dimeihylpyridin-3-yl)methyl]-3-methyl-6,7-dihydrothieno[3,2-c]pyridin-4(5H)-one (mixture of cis- and trans-diastereomers)

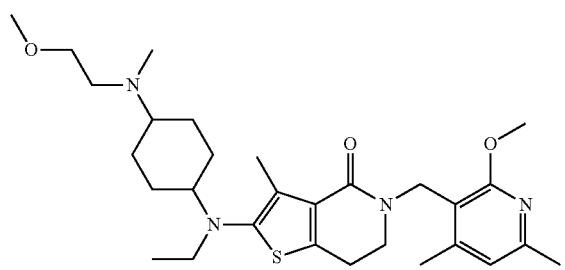

Add 2-[ethyl(4-oxocyclohexyl)amino]-5-[(2-methoxy-4,6-dimethylpyridin-3-yl)methyl]-3-methyl-6,7-dihydrothieno[3,2-c]pyridin-4(5H)-one (0.57 g, 1.25 mmol) to a solution of 2-methoxyethanamine (0.19 g, 2.64 mmol) in MeOH (10 mL) and stir the mixture for 4 hr. Cool to −78° C. and add a 2M solution of LiBH₄ in THF (0.82 mL, 1.63 mmol). Slowly increase the temperature to RT and stir 1 hr. Concentrate the mixture in vacuo, add saturated aqueous NaHCO₃, extract with EtOAc, separate the resulting layers, dry the organic layer over Na₂SO₄, filter, and concentrate the filtrate in vacuo. Dissolve the resulting residue in DCM (6.2 mL) and add 37% formaldehyde in H₂O (0.27 mL, 3.7 mmol), stir the resulting mixture at RT for 15 min, then add sodium triacetoxyborohydride (1.06 g, 5.03 mmol) and stir the resulting mixture at RT overnight. Load the contents of the reaction mixture onto an SCX cartridge, eluting first with MeOH then with 2M NH₃ in MeOH, and concentrate the methanolic ammonia fractions in vacuo to afford the title compound as oil (0.57 g, 86% yield) after solvent evaporation. ES/MS (m/z): 529 (M+H).

Preparation 112

2-[{4-trans-[Cyclopropyl(methyl)amino]cyclohexyl}(ethyl)amino]-5-[(2-methoxy-4,6-dimethylpyridin-3-yl)methyl]-3-methyl-6,7-dihydrothieno[3,2-c]pyridin-4(5H)-one

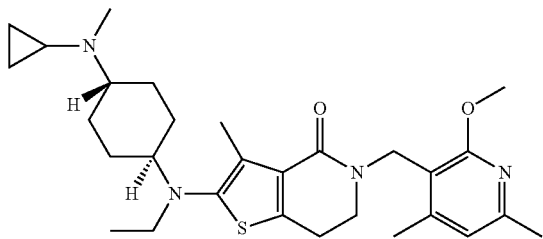 [SMILES: CCN(c1sc2c(c1C)C(=O)N(Cc1c(C)cc(C)nc1OC)CC2)[C@H]1CC[C@H](N(C)C2CC2)CC1]

Add 2-[ethyl(4-oxocyclohexyl)amino]-5-[(2-methoxy-4,6-dimethylpyridin-3-yl)methyl]-3-methyl-6,7-dihydrothieno[3,2-c]pyridin-4(5H)-one (0.57 g, 1.26 mmol) to a solution of cyclopropanamine (0.15 g, 2.641 mmol) in MeOH (10 mL) and stir the mixture for 4 hr. Cool to −78° C., and add a 2M solution of LiBH$_4$ in THF (0.82 mL, 1.64 mmol). Slowly warm the reaction mixture to RT and stir 1 hr. Remove solvent in vacuo, add saturated aqueous NaHCO$_3$ solution, extract with EtOAc, separate the resulting layers, and dry the organic phase over Na$_2$SO$_4$. Filter and concentrate the filtrate in vacuo. Dissolve the resulting residue in DCM (6.2 mL), add 37% formaldehyde solution in H$_2$O (0.27 mL, 3.77 mmol), and stir 15 min. Then, add sodium triacetoxyborohydride (0.8 g, 5.03 mmol) and stir at RT overnight. Load the reaction mixture directly onto an SCX cartridge, eluting first with MeOH then with 2M NH$_3$ in MeOH. Concentrate the methanolic ammonia fraction in vacuo to afford oil (0.56 g, 87% yield) after solvent evaporation, suitable for use without additional purification. ES/MS (m/z): 511 (M+H).

Preparation 113

Methyl 2-bromo-5-{[trans-4-(3-ethoxyazetidin-1-yl)cyclohexyl](ethyl)amino}-4-methylthiophene-3-carboxylate

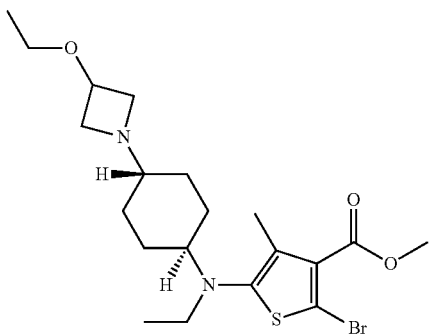 [SMILES: CCOC1CN([C@H]2CC[C@H](N(CC)c3sc(Br)c(C(=O)OC)c3C)CC2)C1]

To a crude sample of methyl 2-bromo-5-[ethyl(4-oxocyclohexyl)amino]-4-methylthiophene-3-carboxylate (2.17 g, 5.80 mmol) in DCM (20 mL), add titanium(IV) isopropoxide (6.79 g, 23.2 mmol) and 3-ethoxyazetidine hydrochloride (1.60 g, 11.6 mmol). Stir the reaction at RT for about 18 hr. Add THF (20 mL), then concentrate the mixture in vacuo to about 20 mL. Cool the resulting mixture to −78° C., then add MeOH (25 mL) followed by the drop wise addition of 2M LiBH$_4$ in THF (4.34 mL, 8.70 mmol). Stir the resulting mixture for about 3 hr, then remove the cold bath and allow the mixture to warm slowly to RT. Dilute the reaction mixture with EtOAc (200 mL) and saturated aqueous NaHCO$_3$ solution (50 mL), filter away the solids, concentrate the filtrate in vacuo, dilute the residue with EtOAc (50 mL), and filter the solids again. Concentrate the organic layer in vacuo to afford the title compound (2.25 g, 78% yield) as yellow gum, suitable for use without separation of the isomers or further chromatography. ES/MS (m/z): ($^{79}$Br/$^{81}$Br) 459/461 (M+H).

Preparation 114

Methyl 2-{2-[(tert-buloxycarbonyl)amino]ethyl}-5-{[trans-4-(3-ethoxyazetidin-1-yl)cyclohexyl](ethyl)amino}-4-methylthiophene-3-carboxylate

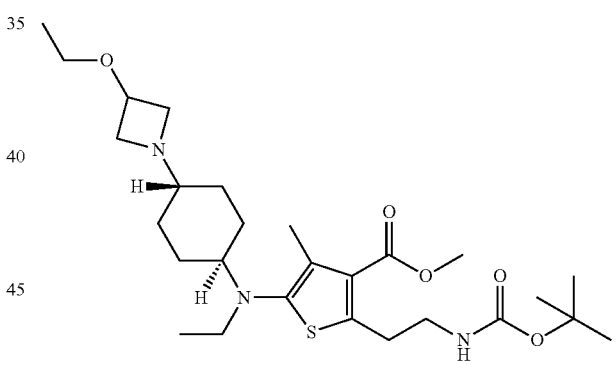

Add potassium tert-butyl N-[2-(trifluoroboranuidyl)ethyl]carbamate (0.47 g, 1.8 mmol) and cesium carbonate (0.89 g, 2.7 mmol, 0.89 g) in water (0.6 mL) to crude methyl 2-bromo-5-{[trans-4-(3-ethoxyazetidin-1-yl)cyclohexyl](ethyl)amino}-4-methylthiophene-3-carboxylate (0.68 g, 1.4 mmol) in toluene (6 mL), then add palladium(II) acetate (0.031 g, 0.14 mmol) and 2-dicyclohexylphosphino-2',6'-diisopropoxy-1,1'-biphenyl (0.13 g, 0.27 mmol). Degas the resulting mixture with streaming N$_2$. Heat the resulting mixture at 100° C. for about 2 hr, dilute the mixture with EtOAc (60 mL), and separate the layers. Dry the organic layer over Na$_2$SO$_4$, filter, and concentrate the filtrate in vacuo. Subject the resulting residue to chromatography on silica, eluting with a gradient of 0-10% 7N NH$_3$ in MeOH/DCM, to afford the title compound (0.401 g, 44% yield) as yellow gum after solvent evaporation. ES/MS (m/z): 524 (M+H).

Preparation 115

Methyl 2-(2-aminoethyl)-5-{[trans-4-(3-ethoxyazetidin-1-yl)cyclohexyl](ethyl)amino}-4-methylthiophene-3-carboxylate

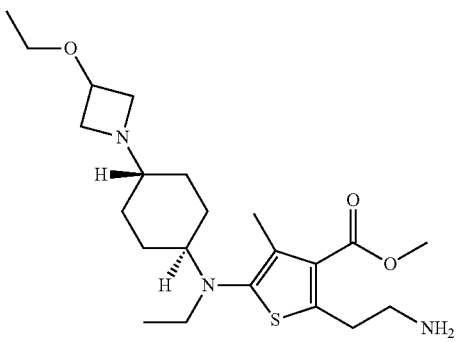 [SMILES: CCOC1CN([C@H]2CC[C@H](N(CC)c3sc(CCN)c(C(=O)OC)c3C)CC2)C1]

Add 4M HCl in dioxane (5 mL, 20 mmol) to methyl 2-{2-[(tert-butoxycarbonyl)amino]ethyl}-5-{[trans-4-(3-ethoxyazetidin-1-yl)cyclohexyl](ethyl)amino}-4-methylthiophene-3-carboxylate (0.401 g, 0.605 mmol) in DCM (5 mL) at RT. Stir the reaction for about 2 hr at RT and concentrate the mixture in vacuo. Add MeOH (5 mL), and concentrate the mixture in vacuo again. Dilute the resulting residue with DCM (25 mL), wash with saturated aqueous NaHCO₃ solution (3 mL), separate the layers, and dry the organic layer over Na₂SO₄. Filter and concentrate the filtrate in vacuo to afford the crude title compound (0.380 g, 95% yield) as yellow gum, suitable for use without additional purification. ES/MS (m/z): 424 (M+H).

Preparation 116

2-{[Trans-4-(3-ethoxyazetidin-1-yl)cyclohexyl] (ethyl)amino}-3-methyl-6,7-dihydrothieno[3,2-c] pyridin-4(5H)-one

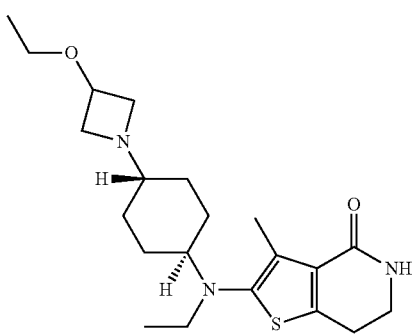 [SMILES: CCOC1CN([C@H]2CC[C@H](N(CC)c3sc4c(c3C)C(=O)NCC4)CC2)C1]

Heat methyl 2-(2-aminoethyl)-5-{[trans-4-(3-ethoxyazetidin-1-yl)cyclohexyl](ethyl)amino}-4-methylthiophene-3-carboxylate (0.380 g, 0.574 mmol) in MeOH (4 mL) to reflux for 3 hr, concentrate the reaction mixture in vacuo, and subject the residue to reverse phase chromatography over C-18 silica (WATERS™ XBRIDGE® OBD, 30×75 min, 5 µm), eluting with a gradient of 20-90% ACN in 10 mM aqueous NH₄CO₃ containing 5% MeOH, to afford the title compound (0.113 g, 50% yield) as off-white gum after solvent evaporation. ES/MS (m/z): 392 (M+H).

Preparation 117

5-{[2-(Benzyloxy)-4,6-dimethylpyridin-3-yl] methyl}-2-{[trans-4-(3-ethoxyazetidin-1-yl)cyclohexyl](ethyl)amino}-3-methyl-6,7-dihydrothieno[3, 2-c]pyridin-4(5H)-one

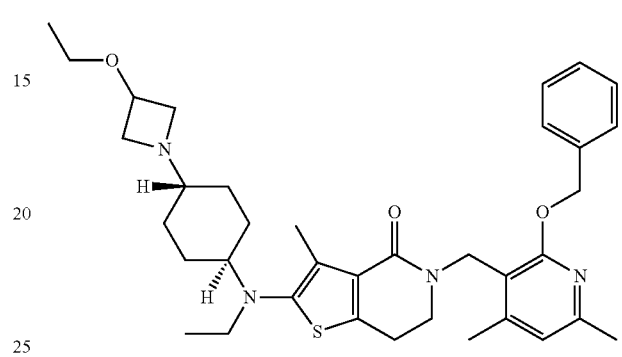

Cool 2-{[trans-4-(3-ethoxy azetidin-1-yl)cyclohexyl] (ethyl)amino}-3-methyl-6,7-dihydrothieno[3,2-c]pyridin-4 (5H)-one (0.113 g, 0.289 mmol) in THF (2 mL) in an ice bath, add 1M KHMDS in THF (0.404 mL, 0.404 mmol), remove the ice bath, warm to RT, and stir the mixture for 30 min Drop wise add 2-benzyloxy-3-(chloromethyl)-4,6-dimethyl-pyridine (0.113 g, 0.433 mmol) in THF (2 mL). Stir the reaction mixture at RT for 22 hr. Quench the reaction mixture with saturated aqueous NH₄Cl (2 mL), extract with EtOAc (40 mL), separate the organic layer, dry over Na₂SO₄, filter, and concentrate the filtrate in vacuo. Subject the resulting residue to chromatography on silica gel, eluting with a gradient of 0-10% 7N NH₃/MeOH in DCM, to afford the title compound (0.084 g, 45% yield) as yellow gum. ES/MS (m/z): 617 (M+H).

Preparation 118

5-[(4-Chloro-2-ethoxy-6-methylpyridin-3-yl) methyl]-2-[1,4-dioxaspiro[4.5]dec-8-yl(ethyl) amino]-3-methyl-6,7-dihydrothieno[3,2-c]pyridin-4 (5H)-one

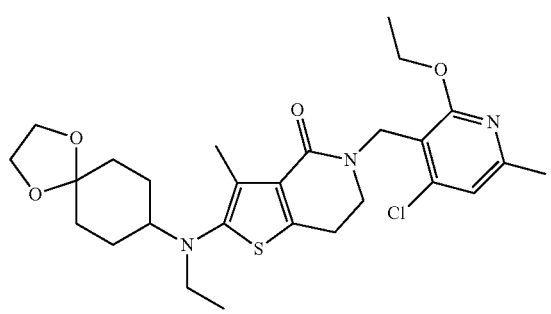 [SMILES: CCOc1nc(C)cc(Cl)c1CN1CCc2sc(N(CC)C3CCC4(CC3)OCCO4)c(C)c2C1=O]

Add pulverized KOH (0.427 g, 7.53 mmol) to a solution of 2-[1,4-dioxaspirol[4.5]dec-8-yl(ethyl)amino]-3-methyl-6,7-dihydrothieno[3,2-c]pyridin-4(5H)-one (0.660 g, 1.88 mmol) in THF (10 mL) in one portion. Stir the resulting mixture for 30 min, add 4-chloro-3-(chloromethyl)-2-ethoxy-6-methylpyridine (0.500 g, 2.27 mmol) in THF (1 mL), and stir the resulting mixture at RT overnight. Quench the mixture with saturated aqueous NaHCO$_3$, extract with DCM, separate the layers, dry the organic phase over anhydrous Na$_2$SO$_4$, filter, and concentrate the filtrate in vacuo. Subject the resulting residue to chromatography on silica, eluting with a gradient of 0-100% EtOAc in hexanes, to afford the title compound (0.988 g, 98% yield), as pale yellow oil after solvent evaporation. ES/MS (m/z): ($^{35}$Cl/$^{37}$Cl) 534/536 (M+H).

Preparation 119

5-[(4-Chloro-6-methyl-2-oxo-1,2-dihydropyridin-3-yl)methyl]-2-[ethyl(4-oxocyclohexyl)amino]-3-methyl-6,7-dihydrothieno[3,2-c]pyridin-4(5H)-one

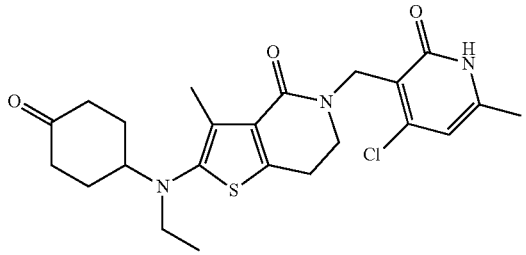 [SMILES: CCN(c1sc2c(c1C)C(=O)N(Cc1c(Cl)cc(C)[nH]c1=O)CC2)C1CCC(=O)CC1]

Add LiCl (0.395 g, 9.22 mmol) and PTSA (1.67 g, 9.21 mmol) to a solution of 5-[(4-chloro-2-ethoxy-6-methylpyridin-3-yl)methyl]-2-[1,4-dioxaspirol[4.5]dec-8-yl(ethyl) amino]-3-methyl-6,7-dihydrothieno[3,2-c]pyridin-4(5H)-one (0.985 g, 1.84 mmol) in DMF (20 mL) and heat the resulting mixture at 70° C. for 1 hr. Increase the temperature to 90° C., stir for 5 hr, cool the mixture to RT, add water, and stir at RT overnight. Quench the mixture with saturated aqueous NaHCO$_3$, extract with DCM, separate the resulting layers, and wash the organic phase with 5% aqueous LiCl. Separate the layers, dry the organic phase over anhydrous Na$_2$SO$_4$, filter, and concentrate the filtrate in vacuo. Subject the resulting residue to chromatography on silica, eluting with a gradient of 0-50% EtOAc in hexanes followed by a gradient of 0-20% MeOH in DCM, to afford the title compound (0.450 g, 26% yield), as orange oil after solvent evaporation. ES/MS (m/z): ($^{35}$Cl/$^{37}$Cl) 462/464 (M+H).

Preparation 120

Methyl 2-(3-{[(benzyloxy)carbonyl]amino}prop-1-yn-1-yl)-5-[2,4-dioxaspiro[4.5]dec-8-yl(ethyl) amino]-4-methylthiophene-3-carboxylate

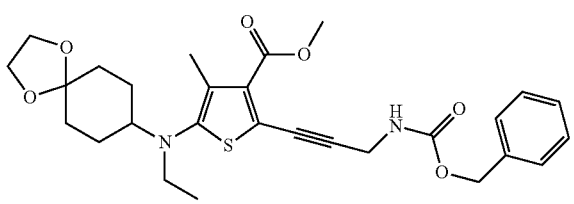 [SMILES: CCN(c1sc(C#CCNC(=O)OCc2ccccc2)c(C(=O)OC)c1C)C1CCC2(CC1)OCCO2]

Add TEA (55.6 g, 550.0 mol) to a mixture of methyl 2-bromo-5-[1,4-dioxaspirol[4.5]dec-8-yl(methyl)amino]-4-methylthiophene-3-carboxylate (7.9 g, 19.0 mmol), CuI (1.5 g, 7.90 mmol), and benzyl N-prop-2-ynylcarbamate (8.9 g, 47 mmol) in THF (200 mL). Degas the mixture with streaming N$_2$ and add bis(triphenylphosphine)palladium (II) dichloride (2.8 g, 3.9 mmol). Stir the mixture at RT overnight. Filter the reaction mixture over diatomaceous earth, and concentrate the filtrate in vacuo. Subject the resulting residue to chromatography on silica, eluting with a gradient of 0-60% EtOAc in hexanes, to afford the title compound (8.2 g, 82% yield) after solvent evaporation. ES/MS (m/z): 513 (M+H).

Preparation 121

Methyl 2-(3-aminopropyl)-5-[1,4-dioxaspiro[4.5]dec-8-yl(ethyl)amino]-4-methylthiophene-3-carboxylate

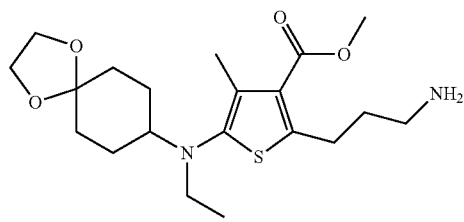 [SMILES: CCN(c1sc(CCCN)c(C(=O)OC)c1C)C1CCC2(CC1)OCCO2]

To a pressure vessel, add a solution of methyl 2-(3-{[(benzyloxy)carbonyl]amino}prop-1-yn-1-yl)-5-[1,4-dioxaspirol[4.5]dec-8-yl(ethyl)amino]-4-methylthiophene-3-carboxylate (7.6 g, 14 mmol) in MeOH (200 mL) containing TEA (1.0 mL, 7.1 mmol) and 10% Pd on carbon (3 g, 2.82 mmol). Fill the reaction vessel with H$_2$ (414 kPa) and stir for 4 hr. Filter the reaction mixture over diatomaceous earth, concentrate the filtrate in vacuo to approximately 150 mL, add 20% Pd(OH)$_2$ on carbon (2.0 g), degas with N$_2$ followed by H$_2$, and stir under an atmosphere of H$_2$ overnight. Filter the reaction mixture over a bed of diatomaceous earth, concentrate in vacuo to about 100 mL, add 20% Pd(OH)$_2$ on carbon (1.2 g) and stir under H$_2$ (414 kPa) overnight. Filter the reaction over diatomaceous earth and concentrate the filtrate in vacuo to afford the title compound (6.5 g, quantitative yield) as brown oil, suitable for use without additional purification. ES/MS (m/z): 397 (M+H).

Preparation 122

2-[1,4-Dioxaspiro[4.5]dec-8-yl(ethyl)amino]-3-methyl-5,6,7,8-tetrahydro-4H-thieno[3,2-c]azepin-4-one

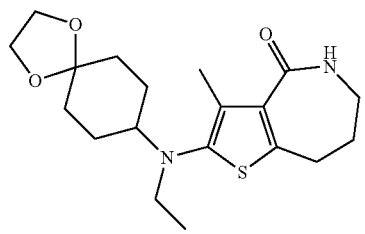 [SMILES: CCN(c1sc2c(c1C)C(=O)NCCC2)C1CCC2(CC1)OCCO2]

Add KOtBu (3 g, 25 mmol) to a solution of methyl 2-(3-aminopropyl)-5-[1,4-dioxaspirol[4.5]dec-8-yl(ethyl)amino]-4-methylthiophene-3-carboxylate (7.6 g, 19 mmol) in THF (200 mL) and TEA (1.0 mL, 7.1 mmol). Heat the mixture at 80° C. for 4 hr, cool to RT, and add water (100 mL). Concentrate the entire mixture in vacuo and treat the resulting residue with a small amount of MeOH until a solid appears. Filter off the resulting solid and concentrate the filtrate in vacuo. Subject the resulting residue to reverse phase chromatography over C-18 silica (Thermo Scientific Hypersil GOLD™), eluting with a gradient of 0-50% ACN containing 0.1% formic acid and water containing 0.1% formic acid, to afford the title compound (1.7 g, 24% yield) as a light brown solid after solvent evaporation. ES/MS (m/z): 365 (M+H).

Preparation 123

5-[(4,6-Dimethyl-2-oxo-1,2-dihydropyridin-3-yl)methyl]-2-[ethyl(4-oxocyclohexyl)amino]-3-methyl-5,6,7,8-tetrahydro-4H-thieno[3,2-c]azepin-4-one

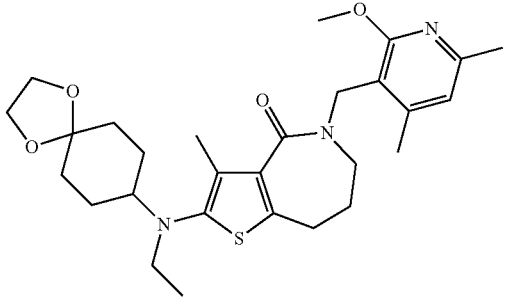 [SMILES: CCN(c1sc2c(c1C)C(=O)N(Cc1c(C)cc(C)nc1OC)CCC2)C1CCC2(CC1)OCCO2]

To a solution of 2-[1,4-dioxaspiro[4.5]dec-8-yl(ethyl)amino]-3-methyl-5,6,7,8-tetrahydro-4H-thieno[3,2-c]azepin-4-one (1.7 g, 4.7 mmol) in dimethyl sulfoxide (20 mL) and THF (20 mL), and add pulverized KOH (1.1 g, 19 mmol). Stir the mixture for 30 min, then add 3-(chloromethyl)-2-methoxy-4,6-dimethyl-pyridine (1.0 g, 5.4 mmol). Stir the resulting mixture for 1 hr, pour the mixture into ice-cold aqueous NaHCO₃ solution, and extract with DCM. Separate the resulting layers and concentrate the organic phase in vacuo to afford the title compound (2.1 g, 61% yield) as brown oil, suitable for use without additional purification. ES/MS (m/z): 514 (M+H).

Preparation 124

5-[(4,6-Dimethyl-2-oxo-1,2-dihydropyridin-3-yl)methyl]-2-[ethyl(4-oxocyclohexyl)amino]-3-methyl-5,6,7,8-tetrahydro-4H-thieno[3,2-c]azepin-4-one

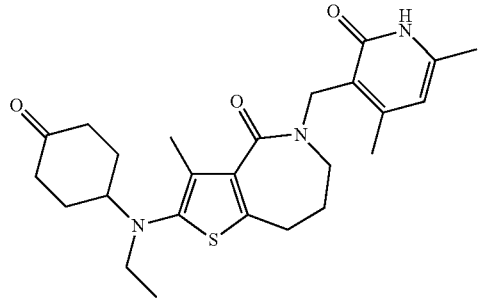 [SMILES: CCN(c1sc2c(c1C)C(=O)N(Cc1c(C)cc(C)[nH]c1=O)CCC2)C1CCC(=O)CC1]

Add LiCl (0.830 g, 19.4 mmol) and PTSA (3.5 g, 19 mmol) to a solution of 2-[1,4-dioxaspiro[4.5]dec-8-yl(ethyl)amino]-5-[(2-methoxy-4,6-dimethylpyridin-3-yl)methyl]-3-methyl-5,6,7,8-tetrahydro-4H-thieno[3,2-c]azepin-4-one (2.0 g, 2.7 mmol, ~70% purity) in DMF (20 mL) and heat the resulting mixture at 70° C. for 1 hr. Cool the reaction mixture to RT, pour into ice-cold saturated aqueous NaHCO₃ solution, extract with DCM (2×100 mL), and separate the layers. Concentrate the combined organic layers in vacuo. Subject the resulting residue to chromatography on silica, eluting with a gradient of 0-10% MeOH in DCM, to afford the title compound (1.8 g, ~85% purity by analytical LCMS) as light brown oil after solvent evaporation. ES/MS (m/z): 456 (M+H).

Preparation 125

Methyl 2-(3-{[(benxyloxy)carbonyl]amino}prop-1-yn-1-yl)-5-[1,4-dioxaspiro[4.5]dec-8-yl(methyl)amino]-4-methylthiophene-3-carboxylate

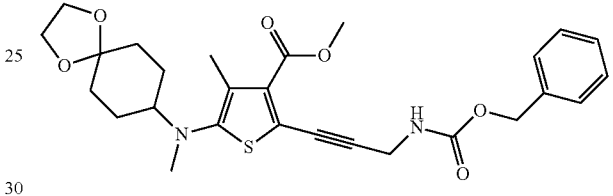

Add TEA (35.4 g, 350.0 mmol) to a suspension of methyl 2-bromo-5-[1,4-dioxaspirol[4.5]dec-8-yl(methyl)amino]-4-methylthiophene-3-carboxylate (5.40 g, 13.0 mmol), CuI (0.987 g, 5.18 mmol) and benzyl N-prop-2-ynylcarbamate (3.17 g 14.3 mmol, 85% purity) in 1,4-dioxane (54 mL). Degas the mixture with streaming N₂, add bis(triphenylphosphine) palladium(II) dichloride (1.84 g, 2.59 mmol), stir the mixture at 40° C. for 1 hr, add additional benzyl N-prop-2-ynylcarbamate (3.17 g, 14.3 mmol, 85% purity), and heat at 40° C. for 1 hr. Concentrate the reaction mixture in vacuo, add DCM/hexanes (approximately 1:1), filter, and concentrate the filtrate in vacuo. Subject the resulting brown oily residue to chromatography on silica, eluting with a gradient of 0-75% MTBE in hexanes, concentrate the chromatography fractions in vacuo, dissolve the resulting residue in MeOH, and concentrate in vacuo again to afford the title compound (5.23 g, 75% yield) as a sticky brown residue. ES/MS (m/z): 513 (M+H).

Preparation 126

Methyl 2-(3-aminopropyl)-5-[1,4-dioxaspiro[4.5]dec-8-yl(methyl)amino]-4-methylthiophene-3-carboxylate

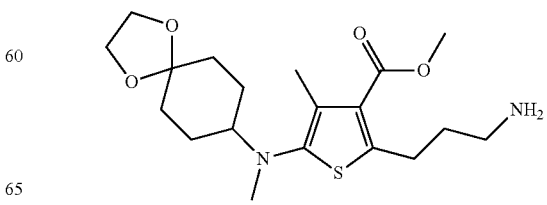

To methyl 2-(3-{[(benzyloxy)carbonyl]amino}prop-1-yn-1-yl)-5-[1,4-dioxaspirol[4.5]dec-8-yl(methyl)amino]-4-methylthiophene-3-carboxylate (5.23 g, 9.18 mmol) in MeOH (45 mL) and EtOAc (15 mL) add TEA (6.40 mL, 45.9 mmol) and 10% Pd on carbon (2.6 g, 2.4 mmol). Evacuate the reaction vessel and stir at RT under H$_2$ (345 kPa) for 5 hr. Add 20% Pd(OH)$_2$ on carbon (2.78 g, 3.96 mmol), evacuate the reaction vessel, charge with H$_2$, and stir for about 17 hr at RT. Add additional 20% Pd(OH)$_2$ on carbon (1.0 g, 1.4 mmol), charge with H$_2$, and stir at RT for 4 hr. Filter the reaction mixture over a bed of diatomaceous earth, and concentrate the filtrate in vacuo. Subject the residue to chromatography on silica, eluting with a gradient of 0-12% 7N methanolic NH$_3$ in DCM. Concentrate the chromatography fractions under reduced pressure, dissolve the resulting residue in MeOH, and concentrate in vacuo again to afford the title compound (2.60 g, 73% yield) as yellow oil. ES/MS (m/z): 383 (M+H).

Preparation 127

2-[1,4-Dioxaspiro[4.5]dec-8-yl(methyl)amino]-3-methyl-5,6,7,8-tetrahydro-4h-thieno[3,2-c]azepin-4-one

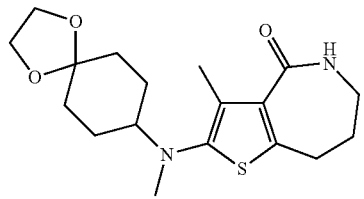 [SMILES: Cc1c(N(C)C2CCC3(CC2)OCCO3)sc2c1C(=O)NCCC2]

Add KOtBu (20% wt. in THF, 5.46 g, 9.72 mmol) to a mixture of methyl 2-(3-aminopropyl)-5-[1,4-dioxaspirol[4.5]dec-8-yl(methyl)amino]-4-methylthiophene-3-carboxylate (2.53 g, 6.48 mmol) in toluene (25 mL). Stir at 120° C. for 1 hr, cool to RT, add propylphosphonic anhydride (50% wt. in ethyl acetate, 0.386 mL 0.648 mmol) and stir for 30 min. Quench the reaction mixture with saturated NH$_4$Cl solution, dilute with EtOAc (about 50 mL), and separate the layers. Dry the organic layer over Na$_2$SO$_4$, filter, and concentrate the filtrate in vacuo to afford the title compound (2.21 g, 97% yield) as yellow oil, suitable for use without additional purification. ES/MS (m/z): 351 (M+H).

Preparation 128

5-{[2-(Benzyloxy)-4,6-dimethylpyridin-3-yl]methyl}-2-[1,4-dioxaspiro[4.5]dec-8-yl(methyl)amino]-3-methyl-5,6,7,8-tetrahydro-4H-thieno[3,2-c]azepin-4-one

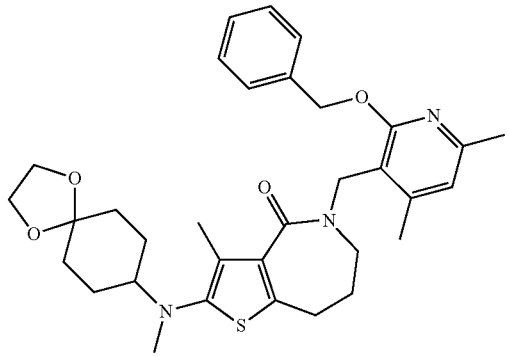 [SMILES: Cc1cc(C)c(CN2CCCc3sc(N(C)C4CCC5(CC4)OCCO5)c(C)c3C2=O)c(OCc2ccccc2)n1]

To a solution of 2-[1,4-dioxaspiro[4.5]dec-8-yl(methyl)amino]-3-methyl-5,6,7,8-tetrahydro-4h-thieno[3,2-c]azepin-4-one (2.21 g, 6.31 mmol) in THF (10 mL) and dimethyl sulfoxide (10 mL) add pulverized KOH (1.43 g, 25.2 mmol) in one portion, stir for 30 min, then add 2-benzyloxy-3-(chloromethyl)-4,6-dimethyl-pyridine (1.98 g, 6.81 mmol, 90% purity) dissolved in THF (2 mL). Stir the resulting mixture at RT for 4 hr, then pour into ice-cold aqueous NaHCO$_3$ solution, and extract with DCM. Separate the layers and concentrate the organic layer in vacuo. Subject the resulting residue to chromatography on silica, eluting with a gradient of 0-50% EtOAc in hexanes, to afford the title compound (3.2 g, 86% yield) after solvent evaporation. ES/MS (m/z): 576 (M+H).

Preparation 129

5-[(4,6-Dimethyl-2-oxo-1,2-dihydropyridin-3-yl)methyl]-3-methyl-2-[methyl(4-oxocyclohexyl)amino]-5,6,7,8-tetrahydro-4H-thieno[3,2-c]azepin-4-one

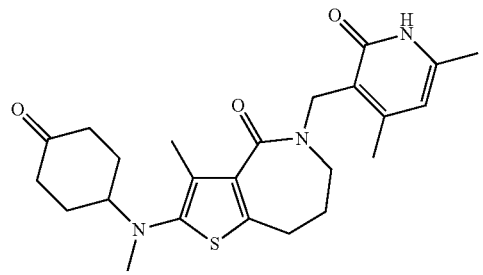 [SMILES: Cc1cc(C)c(CN2CCCc3sc(N(C)C4CCC(=O)CC4)c(C)c3C2=O)c(=O)[nH]1]

Add LiCl (1.4 g, 33 mmol) and PTSA (5.8 g, 32 mmol) to a solution of 5-{[2-(benzyloxy)-4,6-dimethylpyridin-3-yl]methyl}-2-[1,4-dioxaspiro[4.5]dec-8-yl(methyl)amino]-3-methyl-5,6,7,8-tetrahydro-4H-thieno[3,2-c]azepin-4-one (3.2 g, 5.4 mmol) in DMF (30 mL). Heat at 70° C. for 1 hr, cool to RT, pour into ice-cold saturated aqueous NaHCO$_3$ solution, and extract with DCM. Separate the resulting layers and concentrate the organic phase in vacuo. Subject the resulting residue to chromatography on silica, eluting with a gradient of 0-5% 7N methanolic NH$_3$ in DCM, to afford the title compound (1.7 g, 60% yield) as a white solid after solvent evaporation. ES/MS (m/z): 442 (M+H).

Preparation 130

5-[(2-methoxy-4,6-dimethyl-3-pyridyl)methyl]-2-[(1R)-1-{trans-4-[2-methoxyethyl(methyl)amino]cyclohexyl}ethyl]-3-methyl-6,7-dihydrothieno[3,2-c]pyridin-4-one

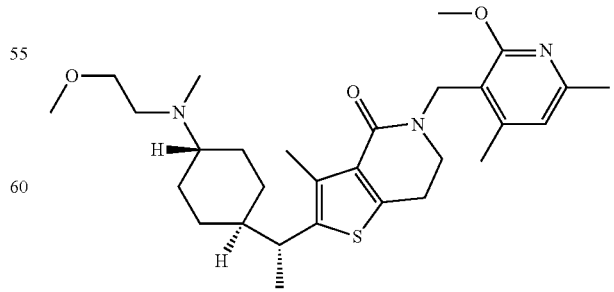

Dissolve 2-methoxyethanamine (100 mg, 1.33 mmol) in MeOH (4 mL) and add 5-[(2-methoxy-4,6-dimethylpyridin- 3-yl)methyl]-3-methyl-2-[(1R)-1-(4-oxocyclohexyl)ethyl]-6,7-dihydrothieno[3,2-c]pyridin-4(5H)-one (160 mg, 0.36 mmol). Stir the mixture for 4 hours. Cool to −78° C. and drop wise add 2M LiBH$_4$ in THF (235 μL, 0.47 mmol). Stir the resulting mixture for 15 minutes and warm to RT with stirring for 1 hr. Concentrate the reaction mixture in vacuo and dilute with DCM and saturated aqueous NaHCO$_3$. Separate the layers, extract the aqueous phase with additional DCM, combine the organic extracts, and dry the organic phase over MgSO$_4$. Filter and concentrate the filtrate to obtain crude 5-[(2-methoxy-4,6-dimethyl-3-pyridyl)methyl]-2-[(1R)-1-{trans-4-[(2-methoxyethylamino)cyclohexyl]ethyl}-3-methyl-6,7-dihydrothieno[3,2-c]pyridin-4-one (150 mg, 83% yield) as oil, sufficient for use in the next step without additional purification. ES/MS (m/z): 500 (M+H).

Dissolve the crude 5-[(2-methoxy-4,6-dimethyl-3-pyridyl)methyl]-2-[(1R)-1-{trans-4-[(2-methoxyethylamino)cyclohexyl]ethyl}-3-methyl-6,7-dihydrothieno[3,2-c]pyridin-4-one (100 mg, 0.20 mmol) in DCM (2 mL) and add a solution of 37% aqueous formaldehyde (0.4 mL, 5.0 mmol); stir the mixture at RT for 15 mm Add Na(OAc)$_3$BH (170 mg, 0.80 mmol) and stir the mixture at RT for about 3 hours. Add an additional solution of 37% aqueous formaldehyde (1.5 mL, 18.75 mmol) to the reaction mixture and stir for 2 hr at RT. Concentrate the reaction mixture in vacuo and add DCM (25 mL). Further suspend the mixture in MeOH (8 mL) with TEA (1.5 mL, 11 mmol). Add a solution of 37% aqueous formaldehyde (6 mL, 80.0 mmol). Stir the mixture at RT for 1 hr. Add Na(OAc)$_3$BH (300 mg, 1.42 mmol) and stir the resulting mixture at RT for approximately 4 hr. Dilute the reaction with DCM (40 mL) and saturated aqueous NaHCO$_3$ (1.0 mL). Separate the layers, dry the organic phase over MgSO$_4$ and concentrate the filtrate in vacuo. Subject the resulting residue to chromatography on silica, eluting with a gradient of 0-10% MeOH in DCM, to afford the title compound (48 mg, 47% yield) after solvent evaporation. ES/MS (m/z): 514 (M+H).

Preparation 131

Methyl 5-[(1R)-1-(1,4-dioxaspiro[4.5]decan-8-yl)ethyl]-2-[3-[(2-methoxy-4,6-dimethyl-3-pyridyl)methylamino]propyl]-4-methyl-thiophene-3-carboxylate

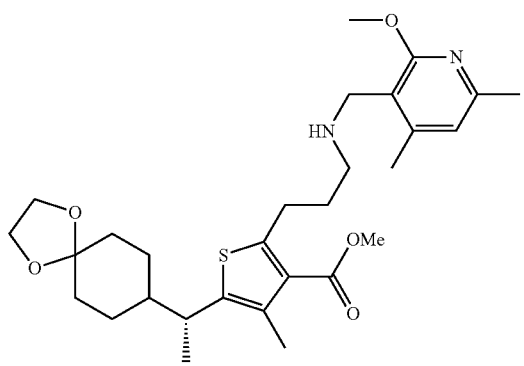 [SMILES: COC(=O)c1c(CCCNCc2c(C)cc(C)nc2OC)sc([C@H](C)C2CCC3(CC2)OCCO3)c1C]

Subject a solution of methyl 2-(3-{[(benzyloxy)carbonyl]amino}prop-1-yn-1-yl)-5-[1,4-dioxaspiro[4.5]dec-8-yl(methyl)amino]-4-methylthiophene-3-carboxylate (803 g, 1.57 mol), 2-methoxy-4,6-dimethyl-pyridine-3-carbaldehyde (314.5 g, 1.90 mol) and palladium Pd(OH)$_2$ on activated carbon (298 g) in EtOH (7.5 L) to hydrogenation at 100 psi at 60° C. Upon ceasing of H$_2$ uptake (18 h), cool the reaction and filter the resulting mixture through diatomaceous earth, rinsing with EtOH (2 L). Remove the solvent under reduced pressure to give the title compound (892 g, >99% yield) as oil. ES/MS (m/z): 531 (M+H).

Preparation 132

5-[(2-Methoxy-4,6-dimethyl-3-pyridyl)methyl]-3-methyl-2-[(1R)-1-(4-oxocyclohexyl)ethyl]-7,8-dihydro-6H-thieno[3,2-c]azepin-4-one

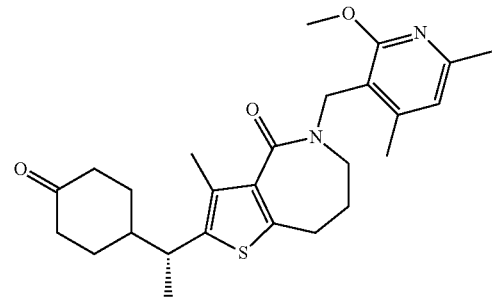 [SMILES: COc1nc(C)cc(C)c1CN1CCCc2sc([C@H](C)C3CCC(=O)CC3)c(C)c2C1=O]

Add potassium trimethylsilanolate (256.7 g, 2.0 mol) to a solution of methyl 5-[(1R)-1-(1,4-dioxaspiro[4.5]decan-8-yl)ethyl]-2-[3-[(2-methoxy-4,6-dimethyl-3-pyridyl)methylamino]propyl]-4-methyl-thiophene-3-carboxylate (531.4 g, 1.0 mol) in THF (6.4 L). Heat the mixture at 65° C. for 18 h, cool to 5° C., and sequentially add TEA (382 ml, 2.7 mol) and triethylamine hydrochloride (471 g, 3.4 mol). After stirring for 10 minutes, add 2,4,6-tripropyl-1,3,5,2,4,6-trioxatriphosphorinane-2,4,6-trioxide in EtOAc (887 ml, 1.5 mol) over a 30 minute period while maintaining the temperature ~5° C. Stir the reaction mixture overnight at RT, and add 2N aqueous HCl (5.0 L, 10.0 mol) at 23° C. Stir the reaction for 16 h, dilute with EtOAc (6.5 L), and neutralize with 2M K$_3$PO$_4$ (6.5 L). Wash the organic layer with saturated aqueous NaCl (3.2 L), separate the layers, dry the organic layer over Na$_2$SO$_4$, filter, and concentrate the resulting filtrate under reduced pressure. Purify the resulting residue by chromatography on silica (4 kg), eluting with a gradient of 10 to 50% EtOAc in heptanes. Triturate the purified fractions with heptanes (2.3 L) and dry under vacuum at 40° C. to obtain the title compound (196.2 g, 43% yield). ES/MS (m/z): 455 (M+H).

Preparation 133

2-[(1R)-1-[4-(3-Methoxyazetidin-1-yl)cyclohexyl]elhyl]-5-[(2-methoxy-4,6-dimethyl-3-pyridyl)methyl]-3-methyl-7,8-dihydro-6H-thieno[3,2-c]azepin-4-one

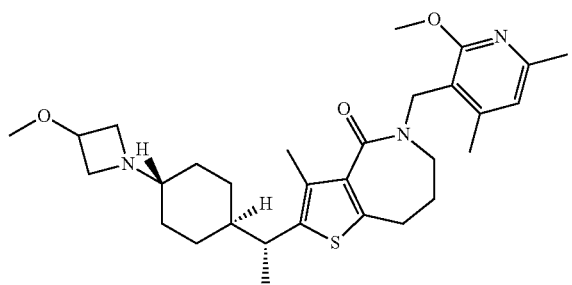

Add 5-[(2-methoxy-4,6-dimethyl-3-pyridyl)methyl]-3-methyl-2-[(1R)-1-(4-oxocyclohexyl)ethyl]-7,8-dihydro-6H-thieno[3,2-c]azepin-4-one (246.3 g, 0.5418 mol) to a solution of 3-methoxyazetidine hydrochloride (186.9 g, 1.51 mol) in MeOH (2.9 L) containing DIPEA (573 ml, 3.29 mol). Stir the resulting reaction mixture at RT overnight. Add THF (991 ml) and cool the solution to −72° C. Add a solution of 2M LiBH₄ in THF (379 ml, 0.758 mol) drop wise over 45 min, while maintaining the internal temperature below −70° C. After stirring for 2.5 h, quench the reaction by adding the reaction mixture to 1M aqueous HCl (6.6 L) over 20 min. Stir the mixture for 10 min and adjust to pH ~9 with 6M aqueous K₂CO₃ (1.25 L). Concentrate the resulting mixture to remove volatiles and dilute the remaining aqueous mixture with EtOAc (6 L). Separate the layers and wash the organic layer sequentially with 3M K₂CO₃ (1.65 L) and saturated aqueous NaCl. Dry the organic layer over Na₂SO₄, filter, and concentrate the filtrate under reduced pressure. Purify the resulting residue over silica gel (3.2 kg), eluting with a gradient of a mixture of 0 to 5% 7N NH3/MeOH in EtOAc, to obtain the title compound (208.6 g, 73% yield) after solvent evaporation. ES/MS (m/z): 526 (M+H).

Example 1

5-[(4,6-Dimethyl-2-oxo-1,2-dihydropyridin-3-yl)methyl]-2-{(1R)-1-[trans-4-(3-methoxyazetidin-1-yl)cyclohexyl]ethyl}-3-methyl-6,7-dihydrothieno[3,2-c]pyridin-4(5H)-one

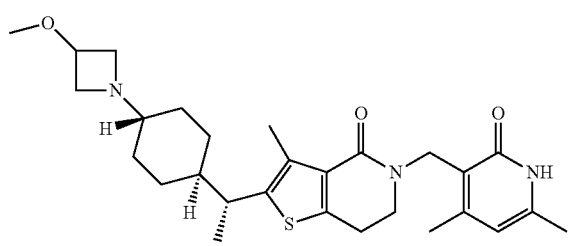

Add LiCl (9.83 g, 230 mmol) and PTSA (41.6 g, 230 mmol) to a solution of 5-[(2-methoxy-4,6-dimethylpyridin-3-yl)methyl]-2-{(1R)-1-[trans-4-(3-methoxyazetidin-1-yl)cyclohexyl]ethyl}-3-methyl-6,7-dihydrothieno[3,2-c]pyridin-4(5H)-one (23.5 g, 45.9 mmol) in DMF (188 mL). Stir the resulting mixture at 50° C. for 8 hr and at RT for 16 hr. Add water (400 mL) and 2M aqueous K₂CO₃ solution (300 mL), extract with EtOAc (2×250 mL), separate the layers, dry the combined organic phases over MgSO₄, filter, and concentrate the filtrate in vacuo. Suspend the resulting solid in heptane (400 mL) and heat at 80° C. for 3 hr. Cool the suspension, filter, and dry under vacuum at 45° C. for 16 hr. Suspend the resulting solid in diisopropyl ether (195 mL), warm at 70° C. for 2 hr, cool the suspension, filter, and dry under vacuum at 45° C. for 16 hr. Suspend the collected solid in water (180 mL) and warm at 70° C. for 5 hr, then at RT for 5 hr. Filter the resulting solids and dry under vacuum at 45° C. for 16 hr to afford the title compound as an off-white solid (16.6 g, 70% yield). ES/MS (m/z): 498 (M+H). $[\alpha]_D^{20}$ 68.93° (c=1.0, MeOH).

Example 2 and 3

Example 2

5-[(4,6-Dimethyl-2-oxo-1,2-dihydropyridin-3-yl)methyl]-3-methyl-2-[(1R)-1-{trans-4-[3-(3-methyl-1H-pyrazol-1-yl)azetidin-1-yl]cyclohexyl}ethyl]6,7-dihydrothieno[3,2-c]pyridin-4(5H)-one

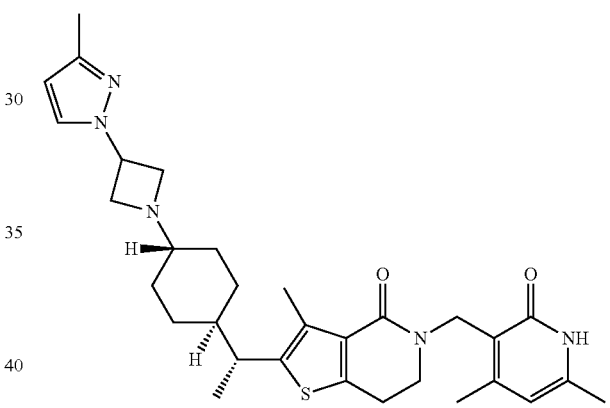

Example 3

5-[(4,6-Dimethyl-2-oxo-1H-pyridin-3-yl)methyl]-3-methyl-2-[(1R)-1-[4-[3-(5-methylpyrazol-1-yl)azetidin-1-yl]cyclohexyl]ethyl]-6,7-dihydrothieno[3,2-c]pyridin-4-one

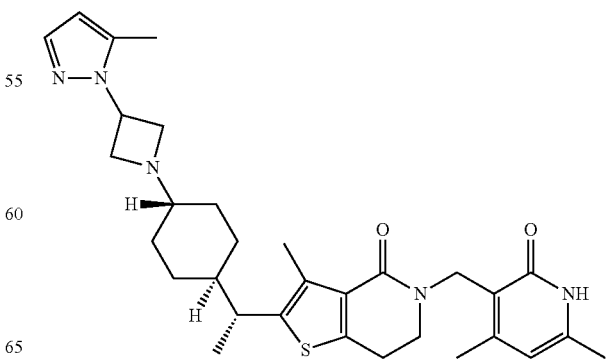

To a solution of 5-[2-methoxy-4,6-dimethylpyridin-3-yl) methyl]-3-methyl-2-[(1R)-1-{trans-4-[3-(3-methyl-1H-pyrazol-1-yl)azetidin-1-yl]cyclohexyl}ethyl]-6,7-dihydrothieno[3,2-c]pyridine-4(5H)-one and 5-[(2-methoxy-4,6-dimethyl-3-pyridyl)methyl]-3-methyl-2-[(1R)-1-[trans-4-[3-(5-methylpyrazol-1-yl)azetidin-1-yl]cyclohexyl]ethyl]-6,7-dihydrothieno[3,2-c]pyridin-4-one (800 mg, 0.925 mmol, mixture of regioisomers) in DMF (5 mL) at 0° C., add LiCl (198 mg, 4.63 mmol) and PTSA (839 mg, 4.63 mmol). Heat the resulting suspension at 50° C. overnight. Add ice-cold saturated aqueous NaHCO$_3$ solution, extract with DCM (2×100 mL), separate the layers, combine organic phases, wash with saturated aqueous NaCl, dry over Na$_2$SO$_4$, filter and concentrate the filtrate in vacuo. Subject the resulting residue to reverse phase chromatography over C-18 silica (XBRIDGE™, 5 µm, 19×100 min, flow rate: 25 mL/min), using a gradient of 40-60% 20 mM aqueous NH$_4$HCO$_3$ (pH 9) in ACN, to afford the title compound as a mixture of regioisomers as a pale yellow solid powder (130 mg, 26%) after solvent evaporation. Separate the regioisomers by preparative SFC chromatography (CHIRALPAK® IA, 35% EtOH (0.2% IPAm)/CO$_2$, 21×250 mm) and the assign structures based on $^1$H and HSQC spectroscopy. Regioisomer 1 (Example 2): 5-[(4,6-Dimethyl-2-oxo-1,2-dihydropyridin-3-yl)methyl]-3-methyl-2-[(1R)-1-{trans-4-[3-(3-methyl-1H-pyrazol-1-yl)azetidin-1-yl]cyclohexyl}ethyl]-6,7-dihydrothieno[3,2-c]pyridin-4(5H)-one, ES/MS (m/z): 548 (M+H), t$_R$=2.93 min (analytical SFC CHIRALPAK® IA, 35% (0.2% IPAm)/CO$_2$, 5 mL/min, 225 nm, 5×25 mm). $^1$H NMR (400.1 MHz, CDCl$_3$): δ 0.87-1.04 (m, 4H), 1.22 (d, J=6.8 Hz, 3H), 1.31-1.25 (m, 1H), 1.60-1.69 (m, 1H), 1.69-1.79 (m, 1H), 1.86-1.91 (m, 1H), 1.92-2.01 (m, 1H), 2.08-2.17 (m, 1H), 2.26 (s, 3H), 2.27 (s, 3H), 2.30 (s, 3H), 2.39 (s, 3H), 2.79-2.89 (m, 3H), 3.33-3.43 (m, 2H), 3.62-3.71 (m, 2H), 3.77 (q, J=6.8 Hz, 2H), 4.71 (s, 2H), 4.85 (quintet, J=7.2 Hz, 1H), 5.92 (s, 1H), 6.01 (d, J=1.9 Hz, 1H), 7.36 (d, J=2.0 Hz, 1H), 12.53-12.55 (bs, 1H). C5 of the pyrazole displays a carbon shift of 128.6 ppm in HSQC spectroscopy. Regioisomer 2 (Example 3): 5-[(4,6-dimethyl-2-oxo-1H-pyridin-3-yl)methyl]-3-methyl-2-[(1R)-1-[4-[3-(5-methylpyrazol-1-yl)azetidin-1-yl]cyclohexyl]ethyl]-6,7-dihydrothieno[3,2-c]pyridin-4-one, ES/MS (m/z): 548 (M+H), t$_R$=3.69 min (analytical SFC CHIRALPAK® IA, 35% (0.2% IPAm)/CO$_2$, 5 mL/min, 225 nm, 5×25 mm). $^1$H NMR (400.1 MHz, CDCl$_3$): δ 0.90-1.04 (m, 4H), 1.21 (d, J=6.9 Hz, 3H), 1.25-1.31 (m, 1H), 1.62-1.67 (m, 1H), 1.79 (s, 1H), 1.84-1.91 (m, 1H), 1.99-2.01 (m, 1H), 2.09-2.19 (m, 1H), 2.23 (s, 3H), 2.26 (s, 3H), 2.30 (s, 3H), 2.39 (s, 3H), 2.81-2.89 (m, 3H), 3.50-3.56 (m, 2H), 3.62-3.71 (m, 2H), 3.79 (q, J=6.7 Hz, 2H), 4.71 (s, 2H), 4.81-4.88 (m, 1H), 5.92 (s, 1H), 5.99 (s, 1H), 7.43 (d, J=1.5 Hz, 1H), 12.32-12.34 (bs, 1H). C3 of the pyrazole displays a carbon shift of 138.4 ppm in HSQC spectroscopy.

Prepare the following compounds essentially by the method of Example 2 utilizing the appropriate 5-[(4,6-dimethyl-2-oxo-1H-pyridin-3-yl)methyl]-3-methyl-2-[(1R)-1-[4-substituted-cyclohexyl]ethyl]-6,7-dihydrothieno[3,2-c]pyridin-4-one and purifying by either normal- or reverse-phase chromatography.

| Example No. | Chemical name | Structure | ES/MS (m/z) (M + H) |
|---|---|---|---|
| 4 | 5-[(4,6-Dimethyl-2-oxo-1,2-dihydropyridin-3-yl)methyl]-3-methyl-2-[(1R)-1-{trans-4-[3-(4-methyl-1H-pyrazol-1-yl)azetidin-1-yl]cyclohexyl}ethyl]-6,7-dihydrothieno[3,2-c]pyridin-4(5H)-one | 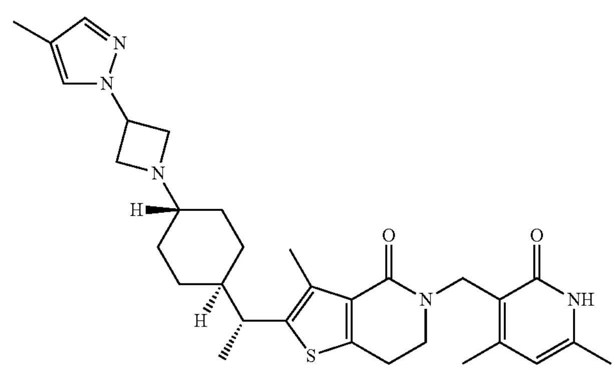 | 548 |
| 5 | 5-[(4,6-Dimethyl-2-oxo-1,2-dihydropyridin-3-yl)methyl]-3-methyl-2-[(1R)-1-{trans-4-[3-(pyrrolidin-1-yl)azetidin-1-yl]cyclohexyl}ethyl]-6,7-dihydrothieno[3,2-c]pyridin-4(5H)-one | 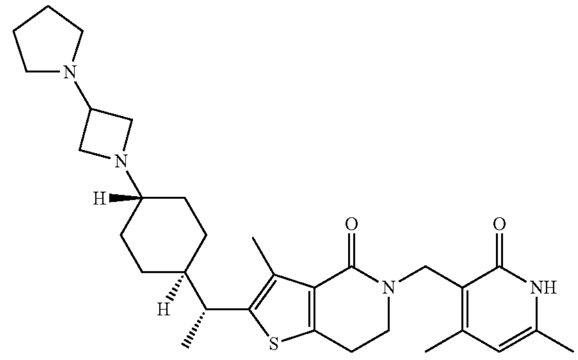 [SMILES: Cc1cc(C)c(CN2CCc3sc([C@H](C)[C@H]4CC[C@H](N5CC(N6CCCC6)C5)CC4)c(C)c3C2=O)c(=O)[nH]1] | 537 |

-continued

| Example No. | Chemical name | Structure | ES/MS (m/z) (M + H) |
|---|---|---|---|
| 6 | 5-[(4,6-Dimethyl-2-oxo-1,2-dihydropyridin-3-yl)methyl]-3-methyl-2-[(1R)-1-{trans-4-[3-(morpholin-4-yl)azetidin-1-yl]cyclohexyl}ethyl]-6,7-dihydrothieno[3,2-c]pyridin-4(5H)-one | 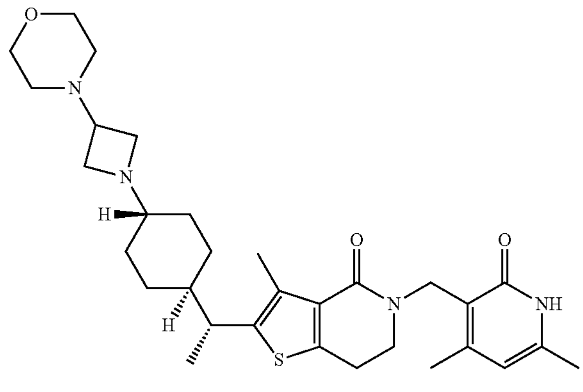 [SMILES: Cc1cc(C)c(CN2CCc3sc([C@H](C)[C@H]4CC[C@H](N5CC(N6CCOCC6)C5)CC4)c(C)c3C2=O)c(=O)[nH]1] | 553 |
| 7 | 5-[(4,6-Dimethyl-2-oxo-1,2-dihydropyridin-3-yl)methyl]-3-methyl-2-[(1R)-1-{trans-4-[3-(1H-1,2,3-triazol-1-yl)azetidin-1-yl]cyclohexyl}ethyl]-6,7-dihydrothieno[3,2-c]pyridin-4(5H)-one | 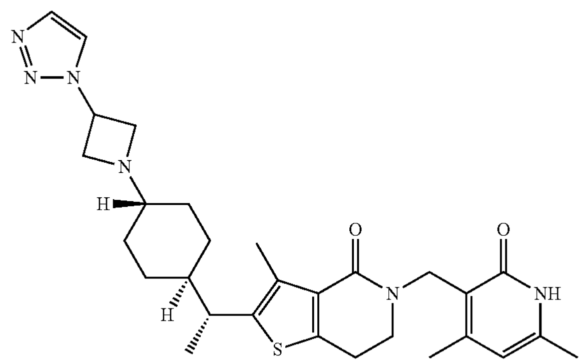 [SMILES: Cc1cc(C)c(CN2CCc3sc([C@H](C)[C@H]4CC[C@H](N5CC(n6ccnn6)C5)CC4)c(C)c3C2=O)c(=O)[nH]1] | 535 |
| 8 | 2-{(1R)-1-[Trans-4-(dimethylamino)cyclohexyl]ethyl}-5-[(4,6-dimethyl-2-oxo-1,2-dihydropyridin-3-yl)methyl]-3-methyl-6,7-dihydrothieno[3,2-c]pyridin-4(5H)-one | 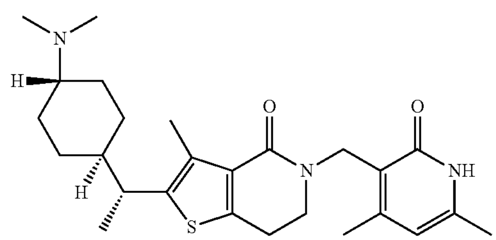 [SMILES: Cc1cc(C)c(CN2CCc3sc([C@H](C)[C@H]4CC[C@H](N(C)C)CC4)c(C)c3C2=O)c(=O)[nH]1] | 458 |

Example 9

2-[(1R)-1-[4-[3-(cyclopropoxy)azetidin-1-yl]cyclohexyl]ethyl]-5-[(4,6-dimethyl-2-oxo-1H-pyridin-3-yl)methyl]-3-methyl-6,7-dihydrothieno[3,2-c]pyridin-4-one

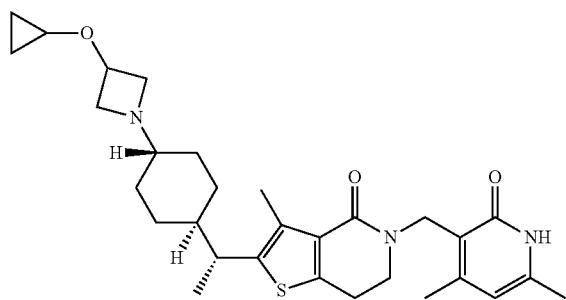 [SMILES: Cc1cc(C)c(CN2CCc3sc([C@H](C)[C@H]4CC[C@H](N5CC(OC6CC6)C5)CC4)c(C)c3C2=O)c(=O)[nH]1]

Stir a mixture of 5-{[2-(benzyloxy)-4,6-dimethylpyridin-3-yl]methyl}-2-[(1R)-1-{trans-4-[3-(cyclopropyloxy) azetidin-1-yl]cyclohexyl}ethyl]-3-methyl-6,7-dihydrothieno[3,2-c]pyridin-4(5H)-one (200 mg, 0.33 mmol) in THF (6 mL) and 1N HCl (10 mL) at 90° C. for 2 hr. Cool to RT and pour the mixture into a saturated aqueous NaHCO₃ solution with ice, and then extract twice with EtOAc. Wash the combined extracts with saturated aqueous NaCl, dry over MgSO₄, filter, and concentrate the filtrate in vacuo. Subject the resulting residue to chromatography on silica, eluting with a gradient of 20-50% of a mixture of (10% 7N NH₃ MeOH) in DCM and DCM to afford 66 mg of the pure product after solvent evaporation. Subject the less pure combined fractions (54 mg after solvent evaporation) by reverse phase chromatography over C-18 silica (Phenomenex LUNA®, 5 μm C-18 AXIA®, 30×75 min, column temperature 25° C., 85 mL/min), using a gradient of 10-75% ACN in 10 mM NH₄HCO₃ (pH 10) in water. Combine similar fractions, concentrate in vacuo, and subject the resulting residue to chromatography on silica, eluting with a gradient of 20-50% of a mixture of (10% 7N NH₃ in MeOH) in DCM and DCM, to afford an additional 22 mg of the title compound after solvent evaporation. Combine the two purified materials as title compound (88 mg, 51% yield). ES/MS (m/z): 524 (M+H). ¹H NMR (400.1 MHz, CDCl₃): 0.40-0.47 (m, 2H), 0.49-0.55 (m, 2H), 0.91-1.01 (m, 4H), 1.20 (d, J=6.9 Hz, 3H), 1.24-1.29 (m, 1H), 1.55-1.65 (m, 1H), 1.67-1.76 (m, 1H), 1.76-1.82 (m, 1H), 1.86-1.97 (m, 2H), 2.30 (s, 3H), 2.26 (s, 3H), 2.38 (s, 3H), 2.77-2.89 (m, 5H), 3.17-3.22 (m, 1H), 3.57-3.69 (m, 4H), 4.71 (s, 2H), 4.20 (quintet, J=6.0 Hz, 1H), 5.92 (s, 1H), 12.81-12.83 (bs, 1H).

Prepare the following compounds essentially by the method of Example 9, using the appropriately substituted 5-[(2-benzyloxy-4,6-dimethyl-3-pyridyl)methyl]-2-[(1R)-1-[4-azetidin-1-yl]cyclohexyl]ethyl]-3-methyl-6,7-dihydrothieno[3,2-c]pyridin-4-one.

| Example No. | Chemical name | Structure | ES/MS (m/z) (M + H) |
|---|---|---|---|
| 10 | 5-[(4,6-Dimethyl-2-oxo-1,2-dihydropyridin-3-yl)methyl]-2-[(1R)-1-{trans-4-[3-(methoxymethyl)azetidin-1-yl]cyclohexyl}ethyl]-3-methyl-6,7-dihydrothieno{3,2-c}pyridin-4(5H)-one | 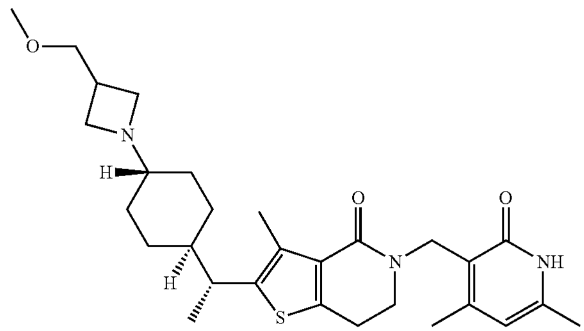 | 512 |
| 11 | 5-[(4,6-Dimethyl-2-oxo-1,2-dihydropyridin-3-yl)methyl]-3-methyl-2-[(1R)-1-{trans-4-[3-(propan-2-yloxy)azetidin-1-yl]cyclohexyl}ethyl]-6,7-dihydrothieno[3,2-c]pyridin-4(5H)-one | 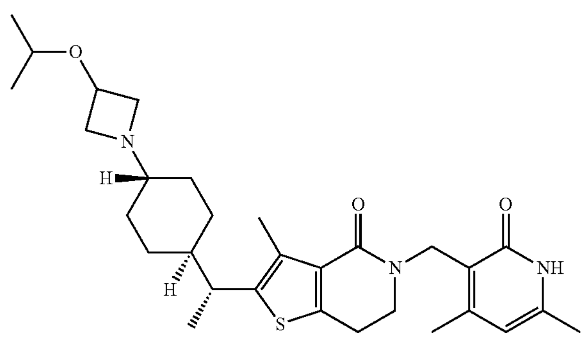 [SMILES: Cc1cc(C)c(CN2CCc3sc([C@H](C)[C@H]4CC[C@H](N5CC(OC(C)C)C5)CC4)c(C)c3C2=O)c(=O)[nH]1] | 526 |
| 12 | 5-[(4,6-Dimethyl-2-oxo-1,2-dihydropyridin-3-yl)methyl]-3-methyl-2-[(1R)-{trans-4-[3-(1H-pyrazol-1-yl)azetidin-1-yl]cyclohexyl}ethyl)-6,7-dihydrothieno[3,2-c]pyridin-4(5H)-one | 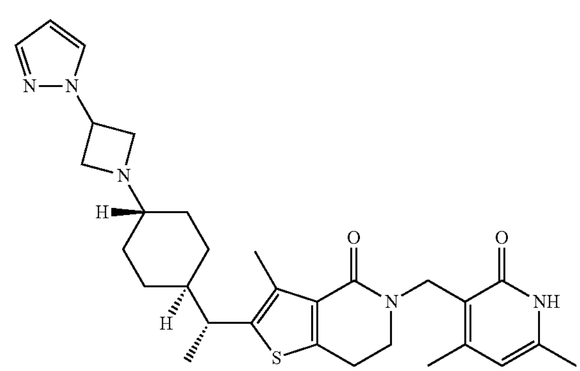 [SMILES: Cc1cc(C)c(CN2CCc3sc([C@H](C)[C@H]4CC[C@H](N5CC(n6cccn6)C5)CC4)c(C)c3C2=O)c(=O)[nH]1] | 534 |

| Example No. | Chemical name | Structure | ES/MS (m/z) (M + H) |
|---|---|---|---|
| 13 | 5-[(4,6-Dimethyl-2-oxo-1,2-dihydropyridin-3-yl)methyl]-3-methyl-2-[(1R)-1-(trans-4-{3-[(3S)-tetrahydrofuran-3-yloxy]azetidin-1-yl}cyclohexyl)ethyl]-6,7-dihydrothieno[3,2-c]pyridin-4(5H)-one | 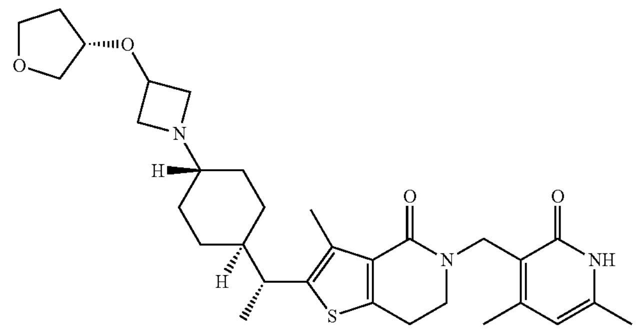 [SMILES: Cc1cc(C)c(CN2CCc3sc([C@H](C)[C@H]4CC[C@H](N5CC(O[C@H]6CCOC6)C5)CC4)c(C)c3C2=O)c(=O)[nH]1] | 554 |
| 14 | 5-[(4,6-Dimethyl-2-oxo-1,2-dihydropyridin-3-yl)methyl]-3-methyl-2-[(1R)-1-(trans-4-{3-[(3R)-tetrahydrofuran-3-yloxy]azetidin-1-yl}cyclohexyl)ethyl]-6,7-dihydrothieno[3,2-c]pyridin-4(5H)-one | 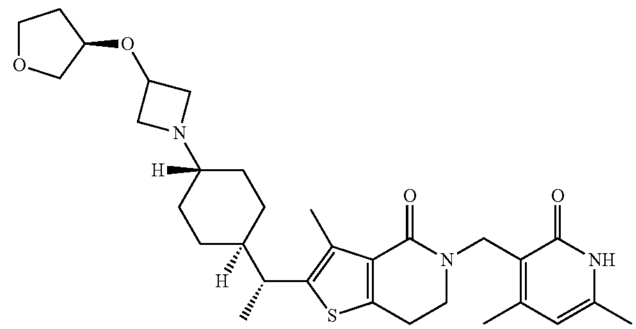 [SMILES: Cc1cc(C)c(CN2CCc3sc([C@H](C)[C@H]4CC[C@H](N5CC(O[C@@H]6CCOC6)C5)CC4)c(C)c3C2=O)c(=O)[nH]1] | 554 |

Example 12: $^1$H NMR (399.8 MHz, CDCl$_3$): 1.05-1.07 (m, 2H), 1.32-1.46 (m, 2H), 1.83-1.85 (m, 2H), 1.93-1.94 (m, 2H), 2.14-2.16 (m, 1H), 2.25 (s, 3H), 2.29 (s, 3H), 2.32 (s, 3H), 2.62 (s, 3H), 2.58-2.67 (m, 1H), 2.76-2.80 (m, 2H), 3.43-3.47 (m, 2H), 3.62-3.66 (m, 2H), 3.77-3.81 (m, 2H), 4.69 (s, 2H), 4.92-4.95 (m, 1H), 5.90 (s, 1H), 6.24 (t, J=2.0 Hz, 1H), 7.46 (d, J=2.1 Hz, 1H), 7.53 (d, J=1.9 Hz, 1H). (Exchangeable NH proton not observed.)

Example 15

2-{(1R)-1-[Trans-4-(azetidin-1-yl)cyclohexyl]ethyl}-5-[(4,6-dimethyl-2-oxo-1,2-dihydropyridin-3-yl)methyl]-3-methyl-6,7-dihydrothioneo[3,2-c]pyridin-4(5H)-one

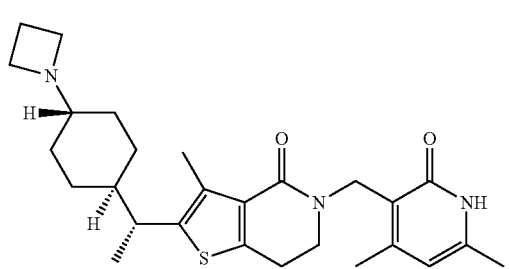 [SMILES: Cc1cc(C)c(CN2CCc3sc([C@H](C)[C@H]4CC[C@H](N5CCC5)CC4)c(C)c3C2=O)c(=O)[nH]1]

Stir a mixture of 2-{(1R)-1-[trans-4-(azetidin-1-yl)cyclohexyl]ethyl}-5-{[2-(benzyloxy)-4,6-dimethylpyridin-3-yl]methyl}-3-methyl-6,7-dihydrothieno[3,2-c]pyridin-4(5H)-one (190 mg, 0.34 mmol) and 10% Pd on carbon (60 mg) in MeOH (15 mL) under H$_2$ at 60 psi overnight. Filter the reaction mixture over a bed of diatomaceous earth and concentrate the filtrate. Subject the resulting residue to chromatography on silica, eluting with a gradient of 0-60% of a mixture of 10% 7N NH$_3$ MeOH/DCM in DCM, to obtain the title compound (117 mg, 73% yield) after solvent evaporation. ES/MS (m/z): 468 (M+H).

Example 16

2-[(1R)-1-{Trans-4-[3-(cyclopropylmethoxy)azetidin-1-yl]cyclohexyl}(ethyl]-5-[(4,6-dimethyl-2-oxo-1,2-dihydropyridin-3-yl)methyl]-3-methyl-6,7-dihydrothieno[3,2- c]pyridin-4(5H)-one

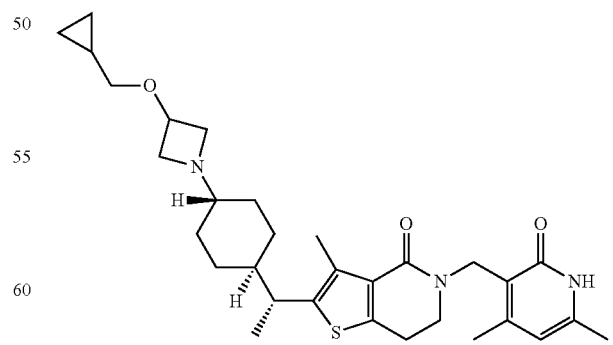

Stir a mixture of 5-{[2-(benzyloxy)-4,6-dimethylpyridin-3-yl]methyl}-2-[(1R)-1-{trans-4-[3-(cyclopropylmethoxy)azetidin-1-yl]cyclohexyl}ethyl]-3-methyl-6,7-dihydrothieno[3,2-c]pyridin-4(5H)-one (96 mg, 0.15 mmol), LiCl (34 mg, 0.79 mmol) and p-toluenesulfonic acid monohydrate (135 mg, 0.77 mmol) in DMF (3 mL) at 62° C. for 1.5 hr and concentrate the reaction mixture in vacuo. Subject the resulting residue to chromatography on silica, eluting with a gradient of 0-70% of a mixture of 10% 2N NH₃ in MeOH/DCM in DCM to give the title compound (40 mg, 48% yield) after solvent evaporation. ES/MS (m/z): 538 (M+H).

Examples 17 and 18

Example 17

5-[(4,6-Dimethyl-2-oxo-1,2-dihydropyridin-3-yl)methyl]-2-[(1R)-{trans-4-[3-(2-methoxyethoxy)(azetidin-1-yl]cyclohexyl}ethyl)]-3-methyl-6,7-dihydrothieno[3,2-c]pyridin-4(5H)-one

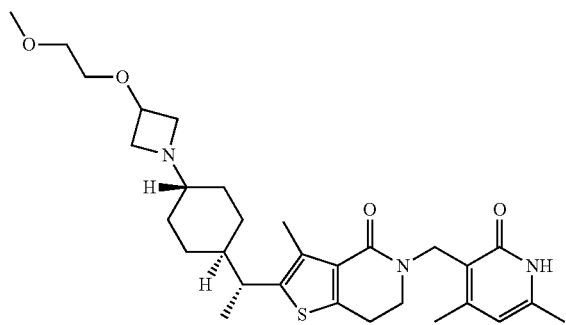

Example 18

5-[(4,6-Dimethyl-2-oxo-1,2-dihydropyridin-3-yl)methyl]-2-[(1R)-{cis-4-[3-(2-methoxyethoxy)azetidin-1-yl]cyclohexyl}(ethyl)]-3-methyl-6,7-dihydrothieno[3,2-c]pyridin-4(5H)-one

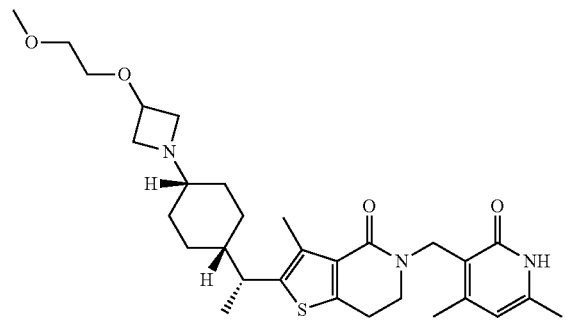

Add LiCl (0.2 g, 5.57 mmol) and PTSA (1.01 g, 5.578 mmol) to a solution of 5-[(2-methoxy-4,6-dimethylpyridin-3-yl)methyl]-2-[(1R)-1-{4-[3-(2-methoxyethoxy)azetidin-1-yl]cyclohexyl}ethyl)]-3-methyl-6,7-dihydrothieno[3,2-c]pyridin-4(5H)-one (0.62 g, 1.11 mmol, mixture of cis- and trans-diastereomers) in DMF (5.6 mL) and stir at 90° C. for 2 hr. Add saturated aqueous NaHCO₃, extract with EtOAc, dry over Na₂SO₄, filter, and concentrate the filtrate in vacuo. Subject the resulting residue to chromatography over SCX (10 g), eluting first with MeOH then with 2M NH₃ in MeOH. Concentrate the MeOH in ammonia fraction in vacuo, and subject the resulting residue to reverse phase chromatography over C-18 silica (Xterra XBRIDGE® column, 5 μm, 19×100 cm), eluting with a gradient of 35-55% 20 mM NH₄CO₃ (pH 9) in water/ACN over 3 min at 25 mL/minute, to afford the first eluting trans-compound Example 17 as a solid (0.148 g, 25% yield) after solvent evaporation, ES/MS (m/z): 541 (M+H), and second eluting cis-compound Example 18 as a solid (0.027 g, 4.5% yield), ES/MS(m/z): 541 (M+H).

Example 19

5-[(4,6-Dimethyl-2-oxo-1,2-dihydropyridin-3-yl)methyl]-2-{[trans-4-(3-methoxyazetidin-1-yl)cyclohexyl](methyl)amino}-3-methyl-6,7-dihydrothieno[3,2-c]pyridin-4(5H)-one

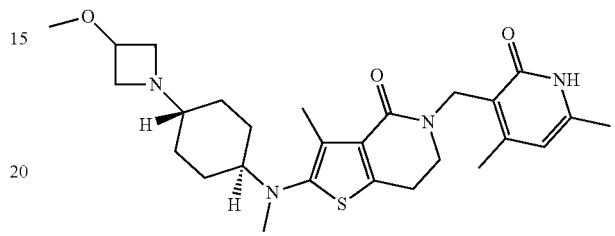

Stir 3-methoxyazetidine hydrochloride (0.304 g, 2.460 mmol) in MeOH (5 mL) and THF (5 mL) with DIPEA (0.308 mL, 1.77 mmol) at RT for 30 min Add 5-[(4,6-dimethyl-2-oxo-1,2-dihydropyridin-3-yl)methyl]-3-methyl-2-[methyl(4-oxocyclohexyl)amino]-6,7-dihydrothieno[3,2-c]pyridin-4(5H)-one (0.28 g, 0.49 mmol) and stir at RT for 1 hr. Cool the mixture to −78° C. and add a solution of 2M LiBH₄ in THF (6.4 mL, 13 mmol), stir the resulting mixture for 1 hr at −78° C., and warm to RT. Pour the reaction mixture into ice-cold saturated NaHCO₃ solution, extract with DCM, separate the layers, dry the organic extracts over Na₂SO₄, filter, and concentrate the organic extract in vacuo. Subject the resulting residue to chromatography on silica, eluting with a gradient of 0-50% of a 10% solution 7N methanolic NH₃ in DCM to DCM. Collect the chromatography fractions containing the trans- and cis-isomers and concentrate in vacuo. Separate the trans- and cis-isomers by reverse phase chromatography on C-18 silica (30 g Thermo Scientific Hypersil GOLD™), eluting with a gradient of 10-100% ACN in 10 mM aqueous NH₄CO₃, to afford the title compound (0.064 g, 26% yield) as a white solid after solvent evaporation. ES/MS (m/z): 499(M+H).

Example 20

5-[(4,6-Dimethyl-2-oxo-1,2-dihydropyridin-3-yl)methyl]-3-methyl-2-(methyl{trans-4-[3-(1H-pyrazol-1-yl)azetidin-1-yl]cyclohexyl}aniino)-6,7-dihydrothieno[3,2-c]pyridin-4(5H)-one

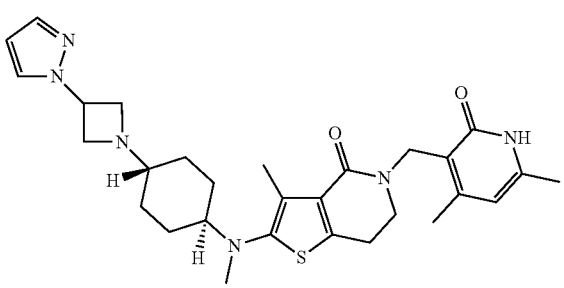 [SMILES: Cc1cc(C)c(CN2CCc3sc(N(C)[C@H]4CC[C@H](N5CC(n6cccn6)C5)CC4)c(C)c3C2=O)c(=O)[nH]1]

Add titanium(IV) isopropoxide (0.373 g, 1.27 mmol) to 5-[(4,6-dimethyl-2-oxo-1,2-dihydropyridin-3-yl)methyl]-3-methyl-2-[methyl(4-oxocyclohexyl)amino]-6,7-dihydrothieno[3,2-c]pyridin-4(5H)-one (0.148 g, 0.32 mmol) in DCM (2.5 mL) at RT followed by 1-(azetidin-3-yl)pyrazole dihydrochloride (0.187 g, 0.955 mmol). After 3 hr, add THF (2.5 mL), then concentrate the mixture to about 2.5 mL in vacuo. Cool the resulting mixture to −78° C., add MeOH (2.5 mL) followed by a solution of 2M LiBH$_4$ in THF (0.24 mL, 0.48 mmol), gradually warm to RT, and stir overnight. Dilute the mixture with DCM (50 mL) and water (10 mL), filter over a bed of diatomaceous earth, and wash the filter cake with DCM (100 mL). Concentrate the filtrate in vacuo and subject the resulting residue to reverse phase chromatography over C-18 silica (WATERS™ XBRIDGE®, 30×75 min, 5 μm), eluting with a gradient of 20-60% ACN in 10 mM aqueous NH$_4$CO$_3$ containing 5% MeOH, to afford the title compound (0.025 g, 14% yield) as thin clear film after solvent evaporation. ES/MS (m/z): 535 (M+H).

Example 21

5-[(4-Chloro-6-methyl-2-oxo-1,2-dihydropyridin-3-yl)methyl]-2-{ethyl[trans-4-(3-methoxyazetidin-1-yl)cyclohexyl]amino}-3-methyl-6,7-dihydrothieno[3,2-c]pyridin-4(5H)-one

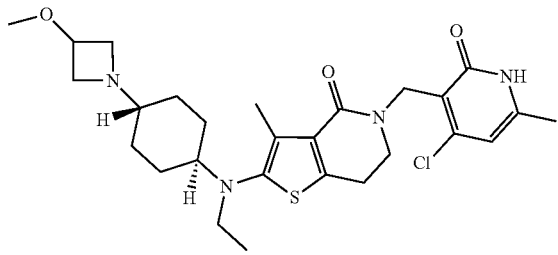

Add 3-methoxyazetidine hydrochloride (0.300 g, 2.43 mmol) in methanol (5 mL) to a round bottom flask containing THF (5 mL) and DIPEA (0.306 mL, 1.75 mmol), stir at RT for 30 min, then add 5-[(4-chloro-6-methyl-2-oxo-1,2-dihydropyridin-3-yl)methyl]-2-[ethyl(4-oxocyclohexyl)amino]-3-methyl-6,7-dihydrothieno[3,2-c]pyridin-4(5H)-one (0.450 g, 0.487 mmol, 50% purity) to the solution, and stir at RT for 1 hr. Cool the reaction mixture to −78° C. and add a solution of 2M LiBH$_4$ in THF (0.63 mL, 1.3 mmol). Stir for 1 hr, then gradually warm the mixture to RT, pour the mixture into ice-cold saturated aqueous NaHCO$_3$, extract with DCM, separate the layers, dry the organic phase over anhydrous Na$_2$SO$_4$, filter, and concentrate the filtrate in vacuo. Subject the resulting residue to chromatography on silica, eluting with a gradient of 0-40% 10% of a mixture of 7N NH$_3$/MeOH in DCM/DCM. To separate the cis- and trans-isomers, evaporate the fractions containing product and subject the resulting residue to reverse phase chromatography over C-18 silica (15.5 g Thermo Scientific Hypersil GOLD™), eluting with a gradient of 10-100% ACN in 10 mM NH$_4$CO$_3$ containing 5% MeOH, to afford the title compound (0.120 g, 46% yield), as a white solid after solvent evaporation. ES/MS (m/z): ($^{35}$Cl/$^{37}$Cl) 533/535 (M+H).

Example 22

5-[(4,6-Dimethyl-2-oxo-1,2-dihydropyridin-3-yl)methyl]-2-{ethyl[trans-4-(3-methoxyazetidin-1-yl)cyclohexyl]amino}-3-methyl-6,7-dihydrothieno[3,2-c]pyridin-4(5H)-one

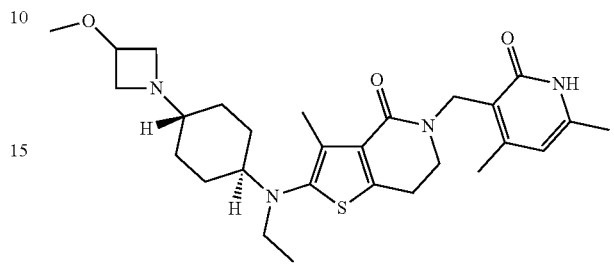

Add LiCl (6.13 g, 143.2 mmol) to a mixture of 2-{ethyl[trans-4-(3-methoxyazetidin-1-yl)cyclohexyl]amino}-5-[(2-methoxy-4,6-dimethylpyridin-3-yl)methyl]-3-methyl-6,7-dihydrothieno[3,2-c]pyridin-4(5H)-one (16.40 g, 28.65 mmol) and PTSA (25.96 g, 143.2 mmol) in DMF (100 mL) and stir at 50° C. for 9 hr and then at RT for 18 hr. Dilute with EtOAc (400 mL) and 4M aqueous K$_2$CO$_3$ solution (200 mL). Separate phases, extract the aqueous phase with EtOAc (3×100 mL), and sequentially wash the combined organic layers with 4M aqueous K$_2$CO$_3$ solution (2×100 mL), water (100 mL), and saturated aqueous NaCl (100 mL). Dry the organic phase over Na$_2$SO$_4$, filter, and concentrate the filtrate in vacuo to afford pale brown solid. Slurry the solid with EtOAc (100 mL) and stir for 1 hr at RT. Add diethyl ether (100 mL), stir for 2 hr at RT, filter the solid, wash with cold diethyl ether (50 mL), and dry under vacuum. Add TEA (21.54 g, 212.8 mmol) to a mixture of the resulting solid in ACN (500 mL) and stir for 24 hr at 85° C. Cool the mixture, concentrate in vacuo, suspend the resulting residue in water (165 mL), and stir for 4 hr at RT. Filter the resulting solid, wash with water (50 mL), and dry under vacuum at 50° C. for 16 hr to afford the title compound (10.83 g, 76% yield) as a pale ivory solid. ES/MS (m/z): 513 (M+H).

Example 23

2-[{Trans-4-[3-(cyclopropyloxy)azetidin-1-yl]cyclohexyl}(ethyl)amino]-5-[(4,6-dimethyl-2-oxo-1,2-dihydropyridin-3-yl)methyl]-3-methyl-6,7-dihydrothieno[3,2-c]pyridin-4(5H)-one

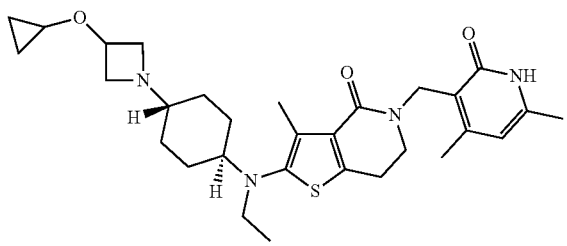 [SMILES: CCN(c1sc2c(c1C)C(=O)N(Cc1c(C)cc(C)[nH]c1=O)CC2)[C@H]1CC[C@H](N2CC(OC3CC3)C2)CC1]

To a round bottom flask, add 3-(cyclopropoxy)azetidine hydrochloride (0.6776 g, 4.529 mmol), MeOH (4 mL), DIPEA (0.5853 g, 4.529 mmol), 5-[(4,6-dimethyl-2-oxo-1, 2-dihydropyridin-3-yl)methyl]-2-[ethyl(4-oxocyclohexyl) amino]-3-methyl-6,7-dihydrothieno[3,2-c]pyridin-4(5H)-one (0.500 g, 1.13 mmol) and THF (20 mL). Stir the resulting solution at RT overnight. Cool the reaction mixture to −78° C. and drop wise add 2M LiBH$_4$ in THF (1.13 mL, 2.26 mmol). Place the reaction in an ice bath at 0° C. and allow to slowly warm to RT over 1.5 hr. Quench the reaction mixture with saturated aqueous NaHCO$_3$ solution, dilute with DCM, separate the layers, and extract the aqueous phase with additional DCM. Combine the organic phases, dry over anhydrous Na$_2$SO$_4$, filter, and concentrate the filtrate in vacuo. Subject the resulting residue to reverse phase chromatography over C-18 silica. Concentrate the desired fractions in vacuo to afford the title compound (0.092 g, 15%) as a white powder. ES/MS (m/z): 539 (M+H).

Example 24 and 25

Example 24

5-[(4,6-Dimethyl-2-oxo-1,2-dihydropyridin-3-yl) methyl]-2-(ethyl{trans-4-[3-(1H-pyrazol-1-yl)azetidin-1-yl]cyclohexyl}amino)-3-methyl-6,7-dihydrothieno[3,2-c]pyridin-4(5H)-one

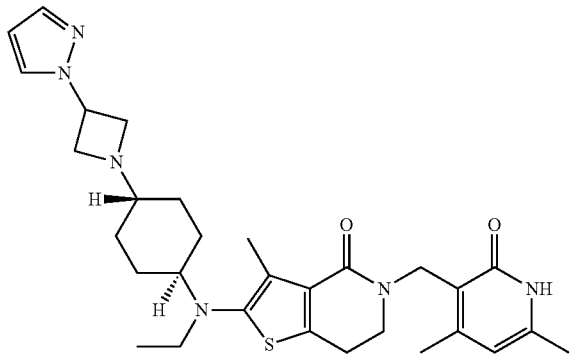 [SMILES: CCN(c1sc2c(c1C)C(=O)N(Cc1c(C)cc(C)[nH]c1=O)CC2)[C@H]1CC[C@H](N2CC(n3cccn3)C2)CC1]

Example 25

5-[(4,6-Dimethyl-2-oxo-1,2-dihydropyridin-3-yl) methyl]-2-(ethyl{cis-4-[3-(1H-pyrazol-1-yl)azetidin-1-yl]cyclohexyl}amino)-3-methyl-6,7-dihydrothieno[3,2-c]pyridin-4(5H)-one

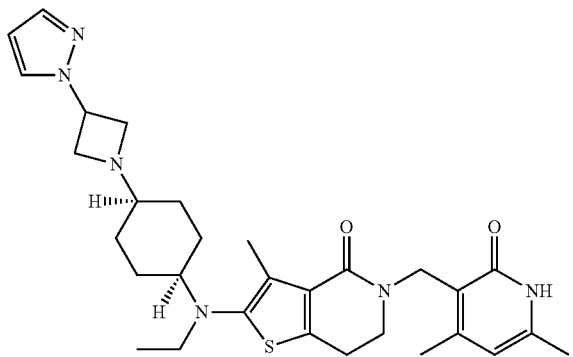 [SMILES: CCN(c1sc2c(c1C)C(=O)N(Cc1c(C)cc(C)[nH]c1=O)CC2)[C@H]1CC[C@@H](N2CC(n3cccn3)C2)CC1]

To a round bottom flask, add 1-(azetidin-3-yl)pyrazole dihydrochloride (0.266 g, 1.36 mmol), MeOH (6.8 mL), and DIPEA (0.239 mL, 1.36 mmol), and stir at RT for 30 min. Add 5-[(4,6-dimethyl-2-oxo-1,2-dihydropyridin-3-yl) methyl]-2-[ethyl(4-oxocyclohexyl)amino]-3-methyl-6,7-dihydrothieno[3,2-c]pyridin-4(5H)-one (0.150 g, 0.340 mmol) to the reaction mixture and stir for 3 hr. Cool the reaction mixture to −78° C., then add 2M LiBH$_4$ in THF (0.255 mL, 0.510 mmol) drop wise and stir for 3 hr. Warm the reaction mixture to RT, pour into ice-cold saturated aqueous NaHCO$_3$ solution, dilute the resulting suspension with DCM/water, and extract three times with DCM. Separate the layers, combine the organic phases, dry over Na$_2$SO$_4$, filter, and concentrate the filtrate in vacuo. Subject the resulting residue to reverse phase chromatography over C-18 silica, eluting with a gradient of 0-55% ACN in 10 mM NH$_4$CO$_3$/water, to afford the trans-title compound Example 24 (0.088 g, 47% yield) as a white solid, ES/MS (m/z): 549 (M+H), and the cis-title compound Example 25 (0.048 g, 26% yield) as a white solid, ES/MS (m/z): 549 (M+H).

Example 26

5-[(4,6-Dimethyl-2-oxo-1,2-dihydropyridim-3-yl) methyl]-2-(ethyl{trans-4-[3-(2-metoxyethoxy)azetidin-1-yl]cyclohexyl}amino)-3-methyl-6,7-dihydrothieno[3,2-c]pyridin-4(5H)-one

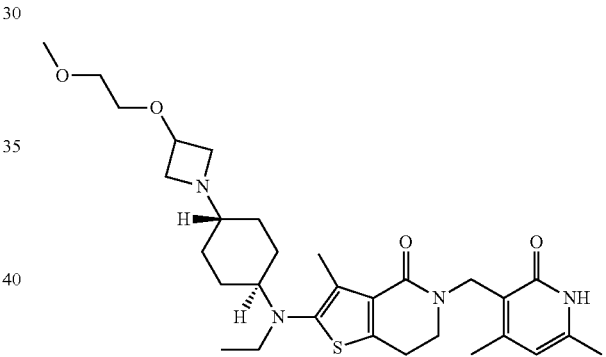

To a round bottom flask, add 3-(2-methoxyethoxy)azetidine hydrochloride (1.5 g, 8.9 mmol) and DIPEA (2 mL, 11.5 mmol) in MeOH (20 mL). Stir at RT for 30 min, then add 5-[(4,6-dimethyl-2-oxo-1,2-dihydropyridin-3-yl) methyl]-2-[ethyl(4-oxocyclohexyl)amino]-3-methyl-6,7-dihydrothieno[3,2-c]pyridin-4(5H)-one (1.0 g, 2.3 mmol) in THF (5 mL) and stir the resulting mixture at RT overnight. Cool the reaction mixture to −78° C. and drop wise add 2M LiBH$_4$ in THF (2.8 mL, 5.6 mmol). Place the reaction in an ice bath and warm slowly to RT for 2 hr. Pour the reaction mixture into ice-cold saturated aqueous NaHCO$_3$ solution, extract with DCM, separate the layers, and concentrate the organic extracts in vacuo. Subject the resulting residue to chromatography on silica, eluting with a gradient of 0-3% of a mixture of 7N NH$_3$/MeOH in DCM, to afford the trans-isomer (0.450 g, 36% yield) as impure light brown solid and the cis-isomer (0.220 g, 17% yield) as light brown oil after solvent evaporation. Subject the trans-isomer to reverse phase chromatography on C-18 silica, eluting with a gradient of 0-60% ACN in 10 mM NH$_4$CO$_3$/water, to afford the trans-title compound (233 mg, 18% yield) as a light brown solid after solvent evaporation. ES/MS (m/z): 557 (M+H). $^1$H NMR (400.1 MHz, CDCl$_3$): 0.94 (t, J=7.0 Hz, 3H), 0.98-1.03 (m, 2H), 1.20-1.28 (m, 2H), 1.78-1.81 (m, 2H), 1.86-1.92 (m, 3H), 2.29 (s, 3H), 2.35 (s, 6H), 2.67-2.77 (m, 1H), 2.83 (t, J=6.6 Hz, 2H), 2.85-2.95 (m, 4H), 3.39 (s, 3H), 3.59 (dd, J=6.1, 7.5 Hz, 2H), 3.52 (s, 4H), 3.69 (t, J=6.6 Hz, 2H), 4.13 (quintet, J=5.9 Hz, 1H), 4.73 (s, 2H), 5.94 (s, 1H), 12.24-12.25 (bs, 1H).

Example 27

2-{[Trans-4-(dimethylamino)cyclohexyl](ethyl)amino}-5-[(4,6-dimethyl-2-oxo-1,2-dihydropyridin-3-yl)methyl]-3-methyl-6,7-dihydrothieno[3,2-c]pyridin-4(5H)-one

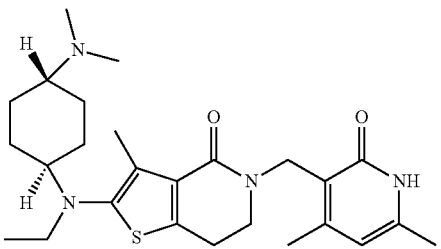 [SMILES: CCN(c1sc2c(c1C)C(=O)N(Cc1c(C)cc(C)[nH]c1=O)CC2)[C@H]1CC[C@H](N(C)C)CC1]

To a 5 mL microwave vial, add 2-[(trans-4-aminocyclohexyl)(ethyl)amino]-5-[(4,6-dimethyl-2-oxo-1,2-dihydropyridin-3-yl)methyl]-3-methyl-6,7-dihydrothieno[3,2-c]pyridin-4(5H)-one (0.050 g, 0.113 mmol), acetic acid (0.019 mL, 0.339 mmol), and 37% aqueous formaldehyde (0.025 mL, 0.3389 mmol) in MeOH (4 mL). Cool the vial to 0° C. and slowly add NaCNBH$_4$ (0.0213 g, 0.3389 mmol) to the reaction mixture. Warm to RT, stir for 4.5 hr, then concentrate the reaction mixture in vacuo. Dilute the resulting residue with DCM and water, separate the layers, and extract the aqueous layer with additional DCM. Combine the organic phases, dry over Na$_2$SO$_4$, filter, and concentrate the filtrate in vacuo. Subject the resulting residue to reverse phase chromatography over C-18 silica (50 g), eluting with ACN in 10 mM NH$_4$CO$_3$/water, to afford the title compound (0.0135 g, 25% yield) as a white powder after solvent evaporation. ES/MS (m/z): 471 (M+H).

Example 28

5-[(4,6-Dimethyl-2-oxo-1,2-dihydropyridin-3-yl)methyl]-2-[ethyl(piperidin-4-yl)amino]-3-methyl-6,7-dihydrothieno[3,2-c]pyridin-4(5H)-one

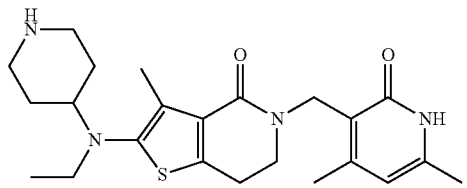 [SMILES: CCN(c1sc2c(c1C)C(=O)N(Cc1c(C)cc(C)[nH]c1=O)CC2)C1CCNCC1]

Add tert-butyl 4-(ethyl{5-[(2-methoxy-4,6-dimethylpyridin-3-yl)methyl]-3-methyl-4-oxo-4,5,6,7-tetrahydrothieno[3,2-c]pyridin-2-yl}amino)piperidine-1-carboxylate (0.700 g, 1.290 mmol) in DMF (6.45 mL) to a microwave vial. Cool to 0° C., then add LiCl (0.276, 6.45 mmol) and PTSA (1.17 g, 6.45 mmol). Heat the resulting mixture to 90° C. overnight, cool the reaction mixture to RT, quench with ice-cold saturated aqueous NaHCO$_3$, and dilute with DCM. Separate the layers, extract the aqueous layer with additional DCM, combine the organic phases, dry over Na$_2$SO$_4$, filter, and concentrate in vacuo. Subject the resulting residue to chromatography on silica, eluting with a gradient of 0-10% 7N NH$_3$ in MeOH/DCM, to afford the title compound (0.284 g, 51% yield) as a beige solid after solvent evaporation. ES/MS (m/z): 429 (M+H).

Examples 29 and 30

Example 29

5-[(4,6-Dimethyl-2-oxo-1,2-dihydropyridin-3-yl)methyl]-2-(ethyl{trans-4-[2-methoxyethyl)(methyl)amino]cyclohexyl}amino)-3-methyl-6,7-dihydrothieno[3,2-c]pyridin-4(5H)-one

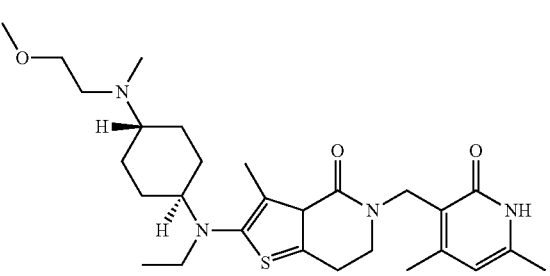

Example 30

5-[(4,6-Dimethyl-2-oxo-1,2-dihydropyridin-3-yl)methyl]-2-(ethyl{cis-4-[(2-methoxyethyl)(methyl)amino]cyclohexyl}amino)-3-methyl-6,7-dihydrothieno[3,2-c]pyridin-4(5H)-one

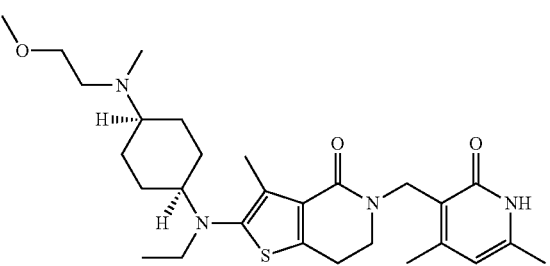

Add LiCl (0.22 g, 5.20 mmol) and PTSA (0.94 g, 5.20 mmol) to a solution of 2-(ethyl {4-[(2-methoxyethyl)(methyl)amino]cyclohexyl}amino)-5-[(2-methoxy-4,6-dimethylpyridin-3-yl)methyl]-3-methyl-6,7-dihydrothieno[3,2-c]pyridin-4(5H)-one (0.55 g, 1.04 mmol, mixture of cis- and trans-diastereomers) in DMF (5.2 mL) and heat at 90° C. in a sealed tube for 1 hr. Cool the reaction to RT, add saturated aqueous NaHCO$_3$ solution, extract with EtOAc, and concentrate the organic extract in vacuo. Load the resulting residue onto an SCX cartridge (25 g), eluting first with MeOH and then with 2M NH$_3$ in MeOH. Concentrate the methanolic ammonia fractions in vacuo and subject the resulting residue to Supercritical Fluid Chromatography (CHIRALCEL® OD, 5 um, 2×25 cm), eluting isocratically at 30% with a mobile phase of $CO_2$/MeOH containing 0.2% DMA at 65 mL/min, to afford the title compounds: 5-[(4,6-dimethyl-2-oxo-1,2-dihydropyridin-3-yl)methyl]-2-(ethyl{trans-4-[(2-methoxyethyl)(methyl)amino]cyclohexyl}amino)-3-methyl-6,7-dihydrothieno[3,2-c]pyridin-4(5H)-one, Example 29, (0.07 g, 13% yield), ES/MS (m/z): 515 (M+H). 5-[(4,6-dimethyl-2-oxo-1,2-dihydropyridin-3-yl)methyl]-2-(ethyl {cis-4-[(2-methoxyethyl)(methyl)amino]cyclohexyl}-amino)-3-methyl-6,7-dihydrothieno[3,2-c]pyridin-4(5H)-one, Example 30, (0.04 g, 8% yield), ES/MS (m/z): 515 (M+H).

Example 31

2-[{Trans-4-[(cyclopropyl(methyl)amino]cyclohexyl}(ethyl)amino]-5-[(4,6-dimethyl-2-oxo-1,2-dihydropyridin-3-yl)methyl]-3-methyl-6,7-dihydrothieno[3,2-c]pyridin-4(5H)-one

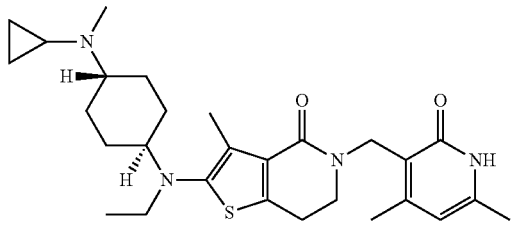 [SMILES: CCN(c1sc2c(c1C)C(=O)N(Cc1c(C)cc(C)[nH]c1=O)CC2)[C@H]1CC[C@H](N(C)C2CC2)CC1]

Add LiCl (0.23 g, 5.38 mmol) and PTSA (0.97 g, 5.38 mmol) to a solution of 2-[{4-trans-[cyclopropyl(methyl)amino]cyclohexyl}(ethyl)amino]-5-[(2-methoxy-4,6-dimethylpyridin-3-yl)methyl]-3-methyl-6,7-dihydrothieno[3,2-c]pyridin-4(5H)-one (0.55 g, 1.07 mmol) in DMF (5.4 mL) and heat 90° C. for 1 hr. Cool to RT and add saturated aqueous $NaHCO_3$ solution, extract with EtOAc, and separate the layers. Dry the organic phase over anhydrous $Na_2SO_4$, filter, concentrate in vacuo, and load the resulting residue onto an SCX cartridge, eluting first with MeOH and then with 2M $NH_3$ in MeOH. Concentrate the methanolic ammonia fraction in vacuo and subject the resulting residue to chromatography by SFC (CHIRALCEL® OD, 5 μm, 2×25 cm), eluting isocratically at 30% with a mobile phase of $CO_2$/MeOH containing 0.2% DMA at 65 mL/minute, to afford the title compound as a solid (0.15 g, 29% yield). ES/MS (m/z): 497 (M+H).

Example 32

5-[(4,6-Dimethyl-2-oxo-1,2-dihydropyridin-3-yl)methyl]-2-{[trans-4-(3-ethoxyazetidin-1-yl)cyclohexyl](ethyl)amino}-3-methyl-6,7-dihydrothieno[3,2-c]pyridin-4(5H)-one

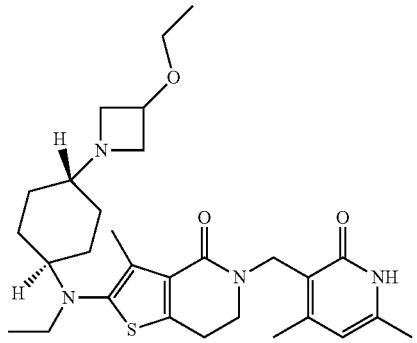 [SMILES: CCOC1CN([C@H]2CC[C@H](N(CC)c3sc4c(c3C)C(=O)N(Cc3c(C)cc(C)[nH]c3=O)CC4)CC2)C1]

Add 10% Pd on carbon (0.035 g, 0.033 mmol) to a solution of 5-{[2-(benzyloxy)-4,6-dimethylpyridin-3-yl]methyl}-2-{[trans-4-(3-ethoxyazetidin-1-yl)cyclohexyl](ethyl)amino}-3-methyl-6,7-dihydrothieno[3,2-c]pyridin-4(5H)-one (0.084 g, 0.13 mmol) in EtOAc (2 mL) and MeOH (2 mL). Charge the reaction vessel with $H_2$ (345 kPa), stir for about 3 hr, filter, and concentrate the reaction mixture in vacuo. Subject the resulting residue to chromatography on silica, eluting with a gradient of 20% EtOAc in DCM followed by 0-10% 7N $NH_3$/MeOH in DCM, to afford the title compound (0.041 g, 57% yield) as yellow gum after solvent evaporation. ES/MS (m/z): 527 (M+H).

Example 33

5-[(4,6-Dimethyl-2-oxo-1,2-dihydropyridin-3-yl)methyl]-2-(ethyl{trans-4-[3-(1H-pyrazol-1-yl)azetidin-1-yl]cyclohexyl}amino)-3-methyl-5,6,7,8-tetrahydro-4h-thieno[3,2-c]azepin-4-one

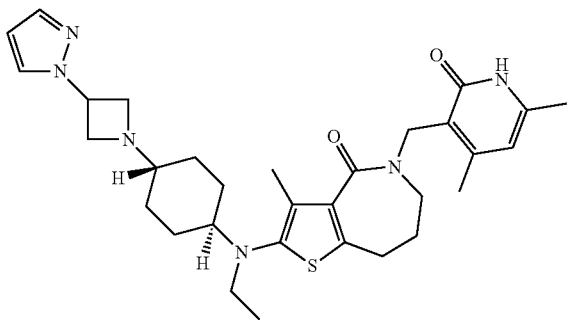 [SMILES: CCN(c1sc2c(c1C)C(=O)N(Cc1c(C)cc(C)[nH]c1=O)CCC2)[C@H]1CC[C@H](N2CC(n3cccn3)C2)CC1]

Add 1-(azetidin-3-yl)pyrazole (0.600 g, 4.87 mmol) to a solution of MeOH (10 mL) containing DIPEA (1.5 mL, 8.6 mmol), stir at RT for 30 min, then add 5-[(4,6-dimethyl-2-oxo-1,2-dihydropyridin-3-yl)methyl]-2-[ethyl(4-oxocyclohexyl)amino]-3-methyl-5,6,7,8-tetrahydro-4H-thieno[3,2-c]azepin-4-one (0.800 g, 1.76 mmol) in THF (10 mL). Stir at RT for 1 hr, cool the reaction mixture to −78° C., and add a solution of 2M $LiBH_4$ in THF (0.9 mL, 1.8 mmol). Stir the resulting mixture for 3 hr, gradually warm to RT, and stir overnight. Pour the reaction mixture into ice-cold saturated $NaHCO_3$ solution, extract with DCM, separate the layers, and concentrate the organic phase in vacuo. Subject the residue to reverse phase chromatography on C-18 silica (100 g, Thermo Scientific Hypersil GOLD™), eluting with a gradient of 0-50% ACN containing 0.1% formic acid and water containing 0.1% formic acid, evaporate the solvent, and subject the resulting residue an additional time to reverse phase chromatography on C-18 silica (100 g, Thermo Scientific Hypersil GOLD™), eluting with a gradient of 0-40% ACN containing 0.1% formic acid and water containing 0.1% formic acid. Treat the combined chromatography fractions with saturated aqueous $NaHCO_3$ solution, extract with DCM, separate the layers, dry the organic phase over $MgSO_4$, filter, concentrate the filtrate in vacuo, and dry in a vacuum oven overnight to afford the title compound as a single isomer (0.047 g, 4.7% yield) as a white solid. ES/MS (m/z): 563 (M+H).

Example 34

5-[(4,6-Dimethyl-2-oxo-1,2-dihydropyridin-3-yl)methyl]-2-{ethyl[trans-4-(3-methoxyazetidin-2-yl)cyclohexyl]amino}-3-methyl-5,6,7,8-tetrahydro-4H-thieno[3,2-c]azepin-4-one

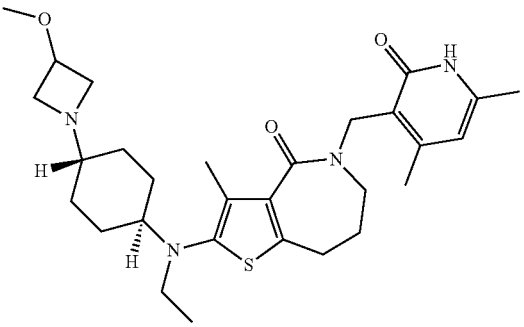

Add 3-methoxyazetidine hydrochloride (0.580 g, 4.69 mmol) to a solution of MeOH (5 mL) and DIPEA (1 mL, 5.7 mmol), stir at RT for 30 min, then add 5-[(4,6-dimethyl-2-oxo-1,2-dihydropyridin-3-yl)methyl]-2-[ethyl(4-oxocyclohexyl)amino]-3-methyl-5,6,7,8-tetrahydro-4H-thieno[3,2-c]azepin-4-one (0.600 g, 1.12 mmol, 85% purity) in THF (5 mL). Stir the resulting mixture at RT for 1 hr, cool to −78° C., and add a solution of 2M LiBH₄ in THF (1.2 mL, 2.4 mmol). Stir the resulting mixture for 1 hr, warm to RT with stirring for 2 hr, then pour the reaction mixture into ice-cold saturated NaHCO₃ solution. Extract with DCM (3×100 mL), separate the layers, and concentrate the organic phase in vacuo. Subject the resulting residue to chromatography on silica, eluting with a gradient of 0-10% MeOH in DCM, to afford a mixture of the trans- and cis-isomers after solvent evaporation. Separate the trans- and cis-isomers by reverse phase chromatography over C-18 silica (100 g, Thermo Scientific Hypersil GOLD™), eluting with a gradient of 0-60% ACN in 10 mM aqueous NH₄CO₃, to afford the title compound (0.0779 g, 13% yield) as a white solid after solvent evaporation. ES/MS (m/z): 527 (M+H).

Example 35

2-[{Trans-4-[3-(cyclopropyloxy)azetidin-1-yl]cyclohexyl}(methyl)amino]-5-[(4,6-dimethyl-2-oxo-1,2-dihydropyridin-3-yl)methyl]-3-methyl-5,6,7,8-tetrahydro-4H-thieno[3,2-c]azepin-4-one

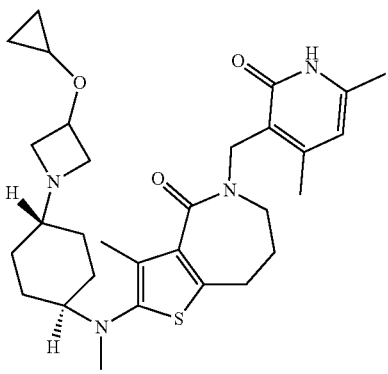 [SMILES: Cc1cc(C)c(CN2CCCc3sc(N(C)[C@H]4CC[C@H](N5CC(OC6CC6)C5)CC4)c(C)c3C2=O)c(=O)[nH]1]

Slurry 3-(cyclopropoxy)azetidine hydrochloride (0.400 g, 2.67 mmol) in MeOH (10 mL), add THF (10 mL) and DIPEA (0.600 mL, 3.44 mmol), stir at RT for 30 min, add 5-[(4,6-dimethyl-2-oxo-1,2-dihydropyridin-3-yl)methyl]-3-methyl-2-[methyl(4-oxocyclohexyl)amino]-5,6,7,8-tetrahydro-4H-thieno[3,2-c]azepin-4-one (0.300 g, 0.577 mmol, 85% purity), and stir the resulting mixture at RT overnight. Cool the mixture to −78° C. and add a solution of 2M LiBH₄ in THF (0.700 mL, 1.4 mmol). Stir the resulting mixture for 1 hr at −78° C. Warm the mixture to RT, stir for 1 hr, pour the reaction mixture into ice-cold saturated NaHCO₃ solution, extract with DCM, separate the layers, and concentrate the organic layer in vacuo. Subject the resulting residue to chromatography on silica, eluting with a gradient of 0-5% 7N methanolic NH₃ in DCM. Collect the chromatography fractions containing the trans- and cis-isomers and concentrate in vacuo. Separate the trans- and cis-isomers by reverse phase chromatography on C-18 silica (40 g, Thermo Scientific Hypersil GOLD™), eluting with a gradient of 5-60% ACN in 10 mM aqueous NH₄CO₃, to afford the title compound (0.0662 g, 21% yield) as a light brown solid after solvent evaporation. ES/MS (m/z): 539 (M+H).

Example 36

5-[(4,6-Dimethyl-2-oxo-1,2-dihydropyridin-3-yl)methyl]-2-{(trans-4-[3-(2-methoxyethoxy)azetidin-1-yl]cyclohexyl}(methyl)amino]-3-methyl-5,6,7,8-tetrahydro-4H-thieno[3,2-c]azepin-4-one

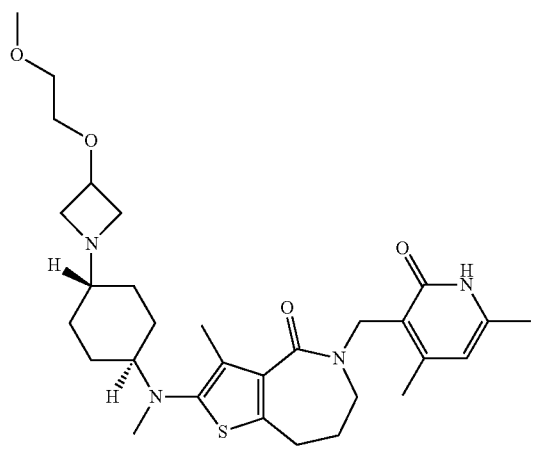 [SMILES: COCCOC1CN([C@H]2CC[C@H](N(C)c3sc4c(c3C)C(=O)N(Cc3c(C)cc(C)[nH]c3=O)CCC4)CC2)C1]

Stir 3-(2-methoxyethoxy)azetidine (0.437 g, 2.460 mmol) in MeOH (5 mL) and THF (5 mL) containing DIPEA (0.418 mL, 2.40 mmol) at RT for 30 min. Add 5-[(4,6-Dimethyl-2-oxo-1,2-dihydropyridin-3-yl)methyl]-3-methyl-2-[methyl(4-oxocyclohexyl)amino]-5,6,7,8-tetrahydro-4H-thieno[3,2-c]azepin-4-one (0.35 g, 0.67 mmol) and stir at RT for 1 hr. Cool the mixture to −78° C. and add a solution of 2M LiBH4 in THF (0.87 mL, 1.7 mmol), stir the resulting mixture for 2 hr at −78° C. and warm to RT overnight. Cool the mixture to −78° C., add a solution of 2M LiBH4 in THF (0.5 mL, 1.0 mmol), and warm to RT. Pour the reaction mixture into ice-cold saturated NaHCO₃ solution, extract with DCM, separate the layers, dry the organic extracts over Na₂SO₄, filter, and concentrate the organic extracts in vacuo. Subject the resulting residue to chromatography on silica, eluting with a gradient of 0-40% of a 10% solution 7N methanolic NH3/DCM in DCM. Collect the chromatography fractions containing the trans- and cis-isomers and concentrate in vacuo. Separate the trans- and cis-isomers by reverse phase chromatography on C-18 silica (15.5 g Thermo Scientific Hypersil GOLD™), eluting with a gradient of 10-100% ACN in 10 mM aqueous NH₄CO₃ containing 5% MeOH, to afford the title compound (0.036 g, 9% yield) as a white solid after solvent evaporation. ES/MS (m/z): 557(M+H).

Example 37

5-[(4,6-Dimethyl-2-oxo-1,2-dihydropyridin-3-yl)methyl]-2-{[trans-4-(3-ethoxyazetidin-1-yl)cyclohexyl](methyl)amino}-3-methyl-5,6,7,8-tetrahydro-4H-thieno[3,2-c]azepin-4-one

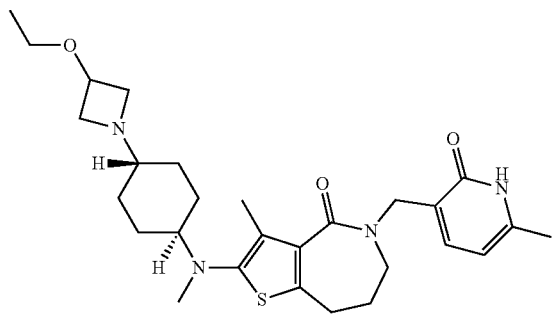 [SMILES: CCOC1CN([C@H]2CC[C@H](N(C)c3sc4c(c3C)C(=O)N(Cc3ccc(C)[nH]c3=O)CCC4)CC2)C1]

To 5-[(4,6-dimethyl-2-oxo-1,2-dihydropyridin-3-yl)methyl]-3-methyl-2-[methyl(4-oxocyclohexyl)amino]-5,6,7,8-tetrahydro-4H-thieno[3,2-c]azepin-4-one (0.320 g, 0.616 mmol) in THF (10 mL), add 3-ethoxyazetidine hydrochloride (0.424 g, 3.08 mmol) in MeOH (5 mL) and DIPEA (0.55 mL, 3.15 mmol). Stir at RT for 30 min. Cool the mixture to −78° C. and slowly add a solution of 2M LiBH₄ in THF (0.650 mL, 1.3 mmol), stir the resulting mixture for 1 hr at −78° C., warm to RT, and stir for 1 hr. Pour the reaction mixture into ice-cold saturated NaHCO₃ solution, extract with DCM, separate the layers, dry the organic extract over Na₂SO₄, filter, and concentrate the filtrate in vacuo. Subject the resulting residue to chromatography on silica, eluting with a gradient of 0-70% of a 10% solution 7N methanolic NH₃ in DCM to DCM. Collect the chromatography fractions containing the trans- and cis-isomers and concentrate in vacuo. Separate the trans- and cis-isomers by reverse phase chromatography on C-18 silica (Phenomenex Luna), eluting with a gradient of 40-75% ACN in 10 mM aqueous NH₄CO₃ containing 5% MeOH, to afford the title compound (0.099 g, 37% yield) as a white solid after solvent evaporation. ES/MS (m/z): 527(M+H).

Example 38

5-[(4,6-Dimeihyl-2-oxo-1,2-dihydropyridin-3-yl)methyl]-2-{(1R)-1-[trans-4-(3-methoxyazetidin-1-yl)cyclohexyl]ethyl}-3-methyl-5,6,7,8-tetrahydro-4H-thieno[3,2-c]azepin-4-one

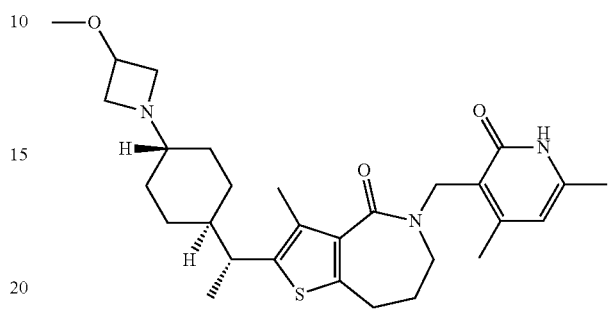

To 3-methoxyazetidine hydrochloride (480 mg, 3.88 mmol) in MeOH (10 mL) and THF (10 mL), add DIPEA (1.0 mL, 5.7 mmol) and stir at RT for 30 min. Add 5-[(4,6-dimethyl-2-oxo-1,2-dihydropyridin-3-yl)methyl]-3-methyl-2-[(1R)-1-(4-oxocyclohexyl)ethyl]-5,6,7,8-tetrahydro-4H-thieno[3,2-c]azepin-4-one (0.25 g, 0.57 mmol) to the solution and stir at RT for 1 hr. Cool the reaction mixture to −78° C. and then add 2M lithium borohydride in THF (1.0 mL, 2.0 mmol). After 3 hr, remove the cold bath and stir for 1 hr at RT. Pour the reaction mixture into an ice-cold saturated aqueous NaHCO₃ solution and concentrate in vacuo. Subject the resulting residue to reverse phase chromatography eluting with a gradient of 0-50% ACN (containing 0.1% formic acid) in water (containing 0.1% formic acid). Collect the pure fractions and concentrate to afford the product as the formic acid salt. Combine the product with material from a previously run reaction of about 2 times the scale following a similar procedure. To the combined product mixture add saturated aqueous NaHCO₃ solution, extract with DCM, wash with brine, dry over MgSO₄ and filter. Concentrate the filtrate in vacuo and dry in an oven overnight to afford the title compound (0.057 g combined mass, 6% combined yield) as a white solid. ES/MS (m/z): 512 (M+H). $[\alpha]_D^{20} = -42.80°$ (c=1.0, MeOH).

Alternative Procedure to Example 38

Add chlorotrimethylsilane (233 ml, 1.83 mol) over a 10 minute period at a temperature of 25 to 34° C. to a mixture of 2-[(1R)-1-[4-(3-methoxyazetidin-1-yl)cyclohexyl]ethyl]-5-[(2-methoxy-4,6-dimethyl-3-pyridyl)methyl]-3-methyl-7,8-dihydro-6H-thieno[3,2-c]azepin-4-one (240 g, 0.456 mol) and NaI (267 g, 1.78 mol) in acetonitrile. Heat the reaction at 33 to 41° C. for 2 h. Cool to RT, and dilute twice with acetonitrile (4 L), concentrating the mixture to the original volume each time under reduced pressure. Dilute the mixture with ethyl acetate (2.4 L) and water (2.4 L), and adjust to approximately pH 10 with NH₄OH (380 ml). Separate the resulting layers wash the organic layer with saturated aqueous NaCl (1.9 L). Dry the organic layer over Na₂SO₄, filter, and remove the solvent under reduced pressure. Purify the resulting residue by filtration over a silica gel plug, eluting first with 10% EtOH in EtOAc, then with a mixture of 5% 7N NH₃ in MeOH and 10% EtOH in EtOAc. Evaporate the methanolic ammonia filtrate and triturate the resulting residue with acetone (3 volumes) at 0° C. Dry under vacuum at RT to obtain the title compound (186.4 g, 80% yield) as a white solid. ES/MS (m/z): 512 (M+H).

Example 39

5-[(4,6-Dimethyl-2-oxo-1H-pyridin-3-yl)methyl]-3-methyl-2-[(1R)-1-[4-(3-pyrazol-1-ylazetidin-1-yl)cyclohexyl]ethyl]-7,8-dihydro-6H-thieno[3,2-c]azepin-4-one

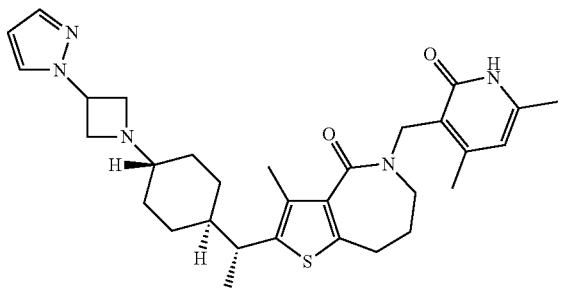 [SMILES: Cc1cc(C)c(CN2CCCc3sc([C@H](C)[C@H]4CC[C@H](N5CC(n6cccn6)C5)CC4)c(C)c3C2=O)c(=O)[nH]1]

Add THF (5 mL) and DIPEA (0.500 mL, 2.87 mmol) to a solution of 1-(azetidin-3-yl)pyrazole (0.380 g, 3.09 mmol) in MeOH (5 mL), stir the resulting mixture at RT for 30 min, add 5-[(4,6-dimethyl-2-oxo-1,2-dihydropyridin-3-yl)methyl]-3-methyl-2-[(1R)-1-(4-oxocyclohexyl)ethyl]-5,6,7,8-tetrahydro-4H-thieno[3,2-c]azepin-4-one (0.400 g, 0.763 mmol, 84% purity), and stir the mixture overnight at RT. Cool the reaction mixture to −78° C., add a solution of 2M LiBH₄ in THF (0.720 mL, 1.4 mmol), stir the resulting mixture at −78° C. for 2 hr, warm to RT, stir for 2 hr, pour the mixture into ice-cold saturated aqueous NaHCO₃ solution, extract with DCM (3×100 mL), separate the layers, and concentrate the combined organic phases in vacuo Subject the resulting residue to reverse phase chromatography over C-18 silica, eluting with a gradient of 5-60% ACN in 10 mM aqueous NH₄CO₃, to afford the title compound (0.110 g, 26% yield) as a white solid after solvent evaporation and vacuum drying. ES/MS (m/z): 548 (M+H).

Example 40

2-{(1R)-1-[Trans-4-(dimethylamino)cyclohexyl]ethyl}-5-[(4,6-dimethyl-2-oxo-1,2-dihydropyridin-3-yl)methyl]-3-methyl-6,7-dihydrothieno[3,2-c]pyridin-4(5H)-one methanesulfonate

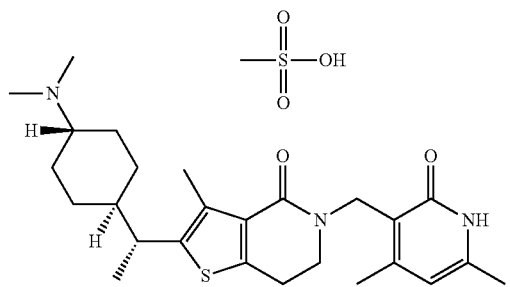

Add MsOH (9.1 mg, 94.3 mmol) to a suspension of 2-{(1R)-1-[trans-4-(dimethylamino)cyclohexyl]ethyl}-5-[(4,6-dimethyl-2-oxo-1,2-dihydropyridin-3-yl)methyl]-3-methyl-6,7-dihydrothieno[3,2-c]pyridin-4(5H)-one (42.9 mg, 90.5 mmol) in MeOH (2 mL) and sonicate to obtain a colorless solution. Concentrate the solution in vacuo to obtain the title compound (47.8 mg, 93.8% yield) as a white solid. ES/MS (m/z): 454.3 (M−H).

Example 41

5-[(4,6-Dimethyl-2-oxo-1,2-dihydropyridin-3-yl)methyl]-3-methyhl-2-[(1R)-1-{trans-4-[3-(5-methyl-1H-pyrazol-1-yl)azetidin-1-yl]cyclohexyl}ethyl]-6,7-dihydrothieno[3,2-c]pyridin-4(5H)-one methanesulfonate

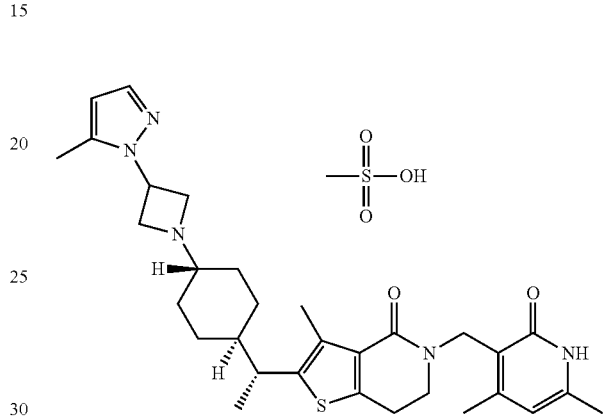

Add a solution of MsOH (1.55 μL, 0.0238 mmol) in MeOH (1 mL) to a solution of 5-[(4,6-dimethyl-2-oxo-1H-pyridin-3-yl)methyl]-3-methyl-2-[(1R)-1-[4-[3-(5-methyl-pyrazol-1-yl)azetidin-1-yl]cyclohexyl]ethyl]-6,7-dihydrothieno[3,2-c]pyridin-4-one (12.7 mg, 0.023 mmol) in MeOH (2 mL). Sonicate the mixture to obtain a clear solution. Concentrate in vacuo and dry the resulting residue in an oven at about 40° C., then at RT for several days, to afford the title compound (13.8 mg, 84% yield) as a white solid. ES/MS (m/z): 548 (M+H).

Example 42

5-[(4,6-Dimethyl-2-oxo-1,2-dihydropyridin-3-yl)methyl]-3-methyl-2-[(1R)-1-{trans-4-[3(3-methyl-1H-pyrazol-1-yl)azetidin-1-yl]cyclohexyl}ethyl]-6,7-dihydrothieno[3,2-c]pyridin-4(5H)-one methanesulfonate

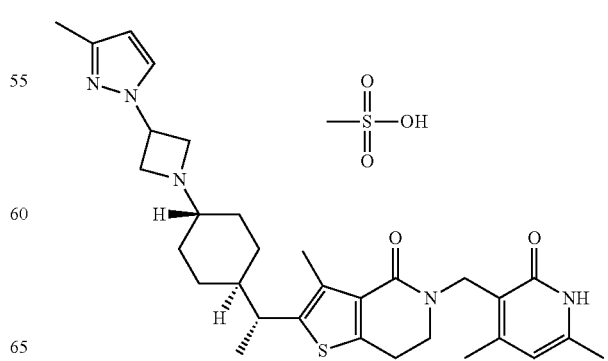

Add MsOH (1.73 μL, 0.0265 mmol) to a suspension of 5-[(4,6-dimethyl-2-oxo-1,2-dihydropyridin-3-yl)methyl]-3-methyl-2-[(1R)-1-{trans-4-[3-(3-methyl-1H-pyrazol-1-yl)azetidin-1-yl]cyclohexyl}ethyl]-6,7-dihydrothieno[3,2-c]pyridin-4(5H)-one (14.5 mg, 0.027 mmol) in MeOH (2 mL). Concentrate the solution in vacuo and dry the resulting residue in a vacuum oven at 50° C. for 2 hr to afford the title compound (15.1 mg, 89% yield) as a white solid. ES/MS (m/z): 548 (M+H).

Example 43

5-[(4,6-Dimethyl-2-oxo-1,2-dihydropyridin-3-yl)methyl]-2-[(1R)-1-{trans-4-[(2-methoxyethyl)(methyl)amino]cyclohexyl}elhyl]-3-methyl-6,7-dihydrthieno[3,2-c]pyridin-4(5H)-one

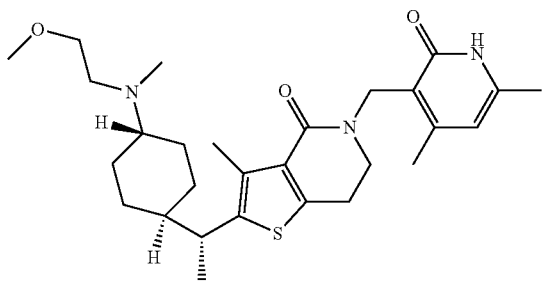

Dissolve 5-[(2-methoxy-4,6-dimethyl-3-pyridyl)methyl]-2-[(1R)-1-{trans-4-[2-methoxyethyl(methyl)amino]cyclohexyl}ethyl]-3-methyl-6,7-dihydrothieno[3,2-c]pyridin-4-one (48.0 mg, 0.093 mmol) in DMF (3.0 mL). Add LiCl (30.0 mg, 0.71 mmol) and PTSA (30 mg, 0.16 mmol). Heat the mixture at 60° C. for 4 hr. Cool to RT and stir overnight. Dilute with EtOAc (30 mL) and water (3 mL). Extract the ethyl acetate layer with water and dry the EtOAc phase over MgSO$_4$. Filter and concentrate the filtrate in vacuo. Subject the resulting residue to chromatography on silica, eluting with a gradient of 0-10% MeOH in DCM, to afford the title compound (47 mg, quantitative yield) as a white powder after solvent removal. ES/MS (m/z): 500 (M+H).

Biological Assays

EZH2 expression has been linked in the literature to multiple types of cancer, for example, lymphomas (Velichutina, I. et al. (2010) Blood 116:5247-55; Sneeringer, C. J. et al. (2010) Proc Natl Acad Sci USA. 107:20980-5; McCabe et al. (2012) Nature 492:108-12. Béguelin, W. et al. (2013) Cancer Cell 23:677-92; Knutson, S. K. et al. Mol Cancer Ther 13:842-54), rhabdoid tumors (Knutson, S. K. et al. (2013) Proc Natl Acad Sci USA. 110: 7922-7), tumors which lack or are defective for SNF5 (Wilson, B. G. et al. (2010) Cancer Cell 18:316-28), sarcomas (Kadoch and Crabtree (2013) Cell 153:71-85; Shen et al. (2016) Sci Rep 6:25239), multiple myeloma (Kalushkova, A. et al. (2010) PLoS One 5:e11483; Popovic, R. et al. (2014) PLoS Genet. 10:e1004566; Hernando, H. et al. (2016) Mol Cancer Ther. 15(2):287-98; Agarwal, P et al. (2016) Oncotarget 7:6809-23), melanoma (Zingg et al. (2015) Nat Commun. 6:6051; Barsotti, A. M. et al. (2015) Oncotarget 6(5):2928-38; Souroullas, G. P. et al. (2016) Nat. Med. 22:632-40), colorectal cancer (Nagarsheth, N. et al. (2016) Cancer Res. 76:275-82), lung cancer (Byers, L. A. et al. (2012) Cancer Discov. 2:798-811; Behrens, C. et al. (2013) Clin Cancer Res. 19:6556-65; Riquelme, E. et al. (2014) Clin Cancer Res. 20:3849-61; Fillmore, C. M. et al. (2015) Nature 520:239-42), kidney cancer (Adelaiye, R. et al. (2015) Mol Cancer Ther. 14(2):513-22), breast cancer (Kleer, C. G. et al. (2003), Proc Natl Acad Sci USA. 100:11606-11; Ren et al. (2012) Cancer Res 72:3091-104), ovarian cancer (Bitler et al. (2015) Nat Med 21:231-8), and prostate cancer (Varambally, S. et al. (2002) Nature 419:624-9; Yu, J. et al. (2007) Cancer Res. 67:10657-63; Varambally, S. et al. (2008) Science 322:1695-9; Yu, J. et al. (2010) Cancer Cell 17:443-54).

The results of the following assays demonstrate that the compounds of examples 1-43 are EZH2 inhibitors and that compounds of the present invention, for example, Examples 1, 9, 13, 22, and 38, herein may be useful in treating cancer. As used herein, "IC$_{50}$" refers to the concentration of an agent which produces 50% of the maximal inhibitory response possible for that agent, (relative IC$_{50}$), or the concentration of an agent which produces 50% inhibition of the target enzyme activity compared to placebo control (absolute IC$_{50}$).

EZH2 WT/Y641N Mut 384-Well Biochemical Assay

The purpose of this assay is to measure the compound effect on the catalytic activity of EZH2 WT/Y641N in the context of the PRC2 complex.

Express FLAG-tagged EZH2 or EZH2 Y641N as the PRC2 5-membered (5-mer) complex consisting of EZH2, EED, SUZ12, RBBP4 and AEBP proteins using a baculovirus expression system in Sf9 cells, and purify using FLAG® Affinity Purification (Sigma-Aldrich). Dilute the enzyme complex into a working stock of 3.33 nM (6.67 nM for mut assay) with Assay Buffer (50 mM Tris-HCl pH 8.5, 10 mM DTT, 0.005% TRITON®-X 100). In the WT assay, dilute non-biotin lysine 27 tri-methylated histone H3 (21-44) co-activator peptide (CPC Scientific Cat #869799) into the above enzyme working solution to a final concentration of 13.33 nM. Co-dilute biotin histone H3 (21-44) peptide substrate (residues 21-44, CPC Scientific Cat#811115) for the WT assay or biotin lysine 27 di-methylated histone H3 (21-44) peptide substrate (CPC Scientific, Cat#830754) for the mut assay with $^3$H-SAM (Adenosyl-L-methionine, S-(methyl)-$^3$H(Adomet), lot 169500/12, 15 Ci/mmol or 0.55 mCi/mL, 36.7 μM, Perkin Elmer NET155) to a final concentration of 4 μM (WT assay) or 2 μM (mut assay) in Assay Buffer.

Add test compounds in 100% DMSO (50 μL of a 4 mM stock for WT assay or 50 μL of a 0.2 mM stock for mut assay) to a 384 well NUNC™ plate (Thermo Scientific, Cat#264573). Place 20 μL 100% DMSO in dilution wells. Perform 3× serial dilutions by transferring 10 μL from one well to the next. In the WT assay, mix 2 μL of serially diluted compound with 38 μL of DMSO in a Labcyte 384 well plate (Cat# P-05525), whereas in the mut assay, transfer all 20 μL of serially diluted compound to a 384-well Labcyte low volume plate (Cat# LP-0200). 200 nL (WT assay) or acoustically transfer 100 nL (mut assay) compound to a recipient 384-well assay plate (Corning 3706). In the WT assay, dispense 15 μL of the enzyme/tri-methyl H3 co-activator peptide mix into the assay plate, followed by 5 μL of the biotin H3 peptide substrate/$^3$H-SAM mix. Seal the plates and shake for 2 hr at RT. Final assay conditions are 2.5 nM enzyme complex, 10 nM tri-methyl histone/co-activator H3 peptide, 1 μM biotin substrate peptide, 1 μM ³H-SAM, and test compound at a top concentration of 1 μM (WT assay); or 5 nM enzyme complex, 0.5 μM biotin substrate peptide, 0.5 μM³H-SAM, and test compound at a top concentration of 1 μM (mut assay). Reconstitute Yttrium Silicate Streptavidin SPA beads (Perkin Elmer, Cat# RPNQ0012) at 1 mg/mL (WT assay) or 0.5 mg/mL (mut assay) in 3 M guanidine-HCL. Add the bead mixture to the assay plates at 20 μL per well, shake for 10 min, and allow to settle for 1 hr at RT prior to counting on a MICROBETA®. Calculate raw data (CPM) and normalize to % inhibition using Genedata Assay Analyzer as % Inhibition=100−[(Test Compound CPM−Median Min CPM)/(Median Max CPM−Median MM CPM)×100]. Plot normalized data and render curves using GENEDATA® Condoseo as % inhibition (y axis) vs. log compound concentration (x-axis), and determine $IC_{50}$ values using a 4-parameter nonlinear logistic fitting algorithm. Compounds within the scope of the invention may be tested in this assay substantially as described above. For example, the compounds of Examples 1 and 20 have biochemical $IC_{50}$ results that demonstrate inhibition of the methyltransferase activity of recombinant WT/mut EZH2 in the context of the PRC2 complex. For example, the compound of Example 1 shows an $IC_{50}$ of 2.06±1.90 nM (n=5) against WT 5-mer EZH2 and 2.11±0.58 nM (n=2) against mut 5-mer EZH2. The compound of Example 22 shows an $IC_{50}$ of 3.29±1.24 nM (n=3) against WT 5-mer EZH2 and 7.21 nM (n=1) against mut 5-mer EZH2. The compound of Example 38 shows an $IC_{50}$ of 0.923±0.091 nM (n=2) against WT 5-mer EZH2 and 2.65 nM (n=1) against mut 5-mer EZH2.

H3K27me3 Cell-Based ELISA

The purpose of this assay is to evaluate the ability of a compound to inhibit the functional activity of EZH2 in cells, via measurement of levels of cell tri-methylated H3K27. Plate Karpas-422 (EZH2 Y641N) cells at 5,000 cells/100 μL/well in black 96-well BD BIOCOAT® Cellware, Poly-Lysine plates (BD Biosciences, Cat#354640). Prepare compound plates in a NUNC™ 96-Well Polypropylene MICROWELL™ Plate (Thermo Scientific Cat# #249944) with the addition of 40 μL/well of 10 mM compound (representing starting final concentration of 20 μM) or 40 μL DMSO, then prepare serial dilutions through the transfer of 20 μL from one well to the next. Add 5 μL of test compound to 245 μL/well of growth media in a separate NUNC™ 96-Well Polypropylene MICROWELL™ Plate, and stamp 11 μL of the compound/media mix onto the cell plates. Place cell plates in a 37° C. incubator for 48 hr. Remove plates from the incubator, place the plates at room temperature for 15-20 min, and spin down the plates at 1000 rpm for 5 min. Fix cells with 30 μL 16% paraformaldehyde for 15 min at RT. Remove the paraformaldehyde and permeabilize cells with 100 μL/well PBS minus calcium or magnesium (−/−) containing 0.1% TRITON® X-100 for 20 min at RT. Wash plates with PBS(−/−) (2×), followed by incubation for 2 hr at RT of 50 μL/well of primary antibody solution (Diagenode anti-H3K27me3 MAb-181-050; 1:3000 dilution in PBS plus calcium and magnesium (+/+) containing 1% BSA). Wash plates with PBS−/−, (3×) followed by incubation with 50 μL/well secondary antibody solution (Invitrogen goat anti-mouse IgG Alexa 488, Cat# A11001; 1:1000 dilution in PBS+/+) for 1 hr at RT in the dark. Wash plates with PBS−/−, (3×), followed by adding 50 μL/well of 5 μg/mL propidium iodide (Invitrogen; Cat# p3566) staining solution in PBS containing 200 μg/mL RNase (Invitrogen; Cat#12091021). Cover plates with black plate seals and scan on ACUMEN® laser scanning cytometer (TTP Lab Tech) with Ex 488 nm/Em 505 nm-530 nm (H3K27m3 signal) and LP655 nm (cell nuclear signal). Compounds within the scope of the invention may be tested in this assay substantially as described above. For example, the compound of Example 1 shows a cell H3K27me3 $IC_{50}$ of 19.2±1.55 nM (n=2) or 23.6±20.5 nM (n=6) in MDA MB-231 and Karpas-422, respectively. The compound of Example 22 shows a cell H3K27me3 $IC_{50}$ of <1 nM (n=1) or 0.0148±0.0147 nM (n=6) in MDA MB-231 and Karpas-422, respectively. The compound of Example 38 shows a cell H3K27me3 $IC_{50}$ of 0.00973±0.00956 nM (n=4) in Karpas-422.

Karpas-422 Proliferation Assay

The purpose of this assay is to demonstrate the ability for test compounds to inhibit the growth of tumor cells in vitro.

Plate Karpas-422 cells at a density of 5000 cells/100 μL/well in 96 well, black 96-well BD BIOCOAT® Cellware, Poly-Lysine plates (BD Biosciences, Cat#354640). 40 μL of 10 mM test compound (representing starting final concentration of 20 μM) or add 100% DMSO to a NUNC™ 96-Well Polypropylene MICROWELL™ Plate (Thermo Scientific Cat# #249944). Perform serial dilutions through the transfer of 20 μL from one well to the next. Add 5 μL of compound to a 245 μL/well of growth media in a separate NUNC™ 96-Well Polypropylene MICROWELL™ Plate, and stamp 11 μL of the compound/media mix onto the cell plates. Incubate cell plates at 37° C. for 7 days. Add 100 μL/well of Cell Titer GLO® reagent (Promega, Cat# G7671) to the cell plates. Shake 2 mm and measure luminescence using a plate reader. Compounds within the scope of the invention may be tested in this assay substantially as described above. For example, the compound of Example 1 shows an $IC_{50}$ of 176±165 nM (n=5). The compound of Example 22 shows an $IC_{50}$ of 84.5±42.7 nM (n=5). The compound of Example 38 shows an $IC_{50}$ of 10.1±4.6 nM (n=4).

Xenograft Studies

The purpose of this assay is to evaluate the ability of a test compound to inhibit tumor EZH2 function and EZH2-mediated tumor growth in vivo.

Conduct in vivo target inhibition and efficacy studies with the compound of Example 1 using the Karpas-422 xenograft model essentially as described in McCabe et al. (2012) Nature 492:108-12, with the following changes/specifications: 1) Use hydroxyethylcellulose (1% HEC/0.25% TWEEN® 80/0.05% antifoam) in place of 20% CAPTISOL® as the formulation vehicle; 2) Administer the compound by oral gavage rather than by intraperitoneal injection; 3) Start compound treatment when tumor volumes reach in range of 150-200 mm³ for efficacy experiments and 300-350 mm³ for target inhibition experiments and; 4) Measure inhibition of tumor methylation or tumor TNFRSF21 expression at day 7 instead of day 10.

ELISA-Based Measurement of Tumor-Derived Tri-Methylated H3K27

To acid-extract histones from tumors, place tumor sections of approximately 0.5 cm by 0.25 cm or 20-30 mg in weight in Lysing Matrix D 500×2 mL Add RNASE/DNASE-free tubes with beads for homogenization (MP Biomedicals, Cat#6913-500). Add 650 μL of Acid Lysis Buffer (0.4 N HCl containing Protease Inhibitor Cocktail Tablets (Roche; Cat#11836153001)). Homogenize tumor samples 2-3 times at speed 6 m/second for 20 seconds in a FASTPREP® FP120 homogenizer. Set samples on ice for 1 hour to separate. Transfer supernatants to an Eppendorf tube and place on a tube rotator to lyse overnight at 4° C. Spin samples down at 8000 rpm for 10 mm at 4° C. Transfer supernatants to a new tube and measure for protein concentration.

Add 150 µL/well of MSD Blocking Solution A (Meso Scale Discovery (MSD); final concentration of 3%) to a MULTI-SPOT® Tri-Methyl-Histone H3(K27) SINGLE-PLEX® plate (MSD; Cat#: N45CA-1). Shake at RT for 1 hr. Wash the plate with 1×MSD Tris Wash Buffer™ (MSD), (3×). Dispense 0.25 µg of tumor lysate in 25 µL Acid Lysis Buffer per well in triplicate. Shake overnight at 4° C. Wash the plate three times with 1×MSD Tris Wash Buffer™. Add 25 µL/well of detection antibody SULFO-TAG™-Trim-ethyl-Histone H3 (K27) diluted to a final concentration of 1.5 µg/µL in Antibody Dilution Buffer (final concentrations of 1% MSD Blocker-A; 0.1% MSD Blocker D-B and 0.1% MSD® Blocker D-G). Shake for 1-2 hr at RT. Wash the plate three times with 1×MSD Tris Wash Buffer. Fix the plate with the addition of 100 µL/well of 4% formaldehyde in PBS. Shake for 30 mm at RT. Wash the plates three times with 1×MSD Tris Wash Buffer. Add 150 µL/well 1×MSD® Read Buffer and measure chemoelectroluminescence using a MSD SECTOR® Imager 6000 instrument. A compound within the scope of the invention may be tested in this assay substantially as described above. For example, BID administration in mice of 50 mpk of the compound of Example 1 results in 53% inhibition of tumor methylation (n=8 mice; p<0.0001). BID administration in mice of 15 mpk of the compound of Example 38 results in 73% inhibition of tumor methylation (n=8 mice; p<0.0001).

qPCR-Based Measurement of Tumor-Derived TNFRSF21 mRNA Expression

To isolate RNA from tumor tissue, place tumor sections of approximately 0.5 cm by 0.25 cm or 20-30 mg in weight in Lysing Matrix D 500×2 mL Add RNASE/DNASE-free tubes with beads for homogenization (MP Biomedicals, REF: 6913-500). Add 650 µL of RLT buffer from RNEASY® Kit (Qiagen; Cat#74104). Homogenize samples 2 to 3 times at speed 6 for 20 seconds in the FASTPREP® FP120 homogenizer. Set samples on ice to cool for 10 mm. Centrifuge at 13 000 rpm for 10 min at 4° C. Place supernatants into a QIA tube and isolate RNA using the RNEASY® Kit (Qiagen; Cat#74104).

Prepare cDNA from 3 µg of tumor RNA using the High Capacity cDNA Reverse Transcription Kit (Applied Biosystems; Cat#4368813) and incubate samples in a PCR Thermocycler using the following cycle conditions: 10 mm at 25° C.; 2 hr at 37° C., hold at 4° C. Amplify cDNA product using Thermo Scientific ABsolute Blue QPCR ROX Mix (Applied Biosystems; Cat# AB-4139) and Taqman probes for TNFRSF21 (Applied Biosystems; Cat# Hs01560899_ml) and housekeeping gene GAPDH (Applied Biosystems; Cat# Hs02758991-gl) in the Applied Biosystems ViiA 7™ Real-Time PCR cycler. Calculate TNFRSF21 cycle threshold values and normalize to its respective sample's GAPDH levels. A compound within the scope of the invention may be tested in this assay substantially as described above. For example, BID administration of 50 mpk of the compound of Example 1 results in a 25-fold increase in tumor TNFRSF21 gene expression (n=8 mice; p<0.0001). BID administration of 15 mpk of the compound of Example 38 results in a 60-fold increase in tumor TNFRSF21 gene expression (n=8 mice; p<0.0001).

Combination Treatments with EZH2 Inhibitors and Other Cancer Chemotherapeutic Agents The following paragraphs provide evidence supporting the use of EZH2 inhibitors, including but not exclusive to Ex. 1 or Ex. 38, alone and/or in combination with Standard of Care (SoC) chemotherapy, in the treatment of ovarian, gastric, lung or colorectal cancers bearing combinations of mutations in components of the SWI/SNF complex and/or MLL complex and/or PI3K pathway. These include but are not exclusive to ovarian cancers lacking ARID1A protein expression combined with mutations in PTEN or PIK3CA and/or constitutive protein expression of Akt phosphorylated on threonine 308 (Thr308). Additionally, these include but are not exclusive to ovarian cancers lacking both SMARCA2 and SMARCA4 protein expression. Additionally, these include but not are not exclusive to gastric cancers bearing heterozygous loss of function (LOF) mutations (including but not limited to nonsense, frameshift and coding-splice mutations) in ARID1A combined with heterozygous LOF mutations in MLL2, and which do not bear homozygous mutations in TP53. Additionally, these include but are not exclusive to gastric cancers bearing a heterozygous LOF mutation (including but not limited to nonsense, frameshift and coding-splice mutations) in ARID1A combined with a mutation in PTEN or PIK3CA and/or constitutive protein expression of Akt phosphorylated on Thr308, and which do not bear a homozygous mutation in TP53. Additionally, these include but are not exclusive to lung cancers with heterozygous LOF mutations in MLL3. Additionally, these include but are not exclusive to colorectal cancers with heterozygous LOF mutations in ARID1A combined with mutations with mutations in PTEN or PIK3CA and/or constitutive protein expression of Akt phosphorylated on Thr308.

Test ovarian cancer cell lines for response to Example 1 or Example 38 in a 7- or 10-day proliferation assay. Optimize each cell line for cell number and splitting schedule which maximizes log phase growth in 96-well format during the 7 or 10-day period. Plate cells in a 96-well black, clear bottom, poly-D-lysine-coated 96-well plate (BD BioSciences; BD BIOCOAT™ Cellware, Poly-Lysine, Cat. #354640) on day 0 in a total volume of 90 µL cell culture media and incubate at 37° C./5% $CO_2$ for 18-24 hrs. On day 1, prepare a compound dilution plate by the addition of 150 µL media containing 2% dimethyl sulfoxide (DMSO; Sigma-Aldrich Cat. #D2438) to columns 3-12 of a 96-well clear flat bottom plate (CORNING® COSTAR® cell culture plate Cat #3596). Prepare 10 mM stocks of Example 1 or Example 38 in 100% DMSO, and further dilute to a working concentration of 200 µM in cell culture media. Add 225 µL of Example 1 or Example 38 to column 2 of the compound dilution plate, and prepare 1:3 10-point serial dilutions of test compound with columns 3 through 12. Add 10 µL of serially diluted compound to cell plates, giving a final test compound concentration range of 1 nM to 20 µM and a final concentration of DMSO of 0.2%. At the end of the 7- or 10-day assay period, subject cells to the CELLTITER-GLO® Luminescent Cell Viability Assay (Promega, Cat. #G7570) as follows: 1) Thaw the CELLTITER-GLO® buffer and equilibrate to room temperature; 2) Equilibrate the lyophilized CELLTITER-GLO® substrate to room temperature; 3) Transfer CELLTITER-GLO® buffer to substrate bottle to form the CELLTITER-GLO® reagent; 4) Equilibrate cell plates to room temperature; 5) For adherent cells only—remove medium from cell plates; 6) Add 25 μL CELLTITER-GLO® reagent to each well; 7) Let plates incubate an additional 20-30 min at room temperature; 8) Read luminescence using the Perkin Elmer EnVision 2104 Multi Detection Microplate Reader.

Derive whole cell lysates of the ovarian cancer cell lines as described in Ye, X. S. et al. (1997) Methods Enzymol. 283:520-32 and measure by Western blot for protein expression of SWI/SNF complex, MLL complex and PI3K pathway components including ARID1A, SMARCA2, SMARCA4 (using 3-8% SDS-PAGE) and Akt phosphorylated on Thr308 (using 4-20% SDS-PAGE), using the following antibodies: anti-ARID1A (Bethyl, Cat. #A301-040A); anti-SMARCA2/BRM (Abcam, Cat. # ab15597); anti-BRG1/SMARCA4 (Bethyl, Cat. #A300-813A) and anti-phospho-Akt (Thr308) Antibody D25E6 (Cell Signaling, Cat. #13038). Use anti-Akt (pan) Antibody 40D4, (Cell Signaling, Cat. #2920) and anti-β-actin AC-74 (Sigma, Cat. #A2228) antibodies to measure total Akt and actin levels as controls for protein loading.

Table 1 summarizes the effect of Example 38 on a panel of ovarian cell lines and show sensitivity to EZH2 inhibitors in ovarian cancer cell lines that are either both ARID1A-negative and phosphorylated on Thr308 on Akt, or lack expression in both SMARCA2 and SMARCA4.

TABLE 1

Effect of Example 38 on the proliferation of 9 ovarian cancer cell lines, as well as their SWI/SNF and PI3K pathway components protein expression profiles.

| Ovarian Cancer Cell Line | Example 38 Proliferation IC50 (μM) | ARID1A | SMARCA2 | SMARCA4 | AKT-pT308 |
|---|---|---|---|---|---|
| COV-434 | 0.02 | + | − | − | − |
| TOV-21G | 0.1 | − | + | + | +++ |
| TOV-112D | 0.2 | + | − | − | − |
| A2780 | 0.2 | − | − | + | + |
| Caov-3 | 8.0 | + | + | + | − |
| OVCAR3 | 8.6 | + | + | + | − |
| SKOV3 | >20 | + | + | + | + |
| HeyA8 | >20 | + | + | + | − |
| HEC59 | >20 | + | + | + | − |

The effect of Example 38 compared to ovarian cancer SoC carboplatin plus paclitaxel is tested in vivo using an A2780 xenograft model. Implant 2 million A2780 cells in 50% MATRIGEL® subcutaneously into the right hind flank of 10 athymic nude mice (Envigo RMS, Inc., Indianapolis, Ind.) per group. Begin treatment when tumors volumes reach 100-150 mm³. Pretreat animals for 5 days with Example 38 followed by co-administration of Example 38 and SoC for at least 23 additional days or until vehicle tumor volumes reach 2000 mm³. Formulate Example 38 in 1% HEC/0.25% TWEEN® 80/0.05% Antifoam and administer at 50 mpk twice a day (BID) by oral gavage (p.o.). Formulate carboplatin (APP Pharmaceuticals NDC 63323-172-60) in phosphate buffered saline (PBS) and administer at 60 mpk very 2 weeks (Q14D) by intraperitoneal (i.p.) injection. Formulate paclitaxel (Hospira, Inc NDC 61703-342-50) in PBS and administer at 10 mpk Q14D by intravenous (IV) injection. Measure tumor growth inhibition as ΔT/C (%), calculated as the mean of individual animal [(tumor volume at Example 38 treatment day 28 minus tumor volume at day 0), divided by (tumor volume at vehicle treatment day 28 minus tumor volume at day 0)], multiplied by 100. Table 2 summarizes the results of the effects of Example 38 and ovarian cancer SoC on A2780 tumor growth on day 28 of treatment. In contrast to the weak effect of SoC alone on A2780 tumor growth, significant inhibition of A2780 tumor growth is observed following treatment with 50 mpk BID p.o. Example 38 alone, and following treatment with 50 mpk QD p.o. Example 38 in combination with SoC.

TABLE 2

Effect of Example 38, ovarian SoC carboplatin plus paclitaxel, and Example 38 in combination with SoC on A2780 tumor growth, on dosing day 28.

| Treatment | Dose and frequency | Route | ΔT/C (%), p-value |
|---|---|---|---|
| Example 38 | 50 mpk BID | p.o. | 10.5 (p < 0.001) |
| carboplatin/paclitaxel | 60 mpk Q14D (carboplatin) 10 mpk Q14D (paclitaxel) | i.p. (carboplatin) IV. (paclitaxel) | 64.9 (p = 0.084) |
| Example 38 + carboplatin/paclitaxel | 50 mpk QD (Ex. 38) 60 mpk Q14D (carboplatin) 10 mpk Q14D (paclitaxel) | p.o. (Ex. 38) i.p. (carboplatin) IV (paclitaxel) | 15.6 (p < 0.001) |

START Discovery (http://startdiscovery.net/) has a platform of patient-derived tumor models. Select two START Discovery ovarian patient-derived models based on presence or absence of SWI/SNF component loss-of-function and PI3K pathway mutations, and test at START Discovery for the effect of Example 1 on tumor growth. Treat 2 groups of 2 mice each for 28 days. Treat Group 1 with ovarian Standard of Care (SoC) compounds carboplatin (formulated in 0.9% NaCl and administered at 60 mpk Q14D i.p.) and paclitaxel (formulated in 0.9% NaCl and administered at 10 mpk Q14D IV). Pretreat group 2 with Example 1 (formulated in 1% HEC/0.25% TWEEN® 80/0.05% Antifoam and administered at 50 mpk BID p.o.) for 5 days, followed by co-administration with Example 1 and SoC for 23 days or until tumor volumes reach 2000 mm³. Monitor models showing tumor stasis or regression with combination treatment at day 28 post dose cessation until tumor re-growth is observed. Compare average % change in tumor volume to baseline tumor volume at day 0, and calculate as the mean of individual animal [(tumor volume at treatment day x minus tumor volume at day 0), divided by tumor volume at day 0], multiplied by 100. Table 3 summarizes the effect of Example 1 treatment on the growth of the two patient-derived ovarian tumor models. ST884—a patient derived ovarian tumor model showing significant tumor growth inhibition with Example 1 treatment bears a homozygous mutation in ARID1A combined with a mutation in PIK3CA. In contrast, ST416—a patient derived ovarian tumor model which is heterozygous mutant ARID1A and no mutation in PIK3CA or PTEN—does not show tumor growth inhibition with Example 1 treatment.

TABLE 3

Effect of ovarian cancer Standard of Care (SoC) carboplatin and paclitaxel, or the combination of Example 1 plus SoC, on the growth of 2 ovarian patient derived tumor models.

| Ovarian Patient-Derived Tumor Model | Average % change in tumor volume | | | Mutation | | | |
|---|---|---|---|---|---|---|---|
| | SoC | Example 1 + SoC | Day | ARID1A LOF | SMARCA2 LOF | SMARCA4 LOF | PIK3CA |
| ST884 | 254 ± 476 | 29 ± 92 | 28 | +/+ | None | none | D478V +/− |
|  | 1713 ± 165 | 29 ± 92 | 47 | | | | |
| ST416 | 1502 ± 464 | 2107 ± 991 | 24 | +/− | none | none | none |

Oncotest (http://www.oncotest.com/) also has an established large collection of patient tumor explants transplanted directly from patients and passaged subcutaneously in nude mice as PDXs. Select 9 Oncotest gastric PDXs based on the presence of loss-of-function (LOF) SWI/SNF and/or MLL complex mutations, and test at Oncotest for effect of Example 1 or vehicle on tumor growth. For models GXA-3011, test 5 animals per group and treat for 28 days with either vehicle (1% HEC/0.25% TWEEN® 80/0.05% Antifoam) or with Example 1 at 50 mpk BID p.o. Monitor models showing tumor stasis or regression at day 28 post dose cessation until tumor re-growth is observed. Calculate ΔT/C (%) as the mean of individual animal [(tumor volume at Example 1 treatment day ≥28 minus tumor volume at day 0), divided by (tumor volume at vehicle treatment day ≥28 minus tumor volume at day 0)], multiplied by 100.

For other Oncotest gastric PDXs, treat 2 groups of 2 mice each for 28 days. Treat group 1 with gastric Standard of Care (SoC) compounds oxaliplatin (formulated in 5% glucose and administered at 8 mpk Q14D i.p.) and paclitaxel (formulated in 0.9% NaCl and administered at 10 mpk Q14D IV). Pretreat group 2 animals with Example 1 (formulated in 1% HEC/0.25% TWEEN® 80/0.05% Antifoam and administered at 50 mpk BID p.o.) for 5 days, followed by co-administration with Example 1 and SoC for 23 days or until tumor volumes reach 2000 mm$^3$. Calculate the average % change in tumor volume as the mean of individual animal [(tumor volume at treatment day ≥28 minus tumor volume at day 0), divided by tumor volume at day 0], multiplied by 100.

Table 4 summarizes the results of the effects of Example 1 treatment on the growth of the patient-derived gastric cancer models (carcinomas or adenocarcinomas), and show that models whose growth is impeded with Example 1 treatment bear two mutations: 1) at least one heterozygous LOF mutation in ARID1A and 2) either a heterozygous LOF in MLL2 (found in PDXs GXA-3052, GXA-3079, GXA-3083) and/or a mutation affecting components of the PI3K pathway (including but not limited to PIK3CA and PTEN; found in PDXs GXA-3002 and GXA-3005). Models whose growth is not inhibited following Example 1 treatment have a homozygous mutation in p53, regardless of LOF mutation status in ARID1A or MLL2 (as in PDX GXA 3011), and regardless of mutation status of the components of the PI3K pathway (as in PDX GXA-3069).

TABLE 4

Effect of SoC oxaliplatin plus paclitaxel, or the combination of Example 1 plus SoC, on the growth of patient-derived gastric cancer models.

| Gastric PDX | ΔT/C (%) Example 1 | Average % change in tumor volume vs. baseline (mean ± standard deviation) | | Day | LOF mutation(s) | | PIK3CA or PTEN mut | TP53 |
|---|---|---|---|---|---|---|---|---|
| | | SoC | Example 1 + SoC | | ARID1A | MLL2 | | |
| GXA 3002 | ND | 262 ± 137 | 122 ± 5 | 28 | wt | wt | PTEN 267fs +/− | wt |
| | | 658 ± 247 | 93 ± 47 | 42 | | | | |
| GXA 3005 | ND | 512 ± 96 | 228 ± 46 | 25 | +/− | wt | PIK3CA C420R +/− | wt |
| | | 838 | 274 | 46 | | | | |
| GXA 3079 | ND | 471 ± 267 | 67 ± 117 | 28 | +/− | +/− | wt | wt |
| | | 940 | 52 ± 75 | 49 | | | | |
| GXA 3083 | ND | 709 | −41 ± 3 | 28 | +/− (2) | +/− | wt | wt |
| GXA 3011 | 141 | ND | ND | 28 | +/− | +/− | wt | 71fs −/−, ins70 −/− |
| GXA 3069 | ND | 488 ± 258 | 235 | 28 | +/− | wt | E545A +/− | R273C −/− |
| GXA 3095 | ND | 348 ± 33 | 326 ± 68 | 28 | −/− | +/− (2) | wt | wt |
| GXA 3096 | ND | 390 | 505 ± 303 | 28 | −/− | wt | D545K +/− P2S +/− | wt |
| GXF 602 | ND | 1346 | 559 ± 123 | 21 | +/− | wt | E542K −/−, E726 +/− | wt |

Similarly, growth of the patient-derived lung tumor model LXFE 937 which bears two heterozygous MLL3 loss of function mutations, is significantly inhibited following treatment with Example 1 in combination with lung cancer SoC gemcitabine (formulated in 0.9% NaCl and administered once a week at 120 mpk i.p) plus cisplatin (formulated in 0.9% NaCl and administered subcutaneously at 3.2 mpk once a week). The data are shown in Table 5.

TABLE 5

Effect of Standard of Care (SoC) gemcitabine plus cisplatin, or the combination of Example 1 plus SoC, on the growth of a lung patient-derived NSCLC squamous cell carcinoma model

| Patient-Derived Tumor Model | Tumor type | SoC | Average % change in tumor volume Example 1 + SoC | Day | LOF Mutation |
|---|---|---|---|---|---|
| LXFE 937 | lung | 11 ± 2 | −29 ± 25 | 28 | MLL3 |
| | | 788 ± 113 | −79 ± 10 | 46 | (+/−) (2) |

Similarly, patient derived colorectal tumor CXF 1034, which does not express ARID1A protein and bears mutations in PIK3CA and PTEN, is significantly growth-inhibited when tested with Example 1 with the SoC combination irinotecan hydrochloride trihydrate (formulated in 0.9% NaCl and administered at 20 mpk Q7D IV) plus oxaliplatin (formulated in 5% glucose and administered at 8 mpk Q14D i.p.) The data are shown in Table 6.

TABLE 6

Effect of Standard of Care (SoC) irinotecan plus oxaliplatin, or the combination of Example 1 plus SoC, on the growth of a patient-derived colorectal carcinoma model.

| Patient-Derived Tumor Model | Tumor type | SoC | Average % change in tumor volume Example 1 + SoC | Day | SWI/SNF/MLL Profile |
|---|---|---|---|---|---|
| CXF 1034 | colorectal | 650 | 221 ± 88 | 28 | ARID1A negative PIK3CA R741* (+/−) PTEN del63 (+/+) |

In conclusion, the results described above provide evidence supporting the use of EZH2 inhibitors, including but not exclusive to Example 1 or Example 38, alone and/or in combination with Standard of Care (SoC) chemotherapy, in the treatment of ovarian, gastric, lung or colorectal cancers bearing combinations of mutations in components of the SWI/SNF complex and/or MLL complex and/or PI3K pathway.

The compounds of the present invention are preferably formulated as pharmaceutical compositions administered by a variety of routes. Most preferably, such compositions are for oral administration. Such pharmaceutical compositions and processes for preparing same are well known in the art. See, e.g., REMINGTON: THE SCIENCE AND PRACTICE OF PHARMACY (D. Troy, et al., eds., 21$^{st}$ ed., Lippincott Williams & Wilkins, 2005).

Dosages for the SoC compounds in patients may be administered as per the approved dosing or may vary according to the recommendation of a physician. Examples of dosing for the SoC compounds may be, for example, as follows: For ovarian cancer, the doses of carboplatin plus paclitaxel may be 175 mg/m2 IV every 3 weeks of paclitaxel followed by 175 mg/m$^2$ IV every 3 weeks of carboplatin. For gastric cancers, the doses of paclitaxel plus oxaliplatin may be 50 mg/m$^2$ IV weekly of paclitaxel and AUC 2 mg/mL weekly of oxaliplatin. For lung cancer, the dosages of gemcitabine plus cisplatin may be 1250 mg/m$^2$ IV every 3 weeks of gemcitabine plus 75 mg/m$^2$ IV every 3 weeks of cisplatin. For colorectal cancers, the doses of irinotecan plus oxaliplatin may be 125 mg/m$^2$ IV weekly or 350 mg/m$^2$ IV every 3 weeks of irinotecan and 85 mg/m2 IV every 2 weeks of oxaliplatin. (Reference for SoC treatment dosages may also be found at http://www.cancertherapyadvisor.com/gastrointestinal-cancers/gastric-cancer-treatment-regimens/article/218159/).

The EZH2 compounds of the present invention are generally effective over a wide dosage range. For example, dosages per day may fall within the daily range of up to 5000 mg/day, preferably about 100-2000 mg/day, administered in one or more doses. It will be understood however that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

We claim:
1. A compound which is

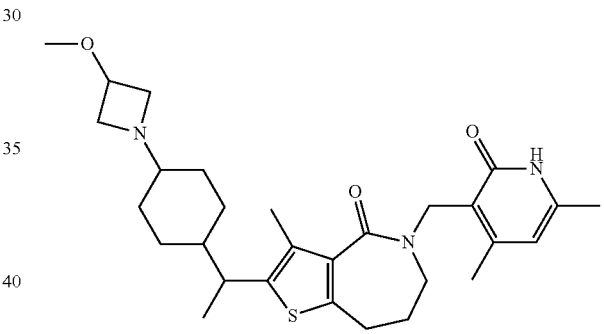

or a pharmaceutically acceptable salt thereof.

2. The compound according to claim 1 which is 5-[(4,6-dimethyl-2-oxo-1,2-dihydropyridin-3-yl)methyl]-2-{(1R)-1-[4-(3-methoxyazetidin-1-yl)cyclohexyl]ethyl}-3-methyl-5,6,7,8-tetrahydro-4H-thieno[3,2-c]azepin-4-one, or a pharmaceutically acceptable salt thereof.

3. The compound according to claim 2 which is 5-[(4,6-dimethyl-2-oxo-1,2-dihydropyridin-3-yl)methyl]-2-{(1R)-1-[trans-4-(3-methoxyazetidin-1-yl)cyclohexyl]ethyl}-3-methyl-5,6,7,8-tetrahydro-4H-thieno[3,2-c]azepin-4-one, or a pharmaceutically acceptable salt thereof.

4. A pharmaceutical composition comprising 5-[(4,6-dimethyl-2-oxo-1,2-dihydropyridin-3-yl)methyl]-2-{(1R)-1-[trans-4-(3-methoxyazetidin-1-yl)cyclohexyl]ethyl}-3-methyl-5,6,7,8-tetrahydro-4H-thieno[3,2-c]azepin-4-one or a pharmaceutically acceptable salt thereof and one or more pharmaceutically acceptable excipients, carriers, or diluents.

5. A method of treating cancer in a patient, wherein the cancer is selected from the group consisting of lymphomas, rhabdoid tumors, tumors which lack or are defective in one or more components of the SWI/SNF complex, MLL complexes, and constitutively active PI3K pathway, sarcomas, multiple myeloma, melanoma, gastrointestinal cancer, colorectal cancer, lung cancer, kidney cancer, breast cancer, ovarian cancer, and prostate cancer comprising administering to the patient, an effective amount of 5-[(4,6-dimethyl-2-oxo-1,2-dihydropyridin-3-yl)methyl]-2-{(1R)-1-[trans-4-(3-methoxyazetidin-1-yl)cyclohexyl]ethyl}-3-methyl-5,6,7,8-tetrahydro-4H-thieno[3,2-c]azepin-4-one or a pharmaceutically acceptable salt thereof.

6. The method according to claim 5 wherein the cancer is diffuse large B-cell lymphoma and follicular lymphoma.

7. The method according to claim 5 wherein the cancer is diffuse large B-cell lymphoma.

8. The method according to claim 5 wherein the cancer is a rhabdoid tumor that lacks SNF5.

9. The method according to claim 5 wherein the cancer is gastric cancer.

10. The method according to claim 5 wherein the cancer is ovarian cancer.

11. The method according to claim 5 wherein the cancer is multiple myeloma.

12. The method according to claim 10 further comprising administering to the patient carboplatin and paclitaxel.

13. The method according to claim 9 further comprising administering to the patient oxaliplatin and paclitaxel.

14. The method according to claim 5 wherein the cancer is lung cancer and further comprising administering to the patient gemcitabine and cisplatin.

15. The method according to claim 5 wherein the cancer is colorectal cancer and further comprising administering to the patient irinotecan and oxaliplatin.

* * * * *